US008835427B2

(12) United States Patent
Liepa et al.

(10) Patent No.: US 8,835,427 B2
(45) Date of Patent: Sep. 16, 2014

(54) FUNGICIDAL HETEROCYCLIC COMPOUNDS

(75) Inventors: Andris Juris Liepa, Victoria (AU); Robert James Pasteris, Newark, DE (US); Thomas Martin Stevenson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/518,943

(22) PCT Filed: Jan. 7, 2011

(86) PCT No.: PCT/US2011/020473
§ 371 (c)(1),
(2), (4) Date: Jun. 25, 2012

(87) PCT Pub. No.: WO2011/085170
PCT Pub. Date: Jul. 14, 2011

(65) Prior Publication Data
US 2012/0309752 A1    Dec. 6, 2012

Related U.S. Application Data

(60) Provisional application No. 61/293,095, filed on Jan. 7, 2010.

(51) Int. Cl.
*C07D 417/04* (2006.01)
*C07D 487/04* (2006.01)
*A01N 43/80* (2006.01)
*A01N 43/90* (2006.01)

(52) U.S. Cl.
USPC .......... 514/228.8; 514/252.02; 514/370; 514/342; 514/256; 514/255.05; 548/181; 546/269.7; 544/238; 544/63; 544/333; 544/405

(58) Field of Classification Search
USPC .......... 544/238, 63, 333, 405; 548/181; 546/269.7; 514/228.8, 252.02, 370, 514/342, 256, 255.05
See application file for complete search history.

(56) References Cited

U.S. PATENT DOCUMENTS

| 4,151,279 A | 4/1979 | Singer |
| 2007/0004741 A1 | 1/2007 | Apodaca et al. |

FOREIGN PATENT DOCUMENTS

| EP | 0 469 685 A1 | 2/1992 |
| EP | 1 790 640 A1 | 5/2007 |
| EP | 2 009 006 A1 | 12/2008 |
| WO | 2007/064553 A2 | 6/2007 |
| WO | 2008/013622 A2 | 1/2008 |
| WO | 2008/013925 A2 | 1/2008 |
| WO | 2008/091594 A2 | 7/2008 |
| WO | 2009/094407 A2 | 7/2009 |
| WO | 2009/094445 A2 | 7/2009 |

OTHER PUBLICATIONS

Keith et al: "Thiadiazolopiperazinyl ureas as inhibitors of fatty acid amide hydrolase", Bioorganic & Medicinal Chemistry Letters, Pergamon, Elsevier Science, GB, vol. 18, No. 17, Sep. 1, 2008, pp. 4838-4843.

*Primary Examiner* — Kahsay Habte
(74) *Attorney, Agent, or Firm* — Renee M. Lett

(57) ABSTRACT

Disclosed are compounds of Formula 1 and Formula 1A including all stereoisomers, N-oxides, and salts thereof,

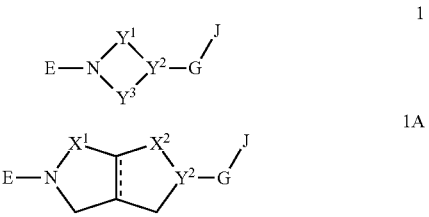

wherein
E, $Y^1$, $Y^2$, $Y^3$, G, J, $X^1$ and $X^2$ are as defined in the disclosure.

Also disclosed are compositions containing the compounds of Formula 1 or Formula 1A and methods for controlling plant disease caused by a fungal pathogen comprising applying an effective amount of a compound or a composition of the invention.

12 Claims, No Drawings

FUNGICIDAL HETEROCYCLIC COMPOUNDS

FIELD OF THE INVENTION

This invention relates to certain heterocyclic compounds, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

Certain pyrazole derivatives of Formula i and their use as fungicides are disclosed in PCT Patent Publication WO 2008/013925

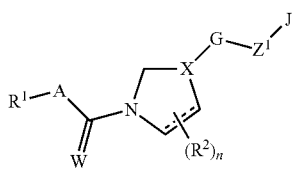

i

SUMMARY OF THE INVENTION

This invention is directed to compounds of Formula 1 and Formula 1A (including all stereoisomers), N-oxides, and salts thereof, agricultural compositions containing them and their use as fungicides:

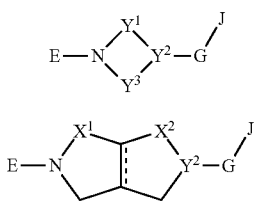

1

1A wherein
E is a radical selected from the group consisting of

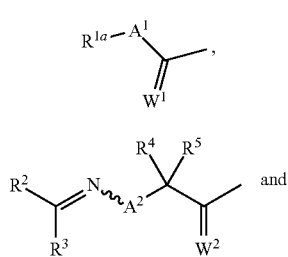

E-1

E-2 and

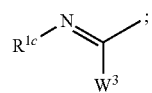

E-3

$Y^1$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(=O)—;

$Y^2$ is a ring member selected from —C($R^{14}$)— and —N—;

$Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(=O)—; or $Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S—, —N($R^{23}$)— and —C(=O)—;

$X^1$ and $X^2$ are each independently a ring member selected from —C($R^{14}$)— and —O—;

G is an optionally substituted 5-membered heterocyclic ring;

J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=NR$^{11}$)$_f$, and the silicon atom ring members are independently selected from SiR$^9$R$^{10}$, each ring or ring system optionally substituted with up to 5 substituents independently selected from R$^6$; or J is C(=W$^4$)NT$^A$T$^B$;

W$^4$ is O or S;

T$^A$ is H or C$_1$-C$_3$ alkyl;

T$^B$ is CR$^{17}$R$^{18}$R$^{19}$,

A$^1$ is CHR$^{15}$, NR$^{16}$ or C(=O);

A$^2$ is —O—, —S—, —N(R$^7$)—, —C(R$^8$)$_2$—, —OC(R$^8$)$_2$—, —SC(R$^8$)$_2$— or —N(R$^7$)C(R$^8$)$_2$—, wherein the bond projecting to the left is connected to —N=C(R$^2$)(R$^3$), and the bond projecting to the right is connected to —C(R$^4$)(R$^5$)—;

W$^1$ and W$^2$ are each independently O or S;

W$^3$ is OR$^{24}$, SR$^{25}$, NR$^{26}$R$^{27}$ or R$^{28}$;

R$^{1a}$ and R$^{1c}$ independently are an optionally substituted phenyl, an optionally substituted naphthalenyl or an optionally substituted 5- to 6-membered heteroaromatic ring; or pyrrolidinyl, piperidinyl or morpholiny, cyano, C$_1$-C$_8$ alkyl, C$_2$-C$_8$ alkenyl, C$_2$-C$_8$ alkynyl, C$_1$-C$_8$ haloalkyl, C$_2$-C$_8$ haloalkenyl, C$_2$-C$_8$ haloalkynyl, C$_3$-C$_8$ cycloalkyl, C$_3$-C$_8$ halocycloalkyl, C$_4$-C$_{10}$ alkylcycloalkyl, C$_4$-C$_{10}$ cycloalkylalkyl, C$_4$-C$_{10}$ halocycloalkylalkyl, C$_5$-C$_{10}$ alkylcycloalkylalkyl, C$_2$-C$_8$ alkoxyalkyl, C$_2$-C$_8$ haloalkoxyalkyl, C$_4$-C$_{10}$ cycloalkoxyalkyl, C$_3$-C$_{10}$ alkoxyalkoxyalkyl, C$_2$-C$_8$ alkylthioalkyl, C$_2$-C$_8$ haloalkylthioalkyl, C$_2$-C$_8$ alkylsulfinylalkyl, C$_2$-C$_8$ alkylsulfonylalkyl, C$_3$-C$_8$ alkoxycarbonylalkyl, C$_3$-C$_8$ haloalkoxycarbonylalkyl, C$_2$-C$_8$ alkylaminoalkyl, C$_3$-C$_{10}$ dialkylaminoalkyl, C$_2$-C$_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_1$-$C_8$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_8$ alkylsulfonylamino or $C_1$-$C_8$ haloalkylsulfonylamino;

$R^2$ is H, halogen, cyano, amino, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_4$-$C_6$ halocycloalkylalkyl, $C_3$-$C_6$ cycloalkenyl, $C_3$-$C_6$ halocycloalkenyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_2$-$C_6$ alkylcarbonyl, $C_2$-$C_6$ haloalkylcarbonyl, $C_4$-$C_6$ cycloalkylcarbonyl, $C_2$-$C_6$ alkoxycarbonyl, $C_4$-$C_6$ cycloalkoxycarbonyl, $C_5$-$C_6$ cycloalkylalkoxycarbonyl, $C_2$-$C_6$ alkylaminocarbonyl, $C_3$-$C_6$ dialkylaminocarbonyl, $C_1$-$C_6$ alkoxy, $C_1$-$C_6$ haloalkoxy, $C_3$-$C_6$ cycloalkoxy, $C_3$-$C_6$ halocycloalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_6$ cycloalkylthio, $C_1$-$C_6$ alkylamino, $C_2$-$C_6$ dialkylamino, $C_1$-$C_6$ haloalkylamino, $C_2$-$C_6$ halodialkylamino, $C_3$-$C_6$ cycloalkylamino, $C_2$-$C_6$ alkylcarbonylamino, $C_2$-$C_6$ haloalkylcarbonylamino, $C_1$-$C_6$ alkylsulfonylamino or $C_1$-$C_6$ haloalkylsulfonylamino;

$R^3$ is H, halogen, cyano, hydroxy, $C_1$-$C_3$ alkyl, $C_1$-$C_3$ haloalkyl, $C_1$-$C_3$ alkoxy or $C_1$-$C_3$ haloalkoxy; or $R^2$ and $R^3$ are taken together with the carbon atom to which they are attached to form a 3- to 7-membered ring containing ring members selected from carbon atoms and up to 4 heteroatoms independently selected from up to 2 O, up to 2 S, up to 2 N and up to 2 Si atoms, wherein up to 3 carbon atom ring members are independently selected from C(=O) and C(=S); the sulfur atom ring members are independently selected from S(=O)$_s$(=NR$^{11}$)$_f$, and the silicon atom ring members are independently selected from SiR$^9$R$^{10}$, the ring optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^4$ is optionally substituted phenyl, optionally substituted naphthalenyl or an optionally substituted 5- to 6-membered heteroaromatic ring; or H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyloxy, $C_2$-$C_4$ haloalkylcarbonyloxy, $C_2$-$C_5$ alkoxycarbonyloxy, $C_2$-$C_5$ alkylaminocarbonyloxy or $C_3$-$C_5$ dialkylaminocarbonyloxy;

$R^5$ is H, $C_1$-$C_3$ alkyl or $C_1$-$C_3$ haloalkyl;

each $R^6$ is independently H, halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino, —NR$^{20}$R$^{21}$ or —ZQ;

each Z is independently a direct bond, O, C(=O), S(O)$_m$, CH(R$^{12}$) or N(R$^{13}$);

each Q is independently phenyl, benzyl, naphthalenyl, a 5- to 6-membered heteroaromatic ring or an 8- to 11-membered heteroaromatic bicyclic ring system, each optionally substituted with up to 2 substituents independently selected from R$^{6b}$ on carbon and nitrogen atom ring members, and each optionally substituted with up to 5 substituents independently selected from R$^{6a}$ on carbon atom ring members and selected from $C_1$-$C_3$ alkyl, $C_1$-$C_3$ alkylcarbonyl, $C_2$-$C_3$ alkoxycarbonyl or $C_1$-$C_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and, C(=S), the sulfur atom ring members are independently selected from S(=O)$_s$(=NR$^{11}$)$_f$, and the silicon atom ring members are independently selected from SiR$^9$R$^{10}$, each ring or ring system optionally substituted with up to 2 substituents independently selected from R$^{6b}$ on carbon and nitrogen atom ring members, and each ring or ring system optionally substituted with up to 5 substituents independently selected from R$^{6a}$ on carbon atom ring members and selected from $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members;

each R$^{6a}$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^6$ and $R^{6a}$ are taken together with the atoms to which they are attached to form a 5- to 7-membered ring containing ring members selected from carbon atoms and optionally up to 3 heteroatoms independently selected from up to 1 O, up to 1 S and up to 1 N atom, the ring optionally substituted with up to 3 substituents independently selected from halogen, cyano, nitro, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members;

each $R^{6b}$ is independently phenyl optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy; or a 5- to 6-membered heteroaromatic ring containing ring members selected from carbon atoms and up to 4 heteroatoms independently selected from up to 2 O, up to 2 S and up to 4 N atoms, and optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members; or a 3- to 7-membered nonaromatic ring containing ring members selected from carbon atoms and up to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^7$ is H, cyano, $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylsulfonyl or $C_1$-$C_4$ haloalkylsulfonyl; or $R^3$ and $R^7$ are taken together with the linking atoms to which they are attached to form a 5- to 7-membered partially saturated ring containing ring members, in addition to the linking atoms, selected from carbon atoms and up to 3 heteroatoms independently selected from up to 1 O, up to 1 S and up to 1 N atom, the ring optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

each $R^8$ is independently H, $C_1$-$C_3$ alkyl or $C_1$-$C_3$ haloalkyl;

each $R^9$ and $R^{10}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each $R^{11}$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylamino, $C_2$-$C_8$ dialkylamino, $C_1$-$C_6$ haloalkylamino or phenyl;

each $R^{12}$ is independently H, $C_1$-$C_4$ alkyl or $C_1$-$C_4$ haloalkyl;

$R^{13}$ is H, $C_1$-$C_4$ alkyl, $C_1$-$C_4$ haloalkyl, $C_3$-$C_6$ cycloalkyl, $C_2$-$C_4$ alkylcarbonyl, $C_2$-$C_4$ haloalkylcarbonyl, $C_2$-$C_4$ alkoxycarbonyl or $C_2$-$C_4$ haloalkoxycarbonyl;

each $R^{14}$ is independently H, halogen, cyano, hydroxy, $C_1$-$C_4$ alkyl, $C_1$-$C_4$ alkenyl, $C_1$-$C_4$ haloalkyl or $C_1$-$C_4$ alkoxy;

$R^{15}$ is H, halogen, cyano, hydroxy, —CHO, $C_1$-$C_4$ alkyl, $C_2$-$C_4$ alkenyl, $C_2$-$C_8$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_3$-$C_5$ alkoxycarbonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

$R^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;

$R^{17}$ is H or $C_1$-$C_4$ alkyl;

$R^{18}$ is phenyl, benzyl, naphthalenyl or a 5- to 6-membered heteroaromatic ring, each optionally substituted with up to 3 substituents independently selected from $R^{22}$;

$R^{19}$ is H, cyano, nitro, $C_1$-$C_6$ alkyl, $C_2$-$C_6$ alkenyl or $C_2$-$C_6$ alkynyl;

each $R^{20}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{21}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —$Z^1Q$;

each $R^{22}$ is independently halogen, cyano, hydroxy, $C_1$-$C_3$ alkyl, $C_1$-$C_3$ haloalkyl or $C_1$-$C_3$ alkoxy; or $R^{19}$ and $R^{22}$ are taken together with the atoms to which they are attached to form a 5- to 7-membered ring containing ring members selected from carbon atoms and up to 4 heteroatoms independently selected from up to 2 O, up to 2 S, up to 2 N and up to 2 Si atoms, wherein up to 2 carbon atom ring members are independently selected from C(=O) and C(=S), the sulfur atom ring members are independently selected from $S(=O)_s(=NR^{11})_f$, and the silicon atom ring members are independently selected from $SiR^9R^{10}$, the ring optionally substituted with up to 4 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members;

each $Z^1$ is independently O, C(=O), $S(O)_m$ or $CH(R^{12})$;

each $R^{23}$ is independently H, —CHO, $C_1$-$C_4$ alkyl, $C_1$-$C_4$ alkenyl, $C_1$-$C_4$ haloalkyl, $C_1$-$C_3$ alkylcarbonyl, $C_2$-$C_4$ alkoxyalkyl, $C_2$-$C_4$ alkoxycarbonyl, $C_2$-$C_4$ alkylaminocarbonyl, $C_4$-$C_7$ dialkylaminocarbonyl or $C_2$-$C_4$ alkylsulfonyl;

each $R^{24}$ and $R^{25}$ is independently $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_2$-$C_6$ alkoxyalkyl, $C_4$-$C_8$ cycloalkoxyalkyl, $C_3$-$C_6$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl;

$R^{26}$ is H, cyano, hydroxy, amino, $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_4$-$C_8$ cycloalkylalkyl, $C_2$-$C_6$ alkoxyalkyl, $C_1$-$C_6$ alkoxy, $C_1$-$C_6$ haloalkoxy, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_1$-$C_6$ alkylamino, $C_2$-$C_8$ dialkylamino, $C_1$-$C_6$ haloalkylamino or $C_2$-$C_8$ halodialkylamino;

$R^{27}$ is H, $C_1$-$C_6$ alkyl, $C_3$-$C_6$ alkenyl, $C_3$-$C_6$ alkynyl, $C_1$-$C_6$ haloalkyl or $C_3$-$C_6$ cycloalkyl; or $R^{26}$ and $R^{27}$ are taken together as —$(CH_2)_4$—, —$(CH_2)_5$— or —$(CH_2)_2O(CH_2)_2$—;

$R^{28}$ is H, halogen, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl or $C_3$-$C_6$ dialkylaminocarbonyl;

each m is independently 0, 1 or 2; and s and f are independently 0, 1 or 2 in each instance of $S(=O)_s(=NR^{11})_f$, provided that the sum of s and f is 1 or 2;

provided that:
(a) when $Y^1$ is a ring-forming chain consisting of 2 chain members and $Y^3$ is a ring-forming chain consisting of 2 or 3 chain members, then at least one of the chain members of $Y^1$ or $Y^3$ is other than $C(R^{14})_2$;
(b) when $Y^1$ is a ring-forming chain consisting of 2 chain members or $Y^3$ is a ring-forming chain consisting of 2 or 3 chain members and when a chain member is —C(=O)—, then said chain member is bonded to other than N-E in Formula 1;
(c) when $X^1$ is —O—, then $X^2$ is —C($R^{14}$)— and the ring is fully saturated; and when $X^2$ is —O—, then $X^1$ is —C($R^{14}$)— and the ring is fully saturated;
(d) when $Y^2$ is N, then the heterocyclic ring G is bonded to $Y^2$ through a carbon atom; and
(f) when $R^{15}$ is hydroxy, then $R^{1a}$ is bonded through a carbon atom to A in Formula 1 or Formula 1A.

More particularly, this invention pertains to a compound of Formula 1 or Formula 1A (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed or bud of a vegetative propagation unit such as tuber, corm or rhizome.

In the above recitations, the term "alkyl", used either alone or in compound words such as "alkylthio" or "haloalkyl" includes straight-chain and branched alkyl, such as, methyl, ethyl, n-propyl, i-propyl, and the different butyl, pentyl and hexyl isomers. "Alkenyl" includes straight-chain and branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain and branched alkynes such as ethynyl, 1-propynyl, 2-propynyl, and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene isomers. "Alkenylene" denotes a straight-chain or branched alkenediyl containing one olefinic bond. Examples of "alkenylene" include $CH=CH$, $CH_2CH=CH$ and $CH=C(CH_3)$.

"Alkoxy" includes, for example, methoxy, ethoxy, n-propyloxy, i-propyloxy, and the different butoxy, pentoxy and hexyloxy isomers. "Alkenyloxy" includes straight-chain and branched alkenyl attached to and linked through an oxygen atom. Examples of "alkenyloxy" include $H_2C=CHCH_2O$, $CH_3CH=CHCH_2O$ and $(CH_3)_2C=CHCH_2O$. "Alkynyloxy" includes straight-chain and branched alkynyloxy moieties. Examples of "alkynyloxy" include $HC\equiv CCH_2O$, $CH_3C\equiv CCH_2O$ and $CH_3C\equiv CCH_2CH_2O$. The term "alkylthio" includes straight-chain and branched alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$, and the different butylsulfinyl, pentylsulfinyl and hexylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different butylsulfonyl, pentylsulfonyl and hexylsulfonyl isomers. "Alkylamino" includes an NH radical substituted with a straight-chain or branched alkyl group. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_1)_2N$ and $CH_3CH_2(CH_3)N$.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3C(=O)$, $CH_3CH_2OC(=O)$, $CH_3CH_2CH_2C(=O)$, $(CH_3)_2CHOC(=O)$, and the different butoxy- and pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$, and the different butylamino- and pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkoxyalkoxy" denotes alkoxy substitution on another alkoxy moiety. "Alkoxyalkoxyalkyl" denotes alkoxyalkoxy substitution on alkyl. Examples of "alkoxyalkoxyalkyl" include $CH_3OCH_2OCH_2$, $CH_3OCH_2OCH_2CH_2$ and $CH_3CH_2OCH_2OCH_2$.

"Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2SCH_2$ and $CH_3CH_2SCH_2CH_2$; "alkylsulfinylalkyl" and "alkylsulfonylalkyl" include the corresponding sulfoxides and sulfones, respectively. "Alkylcarbonylthio" denotes a straight-chain or branched alkylcarbonyl attached to and linked through a sulfur atom. Examples of "alkylcarbonylthio" include $CH_3C(=O)S$, $CH_3CH_2CH_2C(=O)S$ and $(CH_3)_2CHC(=O)S$.

"Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2CH_2NHCH_2$ and $CH_3CH_2NHCH_2CH_2$. Examples of "dialkylaminoalkyl" include $((CH_3)_2CH)_2NCH_2$, $(CH_3CH_2CH_2)_2NCH_2$ and $CH_3CH_2(CH_3)NCH_2CH_2$.

The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$. "Alkylsulfonylamino" denotes an NH radical substituted with alkylsulfonyl. Examples of "alkylsulfonylamino" include $CH_3CH_2S(=O)_2NH$ and $(CH_3)_2CHS(=O)_2NH$.

The term "alkylcarbonyloxy" denotes a straight-chain or branched alkyl bonded to a $C(=O)O$ moiety. Examples of "alkylcarbonyloxy" include $CH_3CH_2C(=O)O$ and $(CH_3)_2CHC(=O)O$. The term "alkylcarbonylalkoxy" denotes alkylcarbonyl bonded to an alkoxy moiety. Examples of "alkylcarbonylalkoxy" include $CH_3C(=O)CH_2CH_2O$ and $CH_3CH_2C(=O)CH_2O$. Examples of "alkoxycarbonyloxy" include $CH_3CH_2CH_2C(=O)O$ and $(CH_3)_2CHOC(=O)O$. "Alkoxycarbonylalkyl" denotes alkoxycarbonyl substitution on a straight-chain or branched alkyl. Examples of "alkoxycarbonylalkyl" include $CH_3C(=O)CH_2CH(CH_3)$, $CH_3CH_2C(=O)CH_2CH_2$ and $(CH_3)_2CHOC(=O)CH_2$.

The term "alkylaminocarbonyloxy" denotes a straight-chain or branched alkylaminocarbonyl attached to and linked through an oxygen atom. Examples of "alkylaminocarbonyloxy" include $(CH_3)_2CHCH_2NHC(=O)O$ and $CH_3CH_2NHC(=O)O$. Examples of "dialkylaminocarbonyloxy" include $CH_3CH_2CH_2(CH_3)NC(=O)O$ and $(CH_3)_2NC(=O)O$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to a straight-chain or branched alkyl group. The term "alkylcycloalkyl" denotes alkyl substitution on a cycloalkyl moiety and includes, for example, ethylcyclopropyl, i-propylcyclobutyl, methylcyclopentyl and methylcyclohexyl. "Cycloalkenyl" includes groups such as cyclopentenyl and cyclohexenyl as well as groups with more than one double bond such as 1,3- or 1,4-cyclohexadienyl.

The term "cycloalkoxy" denotes cycloalkyl attached to and linked through an oxygen atom such as cyclopentyloxy and cyclohexyloxy. The term "cycloalkylthio" denotes cycloalkyl attached to and linked through a sulfur atom such as cyclopropylthio and cyclopentylthio; "cycloalkylsulfonyl" includes the corresponding sulfones. The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy groups bonded to a straight-chain or branched alkyl moiety. "Cycloalkylalkoxy" denotes cycloalkyl substitution on an alkoxy moiety. Examples of "cycloalkylalkoxy" include cyclopropylmethoxy, cyclopentylethoxy, and other cycloalkyl groups bonded to a straight-chain or branched alkoxy moiety.

"Alkylcycloalkylalkyl" denotes an alkyl group substituted with alkylcycloalkyl. Examples of "alkylcycloalkylalkyl" include methylcyclohexylmethyl and ethylcyclopoylmethyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

"Cycloalkylamino" denotes an NH radical substituted with cycloalkyl. Examples of "cycloalkylamino" include cyclopropylamino and cyclohexylamino. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to a straight-chain or branched alkyl group.

"Cycloalkylcarbonyl" denotes cycloalkyl bonded to a $C(=O)$ group including, for example, cyclopropylcarbonyl and cyclopentylcarbonyl. The term "cycloalkoxycarbonyl" means cycloalkoxy bonded to a $C(=O)$ group, for example, cyclopropyloxycarbonyl and cyclopentyloxycarbonyl. "Cycloalkylaminocarbonyl" denotes cycloalkylamino bonded to a $C(=O)$ group, for example, cyclopentylaminocarbonyl and cyclohexylaminocarbonyl. "Cycloalkylalkoxycarbonyl" denotes cycloalkylalkoxy bonded to a $C(=O)$ group. Examples of "cycloalkylalkoxycarbonyl" include cyclopropylethoxycarbonyl and cyclopentylmethoxycarbonyl. "Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkenyl", "haloalkynyl" "haloalkoxy", "haloalkylthio", "haloalkylamino", "haloalkylsulfinyl", "haloalkylsulfonyl", "halocycloalkyl", and the like, are defined analogously to the term "haloalkyl". Examples of "haloalkenyl" include $Cl_2C=CHCH_2$ and $CF_3CH_2CH=CHCH_2$. Examples of "haloalkynyl" include $HC≡CCHCl$, $CF_3C≡C$, $CCl_3C≡C$ and $FCH_2C≡CCH_2$. Examples of "haloalkoxy" include $CF_3O$, $CCl_3CH_2O$, $F_2CHCH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylamino" include $CF_3(CH_3)CHNH$, $(CF_3)_2CHNH$ and $CH_2ClCH_2NH$. Examples of "haloalkylsulfinyl" include $CF_3S(=O)$, $CCl_3S(=O)$, $CF_3CH_2S(=O)$ and $CF_3CF_2S(=O)$. Examples of "haloalkylsulfonyl" include $CF_3S(=O)_2$, $CCl_3S(=O)_2$, $CF_3CH_2S(=O)_2$ and $CF_3CF_2S(=O)_2$. Examples of "halocycloalkyl" include 2-chlorocyclopropyl, 2-fluorocyclobutyl, 3-bromocyclopentyl and 4-chorocyclohexyl. The term "halodialkyl", either alone or in compound words such as "halodialkylamino", means at least one of the two alkyl groups is substituted with at least one halogen atom, and independently each halogenated alkyl group may be partially or fully substituted with halogen atoms which may be the same or different. Examples of "halodialkylamino" include $(BrCH_2CH_2)_2N$ and $BrCH_2CH_2(ClCH_2CH_2)N$.

"Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2CH_2$.

"Trialkylsilyl" includes 3 branched and/or straight-chain alkyl radicals attached to and linked through a silicon atom, such as trimethylsilyl, triethylsilyl and tert-butyldimethylsilyl.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring or ring system means the group does not have any substituents other than its one or more attachments to the remainder of Formula 1 or Formula 1A. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 4. As used herein, the term "optionally substituted" is used interchangeably with the phrase "substituted or unsubstituted" or with the term "(un)substituted." When a group (e.g., J) contains a substituent (e.g., $R^6$) which can be hydrogen, then when this substituent is taken as hydrogen, it is recognized that this is equivalent to said group being unsubstituted.

The number of optional substituents may be restricted by an expressed limitation. For example, the phrase "optionally substituted with up to 3 substituents independently selected from $R^6$" means that 0, 1, 2 or 3 substituents can be present (if the number of potential connection points allows). Similarly, the phrase "optionally substituted with up to 5 substituents independently selected from $R^6$" means that 0, 1, 2, 3, 4 or 5 substituents can be present if the number of available connection points allows. When a range specified for the number of substituents (e.g., x being an integer from 0 to 5 in Exhibit 3) exceeds the number of positions available for substituents on a ring (e.g., 2 positions available for ($R^6$), on J-1 in Exhibit 3), the actual higher end of the range is recognized to be the number of available positions.

When a compound is substituted with a substituent bearing a subscript that indicates the number of said substituents can vary (e.g., ($R^6$), in Exhibit 3 wherein x is 0 to 5), then said substituents are independently selected from the group of defined substituents, unless otherwise indicated. When a variable group is shown to be optionally attached to a position, for example $(R^{6a})_p$ in Exhibit 6 wherein p may be 0, then hydrogen may be at the position even if not recited in the definition of the variable group.

The term "optionally substituted" without recitation of number or identity of possible substituents (e.g., in definition of rings in G and $R^2$ and $R^3$) refers to groups which are unsubstituted or have at least one non-hydrogen substituent that does not extinguish the biological activity possessed by the unsubstituted analog.

Naming of substituents in the present disclosure uses recognized terminology providing conciseness in precisely conveying to those skilled in the art the chemical structure. For sake of conciseness, locant descriptors may be omitted.

As described in the Summary of the Invention $Y^1$ is —N═C($R^{14}$)—, —C($R^{14}$)═N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(═O)—. When $Y^1$ is —N═C($R^{14}$)— or —C($R^{14}$)═N— the bond projecting to the left is connected to the nitrogen atom (i.e. N-E) of Formula 1, and the bond projecting to the right is connected to $Y^2$ in Formula 1. When $Y^1$ is a ring-forming chain, one chain member is —C($R^{14}$)$_2$— and the other member is selected from —C($R^{14}$)$_2$—, —O—, —S—, —N($R^{23}$)— and —C(═O)—. Both members of $Y^1$ may be —C($R^{14}$)$_2$—. When the second chain member is selected from —O—, —S—, —N($R^{23}$)— and —C(═O)—, the resulting ring-forming chain may be connected to the nitrogen atom (i.e. N-E) of Formula 1 and $Y^2$ in Formula 1 in any order. The ring forming chain $Y^1$ may be, for example, —C($R^{14}$)$_2$C($R^{14}$)$_2$—, —C($R^{14}$)$_2$O—, —N$R^{23}$(C$R^{14}$)$_2$— or —S(C$R^{14}$)$_2$— where $R^{14}$ and $R^{23}$ are as defined in the Summary of the Invention and wherein the bond projecting to the left is bonded to either the nitrogen (i.e. N-E) of Formula 1 or $Y^2$ of Formula 1.

As described in the Summary of the Invention, $Y^3$ is —N═C($R^{14}$)—, —C($R^{14}$)═N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(═O)—. When $Y^3$ is —N═C($R^{14}$)— or —C($R^{14}$)═N— the bond projecting to the left is connected to the nitrogen atom (i.e. N-E) of Formula 1, and the bond projecting to the right is connected to $Y^2$ in Formula 1. Both members of $Y^3$ may be —C($R^{14}$)$_2$—. When the second chain member is selected from —O—, —S—, —N($R^{23}$)— and —C(═O)—, the resulting ring-forming chain may be connected to the nitrogen atom (i.e. N-E) of Formula 1 and $Y^2$ in Formula 1 in any order. The ring forming chain $Y^3$ may be, for example, —C($R^{14}$)$_2$C($R^{14}$)$_2$—, —C($R^{14}$)$_2$O—, —N$R^{23}$(C$R^{14}$)$_2$— or —S(C$R^{14}$)$_2$— where $R^{14}$ and $R^{23}$ are as defined in the Summary of the Invention and wherein the bond projecting to the left is bonded to either the nitrogen (i.e. N-E) of Formula 1 or $Y^2$ of Formula 1.

As described in the Summary of the Invention, $Y^3$ is —C($R^{14}$)$_2$N═C($R^{14}$)—, —C($R^{14}$)$_2$C($R^{14}$)═N—, —N═C($R^{14}$)C($R^{14}$)—, —C($R^{14}$)═NC($R^{14}$)$_2$—, or a ring-forming chain consisting of 3 chain members wherein two chain members are —C($R^{14}$)$_2$— and the third chain member is selected from —C($R^{14}$)$_2$—, —O—, —S—, —N($R^{23}$)— and —C(═O)—. When $Y^3$ is —C($R^{14}$)$_2$N═C($R^{14}$)—, —C($R^{14}$)$_2$C($R^{14}$)═N—, —N═C($R^{14}$)C($R^{14}$)—, or —C($R^{14}$)═NC($R^{14}$)$_2$— the bond projecting to the left is connected to the nitrogen atom (i.e. N-E) of Formula 1, and the bond projecting to the right is connected to $Y^2$ in Formula 1. When $Y^3$ is a ring-forming chain consisting of 3 chain members wherein two chain members are —C($R^{14}$)$_2$— and the third chain member is selected from —C($R^{14}$)$_2$—, —O—, —S—, —N($R^{23}$)— and —C(═O)—, the resulting ring-forming chain may be bonded to the nitrogen (i.e. N-E) of Formula 1 and $Y^2$ in any order. For example, $Y^3$ may be —C($R^{14}$)$_2$OC($R^{14}$)$_2$—, —SC($R^{14}$)$_2$C($R^{14}$)$_2$—, or —N($R^{23}$)C($R^{14}$)$_2$C($R^{14}$)$_2$— wherein the bond projecting to the left is bonded to either the nitrogen (i.e. N-E) of Formula 1 or $Y^2$ of Formula 1. Note that all three chain members of $Y^3$ may be —C($R^{14}$)$_2$—.

As described in the Summary of the Invention, $X^1$ and $X^2$ are each independently a ring member selected from —C($R^{14}$)— and —O—. Note that $X^1$ or $X^2$ can not simultaneously be oxygen. Also note, when either $X^1$ or $X^2$ is oxygen, then the other $X^1$ or $X^2$ must be —C($R^{14}$)— and the bicyclic ring system containing $X^1$ and $X^2$ is fully saturated. Further, note that both $X^1$ and $X^2$ may by simultaneously be —C($R^{14}$)—.

Note that when —C(═O)— is selected as a member of ring-forming chains $Y^1$ or $Y^3$, its placement must be other than adjacent to the nitrogen (i.e. N-E) of Formula 1. Ring-forming members $Y^1$ and $Y^3$ can be combined with ring member. $Y^2$ of Formula 1 to form 6- or 7-membered rings such as those shown in Exhibits 1A and 1B below. Note that when $Y^1$ is a ring-forming chain consisting of 2 chain members and $Y^3$ is a ring-forming chain consisting of 2 or 3 chain members then at least one of the chain members of $Y^1$ or $Y^3$ is other than C($R^{14}$)$_2$. For instance when $Y^1$ is —C($R^{14}$)$_2$C($R^{14}$)$_2$—, then at least one member of $Y^3$ must be selected from —O—, —S—, —N($R^{23}$)— and —C(═O)—. Similarly, when $Y^3$ is —C($R^{14}$)$_2$C($R^{14}$)$_2$C($R^{14}$)$_2$—, then at least one ring member of $Y^1$ must be selected from —O—, —S—, —N($R^{23}$)— and —C(═O)—.

Unless otherwise indicated, a "ring" or "ring system" as a component of Formula 1 or Formula 1A (e.g., substituent J and Q) is carbocyclic or heterocyclic. The term "ring system" denotes two or more connected rings. The term "spirocyclic ring system" denotes a ring system consisting of two rings connected at a single atom (so the rings have a single atom in common). Illustrative of a J moiety that is a spirocyclic ring system is J-29-27 shown in Exhibit 3A below. The term "bicyclic ring system" denotes a ring system consisting of two rings sharing two or more common atoms. In a "fused bicyclic ring system" the common atoms are adjacent, and therefore the rings share two adjacent atoms and a bond connecting them. In a "bridged bicyclic ring system" the common atoms are not adjacent (i.e. there is no bond between the bridgehead atoms). A "bridged bicyclic ring system" can be formed by bonding a segment of one or more atoms to nonadjacent ring members of a ring.

A ring, a bicyclic ring system or a spirocyclic ring system can be part of an extended ring system containing more than two rings wherein substituents on the ring, bicyclic ring system or spirocyclic ring system are taken together to form the additional rings, which may be in bicyclic and/or spirocyclic relationships with other rings in the extended ring system. For example, the J moiety J-29-30 shown in Exhibit 3A below consists of a dihydro isoxazoline ring substituted with one $R^6$ substituent which is —ZQ wherein Z is a —CH$_2$— group and Q is a phenyl ring substituted with an $R^{6a}$ substituent (—CH$_2$—) which is taken together with another $R^6$ substituent (—CH$_2$—) on the dihydro isoxazoline ring to form the additional six-membered ring in the ring system.

The term "ring member" refers to an atom (e.g., C, O, N or S) or other moiety (e.g., C(═O), C(═S), Si$R^9R^{10}$ or S(═O)$_s$ (═N$R^{11}$)$_t$) forming the backbone of a ring or ring system. The term "aromatic" indicates that each ring atom is essentially in the same plane and has a p-orbital perpendicular to the ring plane, and that (4n+2) π electrons, where n is a positive integer, are associated with the ring to comply with Hückers rule The term "carbocyclic ring" denotes a ring wherein the atoms forming the ring backbone are selected only from carbon. Unless otherwise indicated; a carbocyclic ring can be a saturated, partially unsaturated, or fully unsaturated ring.

When a fully unsaturated carbocyclic ring satisfies Hückers rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

As used herein, the term "partially unsaturated ring" or "partially unsaturated heterocycle" refers to a ring which contains unsaturated ring atoms and one or more double bonds but which is not aromatic, for example a 4,5-dihydro-1H-pyrazol-1-yl ring.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. When a fully unsaturated heterocyclic ring satisfies Hückers rule, then said ring is also called a "heteroaromatic ring" or aromatic heterocyclic ring. "Saturated heterocyclic ring" refers to a heterocyclic ring containing only single bonds between ring members.

Unless otherwise indicated, heterocyclic rings and ring systems are attached to the remainder of Formula 1 or Formula 1A through any available carbon or nitrogen atom by replacement of a hydrogen on said carbon or nitrogen atom.

The dotted line in Formula 1A and in other rings depicted in the present description (e.g., J-44 and J-45 in Exhibit 3) indicates that the bond can be a single bond or double bond.

The wavy bond between the nitrogen atom and the atom represented by $A^1$ in Formula 1, Formula 1A and in other rings depicted in the present description, indicates a single bond and the geometry about the adjacent double (i.e. the bond linking the nitrogen atom to the substituents $R^2$ and $R^3$) is either cis-(E), trans-(Z), or a mixture thereof.

As noted above, J is (inter alia) a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{11})_f$, and the silicon atom ring members are independently selected from $SiR^9R^{10}$, each ring or ring system optionally substituted with up to 5 substituents independently selected from $R^6$. In this definition the ring members selected from up to 2 O, up to 2 S, up to 4 N and up to 2 Si atoms are optional, because the number of heteroatom ring members may be zero. When no heteroatom ring members are present, the ring or ring system is carbocyclic. If at least one heteroatom ring member is present, the ring or ring system is heterocyclic. The definition of $S(=O)_s(=NR^{11})_f$ allows up to 2 sulfur ring members, which can be oxidized sulfur moieties (e.g., S(=O) or $S(=O)_2$) or unoxidized sulfur atoms (i.e. when s and f are both zero). The nitrogen atom ring members may be oxidized as N-oxides, because compounds relating to Formula 1 and Formula 1A also include N-oxide derivatives. The up to 3 carbon atom ring members selected from C(=O) and C(=S) are in addition to the up to 4 heteroatoms selected from up to 2 O, up to 2 S, up to 4 N and up to 2 Si atoms. As the $R^6$ substituents are optional, 0 to 5 substituents may be present, limited only by the number of available points of attachment on J. When the substituent $R^6$ is H, this is not counted as one of the 5 optional substituents. The substituents on silicon atom ring members are separately defined as $R^9$ and $R^{10}$.

As noted above, $R^2$ and $R^3$ may be taken together with the carbon atom to which they are attached to form a 3- to 7-membered ring. This 3- to 7-membered ring includes as a ring member the carbon atom to which the substituents $R^2$ and $R^3$ are attached. The other 2 to 6 ring members are selected from carbon atoms and up to 4 heteroatoms independently selected from up to 2 O, up to 2 S, up to 2 N and up to 2 Si atoms. In this definition the heteroatoms are optional, because the number of heteroatom ring members may be zero. When no heteroatom ring members are present, the ring is carbocyclic. If at least one heteroatom ring member is present, the ring is heterocyclic. The ring is optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. The nitrogen atom ring members may be oxidized as N-oxides, because compounds relating to Formula 1 and Formula 1A also include N-oxide derivatives.

As noted above, Q is (inter alia) a 3- to 7-membered nonaromatic carbocyclic ring, a 5- to 7-membered nonaromatic heterocyclic ring or an 8- to 11-membered heteroaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{11})_f$, and the silicon atom ring members are independently selected from $SiR^9R^{10}$, each ring or ring system optionally substituted with up to 2 substituents independently selected from $R^{6b}$ on carbon and nitrogen atom ring members, up to 5 substituents independently selected from $R^{6a}$ on carbon atom ring members and selected from H, $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members. In this definition the ring members selected from up to 2 O, up to 2 S, up to 4 N and up to 2 Si atoms are optional, because the number of heteroatom ring members may be zero. When no heteroatom ring members are present, the ring or ring system is carbocyclic. If at least one heteroatom ring member is present, the ring or ring system is heterocyclic. The definition of $S(=O)_s(=NR^{11})_f$ allows up to 2 sulfur ring members, which can be oxidized sulfur moieties (e.g., S(=O) or $S(=O)_2$) or unoxidized sulfur atoms (i.e. when s and f are both zero). The nitrogen atom ring members may be oxidized as N-oxides, because compounds relating to Formula 1 and Formula 1A also include N-oxide derivatives. The up to 3 carbon atom ring members selected from C(=O) and C(=S) are in addition to the up to 4 heteroatoms selected from up to 2 O, up to 2 S, up to 4 N and up to 2 Si atoms.

As noted above, $R^6$ and $R^{6a}$ may be taken together with the atoms to which they are attached to form a 5- to 7-membered ring including as ring members: (a) the two atoms to which the substituents $R^6$ and $R^{6a}$ are directly attached, (b) the intervening (i.e. other linking) atoms of J, Z and Q, to which $R^6$ and $R^{6a}$ can be regarded as indirectly attached and (c) the $R^6$ and $R^{6a}$ substituents. The ring members of the ring are selected from carbon atoms and optionally up to 3 heteroatoms independently selected from up to 1 O, up to 1 S and up to 1 N atom. In this definition the ring members selected from up to 1 O, up to 1 S and up to 1 N atom are optional, because the number of heteroatom ring members may be zero. The ring is optionally substituted with up to 3 substituents independently selected from halogen, cyano, nitro, $C_1$-$C_2$ alkyl and $C_1$-$C_2$ alkoxy on carbon atom ring members and from cyano, $C_1$-$C_2$ alkyl and $C_1$-$C_2$ alkoxy on nitrogen atom ring members. These optional substituents (when present) are attached to available carbon and nitrogen atom ring members in the portion of the ring provided by $R^6$ and $R^{6a}$, and are in addition to substituents attached to J, Z and Q.

As noted above, $R^3$ and $R^7$ may be taken together with the linking atoms to which they are attached to form a 5- to 7-membered partially unsaturated ring. The linking atoms are the carbon atom to which $R^3$ is directly attached, the nitrogen atom to which $R^7$ is directly attached (only present when $A^2$ is —N($R^7$)—) and the intervening nitrogen atom depicted as "=N~" in Formula 1 or Formula 1A (see E-2). Thus, the three linking atoms are "—C=N~N($R^7$)—". The linking atoms provide 3 ring members of the 5- to 7-membered ring. The other 2 to 4 ring members of the ring are provided by the $R^3$ and $R^7$ substituents. These other ring members are selected from carbon atoms and up to 3 heteroatoms independently selected from up to 1 O, up to 1 S and up to 1 N atom. In this definition the ring members selected from up to 1 O, up to 1 S and up to 1 N atom are optional, because the number of heteroatom ring members may be zero. The ring is optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. These optional substituents (when present) are attached to available carbon and nitrogen atom ring members in the portion of the ring provided by $R^3$ and $R^7$, and are in addition to $R^2$ and the remainder of Formula 1 or Formula 1A attached to the ring. The nitrogen atom ring members may be oxidized as N-oxides, because compounds relating to Formula 1 and Formula 1A also include N-oxide derivatives.

As noted above, $R^{19}$ and $R^{22}$ may be taken together with the atoms to which they are attached to form a 5- to 7-membered ring, including as ring members: (a) the two atoms to which the substituents $R^{19}$ and $R^{22}$ are directly attached, (b) the intervening (i.e. other linking) atoms of $R^{18}$, to which $R^{19}$ and $R^{22}$ can be regarded as indirectly attached and (c) the $R^{19}$ and $R^{22}$ substituents. The ring members of the ring are selected from carbon atoms and up to 4 heteroatoms independently selected from up to 2 O, up to 2 S, up to 2 N and up to 2 Si atoms, wherein up to 2 carbon atom ring members are independently selected from C(=O) and C(=S), the sulfur atom ring members are independently selected from S(=O)$_s$ (=NR$^{11}$)$_f$, and the silicon atom ring members are independently selected from SiR$^9$R$^{10}$, the ring optionally substituted with up to 4 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members. In this definition the ring members selected from up to 2 O, up to 2 S, up to 2 N and up to 2 Si atoms are optional, because the number of heteroatom ring members may be zero. The definition of S(=O)$_s$ (=NR$^{11}$)$_f$ allows up to 2 sulfur ring members, which can be oxidized sulfur moieties (e.g., S(=O) or S(=O)$_2$) or unoxidized sulfur atoms (i.e. when s and f are both zero). The nitrogen atom ring members may be oxidized as N-oxides, because compounds relating to Formula 1 and Formula 1A also include N-oxide derivatives. The up to 2 carbon atom ring members selected from C(=O) and C(=S) are in addition to the up to 4 heteroatoms selected from up to 2 O, up to 2 S, up to 2 N and up to 2 Si atoms. The optional substituents (when present) are attached to available carbon and nitrogen atom ring members in the portion of the ring provided by $R^{19}$ and R. The substituents on silicon atom ring members are separately defined as $R^9$ and $R^{10}$.

Compounds of Formula 1 and Formula 1A can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Compounds of Formula 1 and Formula 1A may be present as a mixture of stereoisomers, individual stereoisomers, or as an optically active form. For example, when J is J-29 (see Exhibit 2) bonded at the 3-position to the remainder of Formula 1 and has one $R^6$ substituent other than H at the 5-position, then Formula 1 possesses a chiral center at the carbon atom to which $R^6$ is bonded. The two enantiomers are depicted as Formula 1' and Formula 1" below and chiral center identified with an asterisk (*).

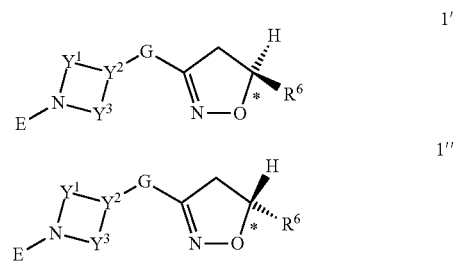

Compounds of Formula 1 and Formula 1A comprise racemic mixtures, for example, equal amounts of the enantiomers of Formulae 1' and 1". In addition, compounds of Formula 1 and Formula 1A include compounds that are enriched compared to the racemic mixture in an enantiomer of Formula 1 or Formula 1A. Also included are the essentially pure enantiomers of compounds of Formula 1 and Formula 1A, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of this invention of Formula 1 and Formula 1A have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 and Formula 1A can comprise additional chiral centers. For example, substituents and other molecular constituents such as $A^1$, $A^2$, $R^{1a}$, $R^{1c}$, $R^2$, $R^3$, $R^4$, $R^6$, $R^{6a}$, $T^B$, J, Q and Z may themselves contain chiral centers. Compounds of Formula 1 and Formula 1A comprise racemic mixtures as well as enriched and essentially pure stereoconfigurations at these additional chiral centers.

Compounds of Formula 1 and Formula 1A can exist as one or more conformational isomers due to restricted rotation about the amide bond (e.g., C(=W$^1$)—N) in Formula 1 or Formula 1A. Compounds of Formula 1 and Formula 1A comprise mixtures of conformational isomers. In addition, compounds of Formula 1 and Formula 1A include compounds that are enriched in one conformer relative to others.

One skilled in the art recognizes that compounds of Formula 1 and Formula 1A can exist in equilibrium with one or more of its respective tautomeric counterparts. Unless otherwise indicated, reference to a compound by one tautomer description is to be considered to include all tautomers. For example, in Formula 1 when E is E-2 and R³ is hydroxy, then reference to the tautomeric form depicted by Formula 1¹ also includes the tautomic form depicted by Formula 1².

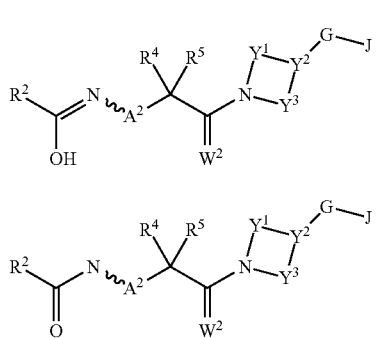

Additionally, some of the unsaturated rings and ring systems depicted in Exhibits 1A, 1B, 2, 2A, 3, 4, 5, 5A and 6 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown.

The compounds of the present invention include N-oxide derivatives of Formula 1 and Formula 1A. One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. When the compounds forming the present mixtures and compositions contain acidic or basic moieties, a wide variety of salts can be formed, and these salts are useful in the present mixtures and compositions for controlling plant diseases caused by fungal plant pathogens (i.e. are agriculturally suitable). When a compound contains a basic moiety such as an amine function, salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound contains an acidic moiety such as a carboxylic acid or phenol, salts include those formed with organic or inorganic bases such as pyridine, triethylamine or ammonia, or amides, hydrides, hydroxides or carbonates of sodium, potassium, lithium, calcium, magnesium or barium.

Compounds selected from Formula 1, Formula 1A, stereoisomers, tautomers, N-oxides, and salts thereof, typically exist in more than one form, thus Formula 1 and Formula 1A includes all crystalline and non-crystalline forms of the compounds that Formula 1 and Formula 1A represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 or Formula 1A can exhibit beneficial effects (e.g., suitability for preparation of useful formulations, improved biological performance) relative to another polymorph or a mixture of polymorphs of the same compound represented by Formula 1 or Formula 1A. Preparation and isolation of a particular polymorph of a compound represented by Formula 1 or Formula 1A can be achieved by methods known to those skilled in the art including, for example, crystallization using selected solvents and temperatures.

Embodiments of the present invention as described in the Summary of the Invention include those described below. In the following Embodiments, Formula 1 and Formula 1A includes geometric and stereoisomers, tautomers, N-oxides, and salts thereof, and reference to "a compound of Formula 1" or "a compound of Formula 1A" includes the definitions of substituents specified in the Summary of the Invention unless further defined in the Embodiments. In the following Embodiments, the phrase "Formula 1 or Formula 1A" is used for convenience, however not all variables are applicable to both a compound Formula 1 and 1A. One skilled in the art, using definitions of substituents specified in the Summary of the Invention, will know which of the following Embodiments are applicable to a compound of Formula 1 and 1A, and which are only applicable to Formula 1 or Formula 1A.

Embodiment 1. A compound of Formula 1 or Formula 1A wherein E is E-3.

Embodiment 2. A compound of Formula 1 or Formula 1A wherein E is E-1 or E-2.

Embodiment 3. A compound of Formula 1 or Formula 1A or Embodiment 2 wherein E is E-1.

Embodiment 4. A compound of Formula 1 or Formula 1A or Embodiment 2 wherein E is E-2.

Embodiment 5. A compound of Formula 1 or Formula 1A or any one of Embodiments 1 through 4 wherein $Y^1$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—.

Embodiment 6. A compound of Formula 1 or Formula 1A or any one of Embodiments 1 through 5 wherein $Y^2$ is a nitrogen ring member.

Embodiment 7. A compound of Formula 1 or Formula 1A or any one of Embodiments 1 through 5 wherein $Y^2$ is a C($R^{14}$) ring member.

Embodiment 8. A compound of Formula 1 or Formula 1A or any one of Embodiments 1 through 7 wherein $Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—; or $Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S— and —N($R^{23}$)—.

Embodiment 9 A compound of Embodiment 8 wherein $Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S— and —N($R^{23}$)—.

Embodiment 10. A compound of any one of Embodiments 1 through 9 wherein $Y^1$, $Y^2$ and $Y^3$ form a ring (hereafter referred to as "L") selected from L-25 through L-59, shown below in Exhibit 1A Exhibit 1A

L-25

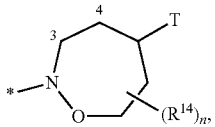

L-26

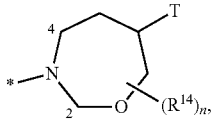

L-27

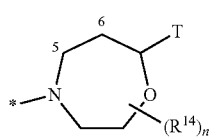

L-28

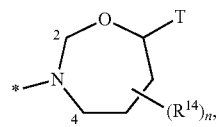

L-29

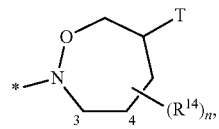

L-30

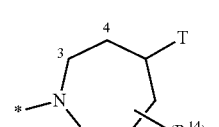

L-31

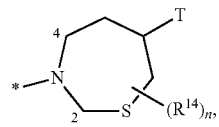

L-32

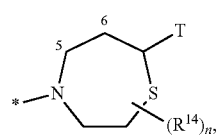

L-33

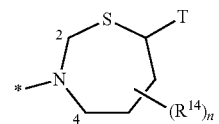

L-34

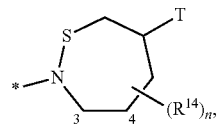

L-35

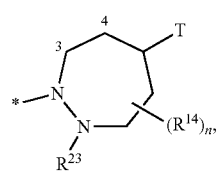

L-36

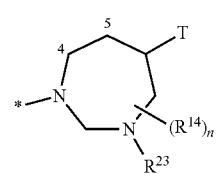

L-37

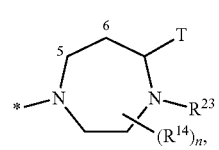

-continued

L-38

L-39

L-40

L-41

L-42

L-43

L-44

L-45

L-46

L-47

-continued

L-48

L-49

L-50

L-51

L-52

L-53

L-54

L-55

L-56

L-57

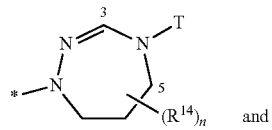

L-58

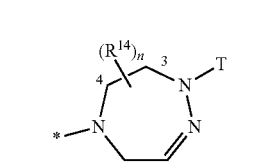

L-59 wherein the bond projecting to the left (i.e. labeled with an astrisk ("*")) is bonded to E in Formula 1 or Formula 1A and the bond projecting to the right (i.e. labeled with a "T") is bonded to G in Formula 1 or Formula 1A; and n is an integer from 0 to 4.

Embodiment 11. A compound of Embodiment 10 wherein L is L-25, L-26 or L-50.

Embodiment 12. A compound of Embodiment 11 wherein L is L-25.

Embodiment 13. A compound of Formula 1 or Formula 1A or any one of Embodiments 1 through 8 wherein $Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—;

Embodiment 14. A compound of Embodiment 13 wherein $Y^1$, $Y^2$ and $Y^3$ form a ring selected from L-1 through L-24, shown below in Exhibit 1B Exhibit 1B

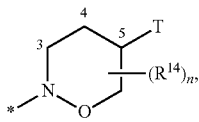

L-1

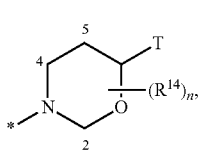

L-2

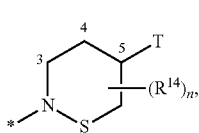

L-3

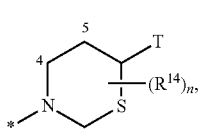

L-4

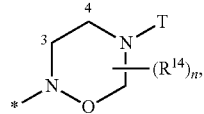

L-5

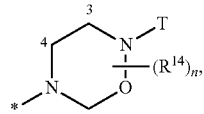

L-6

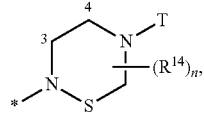

L-7

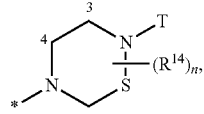

L-8

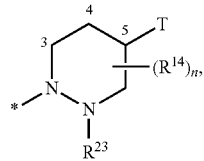

L-9

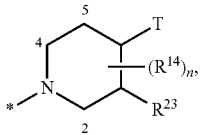

L-10

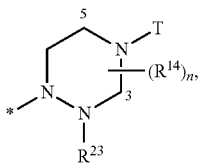

L-11

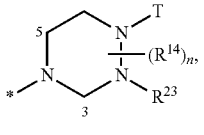

L-12

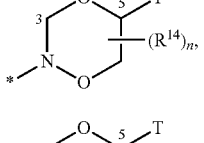

L-13

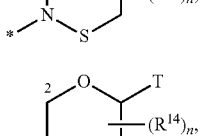

L-14

L-15

-continued

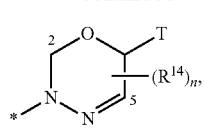
L-16

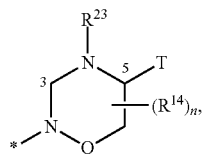
L-17

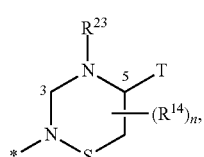
L-18

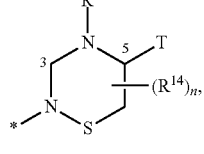
L-19

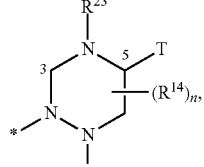
L-20

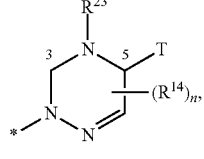
L-21

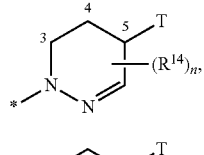
L-22

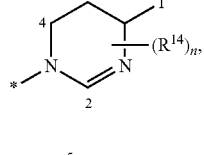
L-23

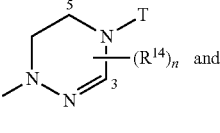
and

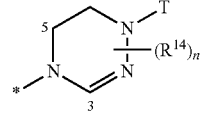
L-24 wherein the bond projecting to the left (i.e. labeled with an astrisk ("*")) is bonded to E in Formula 1 or Formula 1A, and the bond projecting to the right (i.e. labeled with a "T") is bonded to G in Formula 1 or Formula 1A; and n is an integer from 0 to 4.

Embodiment 15. A compound of Embodiment 14 wherein L is L-1, L-2 or L-9.

Embodiment 16. A compound of Embodiment 15 wherein L is L-1 or L-9.

Embodiment 16a. A compound of Formula 1 or Formula 1A or any one of Embodiments 1 through 16 wherein $X^1$ and $X^2$ are each independently a ring member wherein one member is —$C(R^{14})_2$— and the second chain member is —O— and the bicyclic ring containing $X^1$ and $X^2$ is fully saturated; or $X^1$ and $X^2$ are both the ring member is —$C(R^{14})_2$—.

Embodiment 16b. A compound of any one of Embodiments 1 through 16a wherein $Y^2$, $X^1$ and $X^2$ form a ring (hereafter referred to as "L") selected from L-60 through L-65, shown below in Exhibit 1C Exhibit 1C

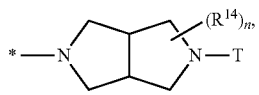
L-60

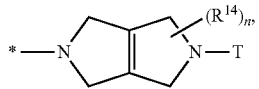
L-61

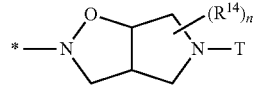
L-62

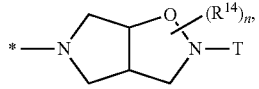
L-63

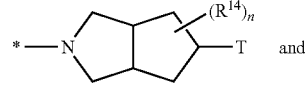
L-64 and

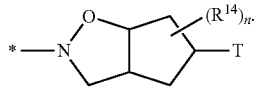
L-65 wherein the bond projecting to the left (i.e. labeled with an astrisk ("*")) is bonded to E in Formula 1 or Formula 1A, and the bond projecting to the right (i.e. labeled with a "T") is bonded to G in Formula 1 or Formula 1A; and n is an integer from 0 to 4.

Embodiment 16c. A compound of Embodiment 16b wherein L is L-60, L-61, L-64 or L-65.

Embodiment 16d. A compound of Embodiment 16c wherein L is L-60 or L-64.

Embodiment 17. A compound of Formula 1 or Formula 1A or any one of Embodiments 1 through 16 wherein G is a 5-membered heterocyclic ring, optionally substituted with up to 2 substituents independently selected from $R^{29}$ on carbon atom ring members and $R^{30}$ on nitrogen atom ring members;

each $R^{29}$ is independently halogen, $C_1$-$C_3$ alkyl or $C_1$-$C_3$ haloalkyl; and each $R^{30}$ is independently $C_1$-$C_3$ alkyl.

Embodiment 17a. A compound of Formula 1 or Formula 1A or any one of Embodiments 1 through 17 wherein G is G-1 through G-48, shown below in Exhibit 2

Exhibit 2
G-1 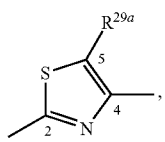
G-2 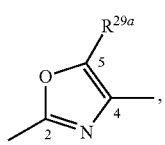
G-3 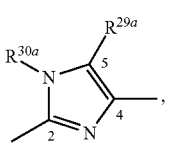
G-4 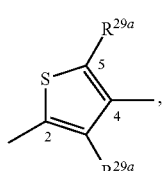
G-5 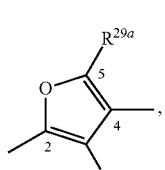
G-6 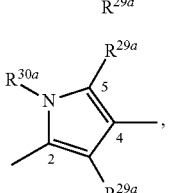
G-7 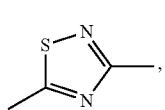
G-8 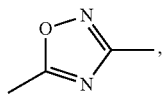
G-9 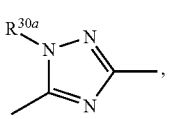
G-10 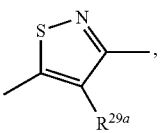
G-11 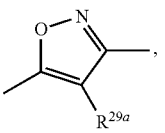
-continued
G-12 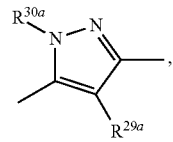
G-13 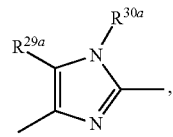
G-14 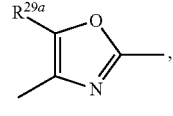
G-15 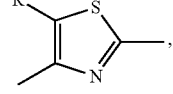
G-16 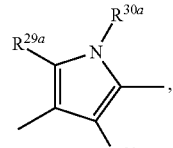
G-17 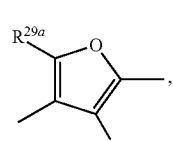
G-18 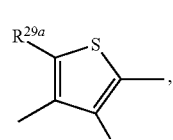
G-19 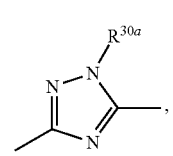
G-20 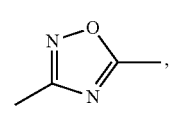
G-21 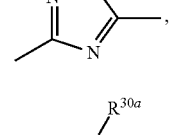
G-22 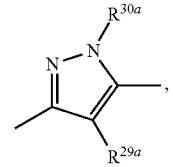

-continued
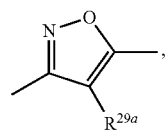 G-23
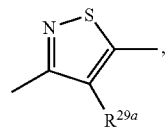 G-24
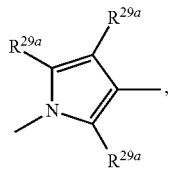 G-25
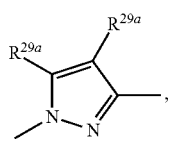 G-26
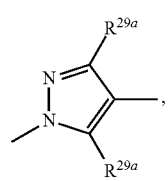 G-27
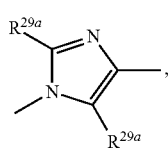 G-28
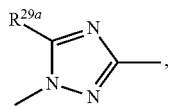 G-29
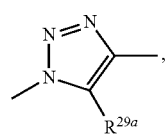 G-30
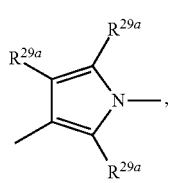 G-31
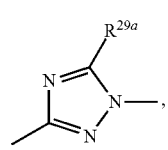 G-32
-continued
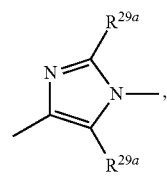 G-33
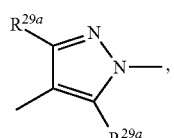 G-34
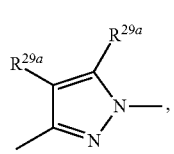 G-35
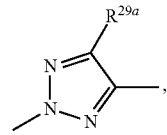 G-36
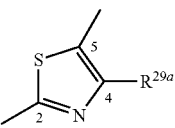 G-37
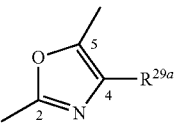 G-38
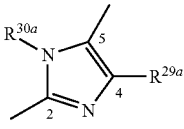 G-39
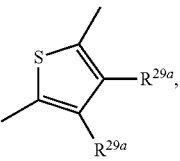 G-40
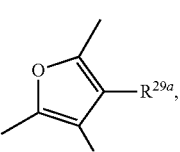 G-41
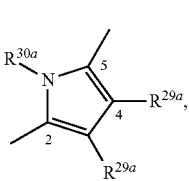 G-42

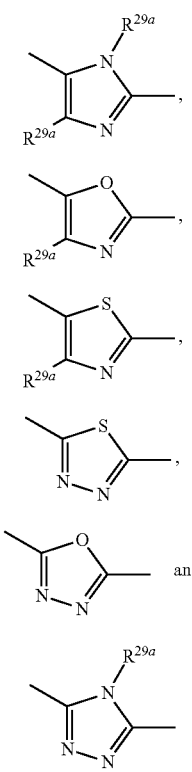

G-43

G-44

G-45

G-46

G-47 and

G-48 wherein the bond projecting to the left is bonded to $Y^2$ in Formula 1 or Formula 1A, and the bond projecting to the right is bonded to J in Formula 1 or Formula 1A; each $R^{29a}$ is independently selected from H and $R^{29}$; and $R^{30a}$ is selected from H and $R^{30}$.

Embodiment 18. A compound of Embodiment 17a wherein G is selected from G-1 through G-3, G-7, G-8, G-10, G-11, G-14, G-15, G-23, G-24, G-26 through G-28, G-30 and G-36 through G-38.

Embodiment 19. A compound of Embodiment 18 wherein G is selected from G-1, G-2, G-7, G-8, G-14, G-15, G-23, G-24, G-26, G-27, G-36, G-37 and G-38.

Embodiment 20. A compound of Embodiment 19 wherein G is selected from G-1, G-2, G-15, G-26, G-27, G-36, G-37 and G-38.

Embodiment 21. A compound of Embodiment 20 wherein G is selected from G-1, G-2, G-15, G-26, G-36 and G-37.

Embodiment 21a. A compound of any one of Embodiments 17 through 21 wherein each $R^{29a}$ is independently H, halogen or $C_1$-$C_3$ alkyl.

Embodiment 21b. A compound of Embodiment 21a wherein each $R^{29a}$ is independently H or methyl.

Embodiment 21c. A compound of Embodiment 21b wherein each $R^{29}$a is H.

Embodiment 21d. A compound of any one of Embodiments 17a through 21c wherein each $R^{30a}$ is independently H or methyl.

Embodiment 21e. A compound of Embodiment 21d wherein each $R^{30a}$ is H.

Embodiment 22. A compound of any one of Embodiments 17 through 21c wherein G is a heterocyclic ring unsubstituted except for its attachments to $Y^2$ and J.

Embodiment 23. A compound of Embodiment 22 wherein G is G-15.

Embodiment 24. A compound of Embodiment 22 wherein G is G-2.

Embodiment 25. A compound of Embodiment 22 wherein G is G-36.

Embodiment 26. A compound of Embodiment 22 wherein G is G-26.

Embodiment 27. A compound of Embodiment 22 wherein G is G-1.

Embodiment 28. A compound of Formula 1 or Formula 1A or any one of Embodiments 1 through 27 wherein J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from $S(=O)_s(=NR^{11})_p$, each ring or ring system optionally substituted with up to 5 substituents independently selected from $R^6$; or J is $C(=W^4)NT^AT^B$.

Embodiment 29. A compound of Embodiment 28 wherein when J is other than $C(=W^4)NT^AT^B$ then J is a ring selected from the group consisting of J-1 through J-82, shown below in Exhibit 3

Exhibit 3

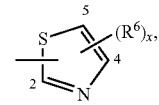 J-1

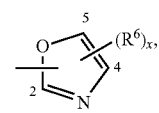 J-2

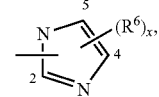 J-3

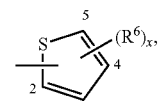 J-4

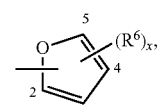 J-5

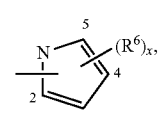 J-6

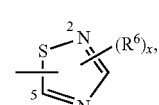 J-7

-continued
J-8
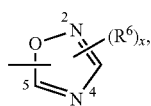
J-9
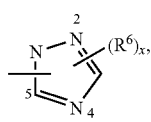
J-10
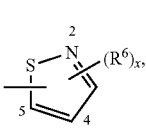
J-11
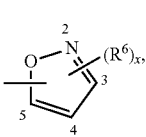
J-12
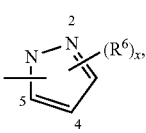
J-13
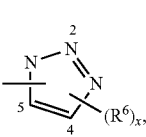
J-14
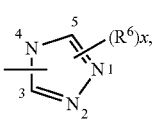
J-15
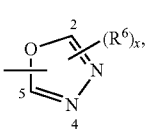
J-16
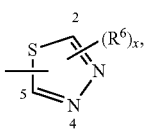
J-17
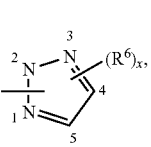
J-18
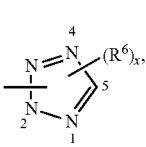
-continued
J-19
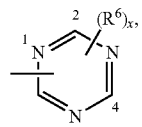
J-20
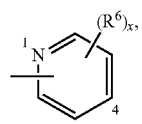
J-21
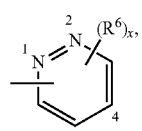
J-22
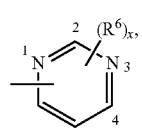
J-23
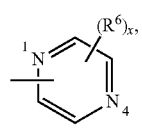
J-24
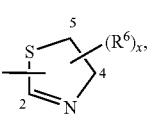
J-25
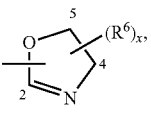
J-26
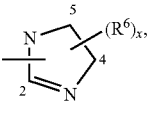
J-27
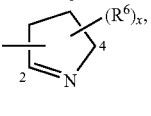
J-28
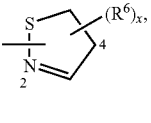
J-29
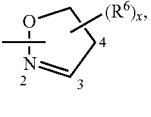
J-30

-continued
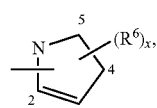 J-31
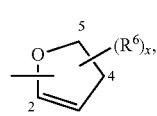 J-32
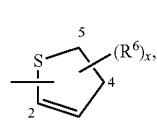 J-33
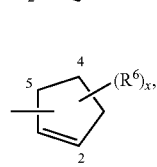 J-34
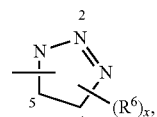 J-35
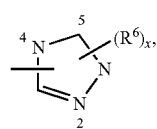 J-36
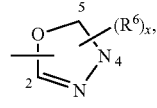 J-37
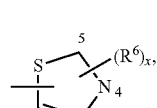 J-38
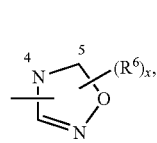 J-39
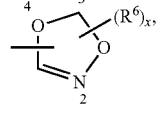 J-40
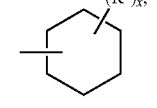 J-41
-continued
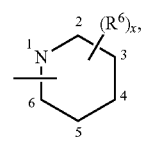 J-42
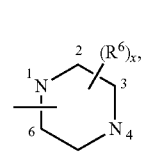 J-43
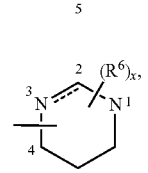 J-44
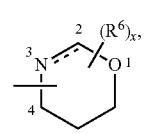 J-45
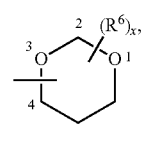 J-46
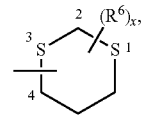 J-47
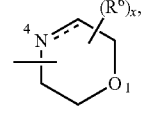 J-48
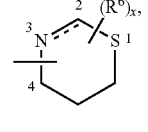 J-49
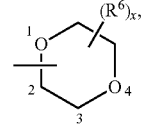 J-50
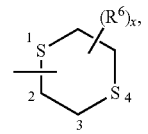 J-51
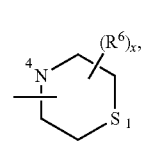 J-52

J-53 through J-73: chemical structure diagrams of heterocyclic ring systems with (R⁶)ₓ substituents.

-continued

J-74
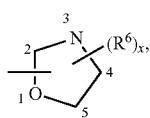

J-75
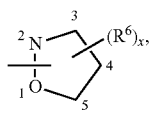

J-76
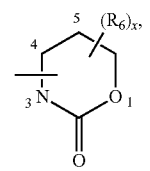

J-77
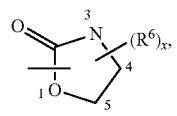

J-78
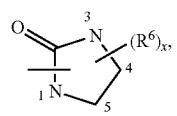

J-79
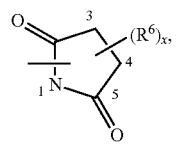

J-80
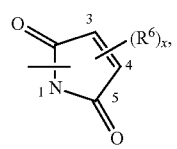

J-81
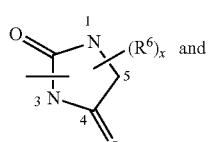

and

J-82
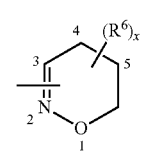

wherein the bond shown projecting to the left is bonded to G in Formula 1 or Formula 1A and to an available carbon or nitrogen atom ring member in the J ring; and x is an integer from 0 to 5.

Embodiment 30. A compound of Embodiment 29 wherein J is a ring selected from the group consisting of J-1 through J-82, x is an integer from 1 to 5, and when x is 2, 3, 4 or 5, then at most one instance of $R^6$ is —ZQ.

Embodiment 31. A compound of Embodiment 29 or 30 wherein J is a ring selected from the group consisting of J-1, J-2, J-3, J-4, J-5, J-7, J-8, J-9, J-10, J-12, J-14, J-15, J-16, J-20, J-24, J-25, J-26, J-29, J-30, J-37, J-38, J-45 and J-69.

Embodiment 32. A compound of Embodiment 29 or 30 wherein J is a ring selected from the group consisting of J-1 through J-82.

Embodiment 33. A compound of Embodiment 31 or 32 wherein J is selected from J-4, J-5, J-8, J-11, J-15, J-16, J-20, J-29, J-30, J-37, J-38 and J-69.

Embodiment 34. A compound of Embodiment 33 wherein J is selected from J-4, J-5, J-11, J-20, J-29, J-37, J-38 and J-69.

Embodiment 35. A compound of Embodiment 34 wherein J is J-11.

Embodiment 36. A compound of Embodiment 34 wherein J is J-29.

Embodiment 37. A compound of Embodiment 34 wherein J is J-69.

Embodiment 38. A compound of any one of Embodiments 29 through 37 wherein x is 1 or 2.

Embodiment 39. A compound of Embodiment 38 wherein x is 1.

Embodiment 40. A compound of Embodiment 36 wherein J is a ring selected from the group consisting of J-29-1 through J-29-58, shown below in Exhibit 3A Exhibit 3A J-29-1
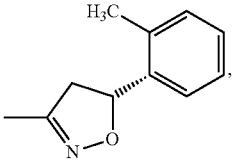

J-29-2
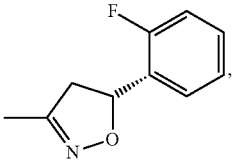

J-29-3
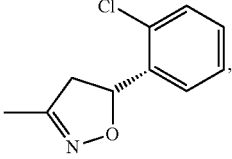

J-29-4
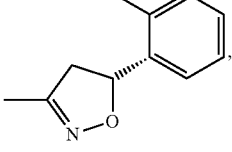

J-29-5
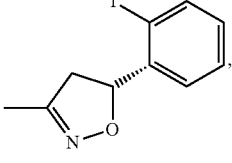

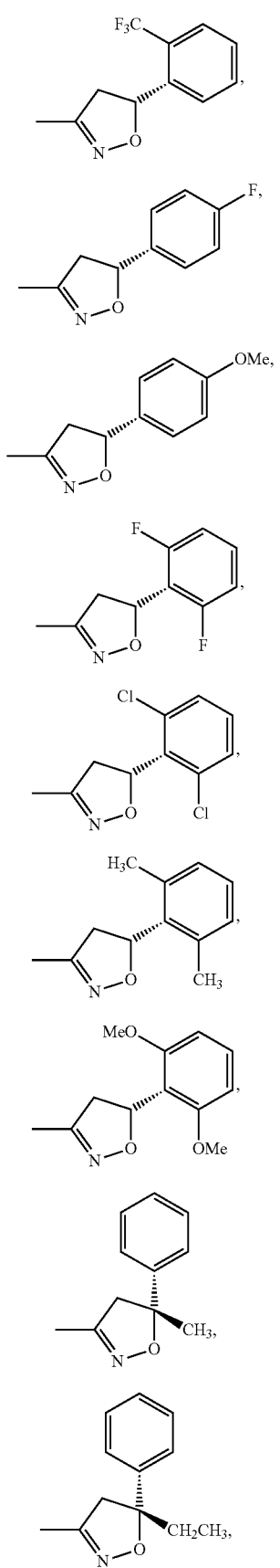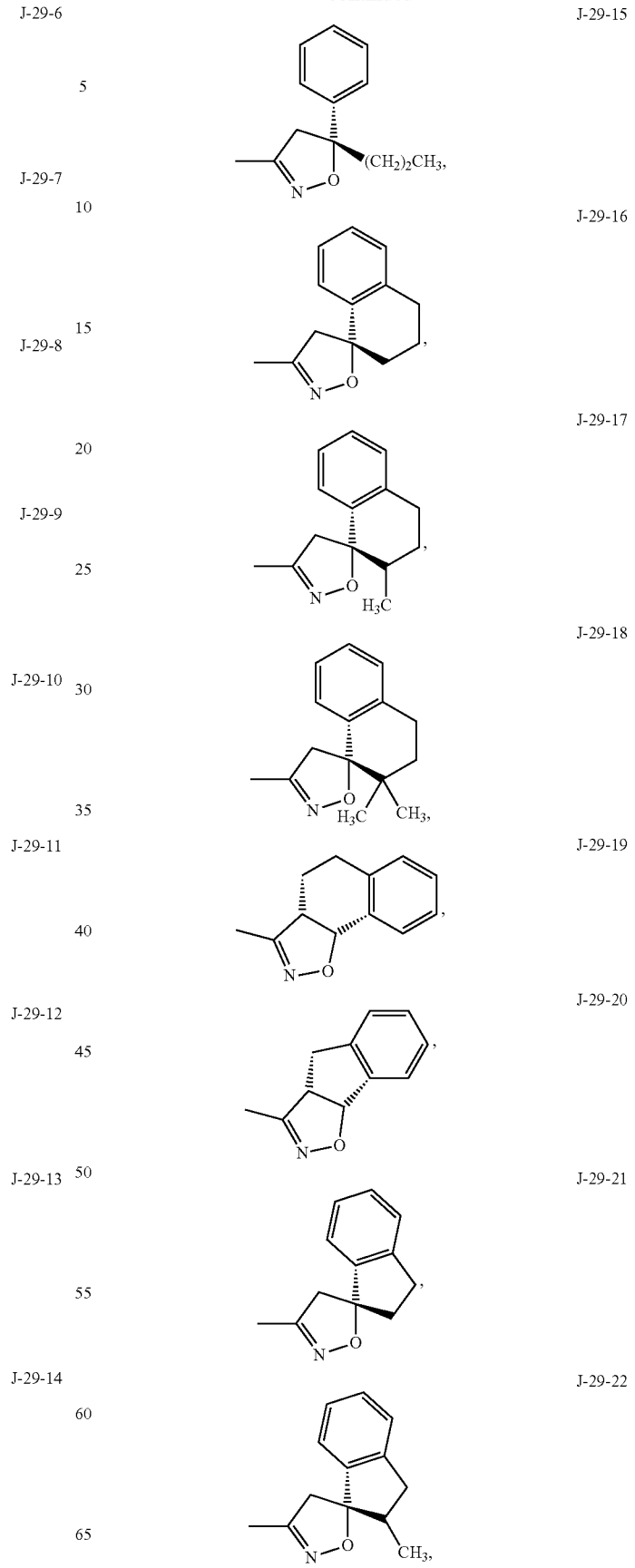

-continued
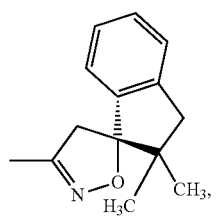 J-29-23
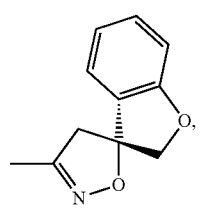 J-29-24
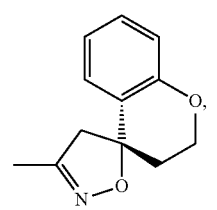 J-29-25
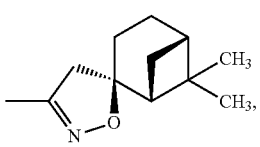 J-29-26
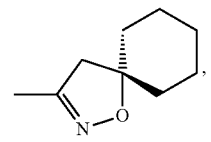 J-29-27
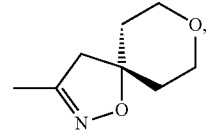 J-29-28
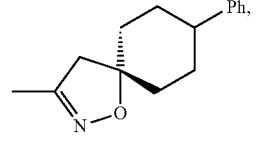 J-29-29
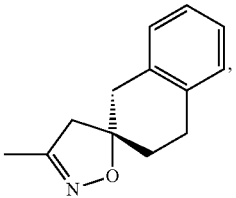 J-29-30
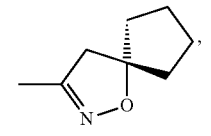 J-29-31
-continued
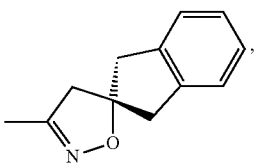 J-29-32
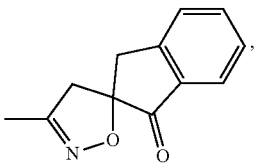 J-29-33
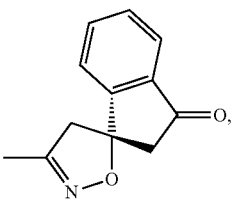 J-29-34
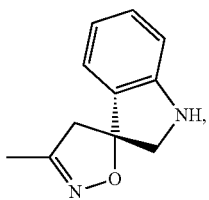 J-29-35
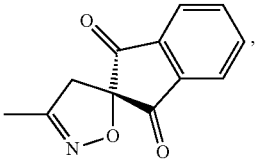 J-29-36
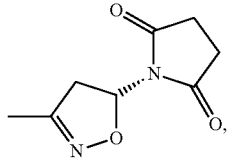 J-29-37
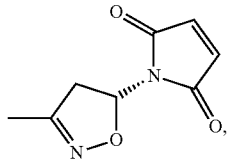 J-29-38
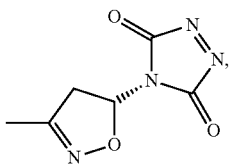 J-29-39

| | |
|---|---|
| J-29-40 | J-29-47 |
| J-29-41 | J-29-48 |
| J-29-42 | J-29-49 |
| J-29-43 | J-29-50 |
| J-29-44 | J-29-51 |
| J-29-45 | J-29-52 |
| | J-29-53 |
| J-29-46 | J-29-54 |

-continued

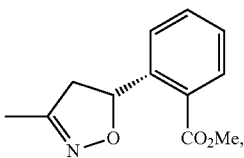
J-29-55

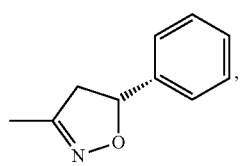
J-29-56

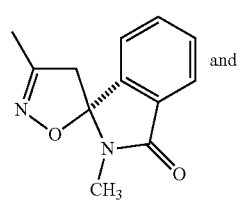
and
J-29-57

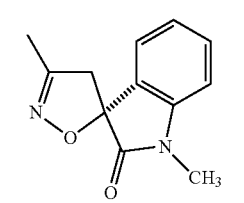
J-29-58 wherein the bond shown projecting to the left is bonded to G in Formula 1 or Formula 1A.

Embodiment 41. A compound of Formula 1 or Formula 1A or any one of Embodiments 1 through 40 wherein each $R^6$ when taken alone (i.e. not taken together with $R^{6a}$) is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —$NR^{20}R^{21}$ or —ZQ.

Embodiment 42. A compound of Embodiment 41 wherein each $R^6$ when taken alone is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{20}R^{21}$ or —ZQ.

Embodiment 43. A compound of Embodiment 42 wherein each $R^6$ when taken alone is independently H, cyano, $C_1$-$C_6$ alkyl, $C_1$-$C_6$ haloalkyl, $C_1$-$C_6$ alkoxy, $C_1$-$C_6$ haloalkoxy, —$NR^{20}R^{21}$ or —ZQ.

Embodiment 44. A compound of Embodiment 43 wherein each $R^6$ when taken alone is independently H, cyano, $C_1$-$C_3$ alkyl, $C_1$-$C_3$ haloalkyl or —ZQ.

Embodiment 45. A compound of Embodiment 44 wherein each $R^6$ when taken alone is —ZQ.

Embodiment 46. A compound of Formula 1 or Formula 1A or any one of Embodiments 1 through 45 wherein each $R^6$ is taken alone.

Embodiment 47. A compound of Formula 1 or any one of Embodiments 1 through 46 wherein each Z is independently a direct bond, O, C(=O), S(=O)$_2$ or CH($R^{12}$).

Embodiment 48. A compound of Embodiment 47 wherein each Z is direct bond.

Embodiment 49. A compound of Formula 1 or Formula 1A or any one of Embodiments 1 through 28 wherein J is C(=$W^4$)N$T^A T^B$.

Embodiment 50. A compound of Embodiment 49 wherein when J is C($W^4$)N$T^A T^B$ then J is selected from the group consisting of J-83 through J-93, shown below in Exhibit 4

Exhibit 4

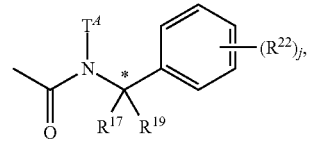
J-83

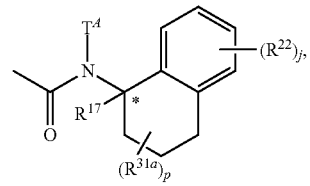
J-84

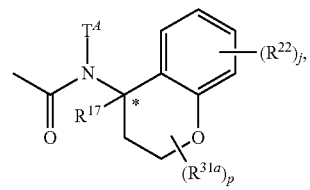
J-85

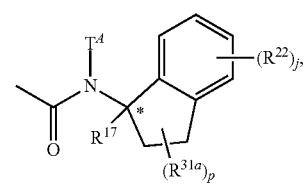
J-86

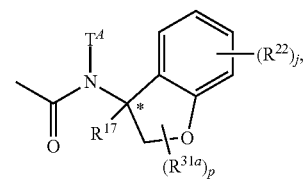
J-87

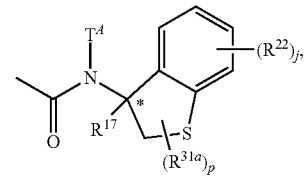
J-88

-continued

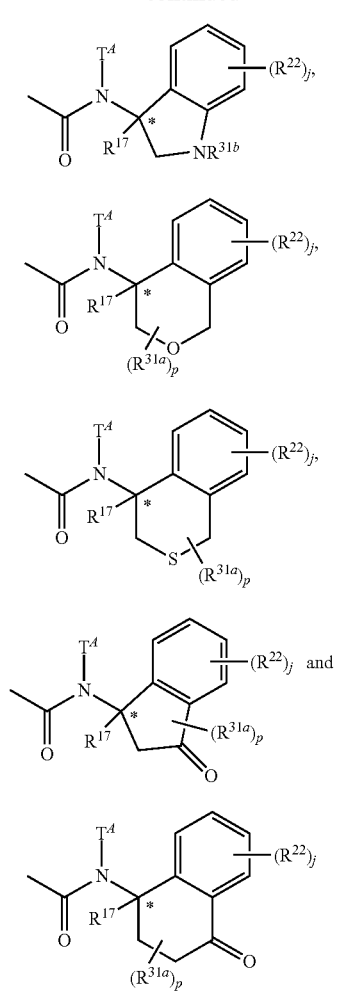

wherein the bond projecting to the left is connected to G in Formula 1 or Formula 1A, and the carbon atom identified with an asterisk (*) contains a stereocenter; each $R^{31a}$ is independently selected from halogen, hydroxy, $C_1$-$C_2$ alkyl and $C_1$-$C_2$ alkoxy and attached to carbon ring members; $R^{31b}$ is selected from halogen, $C_1$-$C_2$ alkyl and $C_1$-$C_2$ alkoxy attached to nitrogen ring members; and each j and p is independently 0, 1 or 2.

Embodiment 51. A compound of Formula 1 or Formula 1A or any one of Embodiments 1 through 28, 49 or 50 wherein $W^4$ is O.

Embodiment 52. A compound of Formula 1 or any one of Embodiments 1 through 28 or 49 through 51 wherein TA is H or methyl.

Embodiment 53. A compound of Formula 1 or Formula 1A or any one of Embodiments 1 through 52 wherein $A^1$ is $CHR^{15}$ or $NR^{16}$.

Embodiment 54. A compound of Formula 1 or Formula 1A or any one of Embodiments 1 through 52 wherein $A^1$ is $NR^{16}$ or C(=O).

Embodiment 55. A compound of Embodiment 53 or Embodiment 54 wherein $A^1$ is $NR^{16}$.

Embodiment 56. A compound of Embodiment 53 wherein $A^1$ is $CHR^{15}$.

Embodiment 57. A compound of Formula 1 or Formula 1A or any one of Embodiments 1 through 52 wherein $A^2$ is —O—, —S—, —N($R^7$)—, —C($R^8$)$_2$— or —OC($R^8$)$_2$— wherein the bond projecting to the left is connected to —N=C($R^2$)($R^3$), and the bond projecting to the right is connected to —C($R^4$)($R^5$)—;

Embodiment 58. A compound of Embodiment 57 wherein $A^2$ is —O—, —S— or —N($R^7$)—.

Embodiment 59. A compound of Embodiment 58 wherein $A^2$ is —O— or —N($R^7$)—.

Embodiment 60. A compound of Formula 1 or Formula 1A or any of Embodiments 1 through 59 wherein $W^1$ is O.

Embodiment 60a. A compound of Formula 1 or Formula 1A or any of Embodiments 1 through 59 wherein $W^2$ is O.

Embodiment 61. A compound of Formula 1 or Formula 1A or any one of Embodiments 1 through 52 wherein W3 is $OR^{24}$, $SR^{25}$ or $NR^{26}R^{27}$.

Embodiment 62. A compound of Embodiment 61 wherein $W^3$ is $OR^{24}$.

Embodiment 63. A compound of Embodiment 61 wherein $W^3$ is $SR^{25}$.

Embodiment 64. A compound of Embodiment 61 wherein $W^3$ is $NR^{26}R^{27}$.

Embodiment 65. A compound of Formula 1 or Formula 1A or any one of Embodiments 1 through 64 wherein $R^{1a}$ and $R^{1c}$ independently are an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ haloalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 66. A compound of Embodiment 65 wherein independently when $R^{1a}$, and $R^{1c}$ are other than an optionally substituted phenyl, an optionally substituted naphthalenyl or an optionally substituted 5- or 6-membered heteroaromatic ring then $R^{1a}$ and $R^{1c}$ are independently cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 67. A compound of Embodiment 66 wherein independently when $R^{1a}$ and $R^{1c}$ are other than an optionally substituted phenyl, an optionally substituted naphthalenyl or an optionally substituted 5- or 6-membered heteroaromatic ring then $R^{1a}$ and $R^{1c}$ are independently $C_1$-$C_8$ alkyl, $C_2$-$C_8$ alkenyl, $C_1$-$C_8$ haloalkyl, $C_2$-$C_8$ alkoxyalkyl, $C_2$-$C_8$ alkylthioalkyl, $C_2$-$C_8$ alkylaminoalkyl, $C_1$-$C_8$ alkoxy, $C_1$-$C_8$ alkylthio, pyrrolidinyl, piperidinyl or morpholinyl.

Embodiment 68. A compound of Embodiment 66 wherein independently when $R^{1a}$ and $R^{1c}$ are other than an optionally substituted phenyl, an optionally substituted naphthalenyl or an optionally substituted 5- or 6-membered heteroaromatic ring then $R^{1a}$ and $R^{1c}$ are independently $C_2$-$C_5$ alkyl, $C_2$-$C_5$ alkenyl, $C_2$-$C_5$ haloalkyl, $C_2$-$C_5$ haloalkenyl, $C_2$-$C_5$ haloalkylthioalkyl, $C_2$-$C_5$ alkoxyalkyl, $C_2$-$C_5$ haloalkoxyalkyl, $C_2$-$C_5$ alkylthioalkyl, $C_2$-$C_5$ alkylaminoalkyl, $C_2$-$C_5$ alkylcarbonyloxy, $C_2$-$C_5$ haloalkylcarbonyloxy, $C_2$-$C_5$ alkoxy, $C_2$-$C_5$ haloalkoxy, $C_2$-$C_5$ alkylthio, $C_2$-$C_5$ alkylamino or $C_2$-$C_5$ alkylcarbonylamino.

Embodiment 69. A compound of Embodiment 68 wherein independently when $R^{1a}$ and $R^{1c}$ are other than an optionally substituted phenyl, an optionally substituted naphthalenyl or an optionally substituted 5- or 6-membered heteroaromatic ring then $R^{1a}$ and $R^{1c}$ are independently $C_3$-$C_5$ alkyl, $C_3$-$C_5$ alkenyl, $C_3$-$C_5$ haloalkyl, $C_3$-$C_5$ haloalkenyl, $C_2$-$C_4$ haloalkylthioalkyl, $C_2$-$C_4$ alkoxyalkyl, $C_2$-$C_4$ haloalkoxyalkyl, $C_2$-$C_4$ alkylthioalkyl, $C_2$-$C_4$ alkylaminoalkyl, $C_2$-$C_3$ alkylcarbonyloxy, $C_2$-$C_3$ haloalkylcarbonyloxy, $C_2$-$C_4$ alkoxy, $C_2$-$C_4$ haloalkoxy, $C_2$-$C_4$ alkylthio, $C_2$-$C_4$ alkylamino or $C_2$-$C_3$ alkylcarbonylamino.

Embodiment 70. A compound of Embodiment 69 wherein independently when $R^{1a}$ and $R^{1c}$ are other than an optionally substituted phenyl, an optionally substituted naphthalenyl or an optionally substituted 5- or 6-membered heteroaromatic ring then $R^{1a}$ and $R^{1c}$ are independently $C_3$-$C_5$ haloalkyl, $C_3$-$C_5$ haloalkenyl, $C_3$-$C_5$ haloalkylthioalkyl, $C_3$-$C_5$ haloalkoxyalkyl, $C_2$-$C_3$ haloalkylcarbonyloxy or $C_2$-$C_4$ haloalkoxy.

Embodiment 71. A compound of Embodiment 70 wherein independently when $R^{1a}$ and $R^{1c}$ are other than an optionally substituted phenyl, an optionally substituted naphthalenyl or an optionally substituted 5- or 6-membered heteroaromatic ring then $R^{1a}$ and $R^{1c}$ are independently $C_4$ haloalkyl, $C_4$ haloalkenyl, $C_3$ haloalkoxyalkyl or $C_3$ haloalkoxy.

Embodiment 72. A compound of Formula 1 or Formula 1A or Embodiment 65 wherein independently when $R^{1a}$ and $R^{1c}$ are an optionally substituted phenyl, an optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 3 independently selected substituents.

Embodiment 73. A compound of Formula 1 or Formula 1A or Embodiment 72 wherein independently when $R^{1a}$ and $R^{1c}$ are an optionally substituted phenyl, an optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 2 independently selected substituents.

Embodiment 74. A compound of Formula 1 or Formula 1A or Embodiments 72 or 73 wherein independently when $R^{1a}$ and $R^{1c}$ are an optionally substituted phenyl, an optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

each $R^{33a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each $R^{33b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 75. The compound of Embodiment 74 wherein independently $R^{1a}$ and $R^{1c}$ is selected from one of U-1 through U-50, shown below in Exhibit 5

Exhibit 5

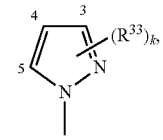

U-1

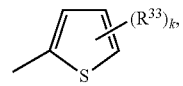

U-2

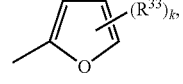

U-3

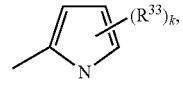

U-4

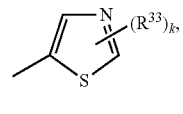

U-5

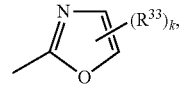

U-6

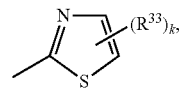

U-7

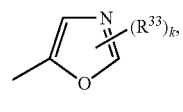

U-8

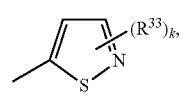

U-9

| | |
|---|---|
| 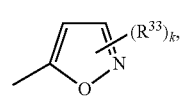 | U-10 |
| 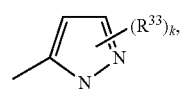 | U-11 |
| 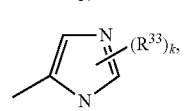 | U-12 |
| 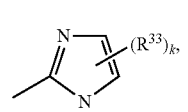 | U-13 |
| 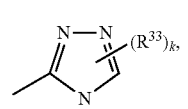 | U-14 |
| 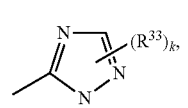 | U-15 |
| 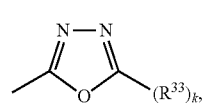 | U-16 |
| 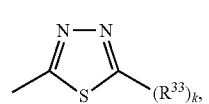 | U-17 |
| 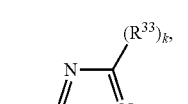 | U-18 |
| 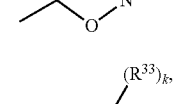 | U-19 |
| 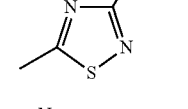 | U-20 |
| 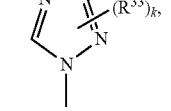 | U-21 |
| 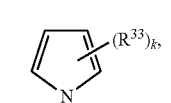 | U-22 |
| 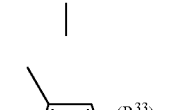 | U-23 |
| | |
|---|---|
| 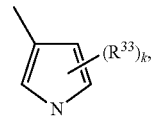 | U-24 |
| 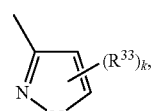 | U-25 |
| 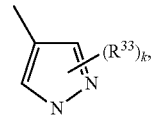 | U-26 |
| 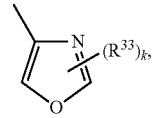 | U-27 |
| 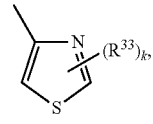 | U-28 |
| 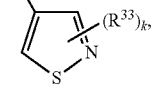 | U-29 |
| 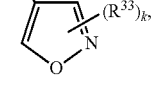 | U-30 |
| 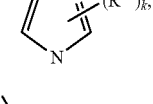 | U-31 |
| 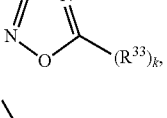 | U-32 |
| 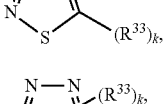 | U-33 |
| 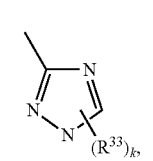 | U-34 |
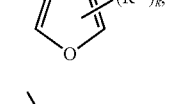
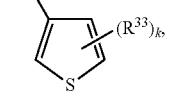

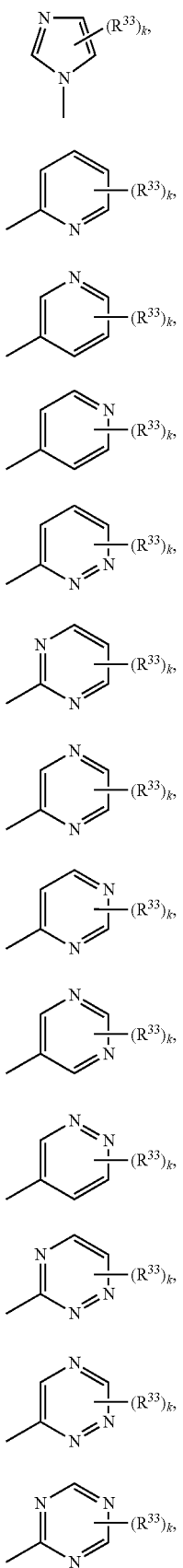
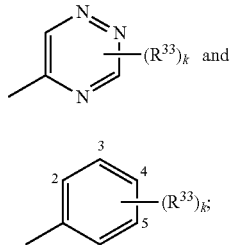

wherein when $R^{33}$ is attached to a carbon ring member, said $R^{33}$ is selected from $R^{33a}$, and when $R^{33}$ is attached to a nitrogen ring member (e.g., in U-4, U-11 through U-15, U-24 through U-26, U-31 or U-35), said $R^{33}$ is selected from $R^{33b}$; and k is 0, 1 or 2.

Embodiment 76. A compound of Embodiment 75 wherein independently $R^{1a}$ and $R^{1c}$ is selected from U-1 through U-5, U-8, U-11, U-13, U-15, U-20 through U-28, U-31, U-36 through U-39 and U-50.

Embodiment 77. A compound of Embodiment 76 wherein independently $R^{1a}$ and $R^{1c}$ is selected from U-1 through U-3, U-5, U-8, U-11, U-13, U-20, U-22, U-23, U-25 through U-28, U-36 through U-39 and U-50.

Embodiment 77a. A compound of Embodiment 77 wherein independently $R^{1a}$ and $R^{1c}$ is selected from U-1 through U-3, U-11, U-13, U-20, U-22, U-23, U-36 through U-39 and U-50.

Embodiment 77b. A compound of Embodiment 77a wherein independently $R^{1a}$ and $R^{1c}$ is U-1, U-20 or U-50.

Embodiment 77c. A compound of Embodiment 77b wherein independently $R^{1a}$ and $R^{1c}$ is U-1 or U-50.

Embodiment 77d. A compound of Embodiment 77c wherein independently $R^{1a}$ and $R^{1c}$ is U-1.

Embodiment 77e. A compound of Embodiment 77b wherein independently $R^{1a}$ and $R^{1c}$ is U-20.

Embodiment 77f. A compound of Embodiment 77b or 77c wherein independently $R^{1a}$ and $R^{1c}$ is U-50.

Embodiment 77g. A compound of Formula 1 or Formula 1A or any one of Embodiments 1 through 77f wherein each $R^{33a}$ is independently halogen, $C_1$-$C_6$ alkyl, $C_1$-$C_6$ haloalkyl or $C_2$-$C_4$ alkoxyalkyl.

Embodiment 77h. A compound of Embodiment 1 through 77g wherein each $R^{33a}$ is independently halogen, $C_1$-$C_3$ alkyl, $C_1$-$C_3$ haloalkyl or $C_2$-$C_3$ alkoxyalkyl.

Embodiment 77i. A compound of Formula 1 or Formula 1A or any one of Embodiments 1 through 77a wherein each $R^{33b}$ is independently $C_1$-$C_6$ alkyl.

Embodiment 78. A compound of Formula 1 or Formula 1A or any one of Embodiments 1 through 52 wherein $R^2$ when taken alone (i.e. not taken together with $R^3$) is H, cyano, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_1$-$C_4$ alkylthio, $C_1$-$C_4$ haloalkylthio, $C_1$-$C_4$ alkylamino, $C_2$-$C_4$ dialkylamino, $C_1$-$C_4$ haloalkylamino or $C_2$-$C_4$ halodialkylamino.

Embodiment 79. A compound of Embodiment 78 wherein $R^2$ when taken alone is H, cyano, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_1$-$C_3$ alkoxy or $C_1$-$C_3$ haloalkoxy.

Embodiment 80. A compound of Embodiment 79 wherein $R^2$ when taken alone is H, $C_1$-$C_3$ alkyl or $C_1$-$C_3$ haloalkyl.

Embodiment 81. A compound of Embodiment 80 wherein $R^2$ when taken alone is H, $C_1$-$C_3$ alkyl or $C_1$-$C_3$ fluoroalkyl.

Embodiment 82. A compound of Embodiment 81 wherein $R^2$ is methyl, trifluoromethyl or $CF_3CH_2$.

Embodiment 83. A compound of Formula 1 or Formula 1A or any one of Embodiments 1 through 52 or 78 through 82 wherein $R^2$ is taken alone.

Embodiment 84. A compound of Formula 1 or Formula 1A or any one of Embodiments 1 through 52 or 78 through 83 wherein $R^3$ when taken alone (i.e. not taken together with $R^2$ or $R^7$) is H, $C_1$-$C_3$ alkyl, $C_1$-$C_3$ alkoxy or $C_1$-$C_3$ haloalkyl.

Embodiment 85. A compound of Embodiment 84 wherein $R^3$ when taken alone is H, $C_1$-$C_3$ alkyl or $C_1$-$C_3$ haloalkyl.

Embodiment 86. A compound of Embodiment 85 wherein $R^3$ when taken alone is H, $C_1$-$C_2$ alkyl or $C_1$-$C_3$ fluoroalkyl.

Embodiment 87. A compound of Embodiment 86 wherein $R^3$ is H, methyl or trifluoromethyl.

Embodiment 88. A compound of Formula 1 or Formula 1A or any one of Embodiments 1 through 52 or 78 through 87 wherein $R^3$ is taken alone.

Embodiment 89. A compound of Formula 1 or Formula 1A or any one of Embodiments 1 through 52 wherein when $R^2$ and $R^3$ are taken together with the carbon atom to which they are attached to form a ring, the ring is 3- to 6-membered and contains ring members selected from carbon atoms and up to 2 heteroatoms independently selected from up to 2 O, up to 2 S and up to 2 N, wherein up to 1 carbon atom ring member is C(=O) or C(=S) and the ring is optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 90. A compound of Formula 1 or Formula 1A or any one of Embodiments 1 through 52 wherein when $R^3$ and $R^7$ are taken together with the linking atoms to which they are attached to form a 5- to 7-membered partially saturated ring containing ring members, in addition to the linking atoms, selected from carbon atoms and up to 3 heteroatoms independently selected from up to 1 O, up to 1 S and up to 1 N atom, the ring is optionally substituted with up to 2 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 91. A compound of Embodiment 90 wherein when $R^3$ and $R^7$ are taken together with the linking atoms to which they are attached to form a 5- to 7-membered partially saturated ring containing ring members, in addition to the linking atoms, selected from carbon atoms and up to 3 heteroatoms independently selected from up to 1 O, up to 1 S and up to 1 N atom, the ring is optionally substituted on carbon atom ring members with up to 2 substituents independently selected from halogen and $C_1$-$C_2$ alkyl.

Embodiment 92. A compound of Embodiment 91 wherein $R^3$ and $R^7$ are taken together with the linking atoms to which they are attached to form the ring defined in Embodiment 91.

Embodiment 93. A compound of Formula 1 or Formula 1A or any one of Embodiments 1 through 52 or 78 through 92 wherein $R^4$ is optionally substituted phenyl, optionally substituted naphthalenyl or an optionally substituted 5- or 6-membered heteroaromatic ring; or H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 94. A compound of Embodiment 93 wherein when $R^4$ is other than optionally substituted phenyl, optionally substituted naphthalenyl or an optionally substituted 5- or 6-membered heteroaromatic ring then $R^4$ is H, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 95. A compound of Embodiment 94 wherein when $R^4$ is other than optionally substituted phenyl, optionally substituted naphthalenyl or an optionally substituted 5- or 6-membered heteroaromatic ring then $R^4$ is H, cyano, hydroxy, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 96. A compound of Formula 1 or Formula 1A or any one of Embodiments 1 through 52 or 78 through 95 wherein $R^4$ is H, cyano, methyl, methoxy or $CH_3C(=O)O—$.

Embodiment 97. A compound of Embodiment 96 wherein $R^4$ is H or methyl.

Embodiment 98. A compound of Embodiment 97 wherein $R^4$ is H.

Embodiment 99. A compound of Formula 1 or Formula 1A or any one of Embodiments 1 through 95 wherein when $R^4$ is optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is substituted with up to 3 optional substituents.

Embodiment 100. A compound of Embodiment 99 wherein when $R^4$ is optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is substituted with up to 2 optional substituents.

Embodiment 101. A compound of Formula 1 or Formula 1A or any one of Embodiments 1 through 52 or 78 through 100 when $R^4$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{32a}$ on carbon ring members and $R^{32b}$ on nitrogen ring members;

each $R^{32a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each $R^{32b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 102. A compound of Embodiment 101 wherein each $R^{32a}$ is independently halogen, $C_1$-$C_2$ alkyl, $C_1$-$C_2$ haloalkyl or $C_1$-$C_2$ alkoxy.

Embodiment 103. A compound of Embodiment 102 wherein each $R^{32a}$ is independently Cl, Br, I, $C_1$-$C_2$ alkyl, trifluoromethyl or methoxy.

Embodiment 104. A compound of Embodiment 103 wherein each $R^{32a}$ is independently Cl, Br, $C_1$-$C_2$ alkyl or trifluoromethyl.

Embodiment 105. A compound of Formula 1 or Formula 1A or any one of Embodiments 2 through 52 or 78 through 104 wherein $R^4$ is other than optionally substituted naphthalenyl.

Embodiment 106. A compound of Formula 1 or Formula 1A or any one of Embodiments 1 through 52 or 78 through 104 wherein when $R^4$ is an optionally substituted 5- to 6-membered heteroaromatic ring then $R^4$ is selected from the group consisting of U-51 through U-60, and when $R^4$ is optionally substituted phenyl then $R^4$ is selected from U-61, shown below in Exhibit 5A Exhibit 5A

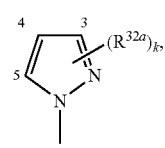
U-51

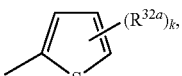
U-52

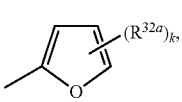
U-53

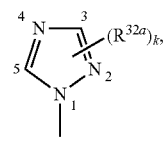
U-54

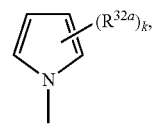
U-55

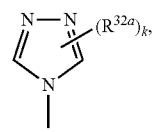
U-56

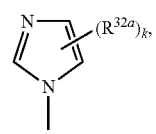
U-57

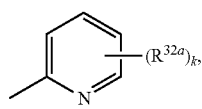
U-58

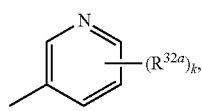
U-59

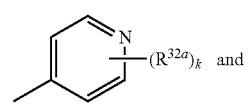
U-60

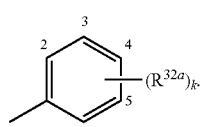
U-61 wherein k is 0, 1 or 2.

Embodiment 107. A compound of Embodiment 106 wherein $R^4$ is selected from the group consisting of U-51 through U-61.

Embodiment 108. A compound of Embodiment 107 wherein $R^4$ is selected from U-51, U-54 and U-61.

Embodiment 109. A compound of Embodiment 108 wherein $R^4$ is U-51.

Embodiment 110. A compound of Formula 1 or Formula 1A or any one of Embodiments 1 through 109 wherein $R^5$ is H or $C_1$-$C_2$ alkyl.

Embodiment 111. A compound of Embodiment 110 wherein $R^5$ is H.

Embodiment 112. A compound of Formula 1 or Formula 1A or any one of Embodiments 1 through 111 wherein each Z is independently a direct bond, O, C(=O), S(O)$_m$ or CH($R^{12}$).

Embodiment 113. A compound of Formula 1 or Formula 1A or any one of Embodiments 1 through 112 wherein each Z is independently a direct bond, O, C(=O), S(=O)$_2$ or CH($R^{12}$).

Embodiment 114. A compound of Embodiment 113 wherein each Z is a direct bond.

Embodiment 115. A compound of Formula 1 or Formula 1A or any one of Embodiments 1 through 114 wherein each Q is independently phenyl, benzyl, naphthalenyl, a 5- to 6-membered heteroaromatic ring or an 8- to 11-membered heteroaromatic bicyclic ring system, each optionally substituted with up to 1 substituent independently selected from $R^{6b}$ on carbon and nitrogen atom ring members, and each optionally substituted with up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl or $C_1$-$C_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S and up to 4 N atoms, wherein up to 3 carbon atom ring members are independently selected from C(=O) and C(=S), the sulfur atom ring members are independently selected from $S(=O)_s(=NR^{11})_f$, each ring or ring system optionally substituted with up to 1 substituent independently selected from $R^{6b}$ on carbon and nitrogen atom ring members, and each ring or ring system optionally substituted with up to 5 substituents independently selected from $R^{6a}$ on carbon atom ring members and selected from $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members.

Embodiment 116. A compound of Embodiment 115 wherein Q is a ring selected from Q-1 through Q-102, shown below in Exhibit 6

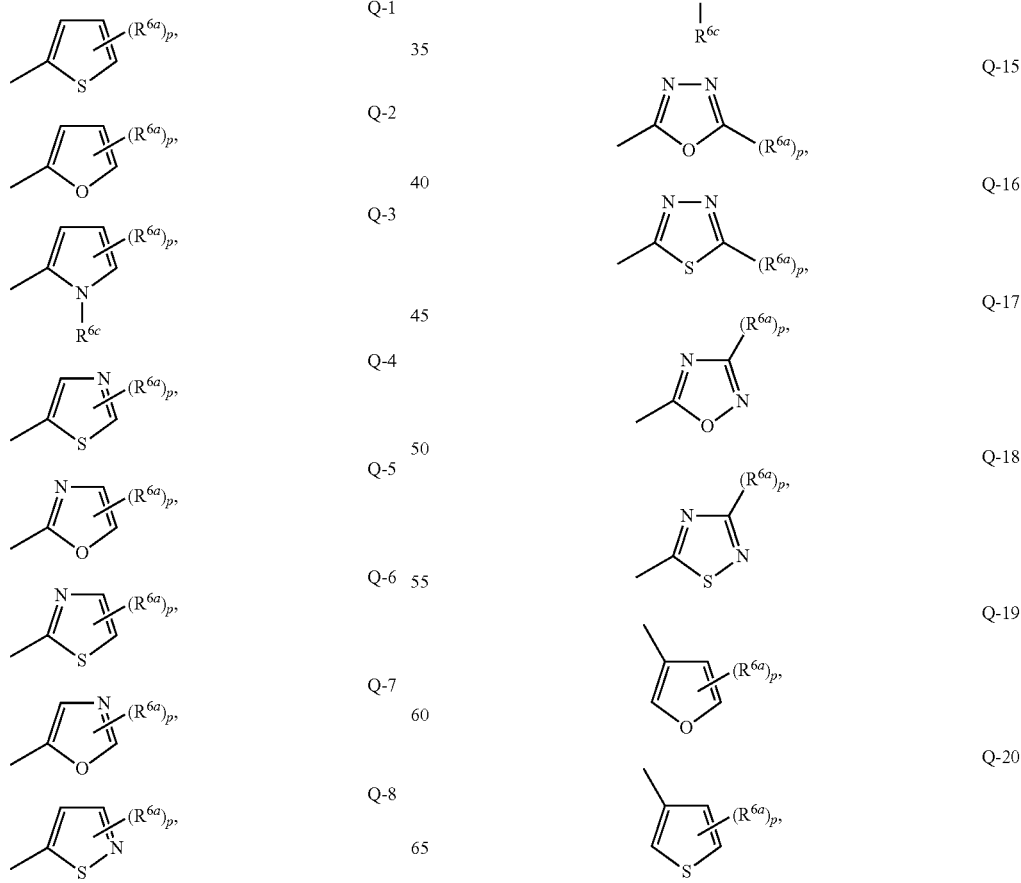

| | |
|---|---|
| Q-21 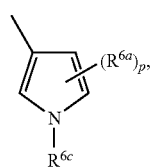 | Q-31 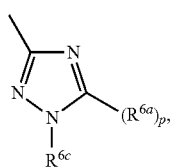 |
| Q-22 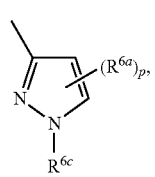 | Q-32 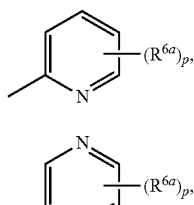 |
| Q-23 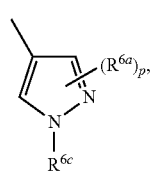 | Q-33 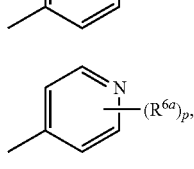 |
| Q-24 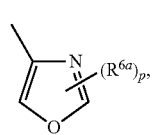 | Q-34 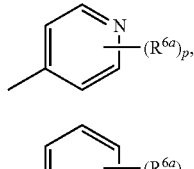 |
| Q-25 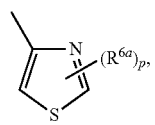 | Q-35 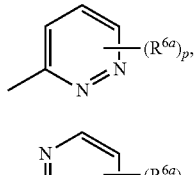 |
| Q-26 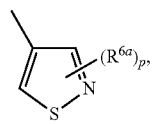 | Q-36 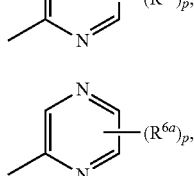 |
| Q-27 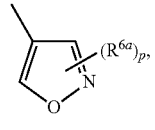 | Q-37 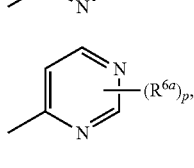 |
| Q-28 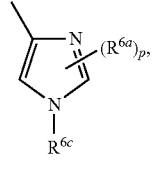 | Q-38 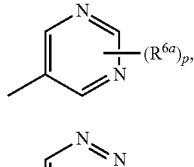 |
| Q-29 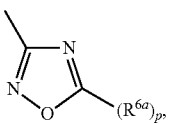 | Q-39 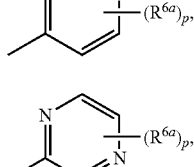 |
| Q-30 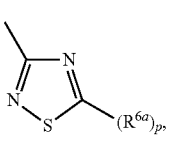 | Q-40 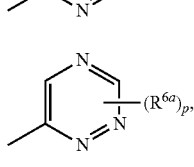 |
| | Q-41 |
| | Q-42 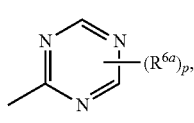 |
| | Q-43 |

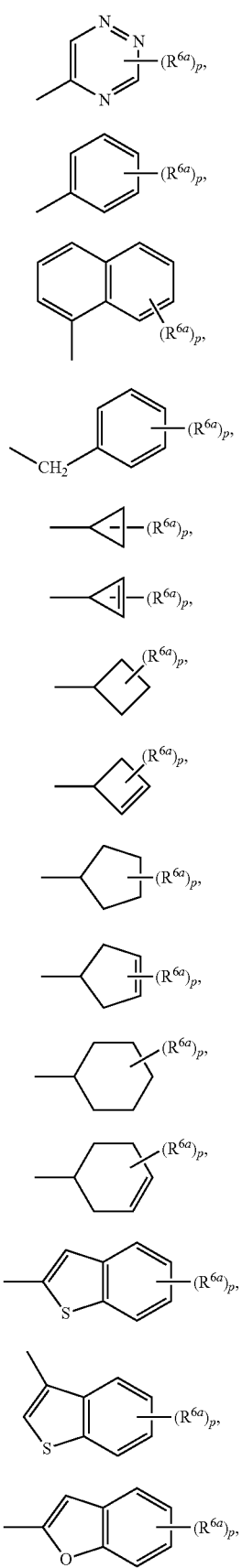
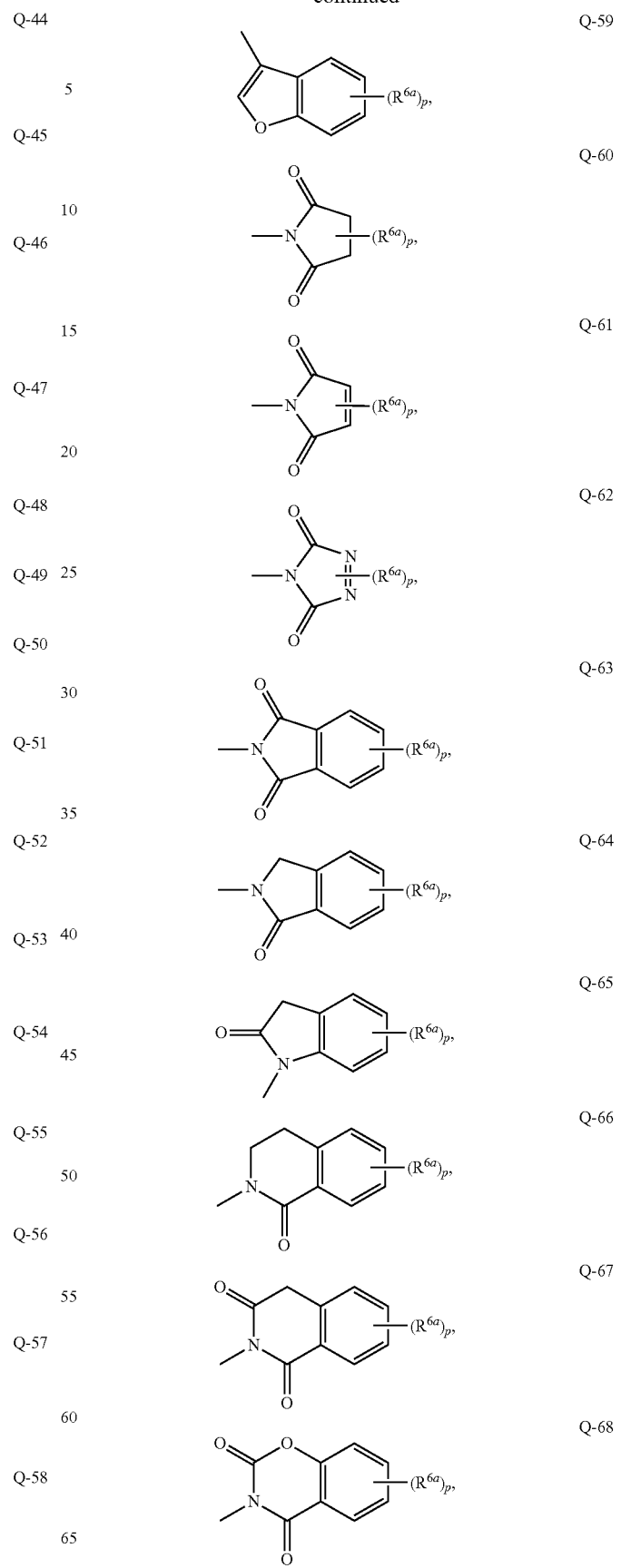

| | |
|---|---|
| 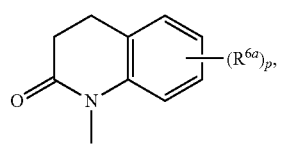 Q-69 | 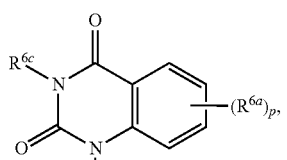 Q-78 |
| 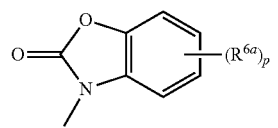 Q-70 | 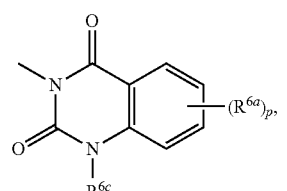 Q-79 |
| 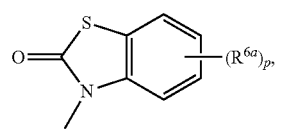 Q-71 | 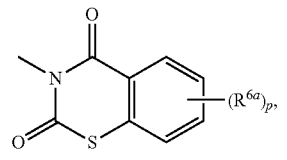 Q-80 |
| 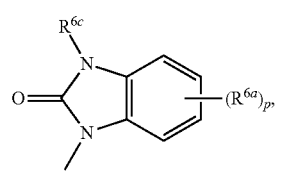 Q-72 | 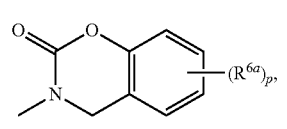 Q-81 |
| 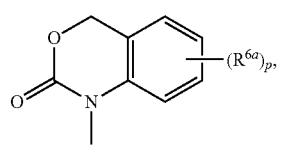 Q-73 | 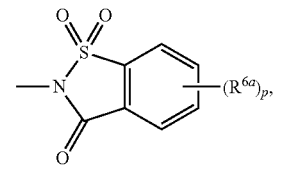 Q-82 |
| 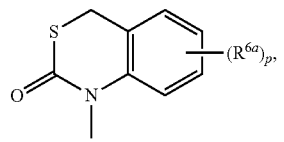 Q-74 | 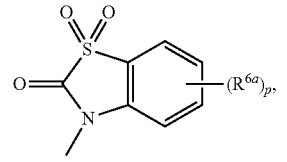 Q-83 |
| 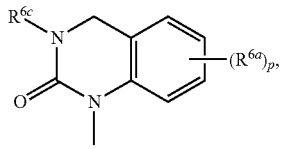 Q-75 | 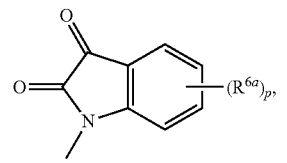 Q-84 |
| 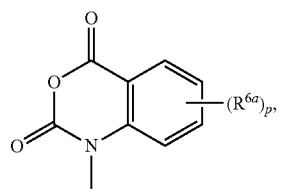 Q-76 | 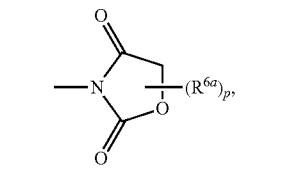 Q-85 |
| 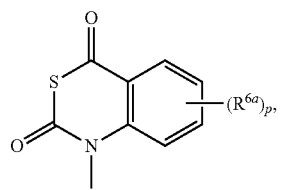 Q-77 | 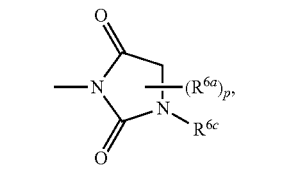 Q-86 |

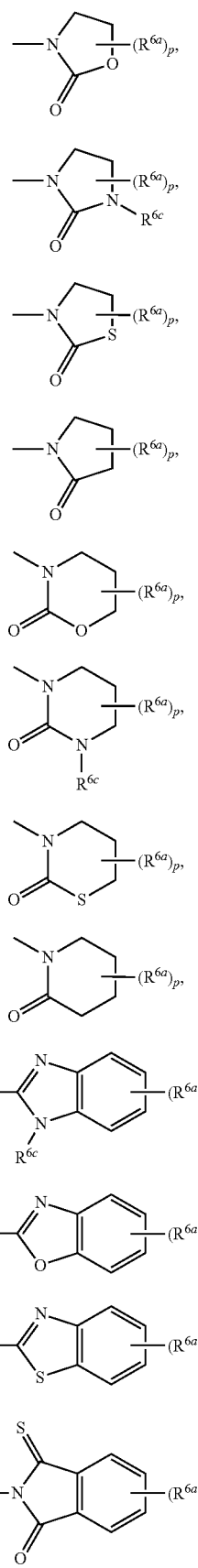
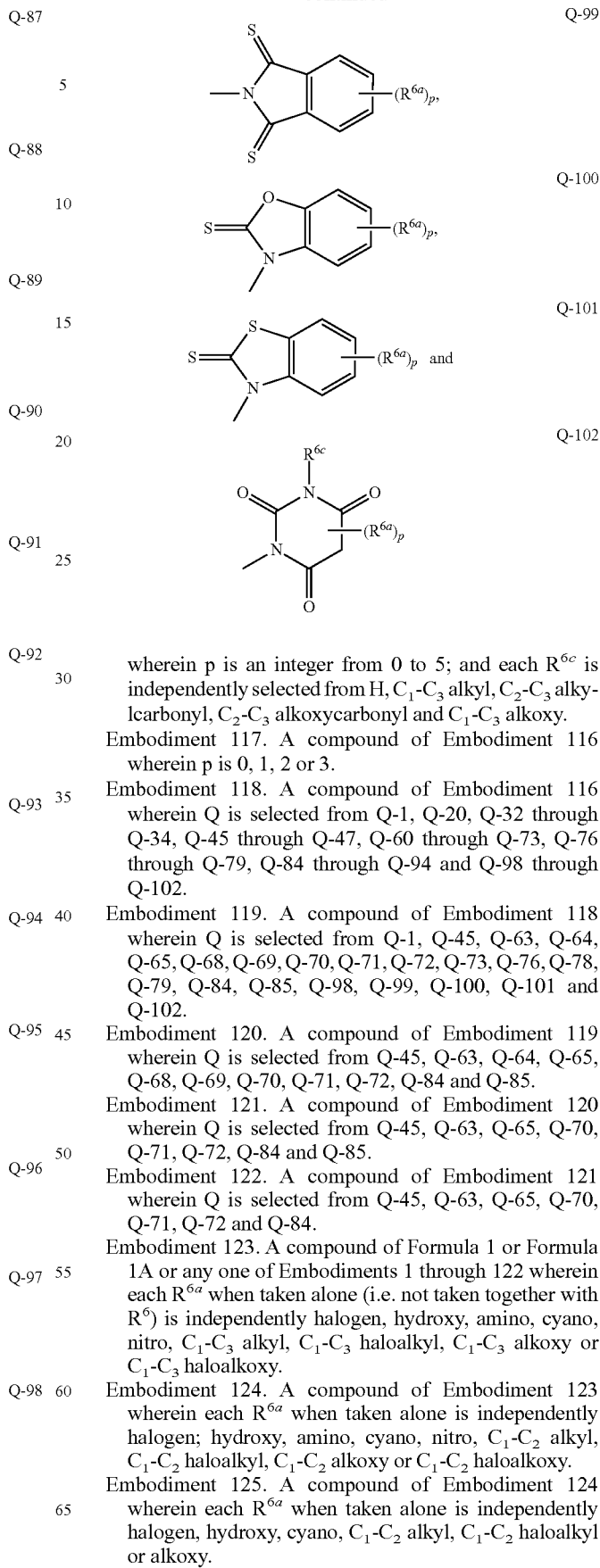

wherein p is an integer from 0 to 5; and each $R^{6c}$ is independently selected from H, $C_1$-$C_3$ alkyl, $C_2$-$C_3$ alkylcarbonyl, $C_2$-$C_3$ alkoxycarbonyl and $C_1$-$C_3$ alkoxy.

Embodiment 117. A compound of Embodiment 116 wherein p is 0, 1, 2 or 3.

Embodiment 118. A compound of Embodiment 116 wherein Q is selected from Q-1, Q-20, Q-32 through Q-34, Q-45 through Q-47, Q-60 through Q-73, Q-76 through Q-79, Q-84 through Q-94 and Q-98 through Q-102.

Embodiment 119. A compound of Embodiment 118 wherein Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102.

Embodiment 120. A compound of Embodiment 119 wherein Q is selected from Q-45, Q-63, Q-64, Q-65, Q-68, Q-69, Q-70, Q-71, Q-72, Q-84 and Q-85.

Embodiment 121. A compound of Embodiment 120 wherein Q is selected from Q-45, Q-63, Q-65, Q-70, Q-71, Q-72, Q-84 and Q-85.

Embodiment 122. A compound of Embodiment 121 wherein Q is selected from Q-45, Q-63, Q-65, Q-70, Q-71, Q-72 and Q-84.

Embodiment 123. A compound of Formula 1 or Formula 1A or any one of Embodiments 1 through 122 wherein each $R^{6a}$ when taken alone (i.e. not taken together with $R^6$) is independently halogen, hydroxy, amino, cyano, nitro, $C_1$-$C_3$ alkyl, $C_1$-$C_3$ haloalkyl, $C_1$-$C_3$ alkoxy or $C_1$-$C_3$ haloalkoxy.

Embodiment 124. A compound of Embodiment 123 wherein each $R^{6a}$ when taken alone is independently halogen; hydroxy, amino, cyano, nitro, $C_1$-$C_2$ alkyl, $C_1$-$C_2$ haloalkyl, $C_1$-$C_2$ alkoxy or $C_1$-$C_2$ haloalkoxy.

Embodiment 125. A compound of Embodiment 124 wherein each $R^{6a}$ when taken alone is independently halogen, hydroxy, cyano, $C_1$-$C_2$ alkyl, $C_1$-$C_2$ haloalkyl or alkoxy.

Embodiment 126. A compound of Formula 1 or Formula 1A or any one of Embodiments 1 through 125 wherein each $R^{6a}$ is taken alone.

Embodiment 127. A compound of Embodiment 126 wherein each $R^{6a}$ is independently halogen, hydroxy, cyano, $C_1$-$C_2$ alkyl or $C_1$-$C_2$ alkoxy.

Embodiment 128. A compound of Embodiment 126 wherein each $R^{6a}$ is independently F, Cl, Br, hydroxy, cyano, methyl or methoxy.

Embodiment 129. A compound of any one of Formula 1 or Formula 1A or any of Embodiments 1 through 122 wherein when $R^6$ and $R^{6a}$ are taken together with the atoms to which they are attached to form a ring, the ring is 5- to 6-membered ring and contains ring members selected from carbon atoms and up to 3 heteroatoms selected from up to 1 O, up to 1 S and up to 1 N atom, and the ring is optionally substituted with up to 2 substituents independently selected from halogen, $C_1$-$C_2$ alkyl and $C_1$-$C_2$ alkoxy on carbon atom ring members and $C_1$-$C_2$ alkyl on nitrogen atom ring members.

Embodiment 130. A compound of Embodiment 129 wherein when $R^6$ and $R^{6a}$ are taken together with the atoms to which they are attached to form a ring, the ring contains ring members selected from carbon atoms and up to 1 heteroatom selected from up to 1 O, up to 1 S and up to 1 N atom, and the ring is optionally substituted on carbon atom ring members with up to 1 substituent independently selected from halogen, $C_1$-$C_2$ alkyl and $C_1$-$C_2$ alkoxy.

Embodiment 131. A compound of Formula 1 or Formula 1A or any one of Embodiments 1 through 130 wherein $R^7$ when taken alone (i.e. not taken together with $R^3$) is H, $C_1$-$C_2$ alkyl, $C_1$-$C_2$ haloalkyl, $CH_3C(=O)$, $CF_3C(=O)$ or $CH_3C(=O)$.

Embodiment 132. A compound of Embodiment 131 wherein $R^7$ when taken alone is H or $C_1$-$C_2$ alkyl.

Embodiment 133. A compound of Embodiment 132 wherein $R^7$ when taken alone is H or methyl.

Embodiment 134. A compound of Formula 1 or Formula 1A or any one of Embodiments 1 through 133 wherein $R^7$ is taken alone.

Embodiment 135. A compound of Formula 1 or Formula 1A or any one of Embodiments 1 through 134 wherein $R^{14}$ is H, cyano, hydroxy, $C_1$-$C_3$ alkyl, $C_1$-$C_3$ haloalkyl or $C_1$-$C_3$ alkoxy.

Embodiment 136. A compound of Embodiment 135 wherein $R^{14}$ is H, cyano, hydroxy, $C_1$-$C_2$ alkyl or $C_1$-$C_2$ alkoxy.

Embodiment 137. A compound of Embodiment 136 wherein $R^{14}$ is H or methyl.

Embodiment 138. A compound of Formula 1 or Formula 1A or any one of Embodiments 1 through 53 or 60 through 137 wherein $A^1$ is $CHR^{15}$.

Embodiment 139. A compound of Embodiment 138 wherein $R^{15}$ is H, halogen, cyano, hydroxy, —CHO, $C_1$-$C_4$ alkyl, $C_1$-$C_4$ haloalkyl, $C_2$-$C_5$ alkoxycarbonyl or $C_1$-$C_4$ alkoxy.

Embodiment 140. A compound of Embodiment 139 wherein $R^{15}$ is H, halogen, cyano, hydroxy, methyl or methoxy.

Embodiment 141. A compound of Embodiment 140 wherein $R^{15}$ is H.

Embodiment 142. A compound of Formula 1 or Formula 1A or any one of. Embodiments 1 through 55 or 60 through 137 wherein $A^1$ is $NR^{16}$.

Embodiment 143. A compound of Embodiments 142 wherein $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment 144. A compound of Embodiment 143 wherein $R^{16}$ is H, methyl, methylcarbonyl or methoxycarbonyl.

Embodiment 145. A compound of Embodiment 144 wherein $R^{16}$ is H.

Embodiment 146. A compound of Formula 1 or Formula 1A or any one of Embodiments 1 through 145 wherein $R^{17}$ is H or methyl.

Embodiment 147. A compound of Formula 1 or Formula 1A or any one of Embodiments 1 through 146 wherein $R^{18}$ is phenyl, benzyl or pyridinyl, each optionally substituted with up to 3 substituents independently selected from $R^{22}$.

Embodiment 148. A compound of Formula 1 or Formula 1A or any one of Embodiments 1 through 147 wherein each $R^{22}$ is independently halogen or $C_1$-$C_3$ alkyl.

Embodiment 149. A compound of Formula 1 or Formula 1A or any one of Embodiments 1 through 148 wherein $R^{19}$ is H or $C_1$-$C_3$ alkyl.

Embodiment 150. A compound of Embodiment 149 wherein $R^{19}$ is H or methyl.

Embodiment 151. A compound of Formula 1 or Formula 1A or any one of Embodiments 1 through 147 wherein when $R^{19}$ and $R^{22}$ are taken together with the atoms to which they are attached to form a 5- to 7-membered ring, the ring contains ring members selected from carbon atoms and up to 2 heteroatoms independently selected from up to 2 O, up to 2 S, up to 2 N, wherein up to 2 carbon atom ring members are independently selected from $C(=O)$ and $C(=S)$, and the sulfur atom ring members are independently selected from $S(=O)_s$ $(=NR^{11})_f$, and the ring is optionally substituted with up to 3 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members.

Embodiment 151a. A compound of Embodiment 151 wherein when $R^{19}$ and $R^{22}$ are taken together with the atoms to which they are attached to form a 5- to 7-membered ring, the ring contains ring members selected from carbon atoms and one heteroatom independently selected from O, S and N.

Embodiment 152. A compound of Formula 1 or Formula 1A or any one of Embodiments 1 through 151a wherein each $R^{21}$ is independently $C_1$-$C_3$ alkyl or $-Z^1Q$.

Embodiment 153. A compound of Embodiment 152 wherein each $R^{21}$ is independently $C_1$-$C_3$ alkyl.

Embodiment 154. A compound of Formula 1 or Formula 1A or any one of Embodiments 1 through 152 wherein each $Z^1$ is independently $C(=O)$ or $S(=O)_2$.

Embodiment 155. A compound of Embodiment 154 wherein each $Z^1$ is $C(=O)$.

Embodiment 156. A compound of Formula 1 or Formula 1A or any one of Embodiments 1 through 155 wherein each $R^{23}$ is independently H, —CHO, $C_1$-$C_4$ alkyl, $C_1$-$C_4$ alkenyl or $C_1$-$C_4$ haloalkyl.

Embodiment 157. A compound of Embodiment 156 wherein each $R^{23}$ is independently H or $CH_3$.

Embodiment 158. A compound of Embodiment 157 wherein each $R^{23}$ is H.

Embodiment 159. A compound of Formula 1 or Formula 1A or any one of Embodiments 1 through 52, 61 through 63 or 65 through 158 wherein each $R^{24}$ and $R^{25}$ independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl.

Embodiment 160. A compound of Embodiment 159 wherein each $R^{24}$ and $R^{25}$ selected from $C_1$-$C_6$ alkyl, $C_3$-$C_4$ alkenyl, $C_3$-$C_4$ alkynyl and $C_1$-$C_4$ haloalkyl.

Embodiment 161. A compound of Embodiment 160 wherein each $R^{24}$ and $R^{25}$ independently is $C_1$-$C_4$ alkyl.

Embodiment 162. A compound of Formula 1 or Formula 1A or any one of Embodiments 1 through 52, 61, or 64 through 158 wherein $R^{26}$ is selected from H, cyano, hydroxy, amino and $C_1$-$C_6$ alkyl.

Embodiment 163. A compound of Formula 1 or Formula 1A or any one of Embodiments 1 through 52, 61 or 64 through 158 wherein $R^{27}$ is selected from H and $C_1$-$C_6$ alkyl.

Embodiment 164. A compound of Formula 1 or Formula 1A or any one of Embodiments 1 through 52, 61 or 64 through 158 wherein $R^{26}$ and $R^{27}$ are taken together as —$(CH_2)_4$—, —$(CH_2)_5$— or —$(CH_2)_2O(CH_2)_2$—.

Embodiment 165. A compound of Embodiment 164 wherein $R^{26}$ and $R^{27}$ are taken together as —$(CH_2)_4$— or —$(CH_2)_2O(CH_2)_2$—.

Embodiment 166. A compound of Embodiment 165 wherein $R^{26}$ and $R^{27}$ are taken together as —$(CH_2)_4$—.

Embodiment 167. A compound of Formula 1 or Formula 1A or any one of Embodiments 1 through 52, 63 or 67 through 158 wherein $R^{28}$ is H, halogen, cyano or $C_1$-$C_4$ alkyl.

Embodiment 168. A compound of Embodiment 167 wherein $R^{28}$ is H, halogen or cyano.

Embodiment 169. A compound of Embodiment 168 wherein $R^{28}$ is Cl or cyano.

Embodiment 170. A compound of Formula 1 or Formula 1A or any one of Embodiments 1 through 52, 57, 60 or 78 through 169 wherein each $R^8$ is independently H, $CH_3$ or $CH_2CF_3$.

Embodiment 171. A compound of Formula 1 or Formula 1A or any one of Embodiments 1 through 170 wherein each $R^{11}$ is independently H, $C_1$-$C_6$ alkyl or $C_3$-$C_8$ cycloalkyl.

Embodiment 172. A compound of Formula 1 or Formula 1A or any one of Embodiments 1 through 171 wherein each $R^{12}$ is independently H, $CH_3$, $CF_3$ or $CH_2CF_3$.

Embodiment 173. A compound of Formula 1 or Formula 1A or any one of Embodiments 1 through 172 wherein each $R^{20}$ is independently H, $CH_3$, $CH_2CF_3$, $CF_3$ or cyclopropyl.

Embodiment 174. A compound of Formula 1 or any one of Embodiments 1 through 172

Embodiment 175. A compound of Formula 1A or any one of Embodiments 1 through 172.

Embodiments of this invention, including Embodiments 1-173 above as well as any other embodiments described herein, can be combined in any manner, and the descriptions of variables in the embodiments pertain not only to the compositions comprising the compounds of Formula 1 and Formula 1A but also to the compounds of Formula 1, Formula 1A the starting compounds and intermediate compounds useful for preparing the compounds of Formula 1 and Formula 1A unless further defined in the Embodiments. In addition, embodiments of this invention, including Embodiments 1-173 above as well as any other embodiments described herein, and any combination thereof, pertain to the compositions and methods of the present invention. Combinations of Embodiments 1-173 are illustrated by:

Embodiment A1. A compound of Formula 1 or Formula 1A wherein
E is E-3;
$Y^1$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—;
$Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—; or
$Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S— and —N($R^{23}$)—;
G is G-1 through G-48 optionally substituted with $R^{29}$ on carbon ring members and optionally substituted with $R^{30}$ on nitrogen ring members;
J is a 5- to 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, wherein up to 3 carbon atom ring members are independently selected from C(=O) and C(=S), and the sulfur atom ring members are independently selected from S(=O)$_s$ (=N$R^{11}$)$_f$, each ring or ring system optionally substituted with up to 5 substituents independently selected from $R^6$; or J is C(=$W^4$)N$T^4T^B$;
$W^3$ is O$R^{24}$, S$R^{25}$ or N$R^{26}R^{27}$;
$W^4$ is O;
$T^4$ is H or methyl;
$R^{1c}$ is an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ haloalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;
$R^6$ is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{20}$R$^{21}$ or —ZQ;

$R^{6a}$ is independently halogen, hydroxy, cyano, $C_1$-$C_2$ alkyl or $C_1$-$C_2$ alkoxy; or $R^6$ and $R^{6a}$ are taken together with the atoms to which they are attached to form a ring, the ring is 5- to 6-membered ring and contains ring members selected from carbon atoms and up to 3 heteroatoms selected from up to 1 O, up to 1 S and up to 1 N atom, and the ring is optionally substituted with up to 2 substituents independently selected from halogen, $C_1$-$C_2$ alkyl and $C_1$-$C_2$ alkoxy on carbon atom ring members and $C_1$-$C_2$ alkyl on nitrogen atom ring members;

Z is independently a direct bond, O, C(=O), S(=O)$_2$ or CH(R$^{12}$);

Q is a ring selected from Q-1 through Q-102 optionally substituted with from 0 to 5 $R^{6a}$ on carbon members and optionally substituted with $R^{6c}$ on nitrogen ring members;

$R^{6c}$ is independently selected from H, $C_1$-$C_3$ alkyl, $C_2$-$C_3$ alkylcarbonyl, $C_2$-$C_3$ alkoxycarbonyl and $C_1$-$C_3$ alkoxy;

$R^{11}$ is independently H, $C_1$-$C_6$ alkyl or $C_3$-$C_8$ cycloalkyl;

$R^{12}$ is independently H, CH$_3$, CF$_3$ or CH$_2$CF$_3$;

$R^{14}$ is H, cyano, hydroxy, $C_1$-$C_3$ alkyl, $C_1$-$C_3$ haloalkyl or $C_1$-$C_3$ alkoxy;

$R^{17}$ is H or methyl $R^{18}$ is phenyl, benzyl or pyridinyl, each optionally substituted with up to 3 substituents independently selected from $R^{22}$;

$R^{19}$ is H or $C_1$-$C_3$ alkyl;

$R^{20}$ is independently H, CH$_3$, CH$_2$CF$_3$, CF$_3$ or cyclopropyl;

$R^{21}$ is independently $C_1$-$C_3$ alkyl or —Z$^1$Q;

$Z^1$ is independently C(=O) or S(=O)$_2$;

$R^{22}$ is independently halogen or $C_1$-$C_3$ alkyl; or $R^{19}$ and $R^{22}$ are taken together with the atoms to which they are attached to form a 3- to 7-membered ring, the ring contains ring members selected from carbon atoms and up to 2 heteroatoms independently selected from up to 2 O, up to 2 S, up to 2 N, wherein up to 2 carbon atom ring members are independently selected from C(=O) and C(=S), and the sulfur atom ring members are independently selected from S(=O)$_s$ (=NR$^{11}$)$_s$ and the ring is optionally substituted with up to 3 substituents independently selected from halogen, cyano, hydroxy, $C_1$-$C_2$ alkyl and $C_1$-$C_2$ alkoxy on carbon atom ring members and cyano, $C_1$-$C_2$ alkyl and $C_1$-$C_2$ alkoxy on nitrogen atom ring members;

$R^{23}$ is independently H, —CHO, $C_1$-$C_4$ alkyl, $C_1$-$C_4$ alkenyl or $C_1$-$C_4$ haloalkyl each $R^{24}$ and $R^{25}$ is independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl;

$R^{26}$ is selected from H, cyano, hydroxy, amino and $C_1$-$C_6$ alkyl;

$R^{27}$ is selected from H, $C_1$-$C_6$ alky; or $R^{26}$ and $R^{27}$ are taken together as —(CH$_2$)$_4$—, —(CH$_2$)$_5$— or (CH$_2$)$_2$O(CH$_2$)$_2$—;

$R^{28}$ is H, halogen, cyano or $C_1$-$C_4$ alkyl;

each $R^{29}$ is independently halogen, $C_1$-$C_3$ alkyl or $C_1$-$C_3$ haloalkyl;

each $R^{30}$ is independently $C_1$-$C_3$ alkyl;

x is an integer from 1 to 5, and when x is 2, 3, 4 or 5, then at most one instance of $R^6$ is —ZQ;

m is 0 or 1; and s and f are 0 or 1 provided that the sum of s and f is 1.

Embodiment A2. A compound of Embodiment A1 wherein
$Y^1$, $Y^2$ and $Y^3$ in Formula 1 form a ring selected from L-1 through L-24;

$Y^2$, $X^1$ and $X^2$ in Formula 1A form a ring selected from L-60 through L-65;

G is selected from G-1, G-2, G-7, G-8, G-14, G-15, G-23, G-24, G-26, G-27, G-36, G-37 and G-38;

J is a ring selected from the group consisting of J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69;

$W^3$ is NR$^{26}$R$^{27}$;

$R^{1c}$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

each $R^{33a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{33b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

Z is a direct bond;

Q is selected from Q-45, Q-63, Q-65, Q-70, Q-71, Q-72, Q-84 and Q-85;

p is 0, 1, 2 or 3; and $R^{6a}$ is F, Cl, Br, hydroxy, cyano, methyl or methoxy.

Embodiment A3. A compound of Formula 1 or Formula 1A wherein

E is E-1 or E-2;

$Y^1$ is —N=C(R$^{14}$)—, —C(R$^{14}$)=N— or a ring-forming chain consisting of 2 chain members wherein one chain member is —C(R$^{14}$)$_2$— and the second chain member is selected from —C(R$^{14}$)$_2$—, —O—, —S— and —N(R$^{23}$)—;

$Y^3$ is —N=C(R$^{14}$)—, —C(R$^{14}$)=N— or a ring-forming chain consisting of 2 chain members wherein one chain member is —C(R$^{14}$)$_2$— and the second chain member is selected from —C(R$^{14}$)$_2$—, —O—, —S— and —N(R$^{23}$)—; or $Y^3$ is —C(R$^{14}$)$_2$N=C(R$^{14}$)—, —C(R$^{14}$)$_2$C(R$^{14}$)=N—, —N=C(R$^{14}$)C(R$^{14}$)$_2$—, —C(R$^{14}$)=NC(R$^{14}$)$_2$— or a ring-forming chain consisting of 3 chain members wherein two chain members are —C(R$^{14}$)$_2$— and the third chain member is selected from —C(R$^{14}$)$_2$—, —O—, —S— and —N(R$^{23}$)—;

G is selected from G-1, G-2, G-15, G-26, G-27, G-36, G-37 and G-38;

each R$^{29}$ is independently halogen, C$_1$-C$_3$ alkyl or C$_1$-C$_3$ haloalkyl;

J is a ring selected from the group consisting of J-4, J-5, J-11, J-20, J-29, J-37, J-38 and J-69;

x is an integer from 1 to 5, and when x is 2, 3, 4 or 5, then at most one instance of R$^6$ is —ZQ;

R$^6$ is H, cyano, C$_1$-C$_6$ alkyl, C$_1$-C$_6$ haloalkyl, C$_3$-C$_8$ cycloalkyl, C$_3$-C$_8$ halocycloalkyl, C$_2$-C$_6$ alkoxyalkyl, C$_1$-C$_6$ alkoxy, C$_1$-C$_6$ haloalkoxy, C$_3$-C$_8$ cycloalkoxy, C$_2$-C$_6$ alkenyloxy, C$_2$-C$_6$ haloalkenyloxy, C$_2$-C$_6$ alkynyloxy, C$_2$-C$_6$ alkoxyalkoxy, C$_2$-C$_6$ alkylcarbonyloxy, C$_2$-C$_6$ haloalkylcarbonyloxy, C$_1$-C$_6$ alkylthio, C$_1$-C$_6$ haloalkylthio, C$_3$-C$_{10}$ trialkylsilyl, —NR$^{20}$R$^{21}$ or —ZQ;

A$^1$ is CHR$^{15}$ or NR$^{16}$;

A$^2$ is —O—, —S—, —N(R$^7$)—, —C(R$^8$)$_2$— or —OC(R$^8$)$_2$—;

W$^1$ is O;

W$^2$ is O;

R$^{1a}$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from R$^{33a}$ on carbon ring members and R$^{33b}$ on nitrogen ring members;

R$^2$ is H, cyano, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_4$ alkoxyalkyl, C$_2$-C$_4$ alkylthioalkyl, C$_2$-C$_4$ alkylcarbonyl, C$_2$-C$_4$ haloalkylcarbonyl, C$_2$-C$_4$ alkoxycarbonyl, C$_1$-C$_4$ alkoxy, C$_1$-C$_4$ haloalkoxy, C$_2$-C$_4$ alkenyloxy, C$_2$-C$_4$ haloalkenyloxy, C$_2$-C$_4$ alkynyloxy, C$_3$-C$_4$ haloalkynyloxy, C$_2$-C$_4$ alkoxyalkoxy, C$_1$-C$_4$ alkylthio, C$_1$-C$_4$ haloalkylthio, C$_1$-C$_4$ alkylamino, C$_2$-C$_4$ dialkylamino, C$_1$-C$_4$ haloalkylamino or C$_2$-C$_4$ halodialkylamino;

R$^3$ is H, C$_1$-C$_3$ alkyl, C$_1$-C$_3$ alkoxy or C$_1$-C$_3$ haloalkyl;

R$^4$ is H or methyl;

R$^{32a}$ is independently halogen, C$_1$-C$_2$ alkyl, C$_1$-C$_2$ haloalkyl or C$_1$-C$_2$ alkoxy;

k is 0, 1 or 2;

R$^5$ is H or C$_1$-C$_2$ alkyl;

R$^7$ is H, C$_1$-C$_2$ alkyl, C$_1$-C$_2$ haloalkyl, CH$_3$C(=O), CF$_3$C(=O) or CH$_3$C(=O);

each R$^8$ is independently H, CH$_3$ or CH$_2$CF$_3$;

Z is a direct bond;

Q is selected from Q-45, Q-63, Q-65, Q-70, Q-71, Q-72, Q-84 and Q-85;

p is 0, 1, 2 or 3; and each R$^{6a}$ is F, Cl, Br, hydroxy, cyano, methyl or methoxy;

R$^{14}$ is H, cyano, hydroxy, C$_1$-C$_3$ alkyl, C$_1$-C$_3$ haloalkyl or C$_1$-C$_3$ alkoxy;

R$^{15}$ is H, halogen, cyano, hydroxy, —CHO, C$_1$-C$_4$ alkyl, C$_1$-C$_4$ haloalkyl, C$_2$-C$_5$ alkoxycarbonyl or C$_1$-C$_4$ alkoxy;

R$^{16}$ is H, methyl, methylcarbonyl or methoxycarbonyl;

R$^{20}$ is independently H, CH$_3$, CH$_2$CF$_3$, CF$_3$ or cyclopropyl;

R$^{21}$ is independently C$_1$-C$_3$ alkyl;

each R$^{23}$ is independently H or CH$_3$;

each R$^{33a}$ is independently halogen, cyano, hydroxy, amino, nitro, C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl; and each R$^{33b}$ is independently C$_1$-C$_6$ alkyl, C$_3$-C$_6$ alkenyl, C$_3$-C$_6$ alkynyl, C$_3$-C$_6$ cycloalkyl, C$_1$-C$_6$ haloalkyl, C$_3$-C$_6$ haloalkenyl, C$_3$-C$_6$ haloalkynyl, C$_3$-C$_6$ halocycloalkyl or C$_2$-C$_4$ alkoxyalkyl.

Embodiment A4. A compound of Embodiment A3 wherein E is E-1;

Y$^1$, Y$^2$ and Y$^3$ in Formula 1 form a ring selected from L-1 through L-24;

Y$^2$, X$^1$ and X$^2$ in Formula 1A form a ring selected from L-60, L-61, L-64 and L-65;

G is selected from G-1, G-2, G-15, G-26, G-36 and G-37;

J is J-29-1 through J-29-58;

R$^{1a}$ is selected from one of U-1 through U-50;

each R$^{33a}$ is independently halogen, cyano, hydroxy, amino, nitro, C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl;

each R$^{33b}$ is independently C$_1$-C$_6$ alkyl, C$_3$-C$_6$ alkenyl, C$_3$-C$_6$ alkynyl, C$_3$-C$_6$ cycloalkyl, C$_1$-C$_6$ haloalkyl, C$_3$-C$_6$ haloalkenyl, C$_3$-C$_6$ haloalkynyl, C$_3$-C$_6$ halocycloalkyl or C$_2$-C$_4$ alkoxyalkyl;

R$^{14}$ is H, cyano, hydroxy, C$_1$-C$_2$ alkyl or C$_1$-C$_2$ alkoxy;

A$^1$ is CHR$^{15}$;

R$^{15}$ is H, halogen, cyano, hydroxy, methyl or methoxy; and

R$^{23}$ is H.

Embodiment A5. A compound of Embodiment A4 wherein;

Y$^1$, Y$^2$ and Y$^3$ in Formula 1 form a ring selected from L-1, L-2 and L-9;

Y$^2$, X$^1$ and X$^2$ in Formula 1A form a ring selected from L-6 and L-64;

R$^{1a}$ is U-1, U-20 or U-50;

R$^{15}$ is H;

k is 1 or 2;

each R$^{33a}$ is independently halogen, C$_1$-C$_3$ alkyl, C$_1$-C$_3$ haloalkyl or C$_2$-C$_3$ alkoxyalkyl;

G is G-1;

R$^{29a}$ is H;

J is J-29; and

R$^6$ is —ZQ;

Q is selected from Q-45, Q-63, Q-65, Q-70, Q-71, Q-72 and Q-84;

each $R^{6a}$ is independently F, Cl, Br, hydroxy, cyano, methyl or methoxy;

$R^{6c}$ is H or methyl; and p is 0, 1 or 2.

Specific embodiments include compounds of Formula 1 and Formula 1A selected from the group consisting of:

1-[4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone, 1-[2-acetyl-4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone;

1-[5-[4-[5-(2,6-Di fluorophenyl)-4,5-dihydro-3-isoxazolyl]-2-thiazolyl]tetrahydro-2H-1,2-oxazin-2-yl]-2-[5-methyl-3-trifluoromethyl)-1H-pyrazol-1-yl]ethanone; and 1-[5-[4-[5-(2,6-difluorophenyl)-4,5-dihydro-3-isoxazolyl]-2-thiazolyl]hexahydropyrrolol[3,4-c]pyrrol-2(1H)-yl]-2-[5-methyl-3-(trifluoromethyl)-1H-pyrazol-1-yl]ethanone.

This invention provides a fungicidal composition comprising a compound of Formula 1 or Formula 1A (including all stereoisomers, N-oxides, and salts thereof), and at least one other fungicide. Of note as embodiments of such compositions are compositions comprising a compound corresponding to any of the compound embodiments described above.

This invention provides a fungicidal composition comprising a compound of Formula 1 or Formula 1A (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 or Formula 1A (including all stereoisomers, N-oxides, and salts thereof). Of note as embodiment of such methods are those comprising applying a fungicidally effective amount of a compound corresponding to any of the compound embodiments describe above. Of particular notes are embodiments where the compounds are applied as compositions of this invention.

One or more of the following methods and variations as described in Schemes 1-30 can be used to prepare the compounds of Formula 1 or Formula 1A. The definitions of $Y^1$, $Y^2$, $Y^3$, $X^1$, $X^2$, G, J, $W^1$, $W^2$, $W^3$, $W^4$, $T^A$, $T^B$, $A^1$, $A^2$, $R^{1a}$, $R^{1c}$, $R^2$, $R^3$, $R^4$, $R^5$, $R^7$, $R^8$, $R^{16}$, $R^{24}$, $R^{25}$, $R^{26}$ and $R^{28}$ in the compounds of Formulae 1-57 below are as defined above in the Summary of the Invention unless otherwise noted. Compounds of Formulae 1a-1i are various subsets of the compounds of Formula 1, and all substituents for Formulae 1a-1i are as defined above for Formula 1.

As shown in Scheme 1, compounds of Formula 1a (Formula 1 wherein E is E-1, $A^1$ is $CHR^{15}$ or C=O) wherein $W^1$ is O can be prepared by coupling an acid chloride of Formula 2 with an amine of Formula 3 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. One skilled in the art will recognize that mixtures may result when an amine of Formula 3 contains a second NH function and standard methods of separation can be employed to isolate the desired isomer.

Scheme 1

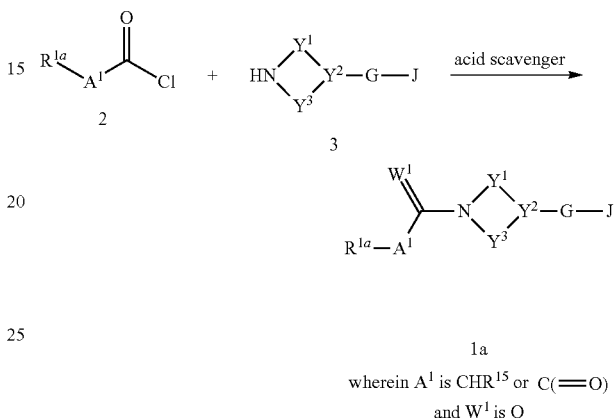

1a
wherein $A^1$ is $CHR^{15}$ or C(=O)
and $W^1$ is O

Acid salts of the Formula 3 amines can also be used in this reaction, provided that at least 2 equivalents of the acid scavenger is present. Typical acids used to form salts with amines include hydrochloric acid, oxalic acid and trifluoroacetic acid. In a subsequent step, amides of Formula 1a wherein $W^1$ is O can be converted to thioamides of Formula 1a wherein $W^1$ is S using a variety of standard thiating reagents such as phosphorus pentasulfide or 2,4-bis(4-methoxyphenyl)-1,3-dithia-2,4-diphosphetane-2,4-disulfide (Lawesson's reagent).

An alternate procedure for the preparation of compounds of Formula 1a wherein $W^1$ is O is depicted in Scheme 2 and involves coupling of an acid of Formula 4 with an amine of Formula 3 (or its acid salt) in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N',N'-tetramethyluronium hexafluoro-phosphate (HBTU). Polymer-supported reagents are again useful here, such as polymer-bound cyclohexylcarbodiimide. These reactions are typically run at 0-40° C. in a solvent such as dichloromethane or acetonitrile in the presence of a base such as triethylamine or N,N-diisopropylethylamine. One skilled in the art will recognize that mixtures may result when an amine of Formula 3 contains a second NH function and standard methods of separation can be employed to isolate the desired isomer.

Scheme 2

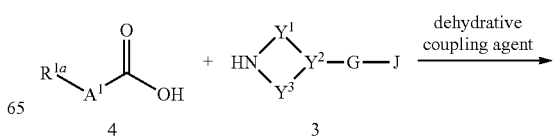

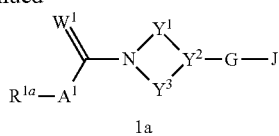

1a wherein $A^1$ is $CHR^{15}$ or
$C(\!=\!O)$ and $W^1$ is O

The acids of Formula 4 are known or can be prepared by methods known to one skilled in the art. For example, $R^{1a}CH_2COOH$ where $R^{1a}$ is linked to the acetic acid residue via a heteroatom can be prepared by reacting the corresponding $R^{1a}H$ with a haloacetic acid or ester in the presence of base; see, for example, U.S. Pat. No. 4,084,955. $R^{1a}CH_2COOH$ wherein $R^{1a}$ is linked to the acetic acid residue via a carbon atom can be prepared from the corresponding $R^{1a}CH_2$-halogen compounds by displacement of the halogen with cyanide followed by hydrolysis; see, for example, K. Adachi, *Yuki Gosei Kagaku Kyokaishi* 1969, 27, 875-876; or from $R^{1a}C(\!=\!O)CH_3$ by the Willgerodt-Kindler reaction; see, for example, H. R. Darabi et al., *Tetrahedron Letters* 1999, 40, 7549-7552 and M. M. Alam and S. R. Adapa, *Synthetic Communications* 2003, 33, 59-63 and references cited therein; or from $R^{1a}Br$ or $R^{1a}I$ by palladium-catalyzed cross-coupling with tert-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

As the synthetic literature includes many amide-forming methods, the synthetic procedures of Schemes 1 and 2 are simply representative examples of a wide variety of methods useful for the preparation of Formula 1 compounds. One skilled in the art also realizes that acid chlorides of Formula 2 can be prepared from acids of Formula 4 by numerous well-known methods.

Certain compounds of Formula 1a (Formula 1 wherein E is E-1, $A^1$ is $CHR^{15}$ or $C\!=\!O$, and $W^1$ is O) wherein $R^1a$ is linked to $A^1$ via a heteroatom can be prepared by reaction of the compound of Formula 5 and a haloacetamide or oxalyl chloride of Formula 6 as shown in Scheme 3. The reaction is carried out in the presence of a base such as sodium hydride, potassium carbonate or triethylamine in a solvent such as tetrahydrofuran, N,N-dimethylformamide or acetonitrile at 0 to 80° C. The haloacetamide of Formula 6 can be prepared by the reaction of an amine of Formula 3 with an α-halo carboxylic acid halide or an α-halo carboxylic acid or its anhydride, analogous to the amide-forming reactions described in Schemes 1 and 2, respectively. The oxalyl chlorides of Formula 6 (i.e. where A is $C(\!=\!O)$) can be prepared by the reaction of an amine of Formula 3 and oxalyl chloride as known to one skilled in the art.

Scheme 3

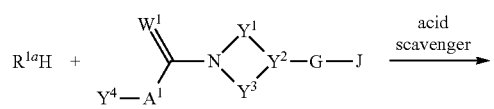

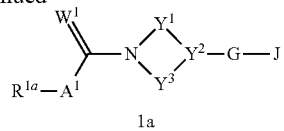

1a wherein $A^1$ is $CHR^{15}$ or
$C(\!=\!O)$ and $W^1$ is O wherein $R^{1a}$ is linked to $A^1$ via a heteroatom; and $Y^4$ is Cl, Br or I.

Compounds of Formula 1b (Formula 1 wherein E is E-1 and $A^1$ is $NR^{16}$), wherein $R^{16}$ is H, and $W^1$ is O or S, can be prepared by reaction of an amine of Formula 3 with an isocyanate or isothiocyanate, respectively, of Formula 7 as depicted in Scheme 4. This reaction is typically carried out at ambient temperature in an aprotic solvent such as dichloromethane or acetonitrile.

Scheme 4

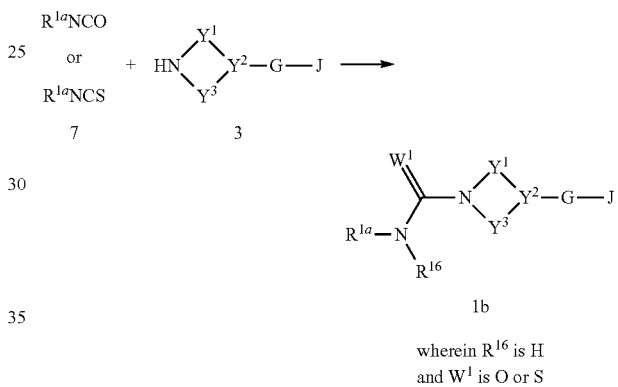

wherein $R^{16}$ is H
and $W^1$ is O or S

Compounds of Formula 1b can also be prepared by the reaction of an amine of Formula 8 with a carbamoyl or thiocarbamoyl chloride or imidazole of Formula 9 as shown in Scheme 5. When $Y^5$ is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 9 (wherein $Y^5$ is Cl) can be prepared from amines of Formula 3 by treatment with phosgene or thiophosgene, respectively, or their equivalents, while carbamoyl or thiocarbamoyl imidazoles of Formula 9 (wherein $Y^5$ is imidazol-1-yl) can be prepared from amines of Formula 3 by treatment with 1,1'-carbonyldiimidazole or 1,1'-thiocarbonyldiimidazole, respectively, according to general methods known to one skilled in the art.

Scheme 5

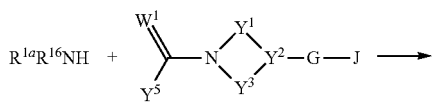

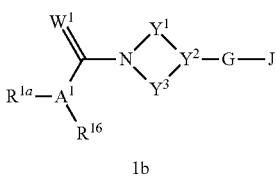

wherein $W^1$ is O or S
and $Y^5$ is Cl or imidazol-1-yl

As shown in Scheme 6, compounds of Formula 1c (Formula 1 wherein E is E-2) wherein $W^2$ is O can be prepared by coupling an acid chloride of Formula 10 with an amine of Formula 3 in the presence of an acid scavenger, analogous to the method described in Scheme 1. In a subsequent step, compounds of Formula 1c wherein $W^2$ is O are converted to the corresponding thioamides wherein $W^2$ is S using a variety of standard thiating reagents such as phosphorus pentasulfide or 2,4-bis(4-methoxyphenyl)-1,3-dithia-2,4-diphosphetane-2,4-disulfide (Lawesson's reagent).

Scheme 6

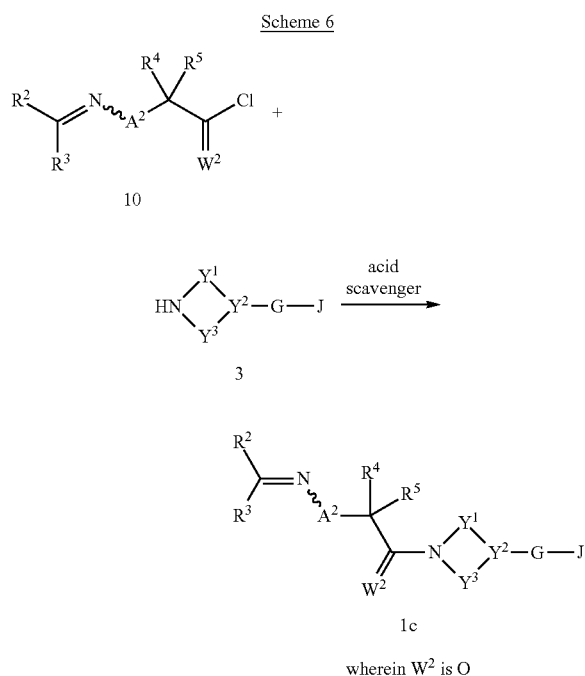

wherein $W^2$ is O

An alternate procedure for the preparation of compounds of Formula 1c (Formula 1 wherein E is E-2 and $W^2$ is O) is depicted in Scheme 7 and involves coupling of an acid of Formula 11 with an amine of Formula 3 (or its acid salt) in the presence of a dehydrative coupling reagent analogous to the method described in Scheme 2. The acids of Formula 11 are known or can be prepared by methods known to one skilled in the art. For leading references see, for example, Schumann, Paquette et al., *J. Med. & Pharm. Chem.* 1962, 5, 464-77; Van Dijk, Jan et al., *J. Med. Chem.* 1977, 20(9), 1199-206; A. Balsamo et al., *J. Med. Chem.* 1989, 32, 1398-1401 and references cited the'rein, and U.S. Pat. No. 4,584,014.

Scheme 7

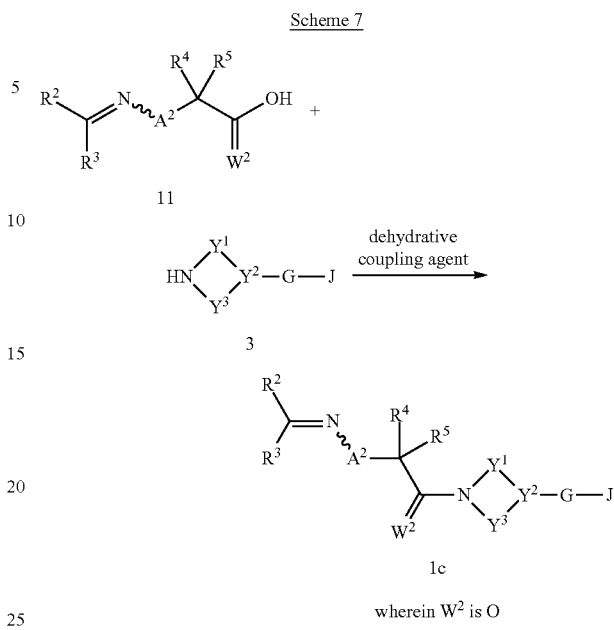

wherein $W^2$ is O

Analogous to Scheme 6, compounds of Formula 1c wherein $W^2$ is O are converted to the corresponding thioamides wherein $W^2$ is S using a variety of standard thiating reagents such as phosphorus pentasulfide or 2,4-bis(4-methoxyphenyl)-1,3-dithia-2,4-diphosphetane-2,4-disulfide (Lawesson's reagent).

Acid chlorides of Formula 10 can be prepared from acids of Formula 11 by numerous well known methods.

As the synthetic literature includes many amide-forming methods, the methods of Schemes 6 and 7 are simply representative examples of a wide variety of methods useful for the preparation of Formula 1 compounds.

Compounds of Formula 1c (Formula 1 wherein E is E-2,) wherein $A^2$ is —O—, —S— and —N($R^7$)— and $W^2$ is O can be prepared by reaction of a compound of Formula 12 and a haloacetamide of Formula 13 wherein Y is Cl, Br or I as shown in Scheme 8. The reaction is carried out in the presence of a base such as sodium hydride or potassium carbonate in a solvent such as tetrahydrofuran, N,N-dimethylformamide or acetonitrile typically at 0 to 80° C. The imines, oximes and hydrazones of Formula 12 are known or can be prepared by methods known in the art; see, for example, S. Dayagi et al., in *The Chemistry of the Carbon-Nitrogen Double Bond*, ed. S. Patci, Interscience, New York 1970; S. R. Sandler et al., *Organic Functional Group Preparations*, Academic Press, New York 1972, 3, 372 and G. Hilgetag et al., *Preparative Organic Chemistry*, John Wiley & Sons, New York 1972, 504-515.

Scheme 8

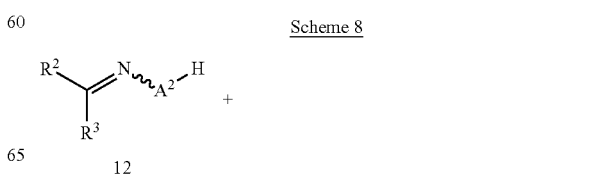

-continued

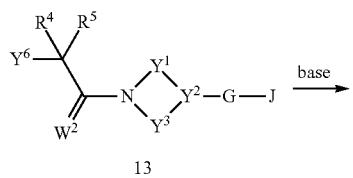

13 wherein $W^2$ is O and $Y^6$ is
Cl, Br or I

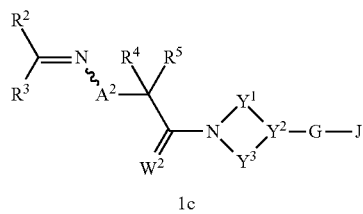

1c wherein $A^2$ is O, S or $NR^7$
and $W^2$ is O

Haloacetamide compounds of Formula 13 can be prepared by the reaction of an amine of Formula 3 with an α-halo carboxylic acid halide or an α-halo carboxylic acid or its anhydride, analogous to the amide-forming reactions described in Schemes 1 and 2, respectively.

Compounds of Formula 1c (Formula 1 wherein E is E-2) wherein $A^2$ is —OC($R^8$)$_2$—, —SC($R^8$)$_2$— or —N($R^7$)C($R^8$)$_2$— and $R^5$ is H can be prepared by a base-catalyzed condensation reaction of a compound of Formula 12a with an α,β-unsaturated amide of Formula 14 as depicted in Scheme 9 wherein V in Formula 12a and C($R^8$)$_2$ in Formula 14 forms $A^2$ in Formula 1c. The reaction is carried out in the presence of a base such as sodium or potassium hydroxide, sodium hydride or potassium carbonate in a solvent such as tetrahydrofuran, N,N-dimethylformamide, ethanol or acetonitrile typically at 0 to 80° C. The α,β-unsaturated amide of Formula 14 can be prepared by coupling of the corresponding α,β-unsaturated acid or acid chloride with an amine of Formula 3 by a method analogous to methods described in Scheme 1 and 2.

Scheme 9

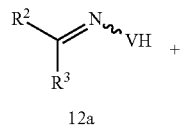

12a wherein V is O, S
or $NR^7$

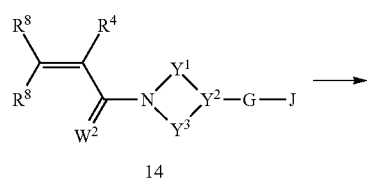

14

-continued

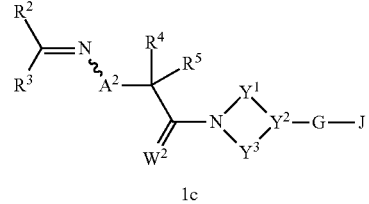

1c wherein $A^2$ is OC($R^8$)$_2$, SC($R^8$)$_2$
and N($R^7$)C($R^8$)$_2$, $W^2$ is O and $R^5$ is H Compounds of Formula 1c (Formula 1 wherein E is E-2) can also be prepared by reacting a compound of Formula 15 with a compound of Formula 16 as illustrated in Scheme 10. The reaction can be carried out in a solvent such as ethanol, tetrahydrofuran or water, and optionally in the presence of an acid catalyst such as acetic acid, hydrochloric acid or sulfuric acid. Acid salts of Formula 16 can also be used in the method of Scheme 10, preferably in the presence of at least one molar equivalent of an acid scavenger such as pyridine or triethylamine. Typical acids used to form salts with amines include hydrochloric acid, oxalic acid and trifluoroacetic acid. The reaction of amines with carbonyl compounds is well known see, for example, S. Dayagi et al. in *The Chemistry of the Carbon-Nitrogen Double Bond*, ed. S. Patei, Interscience, New York 1970; S. R. Sandler et al., *Organic Functional Group Preparations*, Academic Press, New York 1972, 3, 372 and G. Hilgetag et al., *Preparative Organic Chemistry*, John Wiley & Sons, New York 1972, 504-515. Compounds of Formula 15 are known or can be prepared by methods known to one skilled in the art. Compounds of Formula 16 can be prepared directly or by deprotection of corresponding N-protected compounds of Formula 16. The N-protected compounds of Formula 16 can be prepared by methods analogous to those already described for Schemes 1, 2, 3, and 4. The choice and use of a suitable N-protected nitrogen will be apparent to one skilled in the art; for representative examples see T. W. Greene and P. G. M. Wuts, *Protective Groups in Organic Synthesis,* 2nd ed.; Wiley: New York, 1991.

Scheme 10

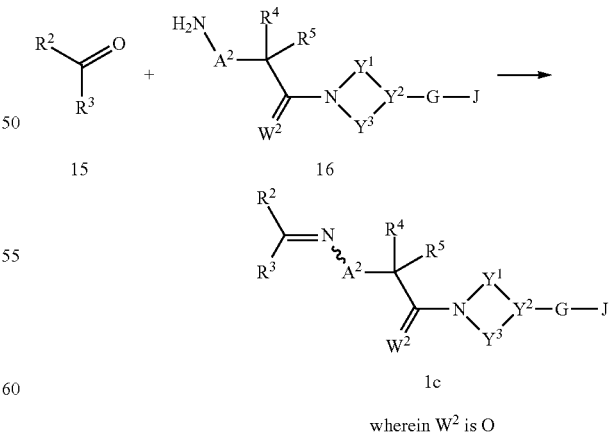

1c wherein $W^2$ is O

As shown in Scheme 11 certain compounds of Formulae 1d-1g (Formula 1 wherein E is E-3 and $W^3$ is $OR^{24}$, $SR^{25}$, $NR^{26}R^{27}$ or CN) can be prepared by reacting an imidoyl chloride of Formula 17 with a compound of Formula 18. in the presence of an acid scavenger. Suitable acid scavengers include, but are not limited to, amine bases such as triethylamine, N,N-diisopropylethylamine and pyridine, hydroxides such as sodium and potassium hydroxide, and carbonates such as sodium carbonate and potassium carbonate. Alternatively, the compounds of Formulae 17 and 18 can be contacted in the absence of an acid scavenger to provide compounds Formulae 1d-1f as the corresponding HCl salts, which are also compounds of the present invention. If desired, the HCl salts can be free-based by standard methods to give compounds of Formulae 1d-1f. Regardless of whether the reaction is conducted with or without an acid scavenger, it is typically conducted in a suitable organic solvent at a temperature between about −20 and 100° C. A variety of solvents can be used to form the suitable solvent for this method, for example nitriles, such as acetonitrile, ethers such as tetrahydrofuran, and halogenated hydrocarbons such as dichloromethane, and amides such as N,N-dimethylformamide, and mixtures thereof. Compounds of Formulae 1d-1g can be generally classified as isoureas, isothioureas, guanidines and cyanoamidines, respectively. For leading references on these classes of compounds see J. Lon Mathias, *Organic Preparations and Procedures International* 1980, 12(5), 309-326; *Comprehensive Organic Chemistry*, vol. 2, I. O, Sutherland, Ed., Pergamon Press, Oxford; *Rodd's Chemistry of Carbon Compounds*, vol. 1C, Elsevier, New York; A. R. Katritzky et al., *J. Organic Chem.* 2004, 69, 309-313. One skilled in the art will recognize that certain compounds of Formulae 1d, 1f and 1g can be prepared from the corresponding compound of Formula 1e by treatment with an appropriate compound of Formula 18. For example, the preparation of thiuronium salts and their conversion to guanidines is described in the literature, see C. R. Rasmussen et al., *Synthesis* 1988, 6, 460-466. Imidoyl chlorides of Formula 17 can be prepared from compounds of Formula 1b (Formula 1 wherein E is E-1, $A^1$ is NH) by treating with thionyl chloride, phosphorous oxychloride or phosphorous pentachloride in a solvent such as dichloromethane. For typical reactions conditions see, for example, W. Zielinski et al., *Heterocycles* 1998, 48, 319-327 or PCT Patent Publication WO/2009/094445. Many compounds of Formula 18 are commercially available and can be prepared by methods well documented in the chemistry art.

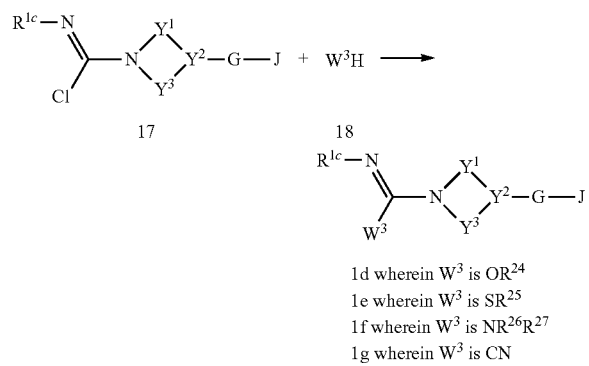

In an alternate procedure shown in Scheme 12, certain compounds of Formulae 1d-1f and Formula 1h (Formula 1 wherein E is E-3 and $W^3$ is $R^{28}$) can be prepared by reacting an amine of Formula 3 with an imidoyl chloride of Formula 19 using conditions analogous to those described in Scheme 11. Many imidoyl chlorides of Formula 19 can be prepared by methods disclosed in the art, for example, see R. Bonnett in The Chemistry of the Carbon-Nitrogen Double Bond, S. Patei, Ed., Interscience Publishers, and references cited therein. Some imidoyl chlorides of Formula 19 are commercially available (e.g., Formula 19 wherein $R^{1c}$ is phenyl, substituted phenyl or lower alkyl and $W^3$ is OMe, SMe, or $N(Me)_2$ can be commercially obtained) and can be prepared by methods documented in the chemistry art.

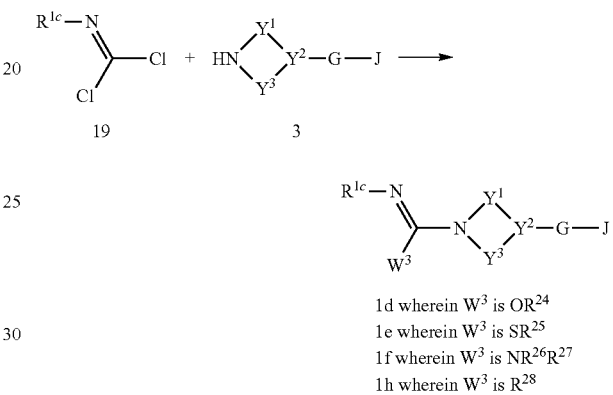

Schemes 11 and 12 are representative of just two methods of preparing compounds of Formula 1e. In another method shown in Scheme 13, compounds of Formula 1e can be prepared by reacting a thiourea of Formula 1b (Formula 1 wherein E is E-1, $A^1$ is NH and $W^1$ is S) with an alkylating or acylating agent of a compound of Formula 20 wherein $Y^6$ is a nucleophic reaction leaving group such as halide (e.g., Cl, Br, I) or sulfonate (e.g., mesylate, triflate, p-toluenesulfonate), and the like. The method can be conducted in the presence of an acid scavenger and a suitable organic solvent at a temperature between about 0 and 100° C. Suitable solvents include, for example, dichloromethane, tetrahydrofuran, acetonitrile, N,N-dimethylformamide, and mixtures thereof. Suitable acid scavengers comprise, for example, amine bases such as triethylamine, N,N-diisopropylethylamine and pyridine, hydroxides such as sodium and potassium hydroxide and carbonates such as sodium carbonate and potassium carbonate. Alternatively, compounds of Formulae 1b and 20 can be contacted in the absence of an acid scavenger to provide the corresponding isothiuronium salts of Formula 1e, which are also compounds of the present invention. In a subsequent reaction the salt can be free-based using standard methods described in the art to provide compounds of Formula 1e. For an example illustrating the preparation of thiuronium salts and their conversion to guanidines see C. R. Rasmussen et al., *Synthesis* 1988, 6, 460-466 or PCT Patent Publication WO/2009/094445. Many compounds of Formula 20 are known and can be prepared by general methods disclosed in the art.

Scheme 13

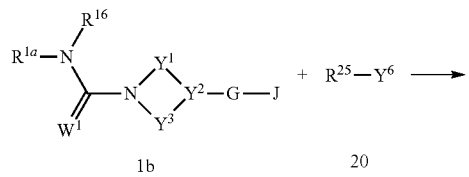

1b
wherein E is E-1 and
$W^1$ is S and $R^{16}$ is H 20
wherein $Y^6$ is
Cl, Br or I

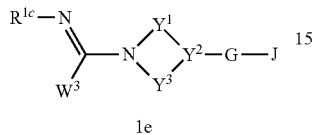

1e
wherein E is E-3
and $W^3$ is $SR^{25}$

Compounds of Formula 1e can also be prepared by reacting an amine of Formula 3 with a dithiocarbamic acid of Formula 21 as illustrated in Scheme 14. The reaction of Scheme 14 is typically conducted in a suitable solvent at a temperature between about 0 to 100° C. Examples of suitable solvents include acetonitrile, tetrahydrofuran, dichloromethane, N,N-dimethylformamide, and mixtures thereof. Dithiocarbamic acids of Formula 21 can be prepared from the corresponding amines, carbon disulfide and two equivalents of a base, followed by treatment with an alkylating agent according to the general method of Alvarez-Ibarra et al., *Organic Preparations and Procedures* 1991, 23(5), 611-616.

Scheme 14

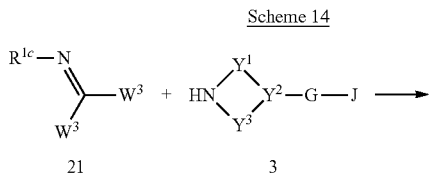

21
wherein $W^3$ is $SR^{25}$

3

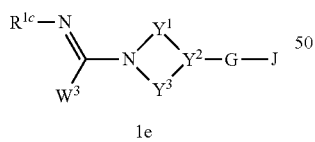

1e
wherein E is E-3,
$W^3$ is $SR^{25}$

Certain compounds of Formula 1h wherein $R^{28}$ is H can be prepared by treating an amine of Formula 3 with a methoxy or ethoxy imine of Formula 22 as shown in Scheme 15. Imines of Formula 22 can be obtained from the corresponding amines. The procedure involves heating the amines with trimethylorthoformate or triethylorthoformate in toluene or xylenes in the presence of a catalytic amount of p-toluenesulfonate.

Scheme 15

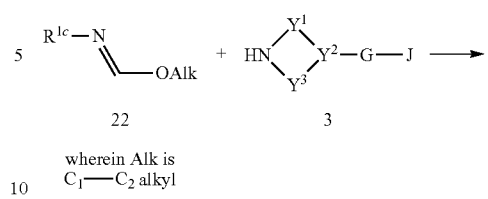

22
wherein Alk is
$C_1$—$C_2$ alkyl

3

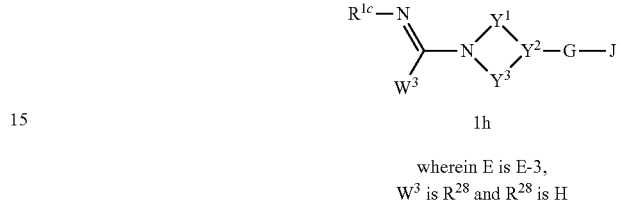

1h
wherein E is E-3,
$W^3$ is $R^{28}$ and $R^{28}$ is H

Compounds of Formula 1 wherein $Y^2$ is $C(R^{14})$ and G is linked to $Y^2$ via a nitrogen atom, can be prepared by displacement of an appropriate leaving group (i.e. $Y^7$) in a compound of Formula 23 with a nitrogen-containing heterocycle of Formula 24 in the presence of a base as depicted in Scheme 16. Suitable bases include sodium hydride or potassium carbonate, and the reaction can be carried out in a solvent such as N,N-dimethylformamide or acetonitrile at 0 to 80° C. Suitable leaving groups in the compounds of Formula 23 include bromide, iodide, mesylate ($OS(O)_2CH_3$), triflate ($OS(O)_2CF_3$) and the like. Compounds of Formula 23 can be prepared from the corresponding compounds wherein $Y^7$ is OH, using general methods known in the art.

Scheme 16

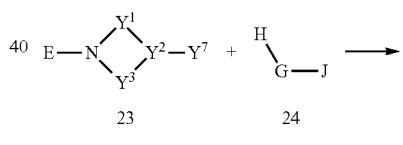

23
$Y^2$ is $CR^{14}$

24
G is bonded to H
through nitrogren

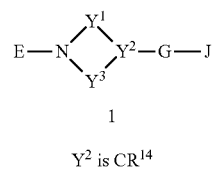

1
$Y^2$ is $CR^{14}$

Compounds of Formula 1 wherein $Y^2$ is a nitrogen atom and G is linked to $Y^2$ through $C(R^{14})$ can be prepared by reaction of a compound of Formula 25 with a heterocyclic compound of Formula 26 wherein $Y^8$ is a leaving group (e.g., bromide, iodide, mesylate ($OS(O)_2CH_3$), triflate ($OS(O)_2CF_3$) and the like) as shown in Scheme 17. The reaction can be carried out in the presence of a base such as potassium carbonate in a solvent such as dimethylsulfoxide, N,N-dimethylformamide or acetonitrile at a temperatures between about 0 to 80° C. Compounds of Formula 26 can be prepared from corresponding compounds wherein $Y^8$ is OH by methods known to one skilled in the art.

Scheme 17

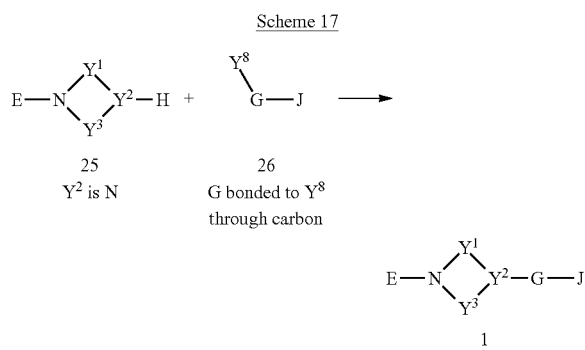

25
$Y^2$ is N

26
G bonded to $Y^8$
through carbon

Compounds of Formula 1 can also be prepared by reaction of a suitably functionalized compound of Formula 27 with a suitably functionalized compound of Formula 28 as shown in Scheme 18. The functional groups $Y^9$ and $Y^{10}$ are selected from, but not limited to, moieties such as aldehydes, ketones, esters, acids, amides, thioamides, nitriles, amines, alcohols, thiols, hydrazines, oximes, amidines, amideoximes, olefins, acetylenes, halides, alkyl halides, methanesulfonates, trifluoromethanesulfonates, boronic acids, boronates, and the like, which under the appropriate reaction conditions, will allow the construction of the various heterocyclic rings G. As an example, reaction of a compound of Formula 27 where $Y^9$ is a thioamide group with a compound of Formula 28 where $Y^{10}$ is a bromoacetyl group will give a compound of Formula 1 where G is a thiazole ring. The synthetic literature describes many general methods for forming 5-membered heteroaromatic rings (e.g., G-1 through G-48); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. The use of intermediates of Formula 27 where $Y^2$ is $C(R^{14})$ and $Y^9$ is Br, I, methanesulfonate or trifluoromethanesulfonate to prepare organozinc reagents for use in cross-coupling reactions with aromatic rings has been described; see, for example, S. Bellotte, *Synlett* 1998, 379-380, and M. Nakamura et al., *Synlett* 2005, 1794-1798. One skilled in the art knows how to select the appropriate functional groups to construct the desired heterocyclic ring G. Compounds of Formula 28 are known or can be prepared by methods known in the art.

Scheme 18

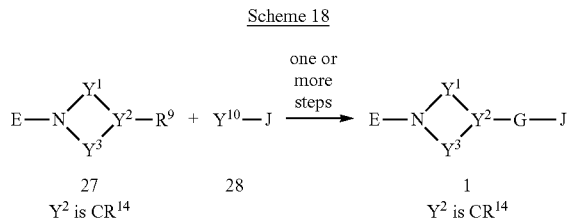

27
$Y^2$ is $CR^{14}$

28

1
$Y^2$ is $CR^{14}$

Compounds of Formula 1 where J is other than C(=$W^4$)$NT^AT^B$ and a nitrogen atom of the J ring is bonded to a carbon atom of G can be prepared by displacement of an appropriate leaving group (i.e. $Y^{11}$) on G of Formula 29 with a compound of Formula 30 in the presence of a base as depicted in Scheme 19. Suitable bases include sodium hydride or potassium carbonate, and the reaction can be carried out in a solvent such as N,N-dimethylformamide or acetonitrile at temperatures between about 0 to 80° C. Suitable leaving groups in the compounds of Formula 29 include, for example, bromide, iodide, mesylate (OS(O)$_2$CH$_3$), triflate (OS(O)$_2$CF$_3$), and the like. Compounds of Formula 29 can be prepared from corresponding compounds wherein $Y^{11}$ is OH by general methods known in the art. The compounds of Formula 30 are known or can be prepared by general methods known in the art.

Scheme 19

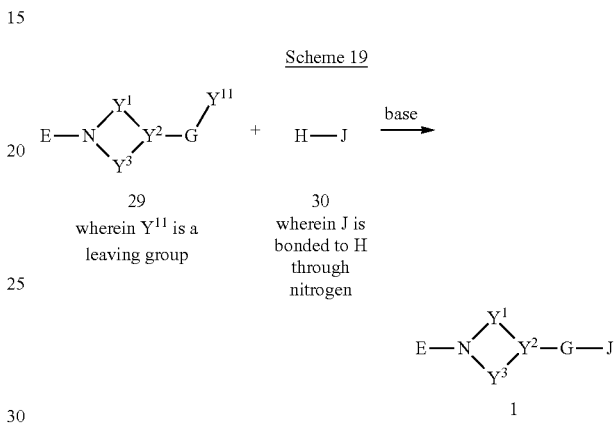

29
wherein $Y^{11}$ is a leaving group 30
wherein J is bonded to H through nitrogen

1

Compounds of Formula 1 where G is bonded to J through a G ring nitrogen can also be prepared by displacement of an appropriate leaving group $Y^{12}$ on J of Formula 32 with a compound of Formula 31 in the presence of a base as depicted in Scheme 20. Suitable bases include sodium hydride or potassium carbonate, and the reaction is carried out in a solvent such as N,N-dimethylformamide or acetonitrile at temperatures between about 0 to 80° C. Suitable leaving groups in the compounds of Formula 32 include, for example, bromide, iodide, mesylate (OS(O)$_2$CH$_3$), triflate (OS(O)$_2$CF$_3$), and the like. Compounds of Formula 32 can be prepared from corresponding compounds wherein $Y^{12}$ is OH by general methods known in the art. Many of the compounds of Formula 32 are known or can be prepared by general methods known in the art.

Scheme 20

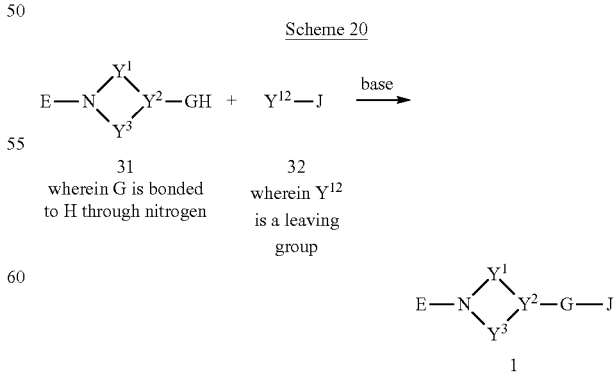

31
wherein G is bonded to H through nitrogen 32
wherein $Y^{12}$ is a leaving group

1

Compounds of Formula 1 wherein J is other than C(=$W^4$)$NT^AT^B$ can also be prepared by reaction of a suitably functionalized compound of Formula 33 with a suitably functionalized compound of Formula 34 as shown in Scheme 21. The functional groups $Y^{13}$ and $Y^{14}$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which, under the appropriate reaction conditions will allow the construction of the various heterocyclic ring J. As an example, reaction of a compound of Formula 33 where $Y^{13}$ is a chloro oxime moiety with a compound of Formula 34 where $Y^{14}$ is a vinyl or acetylene group in the presence of base will provide a compound of Formula 1 where J is an isoxazoline or isoxazole, respectively. The synthetic literature includes many general methods for the formation of carbocyclic and heterocyclic rings and ring systems; see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; the series, *The Chemistry of Heterocyclic Compounds*, E. C. Taylor, editor, Wiley, New York, and *Rodd's Chemistry of Carbon Compounds*, Vol. 2-4, Elsevier, New York. General procedures for cycloaddition of nitrile oxides with olefins are well documented in the chemical literature. For relevant references see Lee, *Synthesis* 1982, 6, 508-509 and Kanemasa et al., *Tetrahedron* 2000, 56, 1057-1064 as well as references cited within. One skilled in the art knows how to select the appropriate functional groups to construct the desired heterocyclic ring J. Compounds of Formula 34 are known or can be prepared by general methods known in the art.

Scheme 21

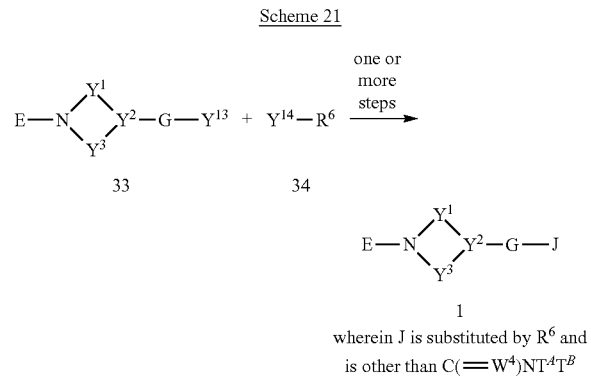

As shown in Scheme 22, compounds of Formula 1i (Formula 1 wherein J is $C(=W^4)NT^AT^B$) wherein $W^4$ is O can be prepared by reacting an acid or acid chloride of Formula 35 with an amine of Formula 36 using standard amide bond forming reactions analogous to those described for Schemes 1 and 2 above. In a subsequent step, amides of Formula 1i wherein $W^4$ is O can be converted to thioamides of Formula 1i wherein $W^4$ is S using a variety of standard thiating reagents such as phosphorus pentasulfide or 2,4-bis(4-methoxyphenyl)-1,3-dithia-2,4-diphosphetane-2,4-disulfide (Lawesson's reagent). Alternate approaches to prepare compounds like those of Formula 1i can be found in Patent Publication WO 2007/014290. Amines of Formula 36 are known or can be prepared by methods known to one skilled in the art.

Scheme 22

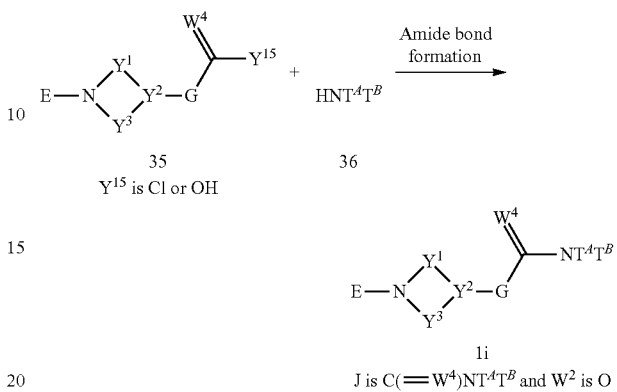

An alternative preparation of compounds of Formula 1 where J is a 5- to 7-membered ring, and 8- to 11-membered bicyclic ring or ring system includes using the Suzuki reaction involving palladium-catalyzed cross-coupling of an iodide or bromide of Formula 37 or 40 with a boronic acid of Formula 38 or 39, respectively, as shown in Scheme 23. Many catalysts are useful for this type of transformation; a typical catalyst is tetrakis(triphenylphosphine)palladium. Solvents such as tetrahydrofuran, acetonitrile, diethyl ether and dioxane are suitable. The Suzuki reaction and related coupling procedures offer many alternatives for creation of the G-J bond. For leading references see for example C. A. Zificsak and D. J. Hlasta, *Tetrahedron* 2004, 60, 8991-9016. For a thorough review of palladium chemistry applicable to the synthesis of G-J bonds see J. J. Li and G. W. Gribble, editors, *Palladium in Heterocyclic Chemistry: A Guide for the Synthetic Chemist*, Elsevier: Oxford, UK, 2000. Many variations of the Suzuki reaction known in the art are useful for preparing compounds of Formula 1.

Scheme 23

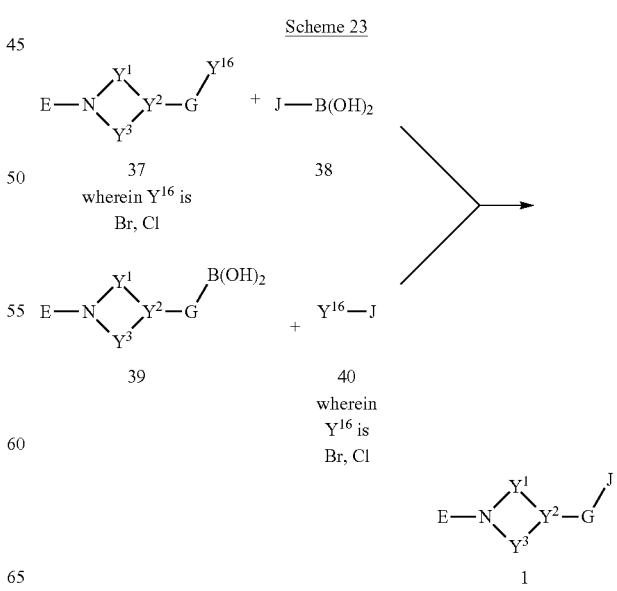

Amines of Formula 3 can be prepared from compounds of Formula 41 wherein $Y^{17}$ is an amine protecting group via a deprotection reaction as shown in Scheme 24. A wide array of amine protecting groups are suitable for the method of Scheme 24 (see, for example, T. W. Greene and P. G. M. Wuts, *Protective Groups in Organic Synthesis,* 2nd ed.; Wiley: New York, 1991), and the choice of the appropriate protecting groups will be apparent to one skilled in chemical synthesis. After deprotection, the amine of Formula 3 can be isolated as its acid salt or the free amine by general methods known in the art.

Scheme 24

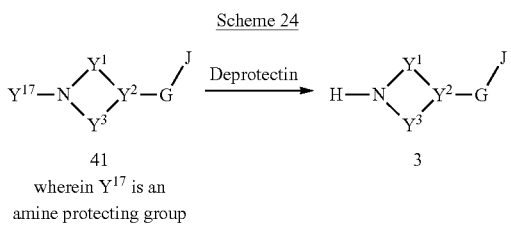

wherein $Y^{17}$ is an amine protecting group

One skilled in the art will recognize that many compounds of Formula 41 can be prepared by methods analogous to those described in Schemes 16 through 23 above where the group E is replaced by $Y^{17}$. Thus, compounds corresponding to Formulae 23, 25, 27, 29, 31, 33, 35, 37 and 39 in which E is replaced by $Y^{17}$ are useful intermediates for the preparation of a compound of Formula 1.

Thioamides of Formula 42 are particularly useful intermediates for preparing compounds of Formula 1 and 41. A thioamide of Formula 42 can be prepared by the addition of hydrogen sulfide to the corresponding nitrile of Formula 43 wherein $Y^2$ is $C(R^{14})$ and $Y^{18}$ is a nitrile moiety as shown in Scheme 25. The methods of Scheme 25 can be carried out by contacting a compound of Formula 43 with hydrogen sulfide in the presence of an amine such as pyridine, diethylamine or diethanolamine. Alternatively, hydrogen sulfide can be used in the form of its bisulfide salt with an alkali metal or ammonia. This type of reaction is well documented in the literature see; for example, European Patent EP 696581.

Scheme 25

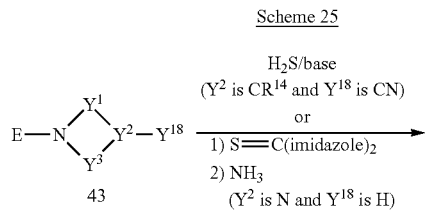

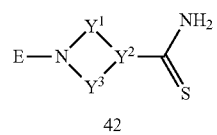

wherein E is E-1, E-2 E-3 or an amine protecting group

As also shown in Scheme 25, a thioamide of Formula 42 can be prepared by the reaction of a compound of Formula 43 (wherein $Y^2$ is a nitrogen atom and $Y^{18}$ is H) is contacted with thiocarbonyl diimidazole followed by treatment with ammonia as described by J. L. Collins, et. al., *J. Med. Chem.* 1998, 41(25), 5037-5054.

One skilled in the art will recognize that the methods of Scheme 1 to Scheme 25 can also be used to prepare compounds of Formula 1A by replacing the core heterocyclic ring shown for compounds of Formula 1 with the core heterocyclic ring shown for compounds of Formula 1A. For example, the method of Scheme 1 can be redrawn as Scheme 1A to illustrate the preparation of compounds of Formula 1Aa.

Scheme 1A

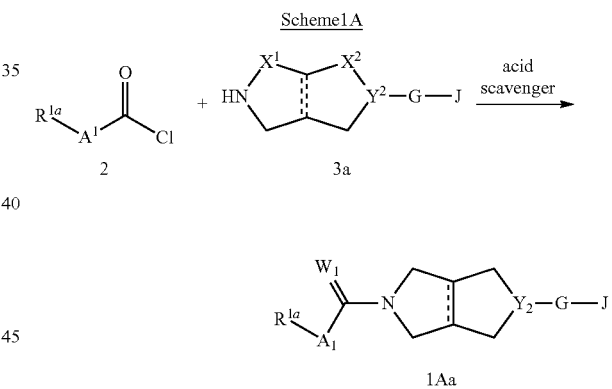

wherein $A^1$ is $CHR^{15}$ or $C(\!=\!O)$ and $W^1$ is O

Halomethyl isoxazoline ketones of Formula 48 are also particularly useful intermediates for preparing certain chiral compounds of Formula 1 and Formula 1A wherein J is, for example, J-29. Halomethyl isoxazoline ketones of Formula 48 can be prepared by the multi-step reaction sequences shown in Scheme 26.

One skilled in the art will recognize that Scheme 26 can also be practiced without the use of a resolving agent, so that a compound of Formula 45 is converted directly to a racemic analog of Formula 44a, which can then be used to prepare racemic analogs of Formulae 47, 48 and certain racemic compounds of Formula 1 and Formula 1A.

Scheme 26

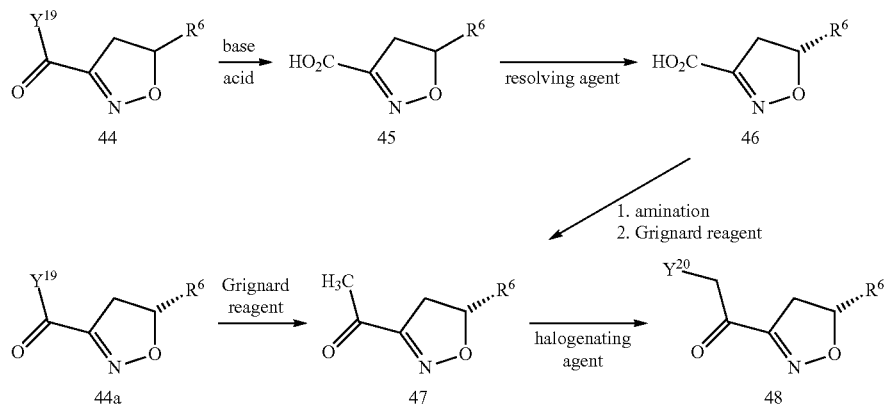

wherein $Y^{19}$ is $C_2$-$C_8$ dialkylamino, $C_2$-$C_6$ haloalkylamino, 1-piperidinyl, 1-pyrrolidinyl or 4-morpholinyl; and $R^6$ is as defined above in the Summary of the Invention.

The preparation of racemic carboxylic acids of Formula 45 can be accomplished according to the well-known methods of basic or acidic hydrolysis of the corresponding compounds of Formula 44, preferably using a slight excess of sodium hydroxide in a water-miscible co-solvent such as methanol or tetrahydrofuran at about 25 to 45° C. The product can be isolated by adjusting the pH of the reaction mixture to about 1 to 3 and followed by filtration or extraction, optionally after removal of the organic solvent by evaporation. The racemic carboxylic acids of Formula 45 can be resolved by classical fractional crystallization of diastereomeric salts of suitable chiral amine bases such as cinchonine, dihydrocinchonine or a mixture thereof. A cinchonine-dihydrocinchonine mixture in about a 85:15 ratio is particularly useful, as it provides, for example, the (R)-configured carboxylic acids of Formula 46, wherein $R^6$ is a substituted phenyl group, as the less soluble salt. Furthermore, these chiral amine bases are readily available on a commercial scale. The halomethyl ketones of Formula 48 can be prepared by first reacting the corresponding amides of Formula 44, either as pure enantiomers (i.e. Formula 44a) or in enantiomerically enriched or racemic mixtures, with one molar equivalent of a methylmagnesium halide (Grignard reagent) in a suitable solvent or solvent mixture such as tetrahydrofuran and toluene at about 0 to 20° C., and the crude ketone products of Formula 47 can be isolated by quenching with aqueous acid, extraction, and concentration. Then the crude ketones of Formula 47 are halogenated with a reagent such as sulfuryl chloride to afford the chloromethyl ketones of Formula 48 wherein $Y^{20}$ is Cl or molecular bromine to afford the corresponding bromomethyl ketones of Formula 48 wherein $Y^{20}$ is Br. The halomethyl ketones of Formula 48 can be purified by crystallization from a solvent such as hexanes or methanol, or can be used without further purification in the condensation reaction with thioamides.

The isoxazoline carboxamides of Formula 44 can be prepared by cycloaddition of the corresponding hydroxamoyl chlorides of Formula 49 with olefin derivatives of Formula 50, as shown in Scheme 27.

Scheme 27

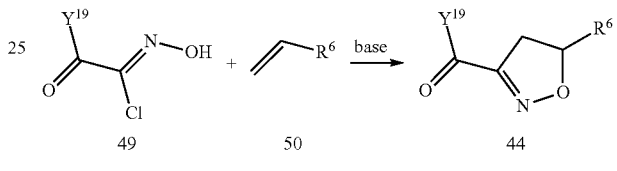

wherein $Y^{19}$ is $C_2$-$C_8$ dialkylamino, $C_2$-$C_6$ haloalkylamino, 1-piperidinyl, 1-pyrrolidinyl or 4-morpholinyl; and $R^6$ is as defined above in the Summary of the Invention.

In this method, all three reacting components (the compounds of Formulae 49 and 50, and the base) are contacted so as to minimize hydrolysis or dimerization of the hydroxamoyl chloride of Formula 49. In one typical procedure, the base, which can either be a tertiary amine base such as triethylamine or an inorganic base such as an alkali metal or alkaline-earth carbonate, bicarbonate or phosphate, is mixed with the olefin derivative of Formula 50, and the hydroxamoyl chloride of Formula 49 is added gradually at a temperature at which the cycloaddition proceeds at a relatively rapid rate, typically between 5 and 25° C. Alternatively, the base can be added gradually to the other two components (the compounds of Formulae 49 and 50). This alternative procedure is preferable when the hydroxamoyl chloride of Formula 49 is substantially insoluble in the reaction medium. The solvent in the reaction medium can be water or an inert organic solvent such as toluene, hexane or even the olefin derivative used in excess. The product can be separated from the salt co-product by filtration or washing with water, followed by evaporation of the solvent. The crude product can be purified by crystallization, or the crude product can be used directly in the methods of Scheme 26. Compounds of Formula 44 are useful precursors to the corresponding methyl ketones of Formula 47 and halomethyl ketones of Formula 48, and are also useful for preparing the resolved enantiomers of the compounds of Formulae 47 and 48 by hydrolysis, resolution, methyl ketone synthesis and halogenation, as shown in Scheme 26.

The core 6-membered and 7-membered heterocyclic ring systems depicted in the above Schemes (see also Exhibits 1A and 1B above for some specific examples) are known or can be prepared by methods known to one skilled in the art. The synthetic literature describes many general methods for forming saturated and partially unsaturated 6- and 7-membered heterocyclic ring systems. See, for example, *Comprehensive Heterocyclic Chemistry*, Vol. 3 and 7, A. R. Katritzky and C. W. Rees editors, Pergamon Press, New York, 1984; *Comprehensive Heterocyclic Chemistry II*, Vol. 6 and 9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. In addition, numerous specific examples of many of these ring systems can be found in the original synthetic literature via structure searches using electronic databases such as Scifinder and Bielstein as known to one skilled in the art. One skilled in the art will know how to select the appropriate protecting groups and functional groups to construct the desired heterocyclic rings.

For example, the intermediate cyano compound 43a wherein the core heterocycle is a hexahydropyridazine (e.g., L-9 in Exhibit 1B above) can be prepared by a three step sequence outlined in Scheme 28. The tetrahydropyridazine 51 is hydroxylated in the presence of mercuric acetate to give compound 52 (see Vartanyan, R. S. et al. *Armyanskii Khimicheskii Zhurnal* 1991, 44(4), 259). The hydroxyl group in compound 52 can be converted into its corresponding mesylate and displaced with a cyanide anion using standard methods to give compound 43a. Detailed description of these transformations can be found in Synthesis Example 1 below.

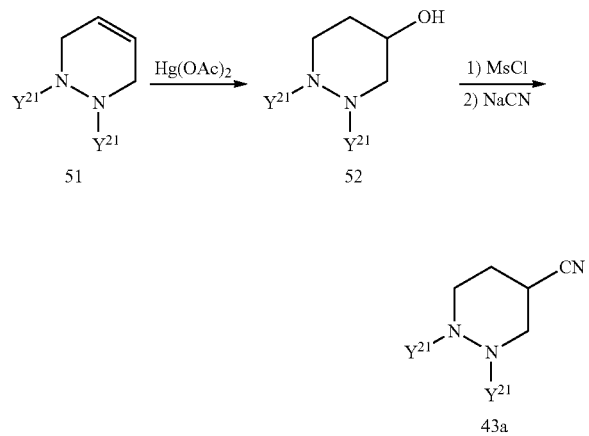

Scheme 28

$Y^{21}$ is an amine protecting group such as ethoxycarbonyl

In a second example, the intermediate cyano compound 43b wherein the core heterocycle is a tetrahydro-1,2-oxazine (e.g., L-1 in Exhibit 1B above) can be prepared in eight steps as outlined in Scheme 29. The primary hydroxyl groups of triol 53 are protected, the secondary hydroxyl group is mesylated and displaced by cyanide followed by deprotection to give cyanodiol 55. Mesylation followed by base treatment gives olefin 56 and the mesyl group is displaced by an O,N di-protected hydroxylamine. The O protecting group can be removed followed by base catalyzed cyclization to provide a compound of Formula 43b. Detailed description of these transformations can be found in Synthesis Example 3 below.

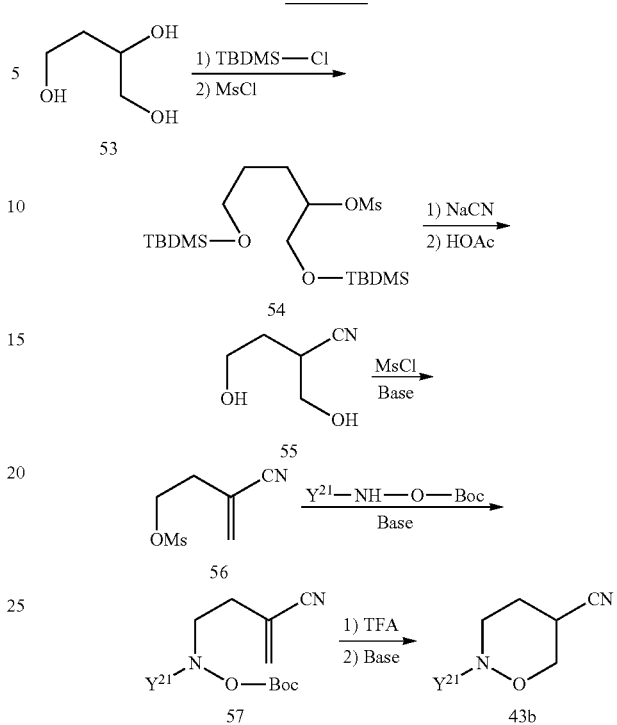

Scheme 29

$Y^{21}$ is an amine protecting group such as ethoxycarbonyl

Alternatively, tetrahydro-1,2-oxazines (e.g. L-1 in Exhibit 1B above) can be prepared by cycloaddition of nitrosyl hydride or nitrosoformaldehyde with substituted dienes as described by Ensley, H. E. and Mahadevan, S., *Tetrahedron Lett.* 1989, 30(25), 3255, or by reaction of substituted 1,4-dibromobutanes with N-hydroxyurethane as described by Riddell, F. G. and Williams, D. A. R., *Tetrahedron* 1974, 30(9), 1083.

Core heterocycles such as tetrahydro-1,3-oxazines (e.g. L-2 in Exhibit 1B) can be prepared by the aminomethylation of vinyl compounds as described by Meisel, S. L., Dickert, J. J., Jr., and Hartough, H. D, *J. Am. Chem. Soc.* 1956, 78, 4782 or by cyclizing substituted 1,4-aminoalcohols with aldehydes or aldeyde equivalents as described by Pandey, G. et al., *Org. Lett.* 2009, 11(12), 2547 and supplemental information provided therein. Core heterocycles such as 1,4,2-tetrahydro dioxazines (e.g. L-13 in Exhibit 1B above) can be prepared by opening a substituted oxirane with methyl hydroxcarbamates followed by cyclization with aldehydes as described by Fruchier, A. et al., *Bull. Soc. Chim. Fr.* 1984, 5-6, Pt. 2, 173. Core heterocycles such as 1,3,4-tetrahydro oxadiazines (e.g. L-15 in Exhibit 1B above) can be prepared from substituted 1,4-amino alcohols by diazotization, reduction to the corresponding hydrazine and cyclization with aldehydes as described by Kalm, M. J. in U.S. Pat. No. 3,251,838.

The core bicyclic heterocyclic ring systems depicted in the above schemes (see Exhibit 1C above for specific examples) are known and can be prepared using by numerous methods described in the chemistry literature. Core heterocycles such as 3,7-diazabicyclo[3.3.0]octanes (e.g., L-60 in Exhibit 1C) can be made by methods disclosed in *J. Med. Chem.* 2009, 52, 4126-4141, PCT Patent Publication WO 2010/108628, U.S. Pat. No. 7,164,019 and references cited therein. Additionally some derivatives are commercially available. Ring core heterocycles such as 3,7-diazabicyclo[3.3.0]oct-5-enes (e.g., L-61 in Exhibit 1C) may be constructed using chemistry described in PCT Patent Publication WO 2010/108628 and U.S. patent application publication 2010/144594 as well as references cited therein. Core heterocycles such as 2-oxa-3,7-diazabicyclo[3.3.0]octanes (e.g., L-63 and L-63 in Exhibit 1C) can be prepared by methods outlined in PCT Patent Publications WO 2007/082262 and WO 2006/002047 as well as references cited therein.

Core heterocycles such as 2-oxa-3-azabicyclo[3.3.0]octanes (e.g., L-65 in Exhibit 1C) can be made by methods outlined in PCT Patent Publication WO 2006/081264.

Core heterocycles such as 3-azabicyclo[3.3.0]octanes (e.g., L-64 in Exhibit 1C) can be made as shown in Scheme 30 below. In this method, a compound of Formula 60 is reacted with tosylmethyl isocyanide as described by Cho et. al., *Bioorganic & Medicinal Chemistry Letters* 2010, 20, 3565-3568 and van Leusen et. al., Organic Reactions, 2001, 57, 417 to provide an a compound of Formula 61. This reaction is typically carried in presence of a solvent such as a mixture dimethoxyethane (DME) and ethanol and in the presence of a strong base such as potassium tert-butoxide. The reaction can be run at a temperature between about 0 to 40° C. Some compounds of Formula 60 are commercially available, others can be prepared using methods described in European Patent 246347, PCT Patent Publication WO 2009/045992 and Org. Lett. 2002, 3983-86.

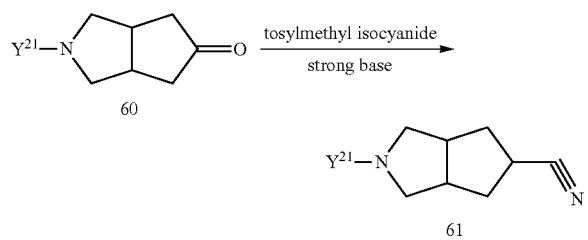

Scheme 30

$Y^{21}$ is a nitrogen protecting group (e.g., Boc)

It is recognized that some reagents and reaction conditions described above for preparing compounds of Formula 1 and Formula 1A may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1 and Formula 1A. One skilled in the art will also recognize that it may be necessary to perform a combination of the steps illustrated in the above schemes in an order other than that implied by the particular sequence presented to prepare the compounds of Formula 1 and Formula 1A.

One skilled in the art will also recognize that compounds of Formula 1, and Formula 1A and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "m" means multiplet, "br m" means broad multiplet and "br s" means broad singlet.

EXAMPLE 1

Preparation of 1-[4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone Step A: Preparation of 5-(2,6-difluorophenyl)-4,5-dihydro-N,N-dimethyl-3-isoxazolecarboxamide To a 1 L round bottom flask equipped with a mechanical stirrer, thermometer and addition funnel was added 2-(dimethylamino)-N-hydroxy-2-oxoethanimidoyl chloride (94.0 g, 0.62 mol) and 2,6-difluorostyrene (84.0 g, 0.60 mol) in chlorobenzene (275 g). The reaction mixture was cooled to 10° C., and then potassium bicarbonate (70 g, 0.70 mol) in water (350 mL) was added dropwise over 1 h while maintaining the temperature between 10 and 15° C. When gas chromatography analysis of the reaction mixture showed about 3% of 2-(dimethylamino)-N-hydroxy-2-oxo-ethanimidoyl chloride remaining, water (200 mL) was added to the reaction mixture and the layers were separated. The organic layer was washed with water (300 mL) and concentrated under reduced pressure. Toluene was added to the resulting residue and the mixture was concentrated under reduced pressure to provide the title compound as an oil (144 g).
$^1$H NMR (CDCl$_3$): δ 3.1 (s, 3H), 3.3 (s, 3H), 3.4 (m, 1H), 3.57 (m, 1H), 6.0 (m, 1H), 6.95 (m, 2H), 7.35 (m, 1H).

Step B: Preparation of 1-(4,5-dihydro-5-(2,6-difluorophenyl)-3-isoxazolyl)ethanone To a 1 L flask equipped with a thermometer and addition funnel was added 5-(2,6-difluorophenyl)-4,5-dihydro-N,N-dimethyl-3-isoxazolecarboxamide (i.e. the product of Step A) (80.0 g, 0.31 mol) and toluene (320 mL). The reaction mixture was cooled to −5° C., and methyl magnesium bromide (3.0 M in tetrahydrofuran, 120 mL, 0.36 mmol) was added dropwise while maintaining the temperature between −10 and −5° C. When gas chromatography analysis of the reaction mixture showed about 2% of 5-(2,6-difluorophenyl)-4,5-dihydro-N,N-dimethyl-3-isoxazolecarboxamide remaining, the reaction mixture was poured into a stirred solution of concentrated hydrochloric acid (80 mL) and water (320 mL) while maintaining the temperature between 10 and 30° C. The organic layer was separated, washed with saturated aqueous sodium chloride solution (80 mL), and then concentrated under reduced pressure. The resulting oil was crystallized from hexanes (100 mL), collected by filtration, washed with hexanes, and dried in a vacuum oven overnight at 23° C. to provide the title compound as a waxy, off-white solid (65 g), melting at 47-50° C.

$^1$H NMR (CDCl$_3$): δ 2.6 (s, 3H), 3.3 (m, 1H), 3.5 (m, 1H), 6.1 (m, 1H), 6.9 (m, 2H), 7.3 (m, 1H).

Step C: Preparation of 2-bromo-1-(4,5-dihydro-5-(2,6-difluorophenyl)-3-isoxazolyl)ethanone To a 500 mL flask equipped with a mechanical stirrer, thermometer, addition funnel and scrubber was added 1-(4,5-dihydro-5-(2,6-difluorophenyl)-3-isoxazolyl)ethanone (i.e. the product of Step B) (60.0 g, 0.27 mmol) and dichloromethane (130 mL). The reaction mixture was heated at 33° C., and then bromine (39.2 mL, 0.24 mol) in dichloromethane (100 mL) was added dropwise via the addition funnel. After about 5 mL of the bromine/dichloromethane solution had been added, the addition was stopped and the reaction mixture was stirred at 33° C. for about 10 minutes, during which time the color of the reaction mixture changed from red to yellow. The reaction mixture was cooled to 5° C., and then the remaining bromine/dichloromethane solution was added dropwise over 90 minutes. After the addition was complete, the reaction mixture was washed with aqueous sodium bisulfite solution (3.5 g in 100 mL of water). The organic layer was concentrated under reduced pressure, hexanes were added, and the resulting solid precipitate was collected by filtration and washed with hexanes to provide the title compound as a brown solid (73 g), which was used without further purification.

Step D: Preparation of 1,2-diethyl tetrahydro 4-hydroxy-1,2-pyridazinedicarboxylate A mixture of 1,2-diethyl-3,6-dihydro-1,2-pyridazinedicarboxylate, (25.0 g, 0.11 mol) and mercuric acetate (52.4 g, 0.165 mol) in tetrahydrofuran (100 mL) and water (100 mL) was stirred at room temperature. After 48 h the reaction mixture was slowly added sodium hydroxide solution (3 M in water, 155 mL), with water bath cooling, followed by the slow addition of sodium borohydride (0.5 M in water) in sodium hydroxide (3 M in water). The reaction mixture was stirred for 24 h, sodium chloride was added and the liquid phases were decanted. The layers were separated and the aqueous phase was extracted with tetrahydrofuran (2×). The combined organic layers were dried over magnesium sulfate, filtered and concentrated under reduced pressure to provide the title compound as a pale-yellow oil (19.25 g), which was used without further purification.

Step E: Preparation of 1,2-diethyl 4-cyanotetrahydro-1,2-pyridazinedicarboxylate To a solution of 1,2-diethyl tetrahydro 4-hydroxy-1,2-pyridazinedicarboxylate (19.0 g, 0.077 mol) (i.e. the product of Step D) in dichloromethane (150 mL) cooled by an ice-bath, was added triethylamine (15 mL, 0.108 mol), followed by methane sulfonyl chloride (7.15 mL, 0.0924 mol) in dichloromethane (50 mL) over a period of 1.5 h while maintaining the temperature of the reaction mixture below 8° C. After stirring for 30 minutes, the reaction mixture was washed with hydrochloric acid (2M in water) (2×), water (2×), dried over magnesium sulfate, filtered and concentrated under reduced pressure to a yellow oil. The yellow oil (about 0.077 mol) and sodium cyanide (15.0 g, 0.308 mol) in dimethyl sulfoxide (DMSO) (350 mL) was stirred at 70° C. for 20 h. More sodium cyanide (5 g, 0.103 mol) was added to the reaction mixture and stirring was continued for another 48 h. The reaction mixture was cooled, poured into water extracted with diethyl ether (3×300 mL). The combined organic extracts were washed with water, dried over magnesium sulfate, filtered and concentrated under reduced pressure to a pale-yellow oil. The yellow oil was adsorbed onto Celite® (diatomaceous filter aid), and then purified by silica gel column chromatography (10% to 60% gradient of ethyl acetate in petroleum ether as eluant) to provide the title compound (5.5 g).

Step F: Preparation of 1,2-diethyl 4-(aminothioxomethyl)tetrahydro-1,2-pyridazinedicarboxylate A mixture of 1,2-diethyl 4-cyanotetrahydro-1,2-pyridazinedicarboxylate (i.e the product of Step E) (5.5 g, 0.024 mol) and thioacetamide (5.5 g, 0.073 mol) in trifluoroacetic acid (about 10 mL) was heated at 50° C. for 20 h. The reaction mixture was cooled, and then partitioned between water and diethyl ether (about 30 mL). The layers were separated and the aqueous layer was extracted with diethyl ether (2×). The combined organic extracts were washed with water (about 30 mL), dried magnesium sulfate, filtered and concentrated under reduce pressure to an orange oil. The oil was adsorbed onto Celite® (diatomaceous filter aid), and then purified by silica gel column chromatography (25% to 60% gradient of ethyl acetate in petroleum ether as eluant) to provide the title compound as a yellow solid (3.97 g).

Step G: Preparation of 1,2-diethyl 4-[4-[5-(2,6-difluorophenyl)-4,5-dihydro-3-isoxazolyl]-2-thiazolyl]tetrahydro-1,2-pyridazinedicarboxylate A mixture of 1,2-diethyl 4-(aminothioxomethyl)tetrahydro-1,2-pyridazinedicarboxylate (i.e. the product of Step F) (2.58 g, 0.0089 mol) and 2-bromo-1-(4,5-dihydro-5-(2,6-difluorophenyl)-3-isoxazolyl)ethanone (i.e the product of Step C) (2.63 g, 0.0086 mol) in methanol (20 mL) were carefully heated to 35° C. No exotherm was observed and the temperature was raised to between 45 to 50° C. and held at this temperature for 1 h. The reaction mixture was neutralised with aqueous sodium acetate (0.73 g in about 20 mL water). The reaction mixture was extracted with diethyl ether (3×), dried magnesium sulfate, filtered, and concentrated under reduced pressure to provide the title compound (4.18 g), which was used without purification.

$^1$H NMR (CDCl$_3$): δ 1.2-1.4 (m, 6H), 1.95-2.1 (m, 1H) 2.1-2.2 (m, 1H), 3.0-3.3 (m, 2H), 3.3-3.45 (m, 1H), 3.6-3.7 (m, 1H), 3.7-3.85 (m, 1H), 4.1-4.3 (m, 4H), 4.3-4.7 (m, 2H), 6.0-6.15 (m, 1H), 6.92 (m, 2H), 7.3 (m, 1H), 7.69 (s, 1H).

Step H: Preparation of 4-[4-[5-(2,6-difluorophenyl)-4,5-dihydro-3-isoxazolyl]-2-thiazolyl]hexahydropyridazine A mixture of 1,2-diethyl 4-[4-[5-(2,6-difluorophenyl)-4,5-dihydro-3-isoxazolyl]-2-thiazolyl]tetrahydro-1,2-pyridazinedicarboxylate (i.e. the product of Step G) (4.09 g, 0.0083 mol) and potassium hydroxide (2.32 g, 0.0414 mol) in ethanol (50 mL) and water (5 mL) was heated at reflux for 20 h. The reaction mixture was cooled, acidified by the addition of concentrated hydrochloric acid, and then warmed to about 70° C. for 10 minutes. The reaction mixture was cooled, neutralised by the addition of sodium bicarbonate. The reaction mixture was concentrated under reduced pressure and the resulting matterial was extracted with diethyl ether (3×), dried over magnesium sulfate, filtered and concentrated under reduced pressure to a tan oil (2.99 g). The oil was adsorbed onto Celite® (diatomaceous filter aid), and then by purified by silica gel column chromatography (5% to 100% gradient of methanol in chloroform as eluant) to provide the title compound (1.275 g).

$^1$H NMR (CDCl$_3$): δ 1.75-1.90 (m, 1H), 2.05-2.20 (m, 1H), 2.75-2.90 (m, 1H), 2.90-3.05 (m, 1H), 3.05-3.30 (m, 4H), 3.30-3.45 (m, 1H), 3.45-3.65 (m, 1H), 3.65-3.70 (m, 1H), 5.90-6.05 (m, 1H), 6.75-6.90 (m, 2H), 7.15-7.30 (m, 1H), 7.58 (s, 1H).

Step I: Preparation of 1-[4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone A mixture of 4-[4-[5-(2,6-difluorophenyl)-4,5-dihydro-3-isoxazolyl]-2-thiazolyl]hexahydropyridazine (i.e. the product of Step H) (0.29 g, 0.83 mmol), 5-methyl-3-(trifluoromethyl)-1H-pyrazole-1-acetic acid (0.19 g, 0.91 mmol) and N,N-dicyclohexylcarbodiimide (0.19 g, 0.91 mmol) in dichloromethane (5 mL) was stirred at room temperature for 48 h. More dichloromethane was added to the reaction mixture, the mixture was filtered, washing thoroughly with dichloromethane. The filtrate was concentrated under reduced pressure and loaded onto a chromatotron plate (4 mm). The plate was eluted with dichloromethane, followed by a gradient of 0.5% to 2% methanol in dichloromethane. Fractions containing product material were further purified by HPLC using an Alltima C18 column (250×22 mm), monitored at wavelength 225 nm and eluted with 60% methanol and 0.1% 2,2,2-trifluoroacetic acid in water to provide the title compound (69 mg), a compound of the present invention.

$^1$H NMR (600 MHz; −40° C., CD$_3$CN): δ 1.95-2.10 (m, 1H), 2.20-2.35 (m, 4H), 2.95-3.15 (m, 2H), 3.40-3.55 (m, 2H), 3.55-3.67 (m, 1H), 3.80-3.95 (m, 1H), 4.50-4.60 (m, 1H), 5.25-5.45 (m, 2H), 6.10-6.20 (m, 1H), 6.50 (s, 1H), 7.05-7.20 (m, 2H), 7.43-7.55 (m, 1H), 7.92 (s, 1H).

EXAMPLE 2

Preparation of 1-[2-Acetyl-4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone A mixture of 1-[4-[4-[5-(2,6-difluorophenyl)-4,5-dihydro-3 isoxazolyl]-2-thiazolyl]tetrahydrol(2H)-pyridazinyl]-2-[5-methyl-3-(trifluoromethyl)-1H-pyrazol-1-yl]ethanone (i.e. the product of Example 1) (0.24 g, 0.44 mmol) in acetic anhydride (2 mL) was heated at 100° C. overnight. The reaction mixture was cooled, water (30 mL) was added and the mixture was stirred for 30 min and then extracted with ethyl acetate. The ethyl acetate extract was washed with saturated aqueous sodium bicarbonate solution and saturated sodium chloride solution, dried over magnesium sulfatate, filtered, and concentrated under reduced pressure. The resulting material was purified by silica gel chromatography (0-100% gradient of ethyl acetate in hexane as eluant) to provide the title compound (150 mg), a compound of the present invention, as a dark foam.

$^1$H NMR (CDCl$_3$): δ 2.00-2.38 (m, 8H), 2.85-3.90 (m, 5H), 4.30-4.80 (m, 2H), 4.90-5.10 (m, 2H), 6.02-6.15 (m, 1H), 6.30-6.40 (m, 1H), 6.85-6.98 (m, 2H), 7.25-7.38 (m, 1H), 7.75 (s, 1H).

EXAMPLE 3

Preparation of 1-[5-[4-[5-(2,6-difluorophenyl)-4,5-dihydro-3-isoxazolyl]-2-thiazolyl]tetrahydro-2H-1,2-oxazin-2-yl]-2-[5-methyl-3-trifluoromethyl)-1H-pyrazol-1-yl]ethanone Step A: Preparation of 2,2,3,3,10,10,11,11-octamethyl-4,9-dioxa-3,10-disiladodecan-6-ol To an ice-bath cooled solution of 1,2,4-butanetriol (12.0 g, 0.113 mol) and imidazole (38.42 g, 0.565 mol) in N,N-dimethylformamide (120 mL) was added t-butyldimethylchlorosilane (35.83 g, 0.238 mol) portionwise over 5-10 min. The mixture was allowed to warm to room temperature and stirred overnight. The reaction mixture was partitioned between water (about 200 mL) and diethyl ether (about 200 mL). The layers were separated and the aqueous fraction was extracted twice with diethyl ether. The combined organic layers were washed with water (200 mL), dried over magnesium sulfate, filtered and concentrated to provide the title compound as a pale yellow oil (38.09 g), which was used without further purification.

Step B: Preparation of 6-methylsulfonyloxy-2,2,3,3,10,10,11,11-octamethyl-4,9-dioxa-3,10-disiladodecane To a solution of 2,2,3,3,10,10,11,11-octamethyl-4,9-dioxa-3,10-disiladodecan-6-ol (i.e. the product of Step A) (36.31 g, 0.109 mol) in dichloromethane (300 mL) cooled to about 0° C. under nitrogen, was added triethylamine (22.8 mL, 0.163 mol), followed by dropwise addition of a solution of methanesulfonyl chloride (10.14 mL, 0.13 mol) in dichloromethane (100 mL), maintaining the reaction mixture below 10° C. The reaction mixture was stirred for another 30 minutes, and then washed with citric acid (about 200 mL, 10%), water (about 200 mL) and sodium bicarbonate (about 200 mL), dried over magnesium sulfate, filtered and concentrated under reduced pressure to provide the title compound as a yellow oil (42.16 g) which was used without further purification.

$^1$H NMR (CDCl$_3$): δ 0.00-0.15 (m, 12H), 0.90 (s, 18H), 1.90 (m, 2H), 3.07 (s, 3H), 3.65-3.85 (m, 4H), 4.80 (m, 1H).

Step C: Preparation of 4-[[(1,1-dimethylethyl)dimethylsilyl]oxy]-2-[[[(1,1-dimethylethyl)dimethylsilyl]oxy]methyl]-butanenitrile A mixture of 6-methylsulfonyloxy-2,2,3,3,10,10,11,11-octamethyl-4,9-dioxa-3,10-disiladodecane (i.e. the product of Step B) (59.29 g, 0.144 mol) and sodium cyanide (15.55 g, 0.317 mol) in DMSO was heated at 90° C. (using an oil bath) for 2 h. The reaction mixture was cooled to room temperature, water (500 mL) was added and the mixture was extracted with diethyl ether (4×250 mL). The combined organic layers were washed with saturated aqueous sodium chloride solution (300 mL), dried over magnesium sulfate, filtered and concentrated under reduced pressure to a dark-yellow oil (48.86 g). The oil was purified by silica gel chromatography (eluting with petroleum ether, followed 1-4% gradient of ethyl acetate in petroleum ether) to provide the title compound (150 mg), a compound of the present invention, as a dark foam. Mixed fractions were combined with mixtures from a previous experiment (total weight 19 g) and purified by silica gel chromatography to provide the title compound (about 11 g).

Step D: Preparation of 2-cyano-1,4-butanediol

A solution of 4-[[(1,1-dimethylethyl)dimethylsilyl]oxy]-2-[[[(1,1-dimethylethyl)dimethylsilyl]oxy]methyl]butanenitrile (14.29 g, 0.041 mol) in tetrahydrofuran (15 mL), water (15 mL) and acetic acid (45 mL) was stirred at room temperature for 5 days. The mixture was concentrated to dryness to give the title compound in quantitative yield which was used without purification.

Step E: Preparation of 4-methylsulfonyloxy-2-(hydroxymethyl) butanenitrile

To a solution of 2-cyano-1,4-butanediol (6.36 g, 0.055 mol) (i.e. the product of Step D) in dichloromethane (70 mL) cooled to 0° C. under nitrogen, was added slowly methanesulfonyl chloride (10.27 mL, 0.133 mol), followed dropwise addition of triethylamine in dichloromethane (30 mL) over about 1 h, while maintaining the reaction mixture temperature below 5° C. Once the addition was complete, as determined by NMR, the reaction mixture was washed with cold hydrochloric acid (1 M, about 50 mL), water (50 mL) and saturated aqueous sodium chloride solution (50 mL), dried over magnesium sulfate, filtered and concentrated under reduced pressure to provide a yellow oil (11.96 g).

A mixture of the yellow oil (11.96 g, 0.044 mol) in dichloromethane (50 mL) was cooled in an ice-bath, and then triethylamine (7.4 mL, 0.053 mol) slowly added. When the addition was complete, the reaction mixture was allowed to warm to room temperature and stirred for 20 h. The reaction mixture was washed twice with hydrochloric acid (2 M, 20 mL), water (20 mL) and saturated aqueous sodium chloride solution (20 mL), dried over magnesium sulfated, filtered and concentrated under reduced pressure to provide the title compound (6.87 g) which was used without purification.

Step F: Preparation of 1,1-dimethylethyl(ethoxycarbonyl)azanyl carbonate

A mixture of hydroxylamine hydrochloride (111.2 g, 1.6 mol), ethyl chloroformate (153 mL, 1.6 mol) and sodium carbonate (250 g, 2.4 mol) in water (750 mL) was stirred at room temperature for 20 h. The reaction mixture was acidified by the addition of hydrochloric acid (6 M), and then extracted with diethyl ether (5×500 mL). The combined organic extracts were dried over magnesium sulfate, filtered and concentrated under reduced pressure to provide a red-tan oil (94.22 g). The resulting oil (24.79 g, 0.236 mol) was combined with di-t-butyldicarbonate (51.53 g, 90.24 mol) and triethylamine (1 mL) in toluene and heated at 70° C. for about 3 h. The reaction mixture was concentrated under reduced pressure to provide the title compound as a pale-yellow oil (45.9 g) which was used without purification.

Step G: Preparation of (3-cyano-3-butene-1-yl)(ethoxycarbonyl)azanyl 1,1-dimethylethyl carbonate A mixture of 4-methylsulfonyloxy-2-(hydroxymethyl) butanenitrile (i.e. the product of Step E) (6.87 g, 0.039 mol), 1,1-dimethylethyl (ethoxycarbonyl)azanyl carbonate (7.65 g, 0.037 mol) (i.e. the product of Step F) and potassium carbonate (10.21 g, 0.074 mol) in N,N-dimethylformamide (50 mL) was stirred at room temperature for 20 h. The reaction mixture was poured onto iced water (100 mL) and extracted with diethyl ether (3×50 mL). The combined organic layers were washed with water (50 mL) and concentrated to a pale-tan oil (10.05 g). The oil was adsorbed onto Celite® (diatomaceous filter aid), and then purified by silica gel chromatography (0-100% gradient of ethyl acetate in petroleum ether as eluant). The appropriate fractions were combined to provide the title compound as a yellow oil (3.78 g).

Step H: Preparation of ethyl 5-cyanotetrahydro-2H-1,2-oxazine-2-carboxylate

A solution of (3-cyano-3-butene-1-yl)(ethoxycarbonyl) azanyl 1,1-dimethylethyl carbonate (i.e. the product of Step G) and trifluoroacetic acid (3 mL) in dichloromethane (40 mL) was stirred at room temperature for 3 days. The reaction mixture was concentrated under reduced pressure to a tan oil. The oil was combined with potassium carbonate (3.6 g, 0.026 mol) in N,N-dimethylformamide (30 mL) and stirred at 80° C. for 24 h. The reaction mixture was concentrated under reduced pressure to near dryness. Methanol and dichloromethane were added and the precipitated solids were removed by filtration. The resulting solid was adsorbed onto Celite® (diatomaceous filter aid), and then purified by silica gel chromatography to provide the title compound as a pale-tan oil (0.645 g).

$^1$H NMR (CDCl$_3$): δ 1.30 (m, 3H), 1.90-2.15 (m, 2H), 2.95 (m, 1H), 3.62 (m, 1H), 3.87 (m, 1H), 4.00-4.18 (m, 2H), 4.18-4.28 (m, 2H).

Step I: Preparation of ethyl 5-(aminothioxomethyl) tetrahydro-2H-1,2-oxazine-2-carboxylate A mixture of ethyl 5-cyanotetrahydro-2H-1,2-oxazine-2-carboxylate (i.e. the product of Step H) (0.63 g, 0.0034 mol) and thioacetamide (0.72 g, 0.0096 mol) in trifluoroacetic acid (about 2 mL) was stirred at 50° C. for 20 h. The reaction mixture was poured into water (10 mL) and extracted with diethyl ether (3×10 mL). The combined organic extracts were washed with water (10 mL), dried over magnesium sulfate, filtered and concentrated to provide an orange oil (about 0.76 g). The resulting oil was adsorbed onto Celite® (diatomaceous filter aid), and then purified by silica gel column chromatography (25% to 50% gradient of ethyl acetate in petroleum ether as eluant) to provide the title compound (0.19 g).

$^1$H NMR (CDCl$_3$): δ 1.30 (m, 3H), 1.85-2.00 (m 1H), 2.00-2.15 (m, 1H), 3.05-3.15 (m, 1H), 3.3-3.43 (m, 1H), 3.95-4.15 (m, 3H), 4.15-4.22 (m, 2H), 7.95 (br s, 1H), 8.08 (br s, 1H).

Step J: Preparation of ethyl 5-[4-[5-(2,6-difluorophenyl)-4,5-dihydro-3-isoxazolyl]-2-thiazolyl]tetrahydro-2H-1,2-oxazine-2-carboxylate A solution of ethyl 5-(aminothioxomethyl)tetrahydro-2H-1,2-oxazine-2-carboxylate (i.e. the product of Step I) (0.19 g, 0.87 mmol) and 2-bromo-1-(4,5-dihydro-5-(2,6-difluorophenyl)-3-isoxazolyl)ethanone (the product of Example 1, Step C) (0.264 g, 0.87 mmol) in methanol (2 mL) was heated at 50° C. for 1 h. Methanol was removed under reduced pressure and the resulting material was partitioned between sodium acetate (10%, 5 mL) and diethyl ether (5 mL). The layers were separated and the aqueous phase was extracted with diethyl ether (2×). The organic fractions were concentrated under reduced pressure to provide the title compound as a pale-tan oil (0.383 g).

$^1$H NMR (CDCl$_3$): δ 1.30 (m, 3H), 2.07-2.17 (m 1H), 2.17-2.30 (m, 1H), 3.50-3.75 (m, 3H), 3.75-3.88 (m, 1H), 4.05-4.12 (m, 1H), 4.12-4.22 (m, 1H), 4.22-4.32 (m, 2H), 4.35-4.45 (m, 1H), 6.03-6.12 (m, 1H), 6.88-6.98 (m, 2H), 7.25-7.38 (m, 1H), 7.70 (s, 1H).

Step K: Preparation of 5-[4-[5-(2,6-difluorophenyl)-4,5-dihydro-3-isoxazolyl]-2-thiazolyl]tetrahydro-2H-1,2-oxazine A solution of ethyl 5-[4-[5-(2,6-difluorophenyl)-4,5-dihydro-3-isoxazolyl]-2-thiazolyl]tetrahydro-2H-1,2-oxazine-2-carboxylate (i.e. the product of Step J) (0.30 g, 0.71 mmol) and potassium hydroxide (0.20 g, 3.50 mmol) in ethanol (10 mL) and water (1 mL) was heated at reflux for 20 h, and then cooled to room temperature. The reaction mixture was acidified by the addition of concentrated hydrochloric acid, heated at 70° C. for about 20 minutes, cooled to room temperature, and then basified by the addition of sodium hydroxide (1%). The reaction mixture was extracted with ethyl acetate (20 mL) and combined organic extracts were concentrated under reduced pressure to provide the title compound as a yellow oil (0.235 g) which was used without purification.
$^1$H NMR (CDCl$_3$): δ 2.00-2.15 (m 1H), 2.15-2.30 (m, 1H), 3.20-4.35 (m, 7H), 4.8-5.8 (br m, 1H), 6.02-6.12 (m, 1H), 6.85-6.95 (m, 2H), 7.25-7.32 (m, 1H), 7.68 (s, 1H).

Step L: Preparation of 1-[5-[4-[5-(2,6-difluorophenyl)-4,5-dihydro-3-isoxazolyl]-2-thiazolyl]tetrahydro-2H-1,2-oxazin-2-yl]-2-[5-methyl-3-trifluoromethyl)-1H-pyrazol-1-yl]ethanone A mixture of 5-[4-[5-(2,6-difluorophenyl)-4,5-dihydro-3-isoxazolyl]-2-thiazolyl]tetrahydro-2H-1,2-oxazine (i.e. the product of Step K) (0.235 g, 0.67 mmol), 5-methyl-3-(trifluoromethyl)-1H-pyrazole-1-acetic acid (0.154 g, 0.74 mmol) and N,N-dicyclohexylcarbodiimide (0.152 g, 0.74 mmol) in dichloromethane was stirred at room temperature for 20 h. The reaction mixture was diluted with more dichloromethane and the urea by-product was removed by filtration. The filtrate was concentrated under reduced pressure to a pale-yellow foam (0.42 g). The resulting foam was dissolved in a minimum amount of dichloromethane and loaded onto a chromatotron plate (2 mm) eluting with a gradient of ethyl acetate in dichloromethane to give the title compound, a compound of the present invention, as a colourless foamy solid (0.101 g).
$^1$H NMR (CDCl$_3$): δ 2.05-2.20 (m, 1H), 2.20-2.35 (m, 4H), 3.403-3.55 (m, 1H), 3.55-3.70 (m, 2H), 3.75-3.88 (m, 1H), 4.08-4.20 (m, 1H), 4.35-4.45 (m, 1H), 4.45-4.55 (m, 1H), 5.08 (s, 2H), 6.02-6.12 (m, 1H), 6.30 (s, 1H), 6.85-6.98 (m, 2H), 7.25-7.38 (m, 1H), 7.72 (s, 1H).

EXAMPLE 4

Preparation of 1-[5-[4-[5-(2,6-difluorophenyl)-4,5-dihydro-3-isoxazolyl]-2-thiazolyl]hexahydropyrrolol[3,4-c]pyrrol-2(1H)-yl]-2-[5-methyl-3-(trifluoromethyl)-1H-pyrazol-1-yl]ethanone Step A: Preparation of 1,1-dimethylethyl 5-(aminothioxomethyl)hexahydropyrrolo[3,4-c]pyrrole-2(1H)-carboxylate To a stirred solution of 1,1-dimethylethyl hexahydropyrrolo[3,4-c]pyrrole-2(1H)-carboxylate ester (4.8 g, 22.55 mmol) in tetrahydrofuran (THF) (60 mL) cooled to 0° C. was added 1,1'-thiocarbonyldiimidazole (4.8 g, 26.97 mmol) in THF (40 mL) drop wise. The reaction mixture was stirred at room temperature for 2 h, cooled to 0° C., and then a solution of ammonia in methanol (saturated) was added drop wise. The reaction mixture was transferred to pressure tube, stirred at room temperature for 16 h, and then concentrated under reduced pressure. The resulting material was partitioned between ethyl acetated (150 mL) and water (150 mL). The organic layer was separated, washed with saturated aqueous sodium chloride solution and concentrated in under reduced pressure. The material obtained was triturated with petroleum ether and filtered to provide title product as white solid (3.4 g) melting at 188.1-190.2° C.
$^1$H NMR (CDCl$_3$): δ 5.59 (s, 2H), 3.7-4.0 (m, 3H), 3.58-3.64 (m, 2H), 3.01-3.36 (m, 5H), 1.46 (s, 9H).

Step B: Preparation of 2-chloro-1-[5-(2,6-difluorophenyl)-4,5-dihydroisoxazol-3-yl]ethanone To a stirred solution of 1,3-dichloro-2-propanone (10.0 g, 78.74 mmol) in diethyl ether and hydrochloric acid (2 M in diethyl ether, 100 mL) cooled to 0° C. was added 1,1-dimethylethyl ester nitrous acid (8.11 g, 78.74 mmol) drop wise. The reaction mixture was stirred at room temperature for 16 h, and then concentrated under reduced pressure to a white semi-solid. The solid was triturated with petroleum ether and 1-chlorobutane (2:1) and filtered to provide 3-chloro-N-hydroxy-2-oxopropanimidoyl chloride as white solid (7.0 g) melting at 98.0-99.3° C.

To a stirred solution of 3-chloro-N-hydroxy-2-oxopropanimidoyl chloride (0.89 g, 5.71 mmol) in acetonitrile (20 mL) was added 2-ethenyl-1,3-difluorobenzene (1.0 g, 7.14 mmol) and sodium bicarbonate (1.8 g, 2.14 mmol) at room temperature. The reaction mixture was stirred at room temperature for 12 h, concentrated in under reduced pressure and the resulting material was partitioned between ethyl acetate (50 mL) and water (50 mL). The organic layer was separated, washed with saturated aqueous sodium chloride solution and concentrated in under reduced pressure. The resulting material was triturated with petroleum ether and filtered to provide the title product as white solid (1.1 g) melting at 82.1-83.4° C.
$^1$H NMR (CDCl$_3$): δ 7.3-7.4 (m, 1H), 6.9-6.98 (m, 2H), 6.1-6.18 (m, 1H), 4.76 (s, 2H), 3.52-3.62 (m, 1H), 3.31-3.4 (m, 1H). 1.46 (s, 9H).

Step C: Preparation of 1,1-dimethylethyl 5-[4-[5-(2,6-difluorophenyl)-4,5-dihydro-3-isoxazolyl]-2-thiazolyl]hexahydropyrrolo[3,4-c]pyrrol-2(1H)-carboxylate To a stirred solution of 1,1-dimethylethyl 5-(aminothioxomethyl)hexahydropyrrolo[3,4-c]pyrrole-2(1H)-carboxylate (i.e. the product of Step A) (0.5 g, 18.42 mmol) in chloroform (20 mL) was added 2-chloro-1-[5-(2,6difluorophenyl)-4,5-dihydroisoxazol-3-yl]ethanone (i.e. the product of Step B) (0.478 g, 18.42 mmol) and pyridine (0.29 g, 37.12 mmol) at room temperature. The reaction mixture was heated at 90° C. for 5 h, cooled to room temperature and concentrated under reduced pressure. The resulting material was dissolved in ethyl acetate (100 mL) and washed with water (100 mL) and saturated aqueous sodium chloride solution (100 mL) and concentrated under reduced pressure. The resulting material was purified by column chromatography (1% methanol/chloroform as eluant) to provide the title product as white solid (0.7 g) melting at 78.9-80.2° C.
$^1$H NMR (CDCl$_3$): δ 7.28 (m, 1H), 6.85-6.93 (m, 3H), 5.99-6.03 (m, 1H), 3.39-3.78 (m, 10H), 3.04 (m, 2H), 1.46 (s, 9H).

Step D: Preparation of 5-[4-[5-(2,6-difluorophenyl)-4,5-dihydro-3-isoxazolyl]-2-thiazolyl]hexahydropyrrolo[3,4-c]pyrrole To a stirred solution of 1,1-dimethylethyl 5-[4-[5-(2,6-difluorophenyl)-4,5-dihydro-3-isoxazolyl]-2-thiazolyl]hexahydropyrrolo[3,4-c]pyrrol-2(1H)-carboxylate (i.e. the product of Step C) (0.6 g, 1.26 mmol) in dichloromethane (15 mL) cooled to 0° C. was added trifluoroacetic acid (2 mL, 26.93 mmol). The reaction mixture was allowed to warm to room temperature, stirred for 3 h, and then concentrated under reduced pressure. The resulting material was dissolved in water (50 ml) and basified by the addition of sodium hydroxide (10%) to pH 12, and then extracted with chloroform (3×50 mL). The combined organic extracts were concentrated under reduced pressure to provide the title product as a white-gummy solid (0.42 g).

$^1$H NMR (CDCl$_3$): δ 7.23-7.31 (m, 1H), 6.85-6.93 (m, 3H), 5.98-6.05 (m, 1H), 3.49-3.71 (m, 4H), 3.37-3.40 (m, 2H), 3.13-3.19 (m, 2H), 2.82-2.97 (m, 4H).

Step E: Preparation of (5-methyl-3-trifluoromethyl-pyrazol-1-yl)acetyl

To a stirred solution of (5-methyl-3-trifluoromethyl-pyrazol-1-yl)acetic acid (0.0885 g, 0.4255 mmol) in dichloromethane (10 mL) was added oxalylchloride (0.108 g, 0.851 mmol) and drop a of DMF. The reaction mixture was stirred at 45° C. for 2 h, and then concentrated under reduced pressure to provide the title compound as a white solid (0.096 g).

$^1$H NMR (CDCl$_3$): δ 6.38 (s, 1H), 5.27 (s, 2H), 2.31 (s, 3H).

Step F: Preparation of 1-[5-[4-[5-(2,6-difluorophenyl)-4,5-dihydro-3-isoxazolyl]-2-thiazolyl]hexahydropyrrolol[3,4-c]pyrrol-2(1H)-yl]-2-[5-methyl-3-(trifluoromethyl)-1H-pyrazol-1-yl]ethanone To a stirred solution of 5-[4-[5-(2,6-difluorophenyl)-4,5-dihydro-3-isoxazolyl]-2-thiazolyl]hexahydropyrrolo[3,4-c]pyrrole (i.e. the product of Step D) (0.16 g, 0.4255 mmol) in chloroform (20 mL) was added trifluoroacetic acid (0.086 g, 0.851 mmol) and (5-methyl-3-trifluoromethyl-pyrazol-1-yl)acetyl chloride (i.e. the product of Step E) (0.096 g, 0.4255 mol) at 0° C. The reaction mixture was stirred at room temperature for 2 h, and then concentrated under reduced pressure. The resulting material was dissolved in ethyl acetate (100 ml) and washed with water (100 ml), saturated aqueous sodium chloride solution (100 ml) and concentrated in under reduced pressure. The resulting material was purified by column chromatography (5% methanol/chloroform as eluant) to provide title product, a compound of the present invention, as white solid (0.18 g).

$^1$H NMR (CDCl$_3$): δ 7.27-7.29 (m, 1H), 6.86-6.92 (m, 3H), 6.32 (s, 1H), 6.0-6.03 (m, 1H), 4.81-4.93 (q, 2H), 3.5-3.88 (m, 10H), 3.1-3.25 (m, 2H), 2.32 (s, 3H).

By the procedures described herein together with methods known in the art, the following compounds of Tables 1 to 9r can be prepared. The following abbreviations are used in the Tables which follow: t means tertiary, s means secondary, n means normal, means iso, c means cyclo, Ac means acetyl (i.e. —C(=O)CH$_3$), Me means methyl, Et means ethyl and Ph means phenyl.

TABLE 1

| $A^1$ is CH$_2$, W$^1$ is O and X is O.<br>R$^{1a}$ | $A^1$ is CH$_2$, W$^1$ is O and X is O.<br>R$^{1a}$ |
|---|---|
| Ph | 3-ethylphenyl |
| 2-methylphenyl | 3-(CF$_3$)phenyl |
| 2-methoxyphenyl | 3-cyanophenyl |
| 2-chlorophenyl | 3-nitrophenyl |
| 2-bromophenyl | 2,5-dichlorophenyl |
| 2-ethoxyphenyl | 5-bromo-2-chlorophenyl |
| 2-(methylthio)phenyl | 2-chloro-5-methylphenyl |
| 3-chlorophenyl | 2-methoxy-5-(CF$_3$)phenyl |
| 3-bromophenyl | 2,5-diethylphenyl |
| 3-iodophenyl | 3-methylpyrazol-1-yl |
| 3-methylphenyl | 3-chloropyrazol-1-yl |
| 2-chloro-5-(CF$_3$)phenyl | 3-bromopyrazol-1-yl |
| 2,5-dibromophenyl | 3-(CF$_3$)pyrazol-1-yl |
| 2-bromo-5-methylphenyl | 3,5-dimethylpyrazol-1-yl |
| 2-bromo-5-(CF$_3$)phenyl | 3-chloro-5-methylpyrazol-1-yl |
| 5-chloro-2-methylphenyl | 3-bromo-5-methylpyrazol-1-yl |
| 5-bromo-2-methylphenyl | 5-methoxy-3-methylpyrazol-1-yl |
| 2,5-dimethylphenyl | 3,5-diethylpyrazol-1-yl |
| 2-methyl-5-(CF$_3$)phenyl | 5-ethyl-3-(CF$_3$)pyrazol-1-yl |
| 5-cyano-2-methylphenyl | 2,5-dimethyl-3-furyl |
| 2-methyl-5-nitrophenyl | 2,5-dimethyl-3-thienyl |
| 5-chloro-2-methoxyphenyl | 2,5-dichloro-3-thienyl |
| 5-bromo-2-methoxyphenyl | 1,4-dimethyl-3-pyrrolyl |
| 2-methoxy-5-methylphenyl | 1,4-dimethyl-3-pyrazolyl |
| 3-ethyl-5-methylpyrazol-1-yl | 1,3-dimethyl-4-pyrazolyl |
| 5-methyl-3-(CF$_3$)pyrazol-1-yl | 2,5-dimethyl-4-oxazolyl |
| 5-methyl-3-(C$_2$F$_5$)pyrazol-1-yl | 2,5-dimethyl-4-thiazolyl |
| 5-chloro-3-methylpyrazol-1-yl | 3,6-dimethyl-2-pyridyl |
| 3,5-dichloropyrazol-1-yl | 2,5-dimethyl-3-pyridyl |
| 5-chloro-3-(CF$_3$)pyrazol-1-yl | 2,5-dimethyl-4-pyridyl |
| 5-bromo-3-methylpyrazol-1-yl | 3,6-dichloro-2-pyridyl |
| 3,5-dibromopyrazol-1-yl | 2,5-dichloro-3-pyridyl |
| 5-bromo-3-(CF$_3$)pyrazol-1-yl | 2,5-dichloro-4-pyridyl |
| 3,5-dimethyl-2-thienyl | 4-bromo-3-pyridazinyl |
| 3,5-dichloro-2-thienyl | 4-(CF$_3$)-2-pyrimidinyl |
| 3,5-dimethyl-2-furyl | 3,6-dimethyl-2-pyrazinyl |
| 4-methyl-2-(CF$_3$)-5-thiazolyl | 2,5-dimethyl-4-pyrimidinyl |
| 4-methyl-2-(CF$_3$)-5-oxazolyl | 4-methoxy-5-pyrimidinyl |
| 1-methyl-4-(CF$_3$)-2-imidazolyl | 3,6-dimethyl-4-pyridazinyl |
| 2,4-dimethyl-1-pyrrolyl | 1-methyl-4-(CF$_3$)imidazol-2-yl |
| 1-methyl-3-(CF$_3$)pyrazol-5-yl | 3,5-bis-(CF$_3$)pyrazol-1-yl |
| 3-bromo-5-(CF$_3$)pyrazol-1-yl | 3-chloro-5-(CF$_3$)-pyrazol-1-yl |
| 3-methyl-5-(CF$_3$)-pyrazol-1-yl | 3,5-bis-(difluoromethoxy)pyrazol-1-yl |
| 3-methoxy-5-(CF$_3$)-pyrazol-1-yl | 3,5-dimethoxypyrazol-1-yl |
| 3,5-dibromopyrazol-1-yl | 5-ethoxy-3-methylpyrazol-1-yl |
| 5-methoxy-3-methylpyrazol-1-yl | 5-ethoxy-3-(CF$_3$)pyrazol-1-yl |
| 5-methoxy-3-(CF$_3$)pyrazol-1-yl | 3,5-dibromotriazol-1-yl |
| 3,5-dichlorotriazol-1-yl | 3-chloro-5-methyltriazol-1-yl |
| 3-methyl-5-chlorotriazol-1-yl | 3-bromo-5-methyltriazol-1-yl |
| 3-methyl-5-bromotriazol-1-yl | 3-(CF$_3$)-5-chlorotriazol-1-yl |
| 3-chloro-5-(CF$_3$)triazol-1-yl | 3-(CF$_3$)-5-bromotriazol-1-yl |
| 3-bromo-5-(CF$_3$)triazol-1-yl | 3,5-bis(CF$_3$)triazol-1-yl |
| n-butyl | Trifluoromethoxyethyl |
| i-amyl | 2-methoxyethoxy |
| 3-methyl-2-buten-1-yl | 3,3,3-trifluoropropoxy |
| propargyl | 2,2,2-trifluoroethylcarbonyloxy |
| 4,4,4-trifluorobutan-1-yl | allyloxy |
| 3,3-dichloro-2-propen-1-yl | propylthio |
| 2-(CF$_3$)cyclopropyl-1-yl | 3,3,3-trifluoropropylthio |
| i-butoxy | 3,3,3-trifluoropropylamino |
| 2,2,2-trifluoroethoxymethyl | |

The present disclosure also includes Tables 1b through 1i, each of which is constructed the same as Table 1 above except that the row heading in Table 1 (i.e. "A$^1$ is CH$_2$, W$^1$ is O and X is O") is replaced with the respective row headings shown below and R$^{1a}$ is define as in Table 1 above. For example, in Table 1b the row heading is "A¹ is NH, W¹ is O and X is O" and R¹ᵃ is as defined in Table 1 above. Thus, the first entry in Table 1b specifically discloses a compound of Formula 1 wherein A¹ is NH, W¹ is O, X is O and R¹ᵃ is phenyl. Tables 1c through 1i are constructed similarly.

| Table Row Heading | A¹ | W¹ | X |
|---|---|---|---|
| 1b | NH | O | O |
| 1c | C=O | O | O |
| 1d | CH₂ | O | NH |
| 1e | NH | O | NH |
| 1f | C=O | O | NH |
| 1g | CH₂ | O | NMe |
| 1h | NH | O | NMe |
| 1i | C=O | O | NMe |

TABLE 1A

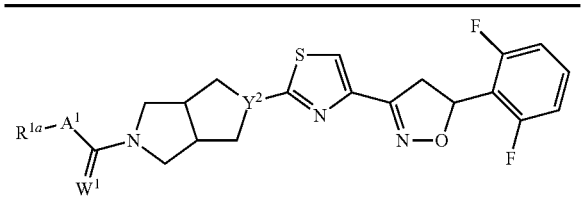

A¹ is CH₂, W¹ is O and Y² is N.

| R¹ᵃ | R¹ᵃ |
|---|---|
| Ph | 3-ethylphenyl |
| 2-methylphenyl | 3-(CF₃)phenyl |
| 2-methoxyphenyl | 3-cyanophenyl |
| 2-chlorophenyl | 3-nitrophenyl |
| 2-bromophenyl | 2,5-dichlorophenyl |
| 2-ethoxyphenyl | 5-bromo-2-chlorophenyl |
| 2-(methylthio)phenyl | 2-chloro-5-methylphenyl |
| 3-chlorophenyl | 2-methoxy-5-(CF₃)phenyl |
| 3-bromophenyl | 2,5-diethylphenyl |
| 3-iodophenyl | 3-methylpyrazol-1-yl |
| 3-methylphenyl | 3-chloropyrazol-1-yl |
| 2-chloro-5-(CF₃)phenyl | 3-bromopyrazol-1-yl |
| 2,5-dibromophenyl | 3-(CF₃)pyrazol-1-yl |
| 2-bromo-5-methylphenyl | 3,5-dimethylpyrazol-1-yl |
| 2-bromo-5-(CF₃)phenyl | 3-chloro-5-methylpyrazol-1-yl |
| 5-chloro-2-methylphenyl | 3-bromo-5-methylpyrazol-1-yl |
| 5-bromo-2-methylphenyl | 5-methoxy-3-methylpyrazol-1-yl |
| 2,5-dimethylphenyl | 3,5-diethylpyrazol-1-yl |
| 2-methyl-5-(CF₃)phenyl | 5-ethyl-3-(CF₃)pyrazol-1-yl |
| 5-cyano-2-methylphenyl | 2,5-dimethyl-3-furyl |
| 2-methyl-5-nitrophenyl | 2,5-dimethyl-3-thienyl |
| 5-chloro-2-methoxyphenyl | 2,5-dichloro-3-thienyl |
| 5-bromo-2-methoxyphenyl | 1,4-dimethyl-3-pyrrolyl |
| 2-methoxy-5-methylphenyl | 1,4-dimethyl-3-pyrazolyl |
| 3-ethyl-5-methylpyrazol-1-yl | 1,3-dimethyl-4-pyrazolyl |
| 5-methyl-3-(CF₃)pyrazol-1-yl | 2,5-dimethyl-4-oxazolyl |
| 5-methyl-3-(C₂F₅)pyrazol-1-yl | 2,5-dimethyl-4-thiazolyl |
| 5-chloro-3-methylpyrazol-1-yl | 3,6-dimethyl-2-pyridyl |
| 3,5-dichloropyrazol-1-yl | 2,5-dimethyl-3-pyridyl |
| 5-chloro-3-(CF₃)pyrazol-1-yl | 2,5-dimethyl-4-pyridyl |
| 5-bromo-3-methylpyrazol-1-yl | 3,6-dichloro-2-pyridyl |
| 3,5-dibromopyrazol-1-yl | 2,5-dichloro-3-pyridyl |
| 5-bromo-3-(CF₃)pyrazol-1-yl | 2,5-dichloro-4-pyridyl |
| 3,5-dimethyl-2-thienyl | 4-bromo-3-pyridazinyl |
| 3,5-dichloro-2-thienyl | 4-(CF₃)-2-pyrimidinyl |
| 3,5-dimethyl-2-furyl | 3,6-dimethyl-2-pyrazinyl |
| 4-methyl-2-(CF₃)-5-thiazolyl | 2,5-dimethyl-4-pyrimidinyl |
| 4-methyl-2-(CF₃)-5-oxazolyl | 4-methoxy-5-pyrimidinyl |
| 1-methyl-4-(CF₃)-2-imidazolyl | 3,6-dimethyl-4-pyridazinyl |
| 2,4-dimethyl-1-pyrrolyl | 1-methyl-4-(CF₃)imidazol-2-yl |
| 1-methyl-3-(CF₃)pyrazol-5-yl | 3,5-bis-(CF₃)pyrazol-1-yl |
| 3-bromo-5-(CF₃)pyrazol-1-yl | 3-chloro-5-(CF₃)-pyrazol-1-yl |
| 3-methyl-5-(CF₃)-pyrazol-1-yl | 3,5-bis-(difluoromethoxy)pyrazol-1-yl |
| 3-methoxy-5-(CF₃)-pyrazol-1-yl | 3,5-dimethoxypyrazol-1-yl |

TABLE 1A-continued

A¹ is CH₂, W¹ is O and Y² is N.

| R¹ᵃ | R¹ᵃ |
|---|---|
| 3,5-dibromopyrazol-1-yl | 5-ethoxy-3-methylpyrazol-1-yl |
| 5-methoxy-3-methylpyrazol-1-yl | 5-ethoxy-3-(CF₃)pyrazol-1-yl |
| 5-methoxy-3-(CF₃)pyrazol-1-yl | 3,5-dibromotriazol-1-yl |
| 3,5-dichlorotriazol-1-yl | 3-chloro-5-methyltriazol-1-yl |
| 3-methyl-5-chlorotriazol-1-yl | 3-bromo-5-methyltriazol-1-yl |
| 3-methyl-5-bromotriazol-1-yl | 3-(CF₃)-5-chlorotriazol-1-yl |
| 3-chloro-5-(CF₃)triazol-1-yl | 3-(CF₃)-5-bromotriazol-1-yl |
| 3-bromo-5-(CF₃)triazol-1-yl | 3,5-bis(CF₃)triazol-1-yl |
| n-butyl | Trifluoromethoxyethyl |
| i-amyl | 2-methoxyethoxy |
| 3-methyl-2-buten-1-yl | 3,3,3-trifluoropropoxy |
| propargyl | 2,2,2-trifluoroethylcarbonyloxy |
| 4,4,4-trifluorobutan-1-yl | allyloxy |
| 3,3-dichloro-2-propen-1-yl | propylthio |
| 2-(CF₃)cyclopropyl-1-yl | 3,3,3-trifluoropropylthio |
| i-butoxy | 3,3,3-trifluoropropylamino |
| 2,2,2-trifluoroethoxymethyl | |

The present disclosure also includes Tables 1Ab through 1Af, each of which is constructed the same as Table 1A above except that the row heading in Table 1A (i.e. "A¹ is CH₂, W¹ is O and Y² is N") is replaced with the respective row headings shown below and R¹ᵃ is define as in Table 1A above. For example, in Table 1Ab the row heading is "A¹ is NH, W¹ is O and Y² is N" and R¹ᵃ is as defined in Table 1A above. Thus, the first entry in Table 1Ab specifically discloses a compound of Formula 1A wherein A¹ is NH, W¹ is O, Y² is N and R¹ᵃ is phenyl. Tables 1Ac through 1Af are constructed similarly.

| Table Row Heading | A¹ | W¹ | Y² |
|---|---|---|---|
| 1Ab | NH | O | N |
| 1Ac | C=O | O | N |
| 1Ad | CH₂ | O | CH |
| 1Ae | NH | O | CH |
| 1Af | C=O | O | CH |

TABLE 2

X is O.

| R² | R³ | R⁴ | R⁵ | A² | W² |
|---|---|---|---|---|---|
| CH₃ | CH₃ | H | H | O | O |
| CH₃ | CH₃ | H | H | S | O |
| CH₃ | CH₃ | H | H | NH | O |
| CH₃ | CH₃ | H | H | N(Me) | O |
| CH₃ | CH₃ | H | H | CH₂ | O |
| CH₃ | CH₃ | H | H | OCH₂ | O |
| CH₃ | CH₃ | H | H | SCH₂ | O |
| CH₃ | CH₃ | H | H | NHCH₂ | O |

TABLE 2-continued

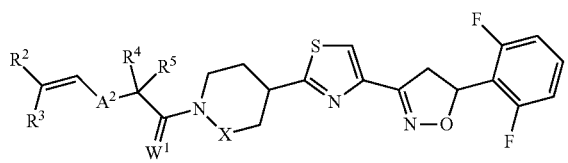

X is O.

| R² | R³ | R⁴ | R⁵ | A² | W² |
|---|---|---|---|---|---|
| CH₃ | CH₃ | H | H | —N(Me)CH₂— | O |
| CH₃ | CH₃ | CH₃ | H | O | O |
| CH₃ | CH₃ | CH₃ | CH₃ | O | O |
| CH₃ | CH₃ | H | H | O | S |
| CF₃ | H | H | H | O | O |
| CF₃ | H | H | H | S | O |
| CF₃ | H | H | H | NH | O |
| CF₃ | H | H | H | N(Me) | O |
| CF₃ | H | H | H | CH₂ | O |
| CF₃ | H | H | H | OCH₂ | O |
| CF₃ | H | H | H | SCH₂ | O |
| CF₃ | H | H | H | NHCH₂ | O |
| CF₃ | H | H | H | —N(Me)CH₂— | O |
| CF₃ | CH₃ | H | H | O | O |
| CF₃ | CH₃ | H | H | S | O |
| CF₃ | CH₃ | H | H | NH | O |
| CF₃ | CH₃ | H | H | N(Me) | O |
| CF₃ | CH₃ | H | H | CH₂ | O |
| CF₃ | CH₃ | H | H | OCH₂ | O |
| CF₃ | CH₃ | H | H | SCH₂ | O |
| CF₃ | CH₃ | H | H | NHCH₂ | O |
| CF₃ | CH₃ | H | H | —N(Me)CH₂— | O |
| CF₃ | H | Me | H | O | O |
| CF₃ | CH₃ | H | Me | O | O |
| CF₃CH₂ | H | H | H | O | O |
| CF₃CH₂ | CH₃ | H | H | O | O |
| Et | H | H | H | O | O |
| Et | CH₃ | H | H | O | O |
| CH₃ | H | H | H | O | O |
| CH₃ | * | H | H | N* | O |
| CF₃ | * | H | H | N* | O |

*R³ and R⁷ are taken together to form a —CH₂CH(CH₃)— bridge.

The present disclosure also includes Tables 2b through 2c, each of which is constructed the same as Table 2 above except that the row heading in Table 2 (i.e. "X is O") is replaced with the respective row headings shown below. For example, in Table 2b the row heading is "X is NH" and $R^2$, $R^3$, $R^4$, $R^5$, $A^2$ and $W^2$ are as defined in Table 2 above. Thus, the first entry in Table 2b specifically discloses a compound of Formula 1 wherein X is NH, $R^2$ is CH₃, $R^3$ is CH₃, $R^4$ is H, $R^5$ is H, $A^2$ is O and $W^2$ is O. Table 2c is constructed similarly.

| Table Row Heading | X |
|---|---|
| 2b | NH |
| 2c | NMe |

TABLE 2A

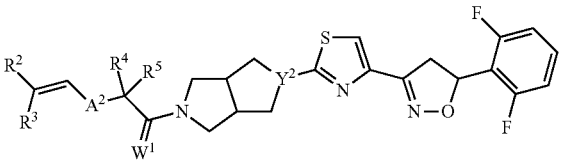

Y² is N.

| R² | R³ | R⁴ | R⁵ | A² | W² |
|---|---|---|---|---|---|
| CH₃ | CH₃ | H | H | S | O |
| CH₃ | CH₃ | H | H | NH | O |
| CH₃ | CH₃ | H | H | N(Me) | O |
| CH₃ | CH₃ | H | H | CH₂ | O |
| CH₃ | CH₃ | H | H | OCH₂ | O |
| CH₃ | CH₃ | H | H | SCH₂ | O |
| CH₃ | CH₃ | H | H | NHCH₂ | O |
| CH₃ | CH₃ | H | H | —N(Me)CH₂— | O |
| CH₃ | CH₃ | CH₃ | H | O | O |
| CH₃ | CH₃ | CH₃ | CH₃ | O | O |
| CH₃ | CH₃ | H | H | O | S |
| CF₃ | H | H | H | O | O |
| CF₃ | H | H | H | S | O |
| CF₃ | H | H | H | NH | O |
| CF₃ | H | H | H | N(Me) | O |
| CF₃ | H | H | H | CH₂ | O |
| CF₃ | H | H | H | OCH₂ | O |
| CF₃ | H | H | H | SCH₂ | O |
| CF₃ | H | H | H | NHCH₂ | O |
| CF₃ | H | H | H | —N(Me)CH₂— | O |
| CF₃ | CH₃ | H | H | O | O |
| CF₃ | CH₃ | H | H | S | O |
| CF₃ | CH₃ | H | H | NH | O |
| CF₃ | CH₃ | H | H | N(Me) | O |
| CF₃ | CH₃ | H | H | CH₂ | O |
| CF₃ | CH₃ | H | H | OCH₂ | O |
| CF₃ | CH₃ | H | H | SCH₂ | O |
| CF₃ | CH₃ | H | H | NHCH₂ | O |
| CF₃ | CH₃ | H | H | —N(Me)CH₂— | O |
| CF₃ | H | Me | H | O | O |
| CF₃ | CH₃ | H | Me | O | O |
| CF₃CH₂ | H | H | H | O | O |
| CF₃CH₂ | CH₃ | H | H | O | O |
| Et | H | H | H | O | O |
| Et | CH₃ | H | H | O | O |
| CH₃ | H | H | H | O | O |
| CH₃ | * | H | H | N* | O |
| CF₃ | * | H | H | N* | O |

*R³ and R⁷ are taken together to form a —CH₂CH(CH₃)— bridge.

The present disclosure also includes Table 2Ab which is constructed the same as Table 2A above except that the row heading in Table 2A (i.e. "Y² is N") is replaced with the row heading "Y² is CH" and $R^2$, $R^3$, $R^4$, $R^5$, $A^2$ and $W^2$ are as defined in Table 2A above. Thus, the first entry in Table 2Ab specifically discloses a compound of Formula 1A wherein Y² is CH, $R^2$ is CH₃, $R^3$ is CH₃, $R^4$ is H, $R^5$ is H, $A^2$ is O and $W^2$ is O.

| Table Row Heading | Y² |
|---|---|
| 2Ab | CH |

TABLE 3

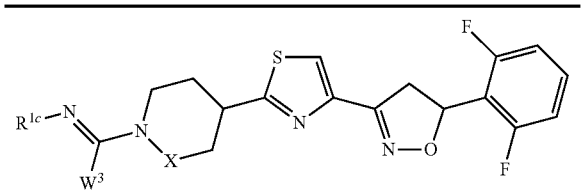

X is O.

| $R^{1c}$ | $W^3$ | $R^{1c}$ | $W^3$ |
|---|---|---|---|
| 2-methylphenyl | OMe | 2-methylphenyl | OMe |
| 2-methoxyphenyl | OMe | 2-methoxyphenyl | OMe |
| 2-chlorophenyl | OMe | 2-chlorophenyl | OMe |
| 2-bromophenyl | OMe | 2-bromophenyl | OMe |
| 2-ethylphenyl | OMe | 2-ethylphenyl | OMe |
| 2-ethoxyphenyl | OMe | 2-ethoxyphenyl | OMe |
| 2-(methylthio)-phenyl | OMe | 2-(methylthio)-phenyl | OMe |
| 2-(trifluoromethoxy)-phenyl | OMe | 2-(trifluoromethoxy)-phenyl | OMe |
| 3-chlorophenyl | OMe | 3-chlorophenyl | OMe |
| 3-bromophenyl | OMe | 3-bromophenyl | OMe |
| 3-methylphenyl | OMe | 3-methylphenyl | OMe |
| 2,5-dimethylphenyl | OMe | 2,5-dimethylphenyl | OMe |
| 2,5-dichlorophenyl | OMe | 2,5-dichlorophenyl | OMe |
| 2-chloro-5-($CF_3$)-phenyl | OMe | 2-chloro-5-($CF_3$)-phenyl | OMe |
| 2,5-dibromophenyl | OMe | 2,5-dibromophenyl | OMe |
| 2-bromo-5-($CF_3$)-phenyl | OMe | 2-bromo-5-($CF_3$)-phenyl | OMe |
| 5-chloro-2-methylphenyl | OMe | 5-chloro-2-methylphenyl | OMe |
| 5-bromo-2-methylphenyl | OMe | 5-bromo-2-methylphenyl | OMe |
| 2-methyl-5-($CF_3$)-phenyl | OMe | 2-methyl-5-($CF_3$)-phenyl | OMe |
| 5-chloro-2-methoxyphenyl | OMe | 5-chloro-2-methoxyphenyl | OMe |
| 5-bromo-2-methoxyphenyl | OMe | 5-bromo-2-methoxyphenyl | OMe |
| 2-methoxy-5-methylphenyl | OMe | 2-methoxy-5-methylphenyl | OMe |
| 2-methoxy-5-($CF_3$)-phenyl | OMe | 2-methoxy-5-($CF_3$)-phenyl | OMe |
| 2,5-diethylphenyl | OMe | 2,5-diethylphenyl | OMe |
| 3,5-dimethylpyrazol-1-yl | OMe | 3,5-dimethylpyrazol-1-yl | OMe |
| 3,5-dichloropyrazol-1-yl | OMe | 3,5-dichloropyrazol-1-yl | OMe |
| 3,5-dibromopyrazol-1-yl | OMe | 3,5-dibromopyrazol-1-yl | OMe |
| 3,5-bis-($CF_3$)-pyrazol-1-yl | OMe | 3,5-bis-($CF_3$)-pyrazol-1-yl | OMe |
| 5-methyl-3-($CF_3$)-pyrazol-1-yl | OMe | 5-methyl-3-($CF_3$)-pyrazol-1-yl | OMe |
| 3,5-dimethyl-1,2,4-triazol-1-yl | OMe | 3,5-dimethyl-1,2,4-triazol-1-yl | OMe |
| 3,5-dichlorol-1,2,4-triazol-1-yl | OMe | 3,5-dichlorol-1,2,4-triazol-1-yl | OMe |
| 3,5-dibromo-1,2,4-triazol-1-yl | OMe | 3,5-dibromo-1,2,4-triazol-1-yl | OMe |
| n-butyl | OMe | n-butyl | OMe |
| i-amyl | OMe | i-amyl | OMe |
| 3-methyl-2-buten-1-yl | OMe | 3-methyl-2-buten-1-yl | OMe |
| propargyl | OMe | propargyl | OMe |
| 4,4,4-trifluorobutan-1-yl | OMe | 4,4,4-trifluorobutan-1-yl | OMe |
| 3,3-dichloro-2-propen-1-yl | OMe | 3,3-dichloro-2-propen-1-yl | OMe |
| 2-($CF_3$)-cyclopropyl-1-yl | OMe | 2-($CF_3$)-cyclopropyl-1-yl | OMe |
| i-butoxy | OMe | i-butoxy | OMe |
| Trifluoromethoxyethyl | OMe | Trifluoromethoxyethyl | OMe |
| 3,3,3-trifluoropropoxy | OMe | 3,3,3-trifluoropropoxy | OMe |
| 2-methylphenyl | SMe | 2-methylphenyl | SMe |
| 2-methoxyphenyl | SMe | 2-methoxyphenyl | SMe |
| 2-chlorophenyl | SMe | 2-chlorophenyl | SMe |
| 2-bromophenyl | SMe | 2-bromophenyl | SMe |

TABLE 3-continued

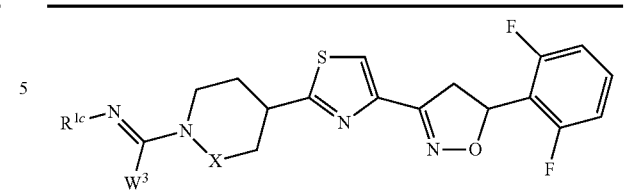

X is O.

| $R^{1c}$ | $W^3$ | $R^{1c}$ | $W^3$ |
|---|---|---|---|
| 2-ethylphenyl | SMe | 2-ethylphenyl | SMe |
| 2-ethoxyphenyl | SMe | 2-ethoxyphenyl | SMe |
| 2-(methylthio)-phenyl | SMe | 2-(methylthio)-phenyl | SMe |
| 2-(trifluoromethoxy)-phenyl | SMe | 2-(trifluoromethoxy)-phenyl | SMe |
| 3-chlorophenyl | SMe | 3-chlorophenyl | SMe |
| 3-bromophenyl | SMe | 3-bromophenyl | SMe |
| 3-methylphenyl | SMe | 3-methylphenyl | SMe |
| 2,5-dimethylphenyl | SMe | 2,5-dimethylphenyl | SMe |
| 2,5-dichlorophenyl | SMe | 2,5-dichlorophenyl | SMe |
| 2-chloro-5-($CF_3$)-phenyl | SMe | 2-chloro-5-($CF_3$)-phenyl | SMe |
| 2,5-dibromophenyl | SMe | 2,5-dibromophenyl | SMe |
| 2-bromo-5-($CF_3$)-phenyl | SMe | 2-bromo-5-($CF_3$)-phenyl | SMe |
| 5-chloro-2-methylphenyl | SMe | 5-chloro-2-methylphenyl | SMe |
| 5-bromo-2-methylphenyl | SMe | 5-bromo-2-methylphenyl | SMe |
| 2-methyl-5-($CF_3$)-phenyl | SMe | 2-methyl-5-($CF_3$)-phenyl | SMe |
| 5-chloro-2-methoxyphenyl | SMe | 5-chloro-2-methoxyphenyl | SMe |
| 5-bromo-2-methoxyphenyl | SMe | 5-bromo-2-methoxyphenyl | SMe |
| 2-methoxy-5-methylphenyl | SMe | 2-methoxy-5-methylphenyl | SMe |
| 2-methoxy-5-($CF_3$)-phenyl | SMe | 2-methoxy-5-($CF_3$)-phenyl | SMe |
| 2,5-diethylphenyl | SMe | 2,5-diethylphenyl | SMe |
| 3,5-dimethylpyrazol-1-yl | SMe | 3,5-dimethylpyrazol-1-yl | SMe |
| 3,5-dichloropyrazol-1-yl | SMe | 3,5-dichloropyrazol-1-yl | SMe |
| 3,5-dibromopyrazol-1-yl | SMe | 3,5-dibromopyrazol-1-yl | SMe |
| 3,5-bis-($CF_3$)-pyrazol-1-yl | SMe | 3,5-bis-($CF_3$)-pyrazol-1-yl | SMe |
| 5-methyl-3-($CF_3$)-pyrazol-1-yl | SMe | 5-methyl-3-($CF_3$)-pyrazol-1-yl | SMe |
| 3,5-dimethyl-1,2,4-triazol-1-yl | SMe | 3,5-dimethyl-1,2,4-triazol-1-yl | SMe |
| 3,5-dichlorol-1,2,4-triazol-1-yl | SMe | 3,5-dichlorol-1,2,4-triazol-1-yl | SMe |
| 3,5-dibromo-1,2,4-triazol-1-yl | SMe | 3,5-dibromo-1,2,4-triazol-1-yl | SMe |
| n-butyl | SMe | n-butyl | SMe |
| i-amyl | SMe | i-amyl | SMe |
| 3-methyl-2-buten-1-yl | SMe | 3-methyl-2-buten-1-yl | SMe |
| propargyl | SMe | propargyl | SMe |
| 4,4,4-trifluorobutan-1-yl | SMe | 4,4,4-trifluorobutan-1-yl | SMe |
| 3,3-dichloro-2-propen-1-yl | SMe | 3,3-dichloro-2-propen-1-yl | SMe |
| 2-($CF_3$)-cyclopropyl-1-yl | SMe | 2-($CF_3$)-cyclopropyl-1-yl | SMe |
| i-butoxy | SMe | i-butoxy | SMe |
| Trifluoromethoxyethyl | SMe | Trifluoromethoxyethyl | SMe |
| 3,3,3-trifluoropropoxy | SMe | 3,3,3-trifluoropropoxy | SMe |
| 2-methylphenyl | $NH_2$ | 2-methylphenyl | $NH_2$ |
| 2-methoxyphenyl | $NH_2$ | 2-methoxyphenyl | $NH_2$ |
| 2-chlorophenyl | $NH_2$ | 2-chlorophenyl | $NH_2$ |
| 2-bromophenyl | $NH_2$ | 2-bromophenyl | $NH_2$ |
| 2-ethylphenyl | $NH_2$ | 2-ethylphenyl | $NH_2$ |
| 2-ethoxyphenyl | $NH_2$ | 2-ethoxyphenyl | $NH_2$ |
| 2-(methylthio)-phenyl | $NH_2$ | 2-(methylthio)-phenyl | $NH_2$ |
| 2-(trifluoromethoxy)- | $NH_2$ | 2-(trifluoromethoxy)- | $NH_2$ |

TABLE 3-continued

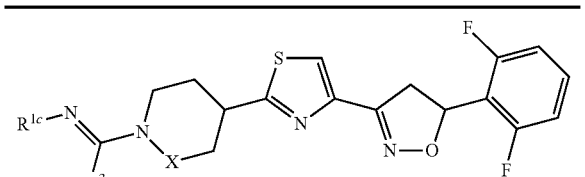

X is O.

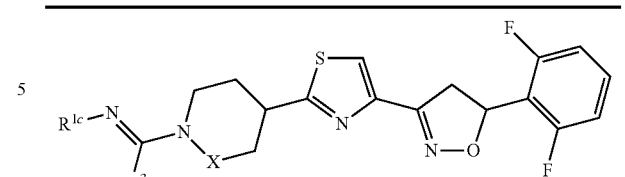

X is O.

| R$^{1c}$ | W$^3$ | R$^{1c}$ | W$^3$ |
|---|---|---|---|
| phenyl | | phenyl | |
| 3-chlorophenyl | NH$_2$ | 3-chlorophenyl | NH$_2$ |
| 3-bromophenyl | NH$_2$ | 3-bromophenyl | NH$_2$ |
| 3-methylphenyl | NH$_2$ | 3-methylphenyl | NH$_2$ |
| 2,5-dimethylphenyl | NH$_2$ | 2,5-dimethylphenyl | NH$_2$ |
| 2,5-dichlorophenyl | NH$_2$ | 2,5-dichlorophenyl | NH$_2$ |
| 2-chloro-5-(CF$_3$)-phenyl | NH$_2$ | 2-chloro-5-(CF$_3$)-phenyl | NH$_2$ |
| 2,5-dibromophenyl | NH$_2$ | 2,5-dibromophenyl | NH$_2$ |
| 2-bromo-5-(CF$_3$)-phenyl | NH$_2$ | 2-bromo-5-(CF$_3$)-phenyl | NH$_2$ |
| 5-chloro-2-methylphenyl | NH$_2$ | 5-chloro-2-methylphenyl | NH$_2$ |
| 5-bromo-2-methylphenyl | NH$_2$ | 5-bromo-2-methylphenyl | NH$_2$ |
| 2-methyl-5-(CF$_3$)-phenyl | NH$_2$ | 2-methyl-5-(CF$_3$)-phenyl | NH$_2$ |
| 5-chloro-2-methoxyphenyl | NH$_2$ | 5-chloro-2-methoxyphenyl | NH$_2$ |
| 5-bromo-2-methoxyphenyl | NH$_2$ | 5-bromo-2-methoxyphenyl | NH$_2$ |
| 2-methoxy-5-methylphenyl | NH$_2$ | 2-methoxy-5-methylphenyl | NH$_2$ |
| 2-methoxy-5-(CF$_3$)-phenyl | NH$_2$ | 2-methoxy-5-(CF$_3$)-phenyl | NH$_2$ |
| 2,5-diethylphenyl | NH$_2$ | 2,5-diethylphenyl | NH$_2$ |
| 3,5-dimethylpyrazol-1-yl | NH$_2$ | 3,5-dimethylpyrazol-1-yl | NH$_2$ |
| 3,5-dichloropyrazol-1-yl | NH$_2$ | 3,5-dichloropyrazol-1-yl | NH$_2$ |
| 3,5-dibromopyrazol-1-yl | NH$_2$ | 3,5-dibromopyrazol-1-yl | NH$_2$ |
| 3,5-bis-(CF$_3$)-pyrazol-1-yl | NH$_2$ | 3,5-bis-(CF$_3$)-pyrazol-1-yl | NH$_2$ |
| 5-methyl-3-(CF$_3$)-pyrazol-1-yl | NH$_2$ | 5-methyl-3-(CF$_3$)-pyrazol-1-yl | NH$_2$ |
| 3,5-dimethyl-1,2,4-triazol-1-yl | NH$_2$ | 3,5-dimethyl-1,2,4-triazol-1-yl | NH$_2$ |
| 3,5-dichlorol-1,2,4-triazol-1-yl | NH$_2$ | 3,5-dichlorol-1,2,4-triazol-1-yl | NH$_2$ |
| 3,5-dibromo-1,2,4-triazol-1-yl | NH$_2$ | 3,5-dibromo-1,2,4-triazol-1-yl | NH$_2$ |
| n-butyl | NH$_2$ | n-butyl | NH$_2$ |
| i-amyl | NH$_2$ | i-amyl | NH$_2$ |
| 3-methyl-2-buten-1-yl | NH$_2$ | 3-methyl-2-buten-1-yl | NH$_2$ |
| propargyl | NH$_2$ | propargyl | NH$_2$ |
| 4,4,4-trifluorobutan-1-yl | NH$_2$ | 4,4,4-trifluorobutan-1-yl | NH$_2$ |
| 3,3-dichloro-2-propen-1-yl | NH$_2$ | 3,3-dichloro-2-propen-1-yl | NH$_2$ |
| 2-(CF$_3$)-clopropyl-1-yl | NH$_2$ | 2-(CF$_3$)-clopropyl-1-yl | NH$_2$ |
| i-butoxy | NH$_2$ | i-butoxy | NH$_2$ |
| Trifluoromethoxyethyl | NH$_2$ | Trifluoromethoxyethyl | NH$_2$ |
| 3,3,3-trifluoropropoxy | NH$_2$ | 3,3,3-trifluoropropoxy | NH$_2$ |
| 2-methylphenyl | NHOH | 2-methylphenyl | NHOH |
| 2-methoxyphenyl | NHOH | 2-methoxyphenyl | NHOH |
| 2-chlorophenyl | NHOH | 2-chlorophenyl | NHOH |
| 2-bromophenyl | NHOH | 2-bromophenyl | NHOH |
| 2-ethylphenyl | NHOH | 2-ethylphenyl | NHOH |
| 2-ethoxyphenyl | NHOH | 2-ethoxyphenyl | NHOH |
| 2-(methylthio)-phenyl | NHOH | 2-(methylthio)-phenyl | NHOH |
| 2-(trifluoromethoxy)-phenyl | NHOH | 2-(trifluoromethoxy)-phenyl | NHOH |
| 3-chlorophenyl | NHOH | 3-chlorophenyl | NHOH |
| 3-bromophenyl | NHOH | 3-bromophenyl | NHOH |
| 3-methylphenyl | NHOH | 3-methylphenyl | NHOH |
| 2,5-dimethylphenyl | NHOH | 2,5-dimethylphenyl | NHOH |
| 2,5-dichlorophenyl | NHOH | 2,5-dichlorophenyl | NHOH |
| 2-chloro-5-(CF$_3$)-phenyl | NHOH | 2-chloro-5-(CF$_3$)-phenyl | NHOH |
| 2,5-dibromophenyl | NHOH | 2,5-dibromophenyl | NHOH |
| 2-bromo-5-(CF$_3$)-phenyl | NHOH | 2-bromo-5-(CF$_3$)-phenyl | NHOH |
| 5-chloro-2-methylphenyl | NHOH | 5-chloro-2-methylphenyl | NHOH |
| 5-bromo-2-methylphenyl | NHOH | 5-bromo-2-methylphenyl | NHOH |
| 2-methyl-5-(CF$_3$)-phenyl | NHOH | 2-methyl-5-(CF$_3$)-phenyl | NHOH |
| 5-chloro-2-methoxyphenyl | NHOH | 5-chloro-2-methoxyphenyl | NHOH |
| 5-bromo-2-methoxyphenyl | NHOH | 5-bromo-2-methoxyphenyl | NHOH |
| 2-methoxy-5-methylphenyl | NHOH | 2-methoxy-5-methylphenyl | NHOH |
| 2-methoxy-5-(CF$_3$)-phenyl | NHOH | 2-methoxy-5-(CF$_3$)-phenyl | NHOH |
| 2,5-diethylphenyl | NHOH | 2,5-diethylphenyl | NHOH |
| 3,5-dimethylpyrazol-1-yl | NHOH | 3,5-dimethylpyrazol-1-yl | NHOH |
| 3,5-dichloropyrazol-1-yl | NHOH | 3,5-dichloropyrazol-1-yl | NHOH |
| 3,5-dibromopyrazol-1-yl | NHOH | 3,5-dibromopyrazol-1-yl | NHOH |
| 3,5-bis-(CF$_3$)-pyrazol-1-yl | NHOH | 3,5-bis-(CF$_3$)-pyrazol-1-yl | NHOH |
| 5-methyl-3-(CF$_3$)-pyrazol-1-yl | NHOH | 5-methyl-3-(CF$_3$)-pyrazol-1-yl | NHOH |
| 3,5-dimethyl-1,2,4-triazol-1-yl | NHOH | 3,5-dimethyl-1,2,4-triazol-1-yl | NHOH |
| 3,5-dichlorol-1,2,4-triazol-1-yl | NHOH | 3,5-dichlorol-1,2,4-triazol-1-yl | NHOH |
| 3,5-dibromo-1,2,4-triazol-1-yl | NHOH | 3,5-dibromo-1,2,4-triazol-1-yl | NHOH |
| n-butyl | NHOH | n-butyl | NHOH |
| i-amyl | NHOH | i-amyl | NHOH |
| 3-methyl-2-buten-1-yl | NHOH | 3-methyl-2-buten-1-yl | NHOH |
| propargyl | NHOH | propargyl | NHOH |
| 4,4,4-trifluorobutan-1-yl | NHOH | 4,4,4-trifluorobutan-1-yl | NHOH |
| 3,3-dichloro-2-propen-1-yl | NHOH | 3,3-dichloro-2-propen-1-yl | NHOH |
| 2-(CF$_3$)-cyclopropyl-1-yl | NHOH | 2-(CF$_3$)-cyclopropyl-1-yl | NHOH |
| i-butoxy | NHOH | i-butoxy | NHOH |
| Trifluoromethoxyethyl | NHOH | Trifluoromethoxyethyl | NHOH |
| 3,3,3-trifluoropropoxy | NHOH | 3,3,3-trifluoropropoxy | NHOH |
| 2-methylphenyl | NHOMe | 2-methylphenyl | NHOMe |
| 2-methoxyphenyl | NHOMe | 2-methoxyphenyl | NHOMe |
| 2-chlorophenyl | NHOMe | 2-chlorophenyl | NHOMe |
| 2-bromophenyl | NHOMe | 2-bromophenyl | NHOMe |
| 2-ethylphenyl | NHOMe | 2-ethylphenyl | NHOMe |
| 2-ethoxyphenyl | NHOMe | 2-ethoxyphenyl | NHOMe |
| 2-(methylthio)-phenyl | NHOMe | 2-(methylthio)-phenyl | NHOMe |
| 2-(trifluoromethoxy)-phenyl | NHOMe | 2-(trifluoromethoxy)-phenyl | NHOMe |
| 3-chlorophenyl | NHOMe | 3-chlorophenyl | NHOMe |
| 3-bromophenyl | NHOMe | 3-bromophenyl | NHOMe |
| 3-methylphenyl | NHOMe | 3-methylphenyl | NHOMe |
| 2,5-dimethylphenyl | NHOMe | 2,5-dimethylphenyl | NHOMe |
| 2,5-dichlorophenyl | NHOMe | 2,5-dichlorophenyl | NHOMe |
| 2-chloro-5-(CF$_3$)-phenyl | NHOMe | 2-chloro-5-(CF$_3$)-phenyl | NHOMe |
| 2,5-dibromophenyl | NHOMe | 2,5-dibromophenyl | NHOMe |

TABLE 3-continued

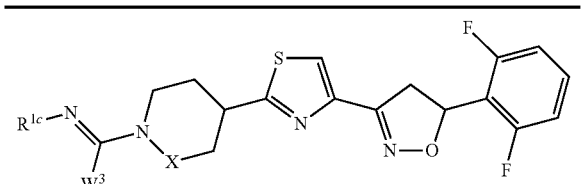

X is O.

| R$^{1c}$ | W$^3$ | R$^{1c}$ | W$^3$ |
|---|---|---|---|
| 2-bromo-5-(CF$_3$)-phenyl | NHOMe | 2-bromo-5-(CF$_3$)-phenyl | NHOMe |
| 5-chloro-2-methylphenyl | NHOMe | 5-chloro-2-methylphenyl | NHOMe |
| 5-bromo-2-methylphenyl | NHOMe | 5-bromo-2-methylphenyl | NHOMe |
| 2-methyl-5-(CF$_3$)-phenyl | NHOMe | 2-methyl-5-(CF$_3$)-phenyl | NHOMe |
| 5-chloro-2-methoxyphenyl | NHOMe | 5-chloro-2-methoxyphenyl | NHOMe |
| 5-bromo-2-methoxyphenyl | NHOMe | 5-bromo-2-methoxyphenyl | NHOMe |
| 2-methoxy-5-methylphenyl | NHOMe | 2-methoxy-5-methylphenyl | NHOMe |
| 2-methoxy-5-(CF$_3$)-phenyl | NHOMe | 2-methoxy-5-(CF$_3$)-phenyl | NHOMe |
| 2,5-diethylphenyl | NHOMe | 2,5-diethylphenyl | NHOMe |
| 3,5-dimethylpyrazol-1-yl | NHOMe | 3,5-dimethylpyrazol-1-yl | NHOMe |
| 3,5-dichloropyrazol-1-yl | NHOMe | 3,5-dichloropyrazol-1-yl | NHOMe |
| 3,5-dibromopyrazol-1-yl | NHOMe | 3,5-dibromopyrazol-1-yl | NHOMe |
| 3,5-bis-(CF$_3$)-pyrazol-1-yl | NHOMe | 3,5-bis-(CF$_3$)-pyrazol-1-yl | NHOMe |
| 5-methyl-3-(CF$_3$)-pyrazol-1-yl | NHOMe | 5-methyl-3-(CF$_3$)-pyrazol-1-yl | NHOMe |
| 3,5-dimethyl-1,2,4-triazol-1-yl | NHOMe | 3,5-dimethyl-1,2,4-triazol-1-yl | NHOMe |
| 3,5-dichlorol-1,2,4-triazol-1-yl | NHOMe | 3,5-dichlorol-1,2,4-triazol-1-yl | NHOMe |
| 3,5-dibromo-1,2,4-triazol-1-yl | NHOMe | 3,5-dibromo-1,2,4-triazol-1-yl | NHOMe |
| n-butyl | NHOMe | n-butyl | NHOMe |
| i-amyl | NHOMe | i-amyl | NHOMe |
| 3-methyl-2-buten-1-yl | NHOMe | 3-methyl-2-buten-1-yl | NHOMe |
| propargyl | NHOMe | propargyl | NHOMe |
| 4,4,4-trifluorobutan-1-yl | NHOMe | 4,4,4-trifluorobutan-1-yl | NHOMe |
| 3,3-dichloro-2-propen-1-yl | NHOMe | 3,3-dichloro-2-propen-1-yl | NHOMe |
| 2-(CF$_3$)-cyclopropyl-1-yl | NHOMe | 2-(CF$_3$)-cyclopropyl-1-yl | NHOMe |
| i-butoxy | NHOMe | i-butoxy | NHOMe |
| Trifluoromethoxyethyl | NHOMe | Trifluoromethoxyethyl | NHOMe |
| 3,3,3-trifluoropropoxy | NHOMe | 3,3,3-trifluoropropoxy | NHOMe |
| 2-methylphenyl | NHNH$_2$ | 2-methylphenyl | NHNH$_2$ |
| 2-methoxyphenyl | NHNH$_2$ | 2-methoxyphenyl | NHNH$_2$ |
| 2-chlorophenyl | NHNH$_2$ | 2-chlorophenyl | NHNH$_2$ |
| 2-bromophenyl | NHNH$_2$ | 2-bromophenyl | NHNH$_2$ |
| 2-ethylphenyl | NHNH$_2$ | 2-ethylphenyl | NHNH$_2$ |
| 2-ethoxyphenyl | NHNH$_2$ | 2-ethoxyphenyl | NHNH$_2$ |
| 2-(methylthio)-phenyl | NHNH$_2$ | 2-(methylthio)-phenyl | NHNH$_2$ |
| 2-(trifluoromethoxy)-phenyl | NHNH$_2$ | 2-(trifluoromethoxy)-phenyl | NHNH$_2$ |
| 3-chlorophenyl | NHNH$_2$ | 3-chlorophenyl | NHNH$_2$ |
| 3-bromophenyl | NHNH$_2$ | 3-bromophenyl | NHNH$_2$ |
| 3-methylphenyl | NHNH$_2$ | 3-methylphenyl | NHNH$_2$ |
| 2,5-dimethylphenyl | NHNH$_2$ | 2,5-dimethylphenyl | NHNH$_2$ |
| 2,5-dichlorophenyl | NHNH$_2$ | 2,5-dichlorophenyl | NHNH$_2$ |
| 2-chloro-5-(CF$_3$)-phenyl | NHNH$_2$ | 2-chloro-5-(CF$_3$)-phenyl | NHNH$_2$ |
| 2,5-dibromophenyl | NHNH$_2$ | 2,5-dibromophenyl | NHNH$_2$ |
| 2-bromo-5-(CF$_3$)-phenyl | NHNH$_2$ | 2-bromo-5-(CF$_3$)-phenyl | NHNH$_2$ |
| 5-chloro-2-methylphenyl | NHNH$_2$ | 5-chloro-2-methylphenyl | NHNH$_2$ |

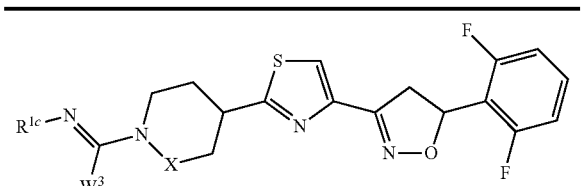

X is O.

| R$^{1c}$ | W$^3$ | R$^{1c}$ | W$^3$ |
|---|---|---|---|
| 5-bromo-2-methylphenyl | NHNH$_2$ | 5-bromo-2-methylphenyl | NHNH$_2$ |
| 2-methyl-5-(CF$_3$)-phenyl | NHNH$_2$ | 2-methyl-5-(CF$_3$)-phenyl | NHNH$_2$ |
| 5-chloro-2-methoxyphenyl | NHNH$_2$ | 5-chloro-2-methoxyphenyl | NHNH$_2$ |
| 5-bromo-2-methoxyphenyl | NHNH$_2$ | 5-bromo-2-methoxyphenyl | NHNH$_2$ |
| 2-methoxy-5-methylphenyl | NHNH$_2$ | 2-methoxy-5-methylphenyl | NHNH$_2$ |
| 2-methoxy-5-(CF$_3$)-phenyl | NHNH$_2$ | 2-methoxy-5-(CF$_3$)-phenyl | NHNH$_2$ |
| 2,5-diethylphenyl | NHNH$_2$ | 2,5-diethylphenyl | NHNH$_2$ |
| 3,5-dimethylpyrazol-1-yl | NHNH$_2$ | 3,5-dimethylpyrazol-1-yl | NHNH$_2$ |
| 3,5-dichloropyrazol-1-yl | NHNH$_2$ | 3,5-dichloropyrazol-1-yl | NHNH$_2$ |
| 3,5-dibromopyrazol-1-yl | NHNH$_2$ | 3,5-dibromopyrazol-1-yl | NHNH$_2$ |
| 3,5-bis-(CF$_3$)-pyrazol-1-yl | NHNH$_2$ | 3,5-bis-(CF$_3$)-pyrazol-1-yl | NHNH$_2$ |
| 5-methyl-3-(CF$_3$)-pyrazol-1-yl | NHNH$_2$ | 5-methyl-3-(CF$_3$)-pyrazol-1-yl | NHNH$_2$ |
| 3,5-dimethyl-1,2,4-triazol-1-yl | NHNH$_2$ | 3,5-dimethyl-1,2,4-triazol-1-yl | NHNH$_2$ |
| 3,5-dichlorol-1,2,4-triazol-1-yl | NHNH$_2$ | 3,5-dichlorol-1,2,4-triazol-1-yl | NHNH$_2$ |
| 3,5-dibromo-1,2,4-triazol-1-yl | NHNH$_2$ | 3,5-dibromo-1,2,4-triazol-1-yl | NHNH$_2$ |
| n-butyl | NHNH$_2$ | n-butyl | NHNH$_2$ |
| i-amyl | NHNH$_2$ | i-amyl | NHNH$_2$ |
| 3-methyl-2-buten-1-yl | NHNH$_2$ | 3-methyl-2-buten-1-yl | NHNH$_2$ |
| propargyl | NHNH$_2$ | propargyl | NHNH$_2$ |
| 4,4,4-trifluorobutan-1-yl | NHNH$_2$ | 4,4,4-trifluorobutan-1-yl | NHNH$_2$ |
| 3,3-dichloro-2-propen-1-yl | NHNH$_2$ | 3,3-dichloro-2-propen-1-yl | NHNH$_2$ |
| 2-(CF$_3$)-cyclopropyl-1-yl | NHNH$_2$ | 2-(CF$_3$)-cyclopropyl-1-yl | NHNH$_2$ |
| i-butoxy | NHNH$_2$ | i-butoxy | NHNH$_2$ |
| Trifluoromethoxyethyl | NHNH$_2$ | Trifluoromethoxyethyl | NHNH$_2$ |
| 3,3,3-trifluoropropoxy | NHNH$_2$ | 3,3,3-trifluoropropoxy | NHNH$_2$ |

The present disclosure also includes Tables 3b through 3c, each of which is constructed the same as Table 3 above except that the Row Heading in Table 3 (i.e. "X is O") is replaced with the respective row headings shown below. For example, in Table 3b the row heading is "X is NH" and R$^{1c}$ and W$^3$ are as defined in Table 3 above. Thus, the first entry in Table 3b specifically discloses a compound of Formula 1 wherein X is NH, R$^{1c}$ is 2-methylphenyl and W$^3$ is methoxy. Table 3c is constructed similarly.

| Table Row Heading | X |
|---|---|
| 3b | NH |
| 3c | N—Me |

TABLE 3A

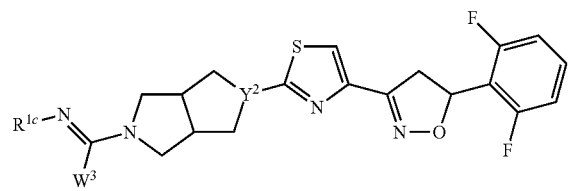

$Y^2$ is N.

| $R^{1c}$ | $W^3$ | $R^{1c}$ | $W^3$ |
|---|---|---|---|
| 2-methylphenyl | OMe | 2-methylphenyl | OMe |
| 2-methoxyphenyl | OMe | 2-methoxyphenyl | OMe |
| 2-chlorophenyl | OMe | 2-chlorophenyl | OMe |
| 2-bromophenyl | OMe | 2-bromophenyl | OMe |
| 2-ethylphenyl | OMe | 2-ethylphenyl | OMe |
| 2-ethoxyphenyl | OMe | 2-ethoxyphenyl | OMe |
| 2-(methylthio)-phenyl | OMe | 2-(methylthio)-phenyl | OMe |
| 2-(trifluoromethoxy)-phenyl | OMe | 2-(trifluoromethoxy)-phenyl | OMe |
| 3-chlorophenyl | OMe | 3-chlorophenyl | OMe |
| 3-bromophenyl | OMe | 3-bromophenyl | OMe |
| 3-methylphenyl | OMe | 3-methylphenyl | OMe |
| 2,5-dimethylphenyl | OMe | 2,5-dimethylphenyl | OMe |
| 2,5-dichlorophenyl | OMe | 2,5-dichlorophenyl | OMe |
| 2-chloro-5-($CF_3$)-phenyl | OMe | 2-chloro-5-($CF_3$)-phenyl | OMe |
| 2,5-dibromophenyl | OMe | 2,5-dibromophenyl | OMe |
| 2-bromo-5-($CF_3$)-phenyl | OMe | 2-bromo-5-($CF_3$)-phenyl | OMe |
| 5-chloro-2-methylphenyl | OMe | 5-chloro-2-methylphenyl | OMe |
| 5-bromo-2-methylphenyl | OMe | 5-bromo-2-methylphenyl | OMe |
| 2-methyl-5-($CF_3$)-phenyl | OMe | 2-methyl-5-($CF_3$)-phenyl | OMe |
| 5-chloro-2-methoxyphenyl | OMe | 5-chloro-2-methoxyphenyl | OMe |
| 5-bromo-2-methoxyphenyl | OMe | 5-bromo-2-methoxyphenyl | OMe |
| 2-methoxy-5-methylphenyl | OMe | 2-methoxy-5-methylphenyl | OMe |
| 2-methoxy-5-($CF_3$)-phenyl | OMe | 2-methoxy-5-($CF_3$)-phenyl | OMe |
| 2,5-diethylphenyl | OMe | 2,5-diethylphenyl | OMe |
| 3,5-dimethylpyrazol-1-yl | OMe | 3,5-dimethylpyrazol-1-yl | OMe |
| 3,5-dichloropyrazol-1-yl | OMe | 3,5-dichloropyrazol-1-yl | OMe |
| 3,5-dibromopyrazol-1-yl | OMe | 3,5-dibromopyrazol-1-yl | OMe |
| 3,5-bis-($CF_3$)-pyrazol-1-yl | OMe | 3,5-bis-($CF_3$)-pyrazol-1-yl | OMe |
| 5-methyl-3-($CF_3$)-pyrazol-1-yl | OMe | 5-methyl-3-($CF_3$)-pyrazol-1-yl | OMe |
| 3,5-dimethyl-1,2,4-triazol-1-yl | OMe | 3,5-dimethyl-1,2,4-triazol-1-yl | OMe |
| 3,5-dichlorol-1,2,4-triazol-1-yl | OMe | 3,5-dichlorol-1,2,4-triazol-1-yl | OMe |
| 3,5-dibromo-1,2,4-triazol-1-yl | OMe | 3,5-dibromo-1,2,4-triazol-1-yl | OMe |
| n-butyl | OMe | n-butyl | OMe |
| i-amyl | OMe | i-amyl | OMe |
| 3-methyl-2-buten-1-yl | OMe | 3-methyl-2-buten-1-yl | OMe |
| propargyl | OMe | propargyl | OMe |
| 4,4,4-trifluorobutan-1-yl | OMe | 4,4,4-trifluorobutan-1-yl | OMe |
| 3,3-dichloro-2-propen-1-yl | OMe | 3,3-dichloro-2-propen-1-yl | OMe |
| 2-($CF_3$)-cyclopropyl-1-yl | OMe | 2-($CF_3$)-cyclopropyl-1-yl | OMe |
| i-butoxy | OMe | i-butoxy | OMe |
| Trifluoromethoxyethyl | OMe | Trifluoromethoxyethyl | OMe |
| 3,3,3-trifluoropropoxy | OMe | 3,3,3-trifluoropropoxy | OMe |
| 2-methylphenyl | SMe | 2-methylphenyl | SMe |
| 2-methoxyphenyl | SMe | 2-methoxyphenyl | SMe |
| 2-chlorophenyl | SMe | 2-chlorophenyl | SMe |

TABLE 3A-continued

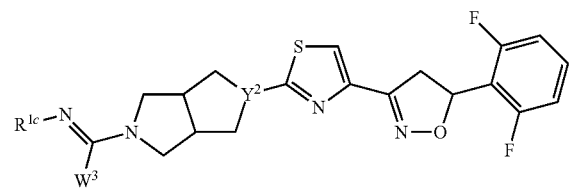

$Y^2$ is N.

| $R^{1c}$ | $W^3$ | $R^{1c}$ | $W^3$ |
|---|---|---|---|
| 2-bromophenyl | SMe | 2-bromophenyl | SMe |
| 2-ethylphenyl | SMe | 2-ethylphenyl | SMe |
| 2-ethoxyphenyl | SMe | 2-ethoxyphenyl | SMe |
| 2-(methylthio)-phenyl | SMe | 2-(methylthio)-phenyl | SMe |
| 2-(trifluoromethoxy)-phenyl | SMe | 2-(trifluoromethoxy)-phenyl | SMe |
| 3-chlorophenyl | SMe | 3-chlorophenyl | SMe |
| 3-bromophenyl | SMe | 3-bromophenyl | SMe |
| 3-methylphenyl | SMe | 3-methylphenyl | SMe |
| 2,5-dimethylphenyl | SMe | 2,5-dimethylphenyl | SMe |
| 2,5-dichlorophenyl | SMe | 2,5-dichlorophenyl | SMe |
| 2-chloro-5-($CF_3$)-phenyl | SMe | 2-chloro-5-($CF_3$)-phenyl | SMe |
| 2,5-dibromophenyl | SMe | 2,5-dibromophenyl | SMe |
| 2-bromo-5-($CF_3$)-phenyl | SMe | 2-bromo-5-($CF_3$)-phenyl | SMe |
| 5-chloro-2-methylphenyl | SMe | 5-chloro-2-methylphenyl | SMe |
| 5-bromo-2-methylphenyl | SMe | 5-bromo-2-methylphenyl | SMe |
| 2-methyl-5-($CF_3$)-phenyl | SMe | 2-methyl-5-($CF_3$)-phenyl | SMe |
| 5-chloro-2-methoxyphenyl | SMe | 5-chloro-2-methoxyphenyl | SMe |
| 5-bromo-2-methoxyphenyl | SMe | 5-bromo-2-methoxyphenyl | SMe |
| 2-methoxy-5-methylphenyl | SMe | 2-methoxy-5-methylphenyl | SMe |
| 2-methoxy-5-($CF_3$)-phenyl | SMe | 2-methoxy-5-($CF_3$)-phenyl | SMe |
| 2,5-diethylphenyl | SMe | 2,5-diethylphenyl | SMe |
| 3,5-dimethylpyrazol-1-yl | SMe | 3,5-dimethylpyrazol-1-yl | SMe |
| 3,5-dichloropyrazol-1-yl | SMe | 3,5-dichloropyrazol-1-yl | SMe |
| 3,5-dibromopyrazol-1-yl | SMe | 3,5-dibromopyrazol-1-yl | SMe |
| 3,5-bis-($CF_3$)-pyrazol-1-yl | SMe | 3,5-bis-($CF_3$)-pyrazol-1-yl | SMe |
| 5-methyl-3-($CF_3$)-pyrazol-1-yl | SMe | 5-methyl-3-($CF_3$)-pyrazol-1-yl | SMe |
| 3,5-dimethyl-1,2,4-triazol-1-yl | SMe | 3,5-dimethyl-1,2,4-triazol-1-yl | SMe |
| 3,5-dichlorol-1,2,4-triazol-1-yl | SMe | 3,5-dichlorol-1,2,4-triazol-1-yl | SMe |
| 3,5-dibromo-1,2,4-triazol-1-yl | SMe | 3,5-dibromo-1,2,4-triazol-1-yl | SMe |
| n-butyl | SMe | n-butyl | SMe |
| i-amyl | SMe | i-amyl | SMe |
| 3-methyl-2-buten-1-yl | SMe | 3-methyl-2-buten-1-yl | SMe |
| propargyl | SMe | propargyl | SMe |
| 4,4,4-trifluorobutan-1-yl | SMe | 4,4,4-trifluorobutan-1-yl | SMe |
| 3,3-dichloro-2-propen-1-yl | SMe | 3,3-dichloro-2-propen-1-yl | SMe |
| 2-($CF_3$)-cyclopropyl-1-yl | SMe | 2-($CF_3$)-cyclopropyl-1-yl | SMe |
| i-butoxy | SMe | i-butoxy | SMe |
| Trifluoromethoxyethyl | SMe | Trifluoromethoxyethyl | SMe |
| 3,3,3-trifluoropropoxy | SMe | 3,3,3-trifluoropropoxy | SMe |
| 2-methylphenyl | $NH_2$ | 2-methylphenyl | $NH_2$ |
| 2-methoxyphenyl | $NH_2$ | 2-methoxyphenyl | $NH_2$ |
| 2-chlorophenyl | $NH_2$ | 2-chlorophenyl | $NH_2$ |
| 2-bromophenyl | $NH_2$ | 2-bromophenyl | $NH_2$ |
| 2-ethylphenyl | $NH_2$ | 2-ethylphenyl | $NH_2$ |
| 2-ethoxyphenyl | $NH_2$ | 2-ethoxyphenyl | $NH_2$ |

TABLE 3A-continued

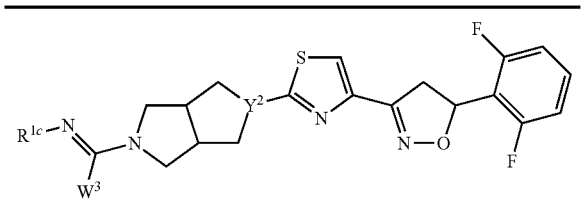

Y² is N.

| R¹ᶜ | W³ | R¹ᶜ | W³ |
|---|---|---|---|
| 2-(methylthio)-phenyl | NH₂ | 2-(methylthio)-phenyl | NH₂ |
| 2-(trifluoromethoxy)-phenyl | NH₂ | 2-(trifluoromethoxy)-phenyl | NH₂ |
| 3-chlorophenyl | NH₂ | 3-chlorophenyl | NH₂ |
| 3-bromophenyl | NH₂ | 3-bromophenyl | NH₂ |
| 3-methylphenyl | NH₂ | 3-methylphenyl | NH₂ |
| 2,5-dimethylphenyl | NH₂ | 2,5-dimethylphenyl | NH₂ |
| 2,5-dichlorophenyl | NH₂ | 2,5-dichlorophenyl | NH₂ |
| 2-chloro-5-(CF₃)-phenyl | NH₂ | 2-chloro-5-(CF₃)-phenyl | NH₂ |
| 2,5-dibromophenyl | NH₂ | 2,5-dibromophenyl | NH₂ |
| 2-bromo-5-(CF₃)-phenyl | NH₂ | 2-bromo-5-(CF₃)-phenyl | NH₂ |
| 5-chloro-2-methylphenyl | NH₂ | 5-chloro-2-methylphenyl | NH₂ |
| 5-bromo-2-methylphenyl | NH₂ | 5-bromo-2-methylphenyl | NH₂ |
| 2-methyl-5-(CF₃)-phenyl | NH₂ | 2-methyl-5-(CF₃)-phenyl | NH₂ |
| 5-chloro-2-methoxyphenyl | NH₂ | 5-chloro-2-methoxyphenyl | NH₂ |
| 5-bromo-2-methoxyphenyl | NH₂ | 5-bromo-2-methoxyphenyl | NH₂ |
| 2-methoxy-5-methylphenyl | NH₂ | 2-methoxy-5-methylphenyl | NH₂ |
| 2-methoxy-5-(CF₃)-phenyl | NH₂ | 2-methoxy-5-(CF₃)-phenyl | NH₂ |
| 2,5-diethylphenyl | NH₂ | 2,5-diethylphenyl | NH₂ |
| 3,5-dimethylpyrazol-1-yl | NH₂ | 3,5-dimethylpyrazol-1-yl | NH₂ |
| 3,5-dichloropyrazol-1-yl | NH₂ | 3,5-dichloropyrazol-1-yl | NH₂ |
| 3,5-dibromopyrazol-1-yl | NH₂ | 3,5-dibromopyrazol-1-yl | NH₂ |
| 3,5-bis-(CF₃)-pyrazol-1-yl | NH₂ | 3,5-bis-(CF₃)-pyrazol-1-yl | NH₂ |
| 5-methyl-3-(CF₃)-pyrazol-1-yl | NH₂ | 5-methyl-3-(CF₃)-pyrazol-1-yl | NH₂ |
| 3,5-dimethyl-1,2,4-triazol-1-yl | NH₂ | 3,5-dimethyl-1,2,4-triazol-1-yl | NH₂ |
| 3,5-dichlorol-1,2,4-triazol-1-yl | NH₂ | 3,5-dichlorol-1,2,4-triazol-1-yl | NH₂ |
| 3,5-dibromo-1,2,4-triazol-1-yl | NH₂ | 3,5-dibromo-1,2,4-triazol-1-yl | NH₂ |
| n-butyl | NH₂ | n-butyl | NH₂ |
| i-amyl | NH₂ | i-amyl | NH₂ |
| 3-methyl-2-buten-1-yl | NH₂ | 3-methyl-2-buten-1-yl | NH₂ |
| propargyl | NH₂ | propargyl | NH₂ |
| 4,4,4-trifluorobutan-1-yl | NH₂ | 4,4,4-trifluorobutan-1-yl | NH₂ |
| 3,3-dichloro-2-propen-1-yl | NH₂ | 3,3-dichloro-2-propen-1-yl | NH₂ |
| 2-(CF₃)-clopropyl-1-yl | NH₂ | 2-(CF₃)-clopropyl-1-yl | NH₂ |
| i-butoxy | NH₂ | i-butoxy | NH₂ |
| Trifluoromethoxyethyl | NH₂ | Trifluoromethoxyethyl | NH₂ |
| 3,3,3-trifluoropropoxy | NH₂ | 3,3,3-trifluoropropoxy | NH₂ |
| 2-methylphenyl | NHOH | 2-methylphenyl | NHOH |
| 2-methoxyphenyl | NHOH | 2-methoxyphenyl | NHOH |
| 2-chlorophenyl | NHOH | 2-chlorophenyl | NHOH |
| 2-bromophenyl | NHOH | 2-bromophenyl | NHOH |
| 2-ethylphenyl | NHOH | 2-ethylphenyl | NHOH |
| 2-ethoxyphenyl | NHOH | 2-ethoxyphenyl | NHOH |
| 2-(methylthio)-phenyl | NHOH | 2-(methylthio)-phenyl | NHOH |
| 2-(trifluoromethoxy)-phenyl | NHOH | 2-(trifluoromethoxy)-phenyl | NHOH |
| 3-chlorophenyl | NHOH | 3-chlorophenyl | NHOH |

TABLE 3A-continued

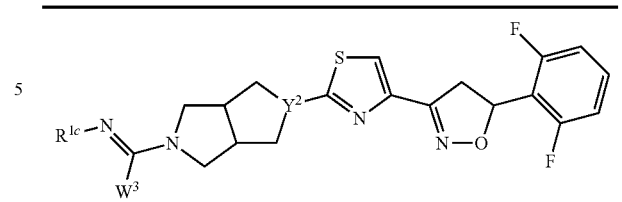

Y² is N.

| R¹ᶜ | W³ | R¹ᶜ | W³ |
|---|---|---|---|
| 3-bromophenyl | NHOH | 3-bromophenyl | NHOH |
| 3-methylphenyl | NHOH | 3-methylphenyl | NHOH |
| 2,5-dimethylphenyl | NHOH | 2,5-dimethylphenyl | NHOH |
| 2,5-dichlorophenyl | NHOH | 2,5-dichlorophenyl | NHOH |
| 2-chloro-5-(CF₃)-phenyl | NHOH | 2-chloro-5-(CF₃)-phenyl | NHOH |
| 2,5-dibromophenyl | NHOH | 2,5-dibromophenyl | NHOH |
| 2-bromo-5-(CF₃)-phenyl | NHOH | 2-bromo-5-(CF₃)-phenyl | NHOH |
| 5-chloro-2-methylphenyl | NHOH | 5-chloro-2-methylphenyl | NHOH |
| 5-bromo-2-methylphenyl | NHOH | 5-bromo-2-methylphenyl | NHOH |
| 2-methyl-5-(CF₃)-phenyl | NHOH | 2-methyl-5-(CF₃)-phenyl | NHOH |
| 5-chloro-2-methoxyphenyl | NHOH | 5-chloro-2-methoxyphenyl | NHOH |
| 5-bromo-2-methoxyphenyl | NHOH | 5-bromo-2-methoxyphenyl | NHOH |
| 2-methoxy-5-methylphenyl | NHOH | 2-methoxy-5-methylphenyl | NHOH |
| 2-methoxy-5-(CF₃)-phenyl | NHOH | 2-methoxy-5-(CF₃)-phenyl | NHOH |
| 2,5-diethylphenyl | NHOH | 2,5-diethylphenyl | NHOH |
| 3,5-dimethylpyrazol-1-yl | NHOH | 3,5-dimethylpyrazol-1-yl | NHOH |
| 3,5-dichloropyrazol-1-yl | NHOH | 3,5-dichloropyrazol-1-yl | NHOH |
| 3,5-dibromopyrazol-1-yl | NHOH | 3,5-dibromopyrazol-1-yl | NHOH |
| 3,5-bis-(CF₃)-pyrazol-1-yl | NHOH | 3,5-bis-(CF₃)-pyrazol-1-yl | NHOH |
| 5-methyl-3-(CF₃)-pyrazol-1-yl | NHOH | 5-methyl-3-(CF₃)-pyrazol-1-yl | NHOH |
| 3,5-dimethyl-1,2,4-triazol-1-yl | NHOH | 3,5-dimethyl-1,2,4-triazol-1-yl | NHOH |
| 3,5-dichlorol-1,2,4-triazol-1-yl | NHOH | 3,5-dichlorol-1,2,4-triazol-1-yl | NHOH |
| 3,5-dibromo-1,2,4-triazol-1-yl | NHOH | 3,5-dibromo-1,2,4-triazol-1-yl | NHOH |
| n-butyl | NHOH | n-butyl | NHOH |
| i-amyl | NHOH | i-amyl | NHOH |
| 3-methyl-2-buten-1-yl | NHOH | 3-methyl-2-buten-1-yl | NHOH |
| propargyl | NHOH | propargyl | NHOH |
| 4,4,4-trifluorobutan-1-yl | NHOH | 4,4,4-trifluorobutan-1-yl | NHOH |
| 3,3-dichloro-2-propen-1-yl | NHOH | 3,3-dichloro-2-propen-1-yl | NHOH |
| 2-(CF₃)-cyclopropyl-1-yl | NHOH | 2-(CF₃)-cyclopropyl-1-yl | NHOH |
| i-butoxy | NHOH | i-butoxy | NHOH |
| Trifluoromethoxyethyl | NHOH | Trifluoromethoxyethyl | NHOH |
| 3,3,3-trifluoropropoxy | NHOH | 3,3,3-trifluoropropoxy | NHOH |
| 2-methylphenyl | NHOMe | 2-methylphenyl | NHOMe |
| 2-methoxyphenyl | NHOMe | 2-methoxyphenyl | NHOMe |
| 2-chlorophenyl | NHOMe | 2-chlorophenyl | NHOMe |
| 2-bromophenyl | NHOMe | 2-bromophenyl | NHOMe |
| 2-ethylphenyl | NHOMe | 2-ethylphenyl | NHOMe |
| 2-ethoxyphenyl | NHOMe | 2-ethoxyphenyl | NHOMe |
| 2-(methylthio)-phenyl | NHOMe | 2-(methylthio)-phenyl | NHOMe |
| 2-(trifluoromethoxy)-phenyl | NHOMe | 2-(trifluoromethoxy)-phenyl | NHOMe |
| 3-chlorophenyl | NHOMe | 3-chlorophenyl | NHOMe |
| 3-bromophenyl | NHOMe | 3-bromophenyl | NHOMe |
| 3-methylphenyl | NHOMe | 3-methylphenyl | NHOMe |
| 2,5-dimethylphenyl | NHOMe | 2,5-dimethylphenyl | NHOMe |

TABLE 3A-continued

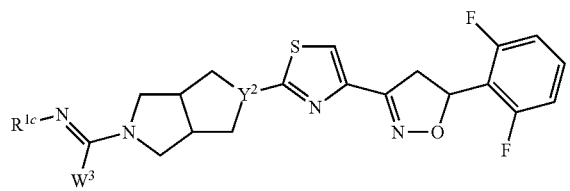

Y² is N.

| R¹ᶜ | W³ | R¹ᶜ | W³ |
|---|---|---|---|
| 2,5-dichlorophenyl | NHOMe | 2,5-dichlorophenyl | NHOMe |
| 2-chloro-5-(CF₃)-phenyl | NHOMe | 2-chloro-5-(CF₃)-phenyl | NHOMe |
| 2,5-dibromophenyl | NHOMe | 2,5-dibromophenyl | NHOMe |
| 2-bromo-5-(CF₃)-phenyl | NHOMe | 2-bromo-5-(CF₃)-phenyl | NHOMe |
| 5-chloro-2-methylphenyl | NHOMe | 5-chloro-2-methylphenyl | NHOMe |
| 5-bromo-2-methylphenyl | NHOMe | 5-bromo-2-methylphenyl | NHOMe |
| 2-methyl-5-(CF₃)-phenyl | NHOMe | 2-methyl-5-(CF₃)-phenyl | NHOMe |
| 5-chloro-2-methoxyphenyl | NHOMe | 5-chloro-2-methoxyphenyl | NHOMe |
| 5-bromo-2-methoxyphenyl | NHOMe | 5-bromo-2-methoxyphenyl | NHOMe |
| 2-methoxy-5-methylphenyl | NHOMe | 2-methoxy-5-methylphenyl | NHOMe |
| 2-methoxy-5-(CF₃)-phenyl | NHOMe | 2-methoxy-5-(CF₃)-phenyl | NHOMe |
| 2,5-diethylphenyl | NHOMe | 2,5-diethylphenyl | NHOMe |
| 3,5-dimethylpyrazol-1-yl | NHOMe | 3,5-dimethylpyrazol-1-yl | NHOMe |
| 3,5-dichloropyrazol-1-yl | NHOMe | 3,5-dichloropyrazol-1-yl | NHOMe |
| 3,5-dibromopyrazol-1-yl | NHOMe | 3,5-dibromopyrazol-1-yl | NHOMe |
| 3,5-bis-(CF₃)-pyrazol-1-yl | NHOMe | 3,5-bis-(CF₃)-pyrazol-1-yl | NHOMe |
| 5-methyl-3-(CF₃)-pyrazol-1-yl | NHOMe | 5-methyl-3-(CF₃)-pyrazol-1-yl | NHOMe |
| 3,5-dimethyl-1,2,4-triazol-1-yl | NHOMe | 3,5-dimethyl-1,2,4-triazol-1-yl | NHOMe |
| 3,5-dichlorol-1,2,4-triazol-1-yl | NHOMe | 3,5-dichlorol-1,2,4-triazol-1-yl | NHOMe |
| 3,5-dibromo-1,2,4-triazol-1-yl | NHOMe | 3,5-dibromo-1,2,4-triazol-1-yl | NHOMe |
| n-butyl | NHOMe | n-butyl | NHOMe |
| i-amyl | NHOMe | i-amyl | NHOMe |
| 3-methyl-2-buten-1-yl | NHOMe | 3-methyl-2-buten-1-yl | NHOMe |
| propargyl | NHOMe | propargyl | NHOMe |
| 4,4,4-trifluorobutan-1-yl | NHOMe | 4,4,4-trifluorobutan-1-yl | NHOMe |
| 3,3-dichloro-2-propen-1-yl | NHOMe | 3,3-dichloro-2-propen-1-yl | NHOMe |
| 2-(CF₃)-cyclopropyl-1-yl | NHOMe | 2-(CF₃)-cyclopropyl-1-yl | NHOMe |
| i-butoxy | NHOMe | i-butoxy | NHOMe |
| Trifluoromethoxyethyl | NHOMe | Trifluoromethoxyethyl | NHOMe |
| 3,3,3-trifluoropropoxy | NHOMe | 3,3,3-trifluoropropoxy | NHOMe |
| 2-methylphenyl | NHNH₂ | 2-methylphenyl | NHNH₂ |
| 2-methoxyphenyl | NHNH₂ | 2-methoxyphenyl | NHNH₂ |
| 2-chlorophenyl | NHNH₂ | 2-chlorophenyl | NHNH₂ |
| 2-bromophenyl | NHNH₂ | 2-bromophenyl | NHNH₂ |
| 2-ethylphenyl | NHNH₂ | 2-ethylphenyl | NHNH₂ |
| 2-ethoxyphenyl | NHNH₂ | 2-ethoxyphenyl | NHNH₂ |
| 2-(methylthio)-phenyl | NHNH₂ | 2-(methylthio)-phenyl | NHNH₂ |
| 2-(trifluoromethoxy)-phenyl | NHNH₂ | 2-(trifluoromethoxy)-phenyl | NHNH₂ |
| 3-chlorophenyl | NHNH₂ | 3-chlorophenyl | NHNH₂ |
| 3-bromophenyl | NHNH₂ | 3-bromophenyl | NHNH₂ |
| 3-methylphenyl | NHNH₂ | 3-methylphenyl | NHNH₂ |
| 2,5-dimethylphenyl | NHNH₂ | 2,5-dimethylphenyl | NHNH₂ |
| 2,5-dichlorophenyl | NHNH₂ | 2,5-dichlorophenyl | NHNH₂ |
| 2-chloro-5-(CF₃)-phenyl | NHNH₂ | 2-chloro-5-(CF₃)-phenyl | NHNH₂ |

TABLE 3A-continued

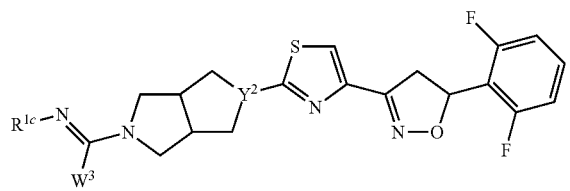

Y² is N.

| R¹ᶜ | W³ | R¹ᶜ | W³ |
|---|---|---|---|
| 2,5-dibromophenyl | NHNH₂ | 2,5-dibromophenyl | NHNH₂ |
| 2-bromo-5-(CF₃)-phenyl | NHNH₂ | 2-bromo-5-(CF₃)-phenyl | NHNH₂ |
| 5-chloro-2-methylphenyl | NHNH₂ | 5-chloro-2-methylphenyl | NHNH₂ |
| 5-bromo-2-methylphenyl | NHNH₂ | 5-bromo-2-methylphenyl | NHNH₂ |
| 2-methyl-5-(CF₃)-phenyl | NHNH₂ | 2-methyl-5-(CF₃)-phenyl | NHNH₂ |
| 5-chloro-2-methoxyphenyl | NHNH₂ | 5-chloro-2-methoxyphenyl | NHNH₂ |
| 5-bromo-2-methoxyphenyl | NHNH₂ | 5-bromo-2-methoxyphenyl | NHNH₂ |
| 2-methoxy-5-methylphenyl | NHNH₂ | 2-methoxy-5-methylphenyl | NHNH₂ |
| 2-methoxy-5-(CF₃)-phenyl | NHNH₂ | 2-methoxy-5-(CF₃)-phenyl | NHNH₂ |
| 2,5-diethylphenyl | NHNH₂ | 2,5-diethylphenyl | NHNH₂ |
| 3,5-dimethylpyrazol-1-yl | NHNH₂ | 3,5-dimethylpyrazol-1-yl | NHNH₂ |
| 3,5-dichloropyrazol-1-yl | NHNH₂ | 3,5-dichloropyrazol-1-yl | NHNH₂ |
| 3,5-dibromopyrazol-1-yl | NHNH₂ | 3,5-dibromopyrazol-1-yl | NHNH₂ |
| 3,5-bis-(CF₃)-pyrazol-1-yl | NHNH₂ | 3,5-bis-(CF₃)-pyrazol-1-yl | NHNH₂ |
| 5-methyl-3-(CF₃)-pyrazol-1-yl | NHNH₂ | 5-methyl-3-(CF₃)-pyrazol-1-yl | NHNH₂ |
| 3,5-dimethyl-1,2,4-triazol-1-yl | NHNH₂ | 3,5-dimethyl-1,2,4-triazol-1-yl | NHNH₂ |
| 3,5-dichlorol-1,2,4-triazol-1-yl | NHNH₂ | 3,5-dichlorol-1,2,4-triazol-1-yl | NHNH₂ |
| 3,5-dibromo-1,2,4-triazol-1-yl | NHNH₂ | 3,5-dibromo-1,2,4-triazol-1-yl | NHNH₂ |
| n-butyl | NHNH₂ | n-butyl | NHNH₂ |
| i-amyl | NHNH₂ | i-amyl | NHNH₂ |
| 3-methyl-2-buten-1-yl | NHNH₂ | 3-methyl-2-buten-1-yl | NHNH₂ |
| propargyl | NHNH₂ | propargyl | NHNH₂ |
| 4,4,4-trifluorobutan-1-yl | NHNH₂ | 4,4,4-trifluorobutan-1-yl | NHNH₂ |
| 3,3-dichloro-2-propen-1-yl | NHNH₂ | 3,3-dichloro-2-propen-1-yl | NHNH₂ |
| 2-(CF₃)-cyclopropyl-1-yl | NHNH₂ | 2-(CF₃)-cyclopropyl-1-yl | NHNH₂ |
| i-butoxy | NHNH₂ | i-butoxy | NHNH₂ |
| Trifluoromethoxyethyl | NHNH₂ | Trifluoromethoxyethyl | NHNH₂ |
| 3,3,3-trifluoropropoxy | NHNH₂ | 3,3,3-trifluoropropoxy | NHNH₂ |

The present disclosure also includes Table 3Ab which is constructed the same as Table 3A above except that the row heading in Table 3A (i.e. "Y² is N") is replaced with the row heading "Y² is NH" and R¹ᶜ and W³ are as defined in Table 3A above. Thus, the first entry in Table 3b specifically discloses a compound of Formula 1A wherein Y² is CH, R¹ᶜ is 2-methylphenyl and W³ is methoxy.

| Table Row Heading | Y² |
|---|---|
| 3Ab | CH |

TABLE 4

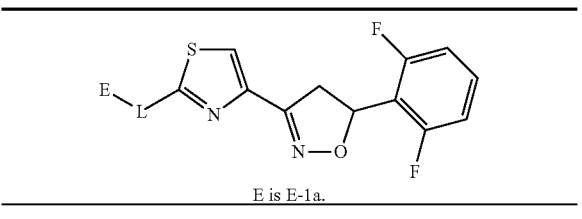

E is E-1a.

| L | R¹⁴ | R²³ |
|---|---|---|
| L-1 | H | — |
| L-2 | H | — |
| L-3 | H | — |
| L-4 | H | — |
| L-5 | H | — |
| L-6 | H | — |
| L-7 | H | — |
| L-8 | H | — |
| L-9 | H | H |
| L-10 | H | H |
| L-11 | H | H |
| L-12 | H | H |
| L-13 | H | — |
| L-14 | H | — |
| L-15 | H | H |
| L-16 | H | — |
| L-17 | H | H |
| L-18 | H | H |
| L-19 | H | H |
| L-20 | H | H |
| L-21 | H | — |
| L-22 | H | — |
| L-23 | H | — |
| L-24 | H | — |
| L-25 | H | — |
| L-26 | H | — |
| L-27 | H | — |
| L-28 | H | — |
| L-29 | H | — |
| L-30 | H | — |
| L-31 | H | — |
| L-32 | H | — |
| L-33 | H | — |
| L-34 | H | — |
| L-35 | H | H |
| L-36 | H | H |
| L-37 | H | H |
| L-38 | H | H |
| L-39 | H | H |
| L-40 | H | — |
| L-41 | H | — |
| L-42 | H | — |
| L-43 | H | — |
| L-44 | H | — |
| L-45 | H | — |
| L-46 | H | — |
| L-47 | H | — |
| L-48 | H | — |
| L-49 | H | — |
| L-50 | H | H |
| L-51 | H | H |
| L-52 | H | H |
| L-53 | H | H |
| L-54 | H | H |
| L-55 | H | — |
| L-56 | H | — |
| L-57 | H | — |
| L-58 | H | — |
| L-59 | H | — |
| L-2 | 2-Me | — |
| L-4 | 4-Me | — |
| L-5 | 6-Me | — |
| L-6 | 6-Me | — |
| L-13 | 3-Me | — |
| L-22 | 2-Me | — |
| L-26 | 2-Me | — |
| L-9 | H | Me |
| L-10 | 2-Me | Me |
| L-11 | H | Me |
| L-12 | H | Me |
| L-15 | H | Me |
| L-35 | H | Me |
| L-50 | H | Me |
| L-9 | H | Ac |
| L-60 | H | — |
| L-61 | H | — |
| L-62 | H | — |
| L-63 | H | — |
| L-64 | H | — |
| L-65 | H | — |

In Table 4 the appropriate L structure from Exhibit 1A, Exhibit 1B and Exhibit 1C above is bonded to the thiazole of the generic Table 4 wherein the bond with the asterisk (*) is connected to the appropriate E value (found below Table 4v) and and "T" is bonded to the 2-position of the thiazole ring. For instance, the first compound listed in Table 4 is a compound of Formula 1 wherein E is E-1a, L is L-1, R¹⁴ is H and there is no value for R²³.

The present disclosure also includes Tables 4b through 4v, each of which is constructed the same as Table 4 above except that the row heading in Table 4 (i.e. "E is E-1a") is replaced with the respective row headings shown below. For example, in Table 4b the row heading is "E is E-1b" and R¹⁴ and R²³ are as defined in Table 4 above. Thus, the first entry in Table 4b specifically discloses a compound of Formula 1 wherein E is E-1b, L is L-1, R¹⁴ is H and there is no value for R²³. Table 4c through 4v are constructed similarly.

| Table Row Heading | E |
|---|---|
| 4b | E-1b |
| 4c | E-1c |
| 4d | E-1d |
| 4e | E-1e |
| 4f | E-1f |
| 4g | E-1g |
| 4h | E-1h |
| 4i | E-1i |
| 4j | E-1j |
| 4k | E-1k |
| 4l | E-1l |
| 4m | E-1m |
| 4n | E-1n |
| 4o | E-2a |
| 4p | E-2b |
| 4q | E-2c |
| 4r | E-2d |
| 4s | E-3a |
| 4t | E-3b |
| 4u | E-3c |
| 4v | E-3d |

Values for variable "E" in Table 4 include E-1a through E-3d:

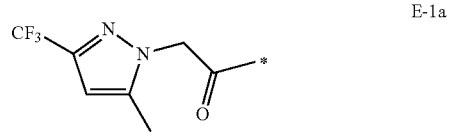

E-1a

-continued

TABLE 5

E is E-1a and X is O.

| G | $R^{29a}$ | $R^{30a}$ |
|---|---|---|
| G-1 | H | — |
| G-2 | H | — |
| G-3 | H | 1-Me |
| G-4 | H | — |
| G-5 | H | — |
| G-6 | H | 1-Me |
| G-7 | — | — |
| G-8 | — | — |
| G-9 | — | H |
| G-10 | H | — |
| G-11 | H | — |
| G-12 | H | 1-Me |
| G-13 | H | H |
| G-14 | H | — |
| G-15 | H | — |
| G-16 | H | 1-Et |
| G-17 | H | — |
| G-18 | H | — |
| G-19 | — | H |
| G-20 | — | — |
| G-21 | — | — |
| G-22 | H | 1-Me |
| G-23 | H | — |
| G-24 | H | — |
| G-25 | H | — |
| G-26 | H | — |
| G-27 | H | — |
| G-28 | H | — |
| G-29 | H | — |
| G-30 | H | — |
| G-31 | H | — |
| G-32 | H | — |
| G-33 | H | — |
| G-34 | H | — |
| G-35 | H | — |
| G-36 | H | — |
| G-37 | H | — |
| G-38 | H | — |
| G-39 | H | 1-Me |
| G-40 | H | — |
| G-41 | H | — |
| G-42 | H | 1-Me |
| G-43 | H | 1-Me |
| G-44 | H | — |
| G-45 | H | — |
| G-46 | — | — |
| G-47 | — | — |
| G-48 | — | 4-Me |
| G-14 | 5-Me | — |
| G-15 | 5-Me | — |
| G-8 | — | 1-Me |
| G-30 | 5-Me | — |
| G-30 | 5-Cl | — |
| G-30 | 5-Br | — |
| G-30 | 5-CN | — |
| G-30 | 5-CF$_3$ | — |

In Table 5 the individual G structures are from Exhibit 2 above (e.g., G-1 through G-48) where the bond projecting to the left is connected to $Y^2$ of Formula 1 and the bond projecting to the right is bonded to the 5-membered isoxazoline ring. For instance, the first compound listed in Table 5 is a comound of Formula 1 wherein E is E-1a (E values from Table 4), X is O, $Y^2$ is C($R^{14}$), G is G-1 (connected to $Y^2$ at the 2-position of the the thiazole ring and connected to the carbon of the 5-membered isoxazoline ring through the 4-position of the thiazole), $R^{29a}$ is H and there is no value for $R^{30a}$.

The present disclosure also includes Tables 5b through 5r, each of which is constructed the same as Table 5 above except that the row heading in Table 5 (i.e. "E is E-1a and X is O") is replaced with the respective row headings shown below. For example, in Table 5b the row heading is "E is E-1g and X is O" and G, $R^{29a}$ and $R^{30}$ are as defined in Table 5 above. Thus, the first entry in Table 5b specifically discloses a compound of Formula 1 wherein E is E-1g, X is O, G is G-1, $R^{29a}$ is H and there is no value for $R^{30a}$. Tables 5c through 5r are constructed similarly.

| Table Row Heading | E | X |
|---|---|---|
| 5b | E-1g | O |
| 5c | E-1h | O |
| 5d | E-2a | O |
| 5e | E-2b | O |
| 5f | E-3a | O |
| 5g | E-1a | NH |
| 5h | E-1g | NH |
| 5i | E-1h | NH |
| 5j | E-2a | NH |
| 5k | E-2b | NH |
| 5l | E-3a | NH |
| 5m | E-1a | N—Me |
| 5n | E-1g | N—Me |
| 5o | E-1h | N—Me |
| 5p | E-2a | N—Me |
| 5q | E-2b | N—Me |
| 5r | E-3a | N—Me |

TABLE 5A

E is E-1a and $Y^2$ is CH.

| G | $R^{29a}$ | $R^{30a}$ |
|---|---|---|
| G-1 | H | — |
| G-2 | H | — |
| G-3 | H | 1-Me |
| G-4 | H | — |
| G-5 | H | — |
| G-6 | H | 1-Me |
| G-7 | — | — |
| G-8 | — | — |
| G-9 | — | H |
| G-10 | H | — |
| G-11 | H | — |
| G-12 | H | 1-Me |
| G-13 | H | H |
| G-14 | H | — |
| G-15 | H | — |
| G-16 | H | 1-Et |
| G-17 | H | — |
| G-18 | H | — |
| G-19 | — | H |
| G-20 | — | — |
| G-21 | — | — |
| G-22 | H | 1-Me |
| G-23 | H | — |
| G-24 | H | — |
| G-25 | H | — |
| G-26 | H | — |
| G-27 | H | — |
| G-28 | H | — |
| G-29 | H | — |
| G-30 | H | — |
| G-31 | H | — |
| G-32 | H | — |
| G-33 | H | — |
| G-34 | H | — |
| G-35 | H | — |
| G-36 | H | — |
| G-37 | H | — |

TABLE 5A-continued

![structure]

E is E-1a and Y² is CH.

| G | R²⁹ᵃ | R³⁰ᵃ |
|---|---|---|
| G-38 | H | — |
| G-39 | H | 1-Me |
| G-40 | H | — |
| G-41 | H | — |
| G-42 | H | 1-Me |
| G-43 | H | 1-Me |
| G-44 | H | — |
| G-45 | H | — |
| G-46 | — | — |
| G-47 | — | — |
| G-48 | — | 4-Me |
| G-14 | 5-Me | — |
| G-15 | 5-Me | — |
| G-8 | — | 1-Me |
| G-30 | 5-Me | — |
| G-30 | 5-Cl | — |
| G-30 | 5-Br | — |
| G-30 | 5-CN | — |
| G-30 | 5-CF₃ | — |

In Table 5A the individual G structures are from Exhibit 2 above (e.g., G-1 through G-48) where the bond projecting to the left is connected to Y² of Formula 1A and the bond projecting to the right is bonded to the 5-membered isoxazoline ring. For instance, the first compound listed in Table 5A is a comound of Formula 1A wherein E is E-1a (E values from Table 4), Y² is CH, G is G-1 (connected to Y² at the 2-position of the thiazole ring and connected to the carbon of the 5-membered isoxazoline ring through the 4-position of the thiazole), R²⁹ᵃ is H and there is no value for R³⁰ᵃ.

The present disclosure also includes Tables 5Ab through 5Al, each of which is constructed the same as Table 5A above except that the row heading in Table 5A (i.e. "E is E-1a and Y² is CH") is replaced with the respective row headings shown below. For example, in Table 5Ab the row heading is "E is E-1g and Y² is CH" and G, R²⁹ᵃ and R³⁰ are as defined in Table 5 above. Thus, the first entry in Table 5Ab specifically discloses a compound of Formula 1A wherein E is E-1g, Y² is CH, G is G-1, R²⁹ᵃ is H and there is no value for R³⁰ᵃ. Tables 5Ac through 5Al are constructed similarly, provided that when Y² is N, then G is not G-25 to G-30 or G-36.

| Table Row Heading | E | Y² |
|---|---|---|
| 5Ab | E-1g | CH |
| 5Ac | E-1h | CH |
| 5Ad | E-2a | CH |
| 5Ae | E-2b | CH |
| 5Af | E-3a | CH |
| 5Ag | E-1a | N |
| 5Ah | E-1g | N |
| 5Ai | E-1h | N |
| 5Aj | E-2a | N |
| 5Ak | E-2b | N |
| 5Al | E-3a | N |

TABLE 6

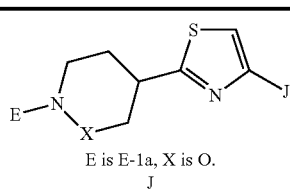

E is E-1a, X is O.

| J |
|---|
| J-29-1 |
| J-29-2 |
| J-29-3 |
| J-29-4 |
| J-29-5 |
| J-29-6 |
| J-29-7 |
| J-29-8 |
| J-29-9 |
| J-29-10 |
| J-29-11 |
| J-29-12 |
| J-29-13 |
| J-29-14 |
| J-29-15 |
| J-29-16 |
| J-29-17 |
| J-29-18 |
| J-29-19 |
| J-29-20 |
| J-29-21 |
| J-29-22 |
| J-29-23 |
| J-29-24 |
| J-29-25 |
| J-29-26 |
| J-29-27 |
| J-29-28 |
| J-29-29 |
| J-29-30 |
| J-29-31 |
| J-29-32 |
| J-29-33 |
| J-29-34 |
| J-29-35 |
| J-29-36 |
| J-29-37 |
| J-29-38 |
| J-29-39 |
| J-29-40 |
| J-29-41 |
| J-29-42 |
| J-29-43 |
| J-29-44 |
| J-29-45 |
| J-29-46 |
| J-29-47 |
| J-29-48 |
| J-29-49 |
| J-29-50 |
| J-29-51 |
| J-29-52 |
| J-29-53 |
| J-29-54 |
| J-29-55 |
| J-29-56 |
| J-29-57 |
| J-29-58 |
| J-83-1 |
| J-84-1 |
| J-85-1 |
| J-86-1 |
| J-87-1 |
| J-88-1 |
| J-89-1 |
| J-90-1 |

TABLE 6-continued

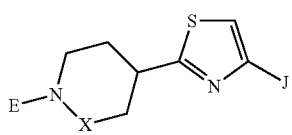

E is E-1a, X is O.

| J |
|---|
| J-92-1 |
| J-93-1 |

In Table 6 the individual structures of each J include J-29-1 through J-29-58 as shown in Exhibits 3A and 4 above. Also in Table 6 the individual structures of each J include J-83-1 through J-93-1 shown below. The bond projecting to the left in each structure of J is connected to the six-membered thiazole ring. When J is represented by one of J-83-1 through J-93-1, then the structure with the carbon atom identified with an asterisk (*) contains a stereocenter.

The present disclosure also includes Tables 6b through 6r, each of which is constructed the same as Table 6 above except that the row heading in Table 6 (i.e. "E is E-1a and X is O") is replaced with the respective row headings shown below. For example, in Table 6b the row heading is "E is E-1g and X is O" and J is as defined in Table 6 above. Thus, the first entry in Table 6b specifically discloses a compound of Formula 1 wherein E is E-1g, X is O, J is J-29-1. Tables 6c through 6r are constructed similarly.

| Table Row Heading | E | X |
|---|---|---|
| 6b | E-1g | O |
| 6c | E-1h | O |
| 6d | E-2a | O |
| 6e | E-2b | O |
| 6f | E-3a | O |
| 6g | E-1a | NH |
| 6h | E-1g | NH |
| 6i | E-1h | NH |
| 6j | E-2a | NH |
| 6k | E-2b | NH |
| 6l | E-3a | NH |
| 6m | E-1a | N—Me |
| 6n | E-1g | N—Me |
| 6o | E-1h | N—Me |
| 6p | E-2a | N—Me |
| 6q | E-2b | N—Me |
| 6r | E-3a | N—Me |

Values for variable "J" in Table 6 above include J-83-1 through J-93-1

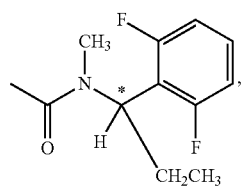

J-83-1

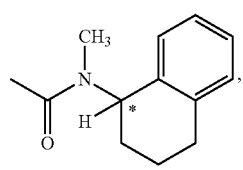

J-84-1

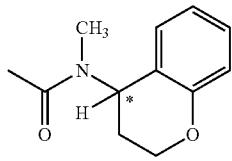

J-85-1

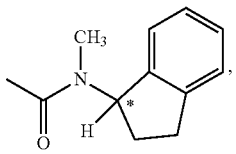

J-86-1

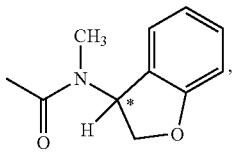

J-87-1

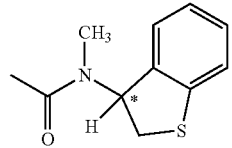

J-88-1

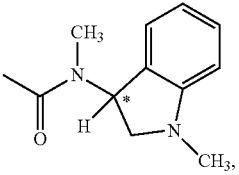

J-89-1

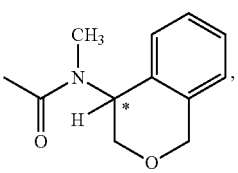

J-90-1

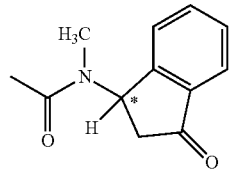

J-92-1

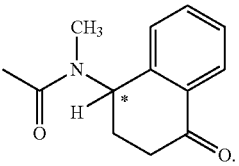

J-93-1

TABLE 6A

E is E-1a, Y² is N.

J
---
J-29-1
J-29-2
J-29-3
J-29-4
J-29-5
J-29-6
J-29-7
J-29-8
J-29-9
J-29-10
J-29-11
J-29-12
J-29-13
J-29-14
J-29-15
J-29-16
J-29-17
J-29-18
J-29-19
J-29-20
J-29-21
J-29-22
J-29-23
J-29-24
J-29-25
J-29-26
J-29-27
J-29-28
J-29-29
J-29-30
J-29-31
J-29-32
J-29-33
J-29-34
J-29-35
J-29-36
J-29-37
J-29-38
J-29-39
J-29-40
J-29-41
J-29-42
J-29-43
J-29-44
J-29-45
J-29-46
J-29-47
J-29-48
J-29-49
J-29-50
J-29-51
J-29-52
J-29-53
J-29-54
J-29-55
J-29-56
J-29-57
J-29-58
J-83-1
J-84-1
J-85-1
J-86-1
J-87-1
J-88-1
J-89-1
J-90-1

TABLE 6A-continued

E is E-1a, Y² is N.

J
---
J-92-1
J-93-1

In Table 6A the individual structures of each J include J-29-1 through J-29-58 as shown in Exhibits 3A and 4 above. Also in Table 6A the individual structures of each J include J-83-1 through J-93-1 shown below. The bond projecting to the left in each structure of J is connected to the six-membered thiazole ring. When J is represented by one of J-83-1 through J-93-1, then the structure with the carbon atom identified with an asterisk (*) contains a stereocenter.

The present disclosure also includes Tables 6Ab through 6Al, each of which is constructed the same as Table 6A above except that the row heading in Table 6A (i.e. "E is E-1a and Y² is N") is replaced with the respective row headings shown below. For example, in Table 6Ab the row heading is "E is E-1g and Y² is N" and J is as defined in Table 6A above. Thus, the first entry in Table 6Ab specifically discloses a compound of Formula 1A wherein E is E-1g, Y² is N, J is J-29-1. Tables 6Ac through 6Al are constructed similarly.

| Table Row Heading | E | Y² |
|---|---|---|
| 6Ab | E-1g | N |
| 6Ac | E-1h | N |
| 6Ad | E-2a | N |
| 6Ae | E-2b | N |
| 6Af | E-3a | N |
| 6Ag | E-1a | CH |
| 6Ah | E-1g | CH |
| 6Ai | E-1h | CH |
| 6Aj | E-2a | CH |
| 6Ak | E-2b | CH |
| 6Al | E-3a | CH |

Values for variable "J" in Table 6A above include J-83-1 through J-93-1

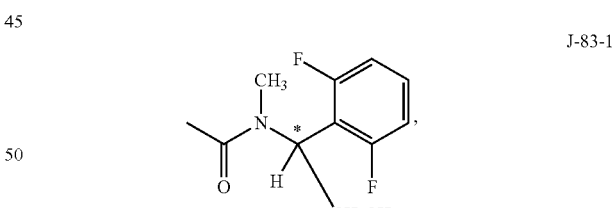

J-83-1

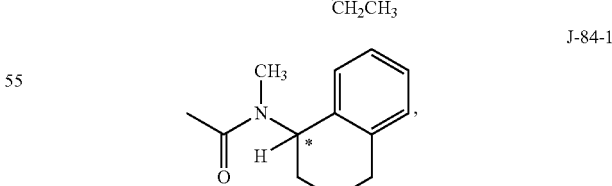

J-84-1

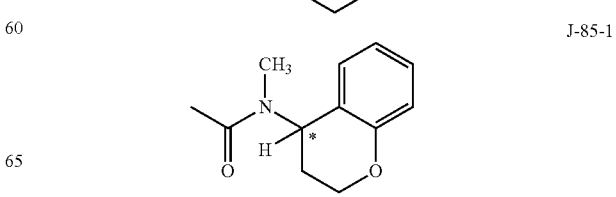

J-85-1

-continued
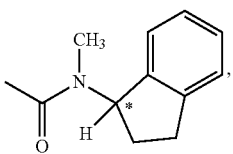
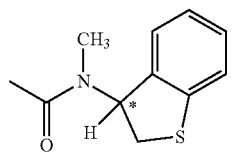
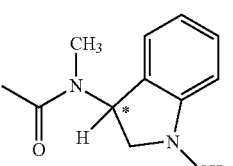
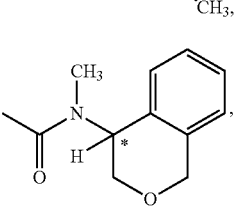
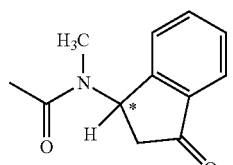
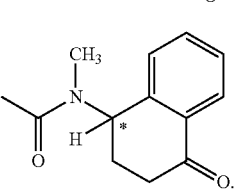
J-86-1
J-87-1
J-88-1
J-89-1
J-90-1
J-92-1
J-93-1
TABLE 7
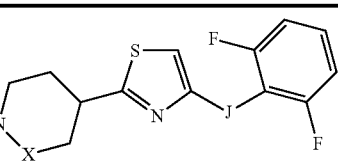
E is E-1a and X is O:
J
J-1 (2/4)
J-1 (2/5)
J-1 (4/2)
J-1 (5/2)
J-2 (2/4)
TABLE 7-continued
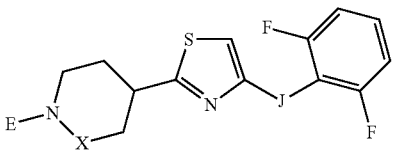
E is E-1a and X is O:
J
J-2 (2/5)
J-2 (4/2)
J-2 (5/2)
J-3 (4/1)
J-4 (2/4)
J-4 (2/5)
J-4 (4/2)
J-4 (5/2)
J-4 (3/5)
J-4 (5/3)
J-5 (2/5)
J-5 (4/2)
J-5 (5/2)
J-5 (3/5)
J-5 (5/3)
J-6 (2/4)
J-6 (3/5)
J-6 (2/5)
J-6 (4/2)
J-6 (5/2)
J-6 (4/2)
J-6 (5/3)
J-6 (3/1)
J-7 (5/3)
J-7 (3/5)
J-8 (5/3)
J-8 (3/5)
J-9 (4/1)
J-10 (3/5)
J-10 (5/3)
J-11 (3/5)
J-11 (5/3)
J-12 (3/1)
J-13 (1/14)
J-13 (4/1)
J-14 (5/3)
J-15 (2/5)
J-16 (2/5)
J-17 (4/2)
J-18 (5/2)
J-19 (2/4)
J-19 (4/2)
J-20 (2/4)
J-20 (2/5)
J-20 (2/6)
J-20 (3/5)
J-20 (4/2)
J20 (5/2)
J-21 (3/5)
J-21 (3/6)
J-21 (5/3)
J-22 (2/4)
J-22 (2/5)
J-22 (4/6)
J-22 (4/2)
J-22 (5/2)
J-23 (2/5)
J-23 (2/6)
J-24 (2/4)
J-24 (2/5)
J-24 (4/2)
J-24 (5/2)
J-25 (2/4)
J-25 (2/5)
J-25 (4/2)
J-25 (5/2)
J-26 (2/4)
J-26 (2/5)
J-26 (4/2)
J-26 (5/2)

TABLE 7-continued

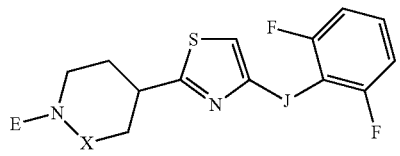

E is E-1a and X is O:
J

| J |
|---|
| J-26 (4/1) |
| J-27 (2/4) |
| J-27 (2/5) |
| J-27 (3/5) |
| J-27 (4/2) |
| J-27 (5/2) |
| J-27 (5/3) |
| J-28 (3/5) |
| J-28 (5/3) |
| J-29 (3/5) |
| J-29 (5/3) |
| J-30 (3/5) |
| J-30 (5/3) |
| J-30 (3/1) |
| J-30 (4/1) |
| J-31 (2/4) |
| J-31 (2/5) |
| J-31 (3/5) |
| J-31 (3/1) |
| J-31 (4/1) |
| J-31 (4/2) |
| J-31 (5/2) |
| J-32 (2/4) |
| J-32 (2/5) |
| J-32 (3/5) |
| J-32 (5/3) |
| J-32 (5/2) |
| J-32 (4/2) |
| J-33 (2/4) |
| J-33 (2/5) |
| J-33 (3/5) |
| J-33 (5/3) |
| J-33 (5/2) |
| J-33 (4/2) |
| J-34 (1/3) |
| J-34 (1/4) |
| J-34 (3/5) |
| J-34 (3/1) |
| J-34 (4/1) |
| J-35 (4/1) |
| J-36 (1/3) |
| J-36 (3/1) |
| J-36 (3/5) |
| J-36 (5/3) |
| J-37 (2/5) |
| J-37 (5/2) |
| J-37 (2/4) |
| J-37 (4/2) |
| J-38 (2/5) |
| J-38 (5/2) |
| J-38 (2/4) |
| J-38 (4/2) |
| J-40 (3/5) |
| J-40 (5/3) |
| J-41 (1/3) |
| J-41 (1/4) |
| J-44 (1/3) |
| J-44 (2/4) |
| J-44 (2/5) |
| J-44 (2/6) |
| J-45 (2/4) |
| J-45 (2/5) |
| J-45 (2/6) |
| J-46 (2/4) |
| J-46 (2/5) |
| J-46 (4/2) |
| J-46 (5/2) |
| J-47 (2/4) |
| J-47 (2/5) |
| J-47 (4/2) |

TABLE 7-continued

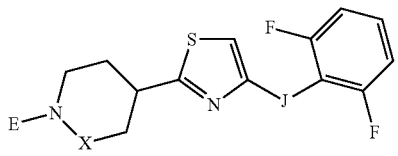

E is E-1a and X is O:
J

| J |
|---|
| J-47 (5/2) |
| J-48 (3/5) |
| J-49 (2/4) |
| J-49 (2/5) |
| J-49 (4/2) |
| J-49 (5/2) |
| J-50 (2/6) |
| J-51 (2/6) |
| J-52 (2/6) |
| J-69 (1/3) |
| J-69 (1/4) |
| J-70 (1/3) |
| J-71 (2/4) |
| J-71 (4/2) |
| J-72 (2/4) |
| J-72 (4/2) |
| J-73 (2/4) |
| J-73 (4/2) |
| J-73 (1/3) |
| J-73 (1/4) |
| J-73 (4/1) |
| J-74 (3/5) |
| J-74 (5/3) |
| J-75 (3/5) |
| J-75 (5/3) |
| J-75 (2/4) |
| J-75 (2/5) |
| J-76 (3/6) |
| J-76 (6/3) |
| J-77 (3/5) |
| J-77 (5/3) |
| J-78 (1/3) |
| J-79 (1/3) |
| J-79 (3/1) |
| J-80 (1/3) |
| J-80 (3/1) |
| J-81 (3/5) |
| J-81 (5/3) |
| J-82 (3/5) |
| J-82 (3/6) |
| J-82 (5/3) |
| J-82 (6/3) |

In Table 7 the individual structures of each J refer to the individual J values from Exhibit 3 (e.g., J-1 through J-82). The numbers in parentheses following J refer to the attachment points of the J ring to the thiazole and the 2,6-difluorophenyl ring. The first number is the ring position on J where the thiazole is attached, and the second number is the ring position on J where the 2,6-difluorophenyl ring is attached.

The present disclosure also includes Tables 7b through 7r, each of which is constructed the same as Table 7 above except that the row heading in Table 7 (i.e. "E is E-1a and X is O") is replaced with the respective row headings shown below. For example, in Table 7b the row heading is "E is E-1g and X is O" and G is as defined in Table 7 above. Thus, the first entry in Table 7b specifically discloses a compound of Formula 1 wherein E is E-1g, X is O, J is J-1 attached at the 2-position of J-1 to the thiazole, and at the 4-position to the 2,6-difluorophenyl ring. Tables 7c through 7r are constructed similarly.

| Table Row Heading | E | X |
|---|---|---|
| 7b | E-1g | O |
| 7c | E-1h | O |
| 7d | E-2a | O |
| 7e | E-2b | O |
| 7f | E-3a | O |

-continued

| Table Row Heading | E | X |
|---|---|---|
| 7g | E-1a | NH |
| 7h | E-1g | NH |
| 7i | E-1h | NH |
| 7j | E-2a | NH |
| 7k | E-2b | NH |
| 7l | E-3a | NH |
| 7m | E-1a | N—Me |
| 7n | E-1g | N—Me |
| 7o | E-1h | N—Me |
| 7p | E-2a | N—Me |
| 7q | E-2b | N—Me |
| 7r | E-3a | N—Me |

TABLE 7A

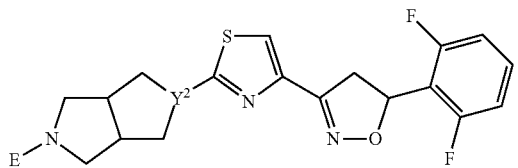

E is E-1a and Y² is N.
J

J-1 (2/4)
J-1 (2/5)
J-1 (4/2)
J-1 (5/2)
J-2 (2/4)
J-2 (2/5)
J-2 (4/2)
J-2 (5/2)
J-3 (4/1)
J-4 (2/4)
J-4 (2/5)
J-4 (4/2)
J-4 (5/2)
J-4 (3/5)
J-4 (5/3)
J-5 (2/5)
J-5 (4/2)
J-5 (5/2)
J-5 (3/5)
J-5 (5/3)
J-6 (2/4)
J-6 (3/5)
J-6 (2/5)
J-6 (4/2)
J-6 (5/2)
J-6 (4/2)
J-6 (5/3)
J-6 (3/1)
J-7 (5/3)
J-7 (3/5)
J-8 (5/3)
J-8 (3/5)
J-9 (4/1)
J-10 (3/5)
J-10 (5/3)
J-11 (3/5)
J-11 (5/3)
J-12 (3/1)
J-13 (1/4)
J-13 (4/1)
J-14 (5/3)
J-15 (2/5)
J-16 (2/5)
J-17 (4/2)
J-18 (5/2)
J-19 (2/4)
J-19 (4/2)
J-20 (2/4)
J-20 (2/5)

TABLE 7A-continued

E is E-1a and Y² is N.
J

J-20 (2/6)
J-20 (3/5)
J-20 (4/2)
J20 (5/2)
J-21 (3/5)
J-21 (3/6)
J-21 (5/3)
J-22 (2/4)
J-22 (2/5)
J-22 (4/6)
J-22 (4/2)
J-22 (5/2)
J-23 (2/5)
J-23 (2/6)
J-24 (2/4)
J-24 (2/5)
J-24 (4/2)
J-24 (5/2)
J-25 (2/4)
J-25 (2/5)
J-25 (4/2)
J-25 (5/2)
J-26 (2/4)
J-26 (2/5)
J-26 (4/2)
J-26 (5/2)
J-26 (4/1)
J-27 (2/4)
J-27 (2/5)
J-27 (3/5)
J-27 (4/2)
J-27 (5/2)
J-27 (5/3)
J-28 (3/5)
J-28 (5/3)
J-29 (3/5)
J-29 (5/3)
J-30 (3/5)
J-30 (5/3)
J-30 (3/1)
J-30 (4/1)
J-31 (2/4)
J-31 (2/5)
J-31 (3/5)
J-31 (3/1)
J-31 (4/1)
J-31 (4/2)
J-31 (5/2)
J-32 (2/4)
J-32 (2/5)
J-32 (3/5)
J-32 (5/3)
J-32 (5/2)
J-32 (4/2)
J-33 (2/4)
J-33 (2/5)
J-33 (3/5)
J-33 (5/3)
J-33 (5/2)
J-33 (4/2)
J-34 (1/3)
J-34 (1/4)
J-34 (3/5)
J-34 (3/1)
J-34 (4/1)
J-35 (4/1)
J-36 (1/3)
J-36 (3/1)
J-36 (3/5)

TABLE 7A-continued

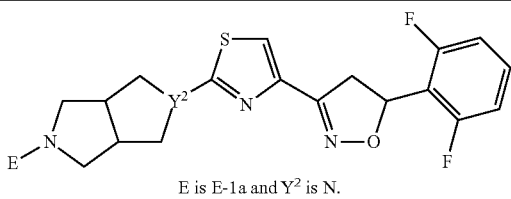

E is E-1a and Y² is N.

| J |
|---|
| J-36 (5/3) |
| J-37 (2/5) |
| J-37 (5/2) |
| J-37 (2/4) |
| J-37 (4/2) |
| J-38 (2/5) |
| J-38 (5/2) |
| J-38 (2/4) |
| J-38 (4/2) |
| J-40 (3/5) |
| J-40 (5/3) |
| J-41 (1/3) |
| J-41 (1/4) |
| J-44 (1/3) |
| J-44 (2/4) |
| J-44 (2/5) |
| J-44 (2/6) |
| J-45 (2/4) |
| J-45 (2/5) |
| J-45 (2/6) |
| J-46 (2/4) |
| J-46 (2/5) |
| J-46 (4/2) |
| J-46 (5/2) |
| J-47 (2/4) |
| J-47 (2/5) |
| J-47 (4/2) |
| J-47 (5/2) |
| J-48 (3/5) |
| J-49 (2/4) |
| J-49 (2/5) |
| J-49 (4/2) |
| J-49 (5/2) |
| J-50 (2/6) |
| J-51 (2/6) |
| J-52 (2/6) |
| J-69 (1/3) |
| J-69 (1/4) |
| J-70 (1/3) |
| J-71 (2/4) |
| J-71 (4/2) |
| J-72 (2/4) |
| J-72 (4/2) |
| J-73 (2/4) |
| J-73 (4/2) |
| J-73 (1/3) |
| J-73 (1/4) |
| J-73 (4/1) |
| J-74 (3/5) |
| J-74 (5/3) |
| J-75 (3/5) |
| J-75 (5/3) |
| J-75 (2/4) |
| J-75 (2/5) |
| J-76 (3/6) |
| J-76 (6/3) |
| J-77 (3/5) |
| J-77 (5/3) |
| J-78 (1/3) |
| J-79 (1/3) |
| J-79 (3/1) |
| J-80 (1/3) |
| J-80 (3/1) |
| J-81 (3/5) |
| J-81 (5/3) |
| J-82 (3/5) |
| J-82 (3/6) |
| J-82 (5/3) |
| J-82 (6/3) |

TABLE 7A-continued

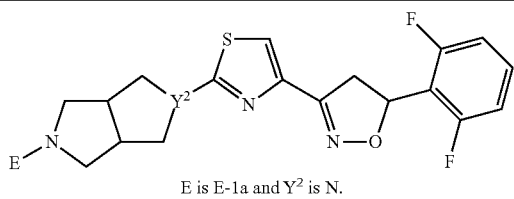

E is E-1a and Y² is N.

J

In Table 7A the individual structures of each J refer to the individual J values from Exhibit 3 (e.g., J-1 through J-82). The numbers in parentheses following J refer to the attachment points of the J ring to the thiazole and the 2,6-difluorophenyl ring. The first number is the ring position on J where the thiazole is attached, and the second number is the ring position on J where the 2,6-difluorophenyl ring is attached.

The present disclosure also includes Tables 7Ab through 7Al, each of which is constructed the same as Table 7A above except that the row heading in Table 7A (i.e. "E is E-1a and Y² is N") is replaced with the respective row headings shown below. For example, in Table 7Ab the row heading is "E is E-1g and Y² is N" and G is as defined in Table 7A above. Thus, the first entry in Table 7Ab specifically discloses a compound of Formula 1A wherein E is E-1g, Y² is N, J is J-1 attached at the 2-position of J-1 to the thiazole, and at the 4-position to the 2,6-difluorophenyl ring. Tables 7Ac through 7Al are constructed similarly.

| Table Row Heading | E | Y² |
|---|---|---|
| 7Ab | E-1g | N |
| 7Ac | E-1g | N |
| 7Ad | E-1h | N |
| 7Ae | E-2a | N |
| 7Af | E-2b | N |
| 7Ag | E-1a | CH |
| 7Ah | E-1g | CH |
| 7Ai | E-1h | CH |
| 7Aj | E-2a | CH |
| 7Ak | E-2b | CH |
| 7Al | E-3a | CH |

TABLE 8

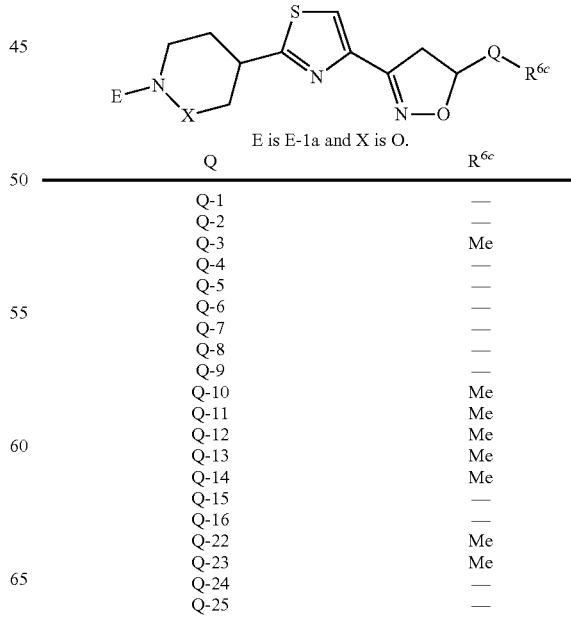

E is E-1a and X is O.

| Q | R^{6c} |
|---|---|
| Q-1 | — |
| Q-2 | — |
| Q-3 | Me |
| Q-4 | — |
| Q-5 | — |
| Q-6 | — |
| Q-7 | — |
| Q-8 | — |
| Q-9 | — |
| Q-10 | Me |
| Q-11 | Me |
| Q-12 | Me |
| Q-13 | Me |
| Q-14 | Me |
| Q-15 | — |
| Q-16 | — |
| Q-22 | Me |
| Q-23 | Me |
| Q-24 | — |
| Q-25 | — |

TABLE 8-continued

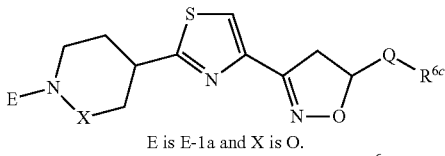

E is E-1a and X is O.

| Q | R6c |
|---|---|
| Q-26 | — |
| Q-27 | — |
| Q-28 | Me |
| Q-29 | — |
| Q-30 | — |
| Q-31 | Me |
| Q-32 | — |
| Q-33 | — |
| Q-34 | — |
| Q-35 | — |
|  | — |
| Q-17 |  |
| Q-18 | — |
| Q-19 | — |
| Q-20 | — |
| Q-21 | Me |
| Q-42 | — |
| Q-43 | — |
| Q-44 | — |
| Q-46 | — |
| Q-48 | — |
| Q-49 | — |
| Q-50 | — |
| Q-51 | — |
| Q-52 | — |
| Q-53 | — |
| Q-36 | — |
| Q-36 | — |
| Q-37 | — |
| Q-38 | — |
| Q-39 | — |
| Q-40 | — |
| Q-41 | — |
| Q-61 | — |
| Q-62 | — |
| Q-63 | — |
| Q-64 | — |
| Q-65 | — |
| Q-66 | — |
| Q-67 | — |
| Q-68 | — |
| Q-69 | — |
| Q-70 | — |
| Q-71 | — |
| Q-72 | Me |
| Q-73 | — |
| Q-74 | — |
| Q-75 | Me |
| Q-76 | — |
| Q-77 | — |
| Q-78 | Me |
| Q-79 | Me |
| Q-80 | — |
| Q-81 | — |
| Q-82 | — |
| Q-83 | — |
| Q-84 | — |
| Q-85 | — |
| Q-86 | Me |
| A-87 | — |
| Q-88 | Me |
| Q-89 | — |
| Q-90 | — |
| Q-91 | — |
| Q-92 | Me |
| Q-93 | — |
| Q-94 | — |
| Q-95 | Me |
| Q-96 | — |
| Q-97 | — |

TABLE 8-continued

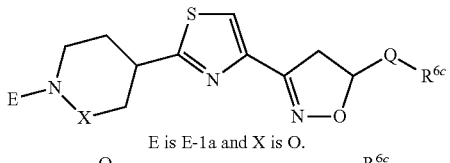

E is E-1a and X is O.

| Q | R6c |
|---|---|
| Q-98 | — |
| Q-99 | — |
| Q-100 | — |
| Q-101 | — |
| Q-102 | Me |

In Table 8 the individual structures of each Q ring refer to the individual Q ring values from Exhibit 6 (e.g., Q-1 through Q-102) and are attached to the 5-position of the isoxazoline ring trough the bond projectin to the left. In Table 8, the Q ring is unsubstituted (i.e. $R^6$ and $R^{6a}$ are both H). When present, the $R^{6c}$ value is listed in Table 8.

The present disclosure also includes Tables 8b through 8r, each of which is constructed the same as Table 8 above except that the row heading in Table 8 (i.e. "E is E-1a and X is O") is replaced with the respective row headings shown below. For example, in Table 8b the row heading is "E is E-1g. and X is O" and Q and $R^{6c}$ are as defined in Table 8 above. Thus, the first entry in Table 8b specifically discloses a compound of Formula 1 wherein E is E-1g, X is O, Q is Q-1 and $R^{6c}$ is H. Tables 8c through 8r are constructed similarly.

| Table Row Heading | E | X |
|---|---|---|
| 8b | E-1g | O |
| 8c | E-1h | O |
| 8d | E-2a | O |
| 8e | E-2b | O |
| 8f | E-3a | O |
| 8g | E-1a | NH |
| 8h | E-1g | NH |
| 8i | E-1h | NH |
| 8j | E-2a | NH |
| 8k | E-2b | NH |
| 8l | E-3a | NH |
| 8m | E-1a | N—Me |
| 8n | E-1g | N—Me |
| 8o | E-1h | N—Me |
| 8p | E-2a | N—Me |
| 8q | E-2b | N—Me |
| 8r | E-3a | N—Me |

TABLE 8A

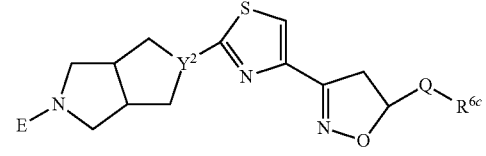

E is E-1a and Y² is O.

| Q | R6c |
|---|---|
| Q-1 | — |
| Q-2 | — |
| Q-3 | Me |
| Q-4 | — |
| Q-5 | — |
| Q-6 | — |
| Q-7 | — |
| Q-8 | — |
| Q-9 | — |
| Q-10 | Me |
| Q-11 | Me |
| Q-12 | Me |

TABLE 8A-continued

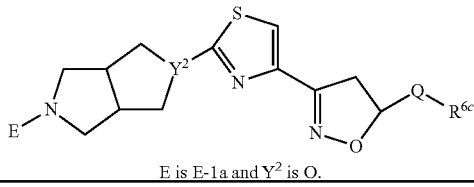

E is E-1a and Y² is O.

| Q | R⁶ᶜ |
|---|---|
| Q-13 | Me |
| Q-14 | Me |
| Q-15 | — |
| Q-16 | — |
| Q-17 | — |
| Q-18 | — |
| Q-19 | — |
| Q-20 | — |
| Q-21 | Me |
| Q-22 | Me |
| Q-23 | Me |
| Q-24 | — |
| Q-25 | — |
| Q-26 | — |
| Q-27 | — |
| Q-28 | Me |
| Q-29 | — |
| Q-30 | — |
| Q-31 | Me |
| Q-32 | — |
| Q-33 | — |
| Q-34 | — |
| Q-35 | — |
| Q-36 | — |
| Q-36 | — |
| Q-37 | — |
| Q-38 | — |
| Q-39 | — |
| Q-40 | — |
| Q-41 | — |
| Q-42 | — |
| Q-43 | — |
| Q-44 | — |
| Q-46 | — |
| Q-48 | — |
| Q-49 | — |
| Q-50 | — |
| Q-51 | — |
| Q-52 | — |
| Q-53 | — |
| Q-54 | — |
| Q-55 | — |
| Q-56 | — |
| Q-57 | — |
| Q-58 | — |
| Q-59 | — |
| Q-60 | — |
| Q-61 | — |
| Q-62 | — |
| Q-63 | — |
| Q-64 | — |
| Q-65 | — |
| Q-66 | — |
| Q-67 | — |
| Q-68 | — |
| Q-69 | — |
| Q-70 | — |
| Q-71 | — |
| Q-72 | Me |
| Q-73 | — |
| Q-74 | — |
| Q-75 | Me |
| Q-76 | — |
| Q-77 | — |
| Q-78 | Me |
| Q-79 | Me |
| Q-80 | — |
| Q-81 | — |

TABLE 8A-continued

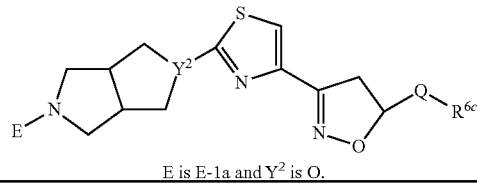

E is E-1a and Y² is O.

| Q | R⁶ᶜ |
|---|---|
| Q-82 | — |
| Q-83 | — |
| Q-84 | — |
| Q-85 | — |
| Q-86 | Me |
| Q-87 | — |
| Q-88 | Me |
| Q-89 | — |
| Q-90 | — |
| Q-91 | — |
| Q-92 | Me |
| Q-93 | — |
| Q-94 | — |
| Q-95 | Me |
| Q-96 | — |
| Q-97 | — |
| A-98 | — |
| Q-99 | — |
| Q-100 | — |
| Q-101 | — |
| Q-102 | Me |

In Table 8A the individual structures of each Q ring refer to the individual Q ring values from Exhibit 6 (e.g., Q-1 throught Q-102) and are attached to the 5-position of the isoxazoline ring trough the bond projectin to the left. In Table 8A, the Q ring is unsubstituted (i.e. R⁶ and R⁶ᵃ are both H). When present, the R⁶ᶜ value is listed in Table 8A.

The present disclosure also includes Tables 8Ab through 8Al, each of which is constructed the same as Table 8A above except that the row heading in Table 8A (i.e. "E is E-1a and Y² is N") is replaced with the respective row headings shown below. For example, in Table 8Ab the row heading is "E is E-1g and Y² is N" and Q and R⁶ᶜ are as defined in Table 8A above. Thus, the first entry in Table 8Ab specifically discloses a compound of Formula 1A wherein E is E-1g, Y² is N, Q is Q-1 and R⁶ᶜ is H. Tables 8Ac through 8Al are constructed similarly.

| Table Row Heading | E | Y² |
|---|---|---|
| 8Ab | E-1g | N |
| 8Ac | E-1h | N |
| 8Ad | E-2a | N |
| 8Ae | E-2b | N |
| 8Af | E-3a | N |
| 8Ag | E-1a | CH |
| 8Ah | E-1g | CH |
| 8Ai | E-1h | CH |
| 8Aj | E-2a | CH |
| 8Ak | E-2b | CH |
| 8Al | E-3a | CH |

TABLE 9

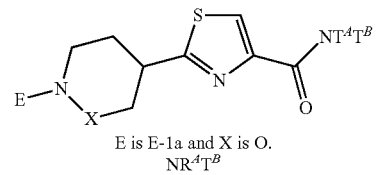

E is E-1a and X is O.
NRᴬTᴮ

(1R)-N-methyl-1-phenylethylamino
(1R)-N-methyl-1-phenylpropylamino

TABLE 9-continued

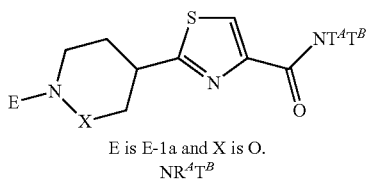

E is E-1a and X is O.
$NR^AT^B$ (1R)-N-methyl-1,2,3,4-tetrahydro-1-naphthalenylamino
N-methyl-4-hydroxy-1,2,3,4-tetrahydro-1-naphthalenylamino
N,2-dimethyl-1,2,3,4-tetrahydro-1-naphthalenylamino
N,2,2-trimethyl-1,2,3,4-tetrahydro-1-naphthalenylamino
N-methyl-4-oxo-1,2,3,4-tetrahydro-1-naphthalenylamino
(1R)-N-methyl-1-indanylamino
N,2-dimethyl-1-indanylamino
N,2,2-trimethyl-1-indanylamino
N-methyl-3-hydroxy-1-indanylamino
N-methyl-3-oxo-1-indanylamino
(1R)-N-ethyl-1-phenylethylamino
(1R)-N-propyl-1-phenylethylamino
(1R)-NH-1-phenylethylamino
(1R)-N-methyl-1-(2-methylphenyl)ethylamino
(1R)-N-methyl-1-(2-fluorophenyl)ethylamino
(1R)-N-methyl-1-(2-chlorophenyl)ethylamino
(1R)-N-methyl-1-(2-bromophenyl)ethylamino
(1R)-N-methyl-1-(2-cyanophenyl)ethylamino
(1R)-N-methyl-1-(2-trifluoromethylphenyl)ethylamino
(1R)-N-methyl-1-(2-methoxyphenyl)ethylamino
(1R)-N-methyl-1-(2,6-dimethylphenyl)ethylamino
(1R)-N-methyl-1-(2,6-dimethoxyphenyl)ethylamino
(1R)-N-methyl-1-(2,6-difluorophenyl)ethylamino
(1R)-N-methyl-1-(2,6-dichlorophenyl)ethylamino
(1R)-N-methyl-1-(2,6-difluorophenyl)propylamino
(1R)-N-methyl-1-(2,6-difluorophenyl)butylamino The present disclosure also includes Tables 9b through 9r, each of which is constructed the same as Table 9 above except that the row heading in Table 9 (i.e. "E is E-1a and X is O") is replaced with the respective Table Row Heading shown below. For example, in Table 9b the row heading is "E is E-1g and X is O" and $NT^AT^B$ is as defined in Table 9 above. Thus, the first entry in Table 9b specifically discloses a compound of Formula 1 wherein E is E-1g, X is O and $NT^AT^B$ is (1R)—N-methyl-1-phenylethylamino. Tables 9c through 9r are constructed similarly.

| Table Row Heading | E | X |
|---|---|---|
| 9b | E-1g | O |
| 9c | E-1h | O |
| 9d | E-2a | O |
| 9e | E-2b | O |
| 9f | E-3a | O |
| 9g | E-1a | NH |
| 9h | E-1g | NH |
| 9i | E-1h | NH |
| 9j | E-2a | NH |
| 9k | E-2b | NH |
| 9l | E-3a | NH |
| 9m | E-1a | N—Me |
| 9n | E-1g | N—Me |
| 9o | E-1h | N—Me |
| 9p | E-2a | N—Me |
| 9q | E-2b | N—Me |
| 9r | E-3a | N—Me |

TABLE 9A

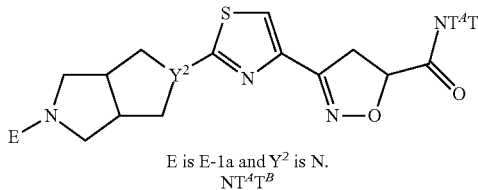

E is E-1a and $Y^2$ is N.
$NT^AT^B$ (1)-N-methyl-1-phenylethylamino
(1R)-N-methyl-1-phenylpropylamino
(1R)-N-methyl-1,2,3,4-tetrahydro-1-naphthalenylamino
N-methyl-4-hydroxy-1,2,3,4-tetrahydro-1-naphthalenylamino
N,2-dimethyl-1,2,3,4-tetrahydro-1-naphthalenylamino
N,2,2-trimethyl-1,2,3,4-tetrahydro-1-naphthalenylamino
N-methyl-4-oxo-1,2,3,4-tetrahydro-1-naphthalenylamino
(1R)-N-methyl-1-indanylamino
N,2-dimethyl-1-indanylamino
N,2,2-trimethyl-1-indanylamino
N-methyl-3-hydroxy-1-indanylamino
N-methyl-3-oxo-1-indanylamino
(1R)-N-ethyl-1-phenylethylamino
(1R)-N-propyl-1-phenylethylamino
(1R)-NH-1-phenylethylamino
(1R)-N-methyl-1-(2-methylphenyl)ethylamino
(1R)-N-methyl-1-(2-fluorophenyl)ethylamino
(1R)-N-methyl-1-(2-chlorophenyl)ethylamino
(1R)-N-methyl-1-(2-bromophenyl)ethylamino
(1R)-N-methyl-1-(2-cyanophenyl)ethylamino
(1R)-N-methyl-1-(2-trifluoromethylphenyl)ethylamino
(1R)-N-methyl-1-(2-methoxyphenyl)ethylamino
(1R)-N-methyl-1-(2,6-dimethylphenyl)ethylamino
(1R)-N-methyl-1-(2,6-dimethoxyphenyl)ethylamino
(1R)-N-methyl-1-(2,6-difluorophenyl)ethylamino
(1R)-N-methyl-1-(2,6-dichlorophenyl)ethylamino
(1R)-N-methyl-1-(2,6-difluorophenyl)propylamino
(1R)-N-methyl-1-(2,6-difluorophenyl)butylamino The present disclosure also includes Tables 9Ab through 9A1, each of which is constructed the same as Table 9A above except that the row heading in Table 9A (i.e. "E is E-1a and $Y^2$ is N") is replaced with the respective Table Row Heading shown below. For example, in Table 9Ab the row heading is "E is E-1g and $Y^2$ is N" and $NT^AT^B$ is as defined in Table 9A above. Thus, the first entry in Table 9Ab specifically discloses a compound of Formula 1A wherein E is E-1g, $Y^2$ is N and $NT^AT^B$ is (1R)—N-methyl-1-phenylethylamino. Tables 9Ac through 9Al are constructed similarly.

| Table Row Heading | E | X |
|---|---|---|
| 9Ab | E-1g | N |
| 9Ac | E-1h | N |
| 9Ad | E-2a | N |
| 9Ae | E-2b | N |
| 9Af | E-3a | N |

| Table Row Heading | E | $Y^2$ |
|---|---|---|
| 9g | E-1a | CH |
| 9h | E-1g | CH |
| 9Ai | E-1h | CH |
| 9Aj | E-2a | CH |
| 9Ak | E-2b | CH |
| 9Al | E-3a | CH |

Formulation/Utility

A compound of Formula 1 or Formula 1A of this invention including N-oxides and salts thereof will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 or Formula 1A and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

EXAMPLE A

High Strength Concentrate

| | |
|---|---|
| Compound 2 | 98.5% |
| silica aerogel | 0.5% |
| synthetic amorphous fine silica | 1.0% |

EXAMPLE B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

Granule

| | |
|---|---|
| Compound 3 | 10.0% |
| attapulgite granules (low volatile matter, 0.71/0.30 mm; U.S.S. No. 25-50 sieves) | 90.0% |

EXAMPLE D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

Emulsifiable Concentrate

| | |
|---|---|
| Compound 2 | 10.0% |
| polyoxyethylene sorbitol hexoleate | 20.0% |
| $C_6$-$C_{10}$ fatty acid methyl ester | 70.0% |

EXAMPLE F

Microemulsion

| | |
|---|---|
| Compound 3 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

Seed Treatment

| | |
|---|---|
| Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and

*Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 or Formula 1A (in a fungicidally effective amount) and at least one additional biologically active Compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1 or Formula 1A, to form a premix, or one or more other biologically active compounds or agents can be formulated separately from the compound of Formula 1 or Formula 1A, and the formulations combined together before application (e.g., in a spray tank) or, alternatively, applied in succession.

Of note is a composition which in addition to the compound of Formula 1 or Formula 1A include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-)pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, N-[2-(1S,2R)-[1,1'-bicyclopropyl]-2-ylphenyl]-3-(difluoromethyl)-1-methyl-1H-pyrazole-4-carboxamide and penflufen (N-[2-(1,3-dimethyl-butyl)phenyl]-5-fluoro-1,3-dimethyl-1H-pyrazole-4-carboxamide). The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071), picoxystrobin and pyraoxystrobin (SYP-3343). The methoxycarbamates include pyraclostrobin and pyrametostrobin (SYP-4155). The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide.
The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen and tebufloquin are examples of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintoiene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzehe-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb, valifenalate and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamatc fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide. Resistance Action Committee (FRAC) code M3), (45.4) "phthalimide fungicides" (Fungicide Resistance Action Committee (FRAC) code M4), (45.5) "chloronitrilc fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7), (46.4) "benzophenone fungicides" (Fungicide Resistance Action Committee (FRAC) code U8) and (46.5) "triazolopyrimidine fungicides". The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone. The triazolopyrimidines include ametoctradin. The (b46) class also includes bethoxazin, neo-asozin (ferric methanearsonate), pyrrolnitrin, quinomethionate, N-[2-[4-[[3-(4-chloro-phenyl)-2-propyn-1-yl]oxy]-3-methoxyphenyl]ethyl]-3-methyl-2-[(methylsulfonyl)amino]-butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]-propyl]carbamate, 5-chloro-6-(2,4,6-trifluorophenyl)-7-(4-methylpiperidin-1-yl)[1,2,4]-triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl] methylene]-benzeneacetamide, N'-[4-[4-chloro-3-(trifluoromethyl)phenoxy]-2,5-dimethylphenyl]-N-ethyl-N-methylmethanimidamide, 1-[(2-propenylthio)carbonyl]-2-(1-methylethyl)-4-(2-methylphenyl)-5-amino-1H-pyrazol-3-one, N-[9-(dichloromethylene)-1,2,3,4-tetrahydro-1,4-methanonaphthalen-5-yl]-3-(difluoromethyl)-1-methyl-1H-pyrazole-4-carboxamide, 3-(di-fluoromethyl)-N-[9-(difluoromethylene)-1,2,3,4-tetrahydro-1,4-methanonaphthalen-5-yl]-1-methyl-1H-pyrazole-4-carboxamide, N-[9-(dibromomethylene)-1,2,3,4-tetrahydro-1,4-methanonaphthalen-5-yl]-3-(difluoromethyl)-1-methyl-1H-pyrazole-4-carboxamide, N-[9-(dibromomethylene)-1,2,3,4-tetrahydro-1,4-methanonaphthalen-5-yl]-1-methyl-3-(trifluoromethyl)-1H-pyrazole-4-carboxamide, N-[9-(difluoromethylene)-1,2,3,4-tetrahydro-1,4-methanonaphthalen-5-yl]-1-methyl-3-(trifluoromethyl)-1H-pyrazole-4-carboxamide and N-[9-(dichloromethylene)-1,2,3,4-tetrahydro-1,4-methanonaphthalen-5-yl]-1-methyl-3-(trifluoromethyl)-1H-pyrazole-4-carboxamide.

Therefore of note is a mixture (i.e. composition) comprising a compound of Formula 1 or Formula 1A and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 or Formula 1A and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, milbemycin oxime, monocrotophos, methoxyfenozide, nicotine, nitenpyram, nithiazine, novaluron, noviflumuron (X DE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 or Formula 1A is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 or Formula 1A alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 or Formula 1A with at least one other fungicidal active ingredient. Of particular note is such a combination where the other fungicidal active ingredient has different site of action from the compounds of Formula 1 and Formula 1A. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 or Formula 1A include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

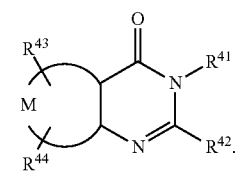

wherein M forms a fused phenyl, thiophene or pyridine ring; $R^{41}$ is $C_1$-$C_6$ alkyl; $R^{42}$ is $C_1$-$C_6$ alkyl or $C_1$-$C_6$ alkoxy; $R^{43}$ is halogen; and $R^{44}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propyl-thieno[2,3-d]pyrimidin-4(3H)-one, 6-bromo-2-propoxy-3-propylthieno[2,3-d]pyrimidin-4(3H)-one; 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propyl-thieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 or Formula 1A with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Preferred for better control of plant diseases caused by fungal plant pathogens (e.g., lower use rate or broader spectrum of plant pathogens controlled) or resistance management are mixtures of a compound of this invention with a fungicide selected from the group azoxystrobin, kresoxim-methyl, trifloxystrobin, pyraclostrobin, picoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, tebuconazole, triticonazole, famoxadone and penthiopyrad.

Specifically preferred mixtures (compound numbers refer to compounds in Index Tables A-B) are selected from the group: combinations of Compound 1, Compound 2, or Compound 3 with azoxystrobin, combinations of Compound 1, Compound 2 or Compound 3, with kresoxim-methyl, combinations of Compound 1, Compound 2 or Compound 3, with trifloxystrobin, combinations of Compound 1, Compound 2 or Compound 3 with pyraclostrobin, combinations of Compound 1, Compound 2 or Compound 3 with picoxystrobin, combinations of Compound 1, Compound 2 or Compound 3 with dimoxystrobin, combinations of Compound 1, Compound 2 or Compound 3 with metominostrobin/fenominostrobin, combinations of Compound 1, Compound 2 or Compound 3 with quinoxyfen, combinations of Compound 1, Compound 2 or Compound 3 with metrafenone, combinations of Compound 1, Compound 2 or Compound 3 with cyflufenamid, combinations of Compound 1, Compound 2 or Compound 3 with fenpropidine, combinations of Compound 1, Compound 2 or Compound 3 with fenpropimorph, combinations of Compound 1, Compound 2 or Compound 3 with cyproconazole, combinations of Compound 1, Compound 2 or Compound 3 with epoxiconazole, combinations of Compound 1, Compound 2 or Compound 3 with flusilazole, combinations of Compound 1, Compound 2 or Compound 3 with metconazole, combinations of Compound 1, Compound 2 or Compound 3 with propiconazole, combinations of Compound 1, Compound 2 or Compound 3 with prothioconazole, combinations of Compound 1, Compound 2 or Compound 3 with tebuconazole, combinations of Compound 1, Compound 2 or Compound 3 with triticonazole, combinations of Compound 1, Compound 2 or Compound 3 with famoxadone, and combinations of Compound 1, Compound 2 or Compound 3 with penthiopyrad.

The rate of application required for effective control (i.e. "biologically effective amount") will depend on such factors as the plant diseases to be controlled, the location, time of year, host crop, ambient moisture, temperature, and the like. One skilled in the art can easily determine through simple experimentation the biologically effective amount necessary for the desired level of plant disease control. The following Tests A-C demonstrate the control efficacy of compounds of this invention on specific pathogens. The pathogen control protection afforded by the compounds is not limited, however, to these Tests (i.e. Tests A-C below). Descriptions of the compounds are provided in Index Tables A-B below. The following abbreviations are used in the index tables: Me is methyl, Ph is phenyl, MeO is methoxy, CN is cyano, $NO_2$ is nitro and Ac means acetyl. The abbreviation "Cmpd. No." means compound number, and "Ex." stands for "Example" and is followed by a number indicating in which example the compound is prepared. The numerical value reported in under the column heading "AP+(M+1)", is the molecular weight of the highest isotopic abundance parent ion (M+1) formed by addition of H+(molecular weight of 1) to the molecule, observed by mass spectrometry using atmospheric pressure chemical ionization (AP+). The presence of molecular ions containing one or higher atomic weight isotopes of lower abundance (e.g., $^{37}Cl$, $^{81}Br$) is not reported.

INDEX TABLE A

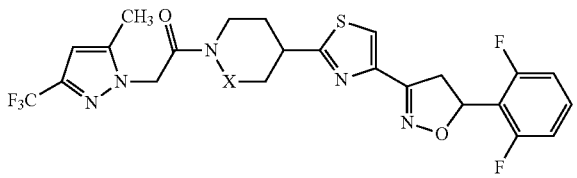

| Cmpd. No. | X | AP+ (M + 1) | $^1$H NMR |
|---|---|---|---|
| 1 (Ex. 1) | NH | 541 | * |
| 2 (Ex. 2) | N—Ac | 583 | * |
| 3 (Ex. 3) | O | 542 | * |

*See Index Table C for $^1$H NMR data

INDEX TABLE B

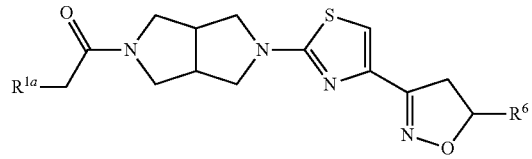

| Cmpd. No. | $R^{1a}$ | $R^6$ | MS (M + 1) | $^1$H NMR |
|---|---|---|---|---|
| 4 | 2,5-di-Me—Ph | 2,6-di-F—Ph | 523 | * |
| 5 | 2,5-di-Me—Ph | Ph | 487 | * |
| 6 (Ex. 4) | 5-Me-3-CF$_3$-pyrazol-1-yl | 2,6-di-F—Ph | 567 | * |
| 7 | 5-Me-3-CF$_3$-1H-pyrazol-1-yl, | Ph | 531 | * |

*See Index Table C for $^1$H NMR data.

INDEX TABLE C

| Compd. No. | $^1$H NMR Data (CDCl3 solution unless indicated otherwise)$^a$ |
|---|---|
| 1 | δ (−40° C., CD$_3$CN): 1.95-2.10 (m, 1H), 2:20-2.35 (m, 4H), 2.95-3.15 (m, 2H), 3.40-3.55 (m, 2H), 3.55-3.67 (m, 1H), 3.80-3.95 (m, 1H), 4.50-4.60 (m, 1H), 5.25-5.45 (m, 2H), 6.10-6.20 (m, 1H), 6.50 (s, 1H), 7.05-7.20 (m, 2H), 7.43-7.55 (m, 1H), 7.92 (s, 1H). |
| 2 | δ 2.00-2.38 (m, 8H), 2.85-3.90 (m, 5H), 4.30-4.80 (m, 2H), 4.90-5.10 (m, 2H), 6.02-6.15 (m, 1H), 6.30-6.40 (m, 1H), 6.85-6.98 (m, 2H), 7.25-7.38 (m, 1H), 7.75 (s, 1H). |
| 3 | δ 2.05-2.20 (m, 1H), 2.20-2.35 (m, 4H), 3.40-3.55 (m, 1H), 3.55-3.70 (m, 2H), 3.75-3.88 (m, 1H), 4.08-4.20 (m, 1H), 4.35-4.45 (m, 1H), 4.45-4.55 (m, 1H), 5.08 (s, 2H), 6.02-6.12 (m, 1H), 6.30 (s, 1H), 6.85-6.98 (m, 2H), 7.25-7.38 (m, 1H), 7.72 (s, 1H). |
| 4 | δ 7.26-7.29 (m, 1H), 6.68-6.98 (m, 6H), 6.0-6.06 (m, 1H), 3.53-3.83 (m, 5H), 3.47 (s, 2H), 3.39-3.44 (m, 5H), 3.08-3.11 (m, 2H), 2.27 (s, 3H), 2.23 (s, 3H). |
| 5 | δ 7.31-7.40 (m, 5H), 7.05-7.06 (d, 1H), 6.93-6.98 (m, 2H), 6.81 (s, 1H), 5.68-5.72 (m, 1 H), 3.71-3.83 (m, 5H), 3.58 (s, 2H), 3.28-3.58 (m, 5H), 3.05-3.15 (m, 2H), 2.27 (s, 3H), 2.23 (s, 3H). |
| 6 | δ 7.27-7.29 (m, 1H), 6.86-6.92 (m, 3H), 6.32 (s, 1H), 6.0-6.03 (m, 1H), 4.81-4.93 (q, 2H), 3.5-3.88 (m, 10H), 3.1-3.25 (m, 2H), 2.32 (s, 3H). |
| 7 | δ 7.31-7.40 (m, 5H), 6.82 (s, 1H), 6.32 (s, 1H), 5.68-5.73 (m, 1H), 4.85-4.89 (q, 2H), 3.74-3.88 (m, 5H), 3.1-3.53 (m, 7H), 2.32 (s, 3H). |

$^a$$^1$H NMR data are in ppm downfield from tetramethylsilane. Couplings are designated by (s)—singlet, (d)—doublet, (q)—quartete and (m)—multiplet.

Biological Examples of the Invention

General protocol for preparing test suspensions for Tests A-C: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-C. Spraying a 200 ppm test suspension to the point of run-off on the test plants was the equivalent of a rate of 800 g/ha. Unless otherwise indicated, the rating values indicate a 200 ppm test suspension was used. (An asterisk "*" next to the rating value indicates a 40 ppm test suspension was used.)

Test A

Grape seedlings were inoculated with a spore suspension of *Plasmopara viticola* (the causal agent of grape downy mildew) and incubated in a saturated atmosphere at 20° C. for 24 h. After a short drying period, the grape seedlings were sprayed with the test suspension to the point of run-off, then moved to a growth chamber at 20° C. for 5 days, and then back to a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test C

Tomato seedlings were inoculated with a spore suspension of *Phytophthora infestans* (the causal agent of tomato late blight) and incubated in a saturated atmosphere at 20° C. for 17 h. After a short drying period, the tomato seedlings were sprayed with a test suspension to the point of run-off and then moved to a growth chamber at 20° C. for 4 days, after which time visual disease ratings were made.

In addition to Tests A-C, the compounds were also sprayed on 2 separate sets of tomato plants, which were inoculated with *Botrytis cinerea* or *Alternaria solani* 24 h after treatment, and wheat plants, which were inoculated with *Blumeria graminis* f. sp. *tritici*. Test compounds did not show activity against these additional pathogens under the test conditions at the application rates tested.

Results for Tests A-C are given in Table A. In the table, a rating of 100 indicates 100% disease control and a rating of 0 indicates no disease control (relative to the controls). An asterisk "*" next to the rating value indicates a 40 ppm test suspension was used.

TABLE A

| Cmpd. No | Test A | Test B | Test C |
| --- | --- | --- | --- |
| 1 | 99* | 100* | 99* |
| 2 | 89* | 100* | 98* |
| 3 | 100* | 100* | 99* |
| 4 | 99* | 100* | 99* |
| 5 | 81* | 92* | 64* |
| 6 | 99* | 100* | 99* |
| 7 | 57* | 100* | 99* |

What is claimed is:

1. A compound selected from Formula 1 or Formula 1A, N-oxides and salts thereof,

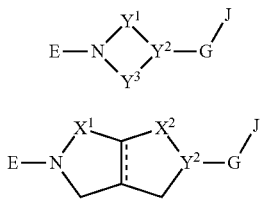

1

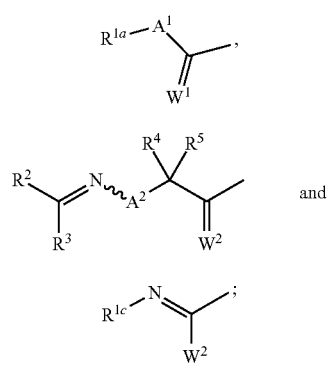

1A wherein

E is a radical selected from the group consisting of

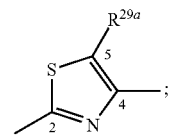

E-1

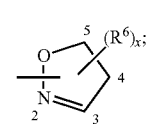

E-2 and

E-3

$Y^1$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(=O)—;

$Y^2$ is a ring member selected from —C($R^{14}$)— and —N—;

$Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S—, —N($R^{23}$)— and —C(=O)—; or $Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S—, —N($R^{23}$)— and —C(=O)—;

$X^1$ and $X^2$ are each independently a ring member selected from —C($R^{14}$)— and —O—;

G is

G-1 wherein the bond projecting to the left is bonded to $Y^2$ in Formula 1 or Formula 1A, and the bond projecting to the right is bonded to J in Formula 1 or Formula 1A; each $R^{29a}$ is independently selected from H and $R^{29}$;

J is

J-29 wherein the bond shown projecting to the left is bonded to G in Formula 1 or Formula 1A and to an available carbon or nitrogen atom ring member in the J ring; and x is an integer from 0 to 5;

$A^1$ is $CHR^{15}$, $NR^{16}$ or C(=O);

$A^2$ is —O—, —S—, —N($R^7$)—, —C($R^8$)$_2$—, —OC($R^8$)$_2$—, —SC($R^8$)$_2$— or —N($R^7$)C($R^8$)$_2$—, wherein the bond projecting to the left is connected to —N=C($R^2$)($R^3$), and the bond projecting to the right is connected to —C($R^4$)($R^5$)—;

$W^1$ and $W^2$ are each independently O or S;

$W^3$ is $OR^{24}$, $SR^{25}$, $NR^{26}R^{27}$ or $R^{28}$;

$R^{1a}$ and $R^{1c}$ independently are an optionally substituted phenyl, an optionally substituted naphthalenyl or an optionally substituted 5- to 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

or pyrrolidinyl, piperidinyl or morpholinyl, cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{10}$ alkylcycloalkylalkyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_1$-$C_8$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_8$ alkylsulfonylamino or $C_1$-$C_8$ halo alkylsulfonylamino;

$R^2$ is H, halogen, cyano, amino, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_4$-$C_6$ halocycloalkylalkyl, $C_3$-$C_6$ cycloalkenyl, $C_3$-$C_6$ halocycloalkenyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_2$-$C_6$ alkylcarbonyl, $C_2$-$C_6$ haloalkylcarbonyl, $C_4$-$C_6$ cycloalkylcarbonyl, $C_2$-$C_6$ alkoxycarbonyl, $C_4$-$C_6$ cycloalkoxycarbonyl, $C_5$-$C_6$ cycloalkylalkoxycarbonyl, $C_2$-$C_6$ alkylaminocarbonyl, $C_3$-$C_6$ dialkylaminocarbonyl, $C_1$-$C_6$ alkoxy, $C_1$-$C_6$ haloalkoxy, $C_3$-$C_6$ cycloalkoxy, $C_3$-$C_6$ halocycloalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_6$ cycloalkylthio, $C_1$-$C_6$ alkylamino, $C_2$-$C_6$ dialkylamino, $C_1$-$C_6$ haloalkylamino, $C_2$-$C_6$ halodialkylamino, $C_3$-$C_6$ cycloalkylamino, $C_2$-$C_6$ alkylcarbonylamino, $C_2$-$C_6$ haloalkylcarbonylamino, $C_1$-$C_6$ alkylsulfonylamino or $C_1$-$C_6$ haloalkylsulfonylamino;

$R^3$ is H, halogen, cyano, hydroxy, $C_1$-$C_3$ alkyl, $C_1$-$C_3$ haloalkyl, $C_1$-$C_3$ alkoxy or $C_1$-$C_3$ haloalkoxy; or $R^2$ and $R^3$ are taken together with the carbon atom to which they are attached to form a 3- to 7-membered ring containing ring members selected from carbon atoms and up to 4 heteroatoms independently selected from up to 2 O, up to 2 S, up to 2 N and up to 2 Si atoms, wherein up to 3 carbon atom ring members are independently selected from C(=O) and C(=S), the sulfur atom ring members are independently selected from S(=O)$_s$(=NR$^{11}$)$_f$ and the silicon atom ring members are independently selected from SiR$^9$R$^{10}$, the ring optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^4$ is optionally substituted phenyl, optionally substituted naphthalenyl or an optionally substituted 5- to 6-membered heteroaromatic ring; or H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyloxy, $C_2$-$C_4$ haloalkylcarbonyloxy, $C_2$-$C_5$ alkoxycarbonyloxy, $C_2$-$C_5$ alkylaminocarbonyloxy or $C_3$-$C_5$ dialkylaminocarbonyloxy;

$R^5$ is H, $C_1$-$C_3$ alkyl or $C_1$-$C_3$ haloalkyl;

each $R^6$ is independently H, halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino, —NR$^{20}$R$^{21}$ or —ZQ;

each Z is independently a direct bond, O, C(=O), S(O)$_m$, CH(R$^{12}$) or N(R$^{13}$);

each Q is independently phenyl, benzyl, naphthalenyl, a 5- to 6-membered heteroaromatic ring or an 8- to 11-membered heteroaromatic bicyclic ring system, each optionally substituted with up to 2 substituents independently selected from R$^{6b}$ on carbon and nitrogen atom ring members, and each optionally substituted with up to 5 substituents independently selected from R$^{6a}$ on carbon atom ring members and selected from $C_1$-$C_3$ alkyl, $C_2$-$C_3$ alkylcarbonyl, $C_2$-$C_3$ alkoxycarbonyl or $C_1$-$C_3$ alkoxy on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S(=O)$_s$(=NR$^{11}$)$_f$ and the silicon atom ring members are independently selected from SiR$^9$R$^{10}$, each ring or ring system optionally substituted with up to 2 substituents independently selected from R$^{6b}$ on carbon and nitrogen atom ring members, and each ring or ring system optionally substituted with up to 5 substituents independently selected from R$^{6b}$ on carbon atom ring members and selected from $C_1$-$C_3$ alkyl, $C_2$-$C_3$ alkylcarbonyl, $C_2$-$C_3$ alkoxycarbonyl and $C_1$-$C_3$ alkoxy on nitrogen atom ring members;

each $R^{6a}$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or each $R^{6b}$ is independently phenyl optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy; or a 5- to 6-membered heteroaromatic ring containing ring members selected from carbon atoms and up to 4 heteroatoms independently selected from up to 2 O, up to 2 S and up to 4 N atoms, and optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members; or a 3- to 7-membered nonaromatic ring containing ring members selected from carbon atoms and up to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^7$ is H, cyano, $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylsulfonyl or $C_1$-$C_4$ haloalkylsulfonyl; or $R^3$ and $R^7$ are taken together with the linking atoms to which they are attached to form a 5-to 7-membered partially saturated ring containing ring members, in addition to the linking atoms, selected from carbon atoms and up to 3 heteroatoms independently selected from up to 1 O, up to 1 S and up to 1 N atom, the ring optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

each $R^8$ is independently H, $C_1$-$C_3$ alkyl or $C_1$-$C_3$ haloalkyl;

each $R^9$ and $R^{10}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each $R^{11}$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylamino, $C_2$-$C_8$ dialkylamino, $C_1$-$C_6$ haloalkylamino or phenyl;

each $R^{12}$ is independently H, $C_1$-$C_4$ alkyl or $C_1$-$C_4$ haloalkyl;

$R^{13}$ is H, $C_1$-$C_4$ alkyl, $C_1$-$C_4$ haloalkyl, $C_3$-$C_6$ cycloalkyl, $C_2$-$C_4$ alkylcarbonyl, $C_2$-$C_4$ haloalkylcarbonyl, $C_2$-$C_4$ alkoxycarbonyl or $C_2$-$C_4$ haloalkoxycarbonyl;

each $R^{14}$ is independently H, halogen, cyano, hydroxy, $C_1$-$C_4$ alkyl, $C_1$-$C_4$ alkenyl, $C_1$-$C_4$ haloalkyl or $C_1$-$C_4$ alkoxy;

$R^{15}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_3$-$C_5$ alkoxycarbonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

$R^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;

each $R^{20}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{21}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —$Z^1Q$;

each $Z^1$ is independently O, C(=O), S(O)$_m$ or CH($R^{12}$);

each $R^{23}$ is independently H, —CHO, $C_1$-$C_4$ alkyl, $C_1$-$C_4$ alkenyl, $C_1$-$C_4$ haloalkyl, $C_1$-$C_3$ alkylcarbonyl, $C_2$-$C_4$ alkoxyalkyl, $C_2$-$C_4$ alkoxycarbonyl, $C_2$-$C_4$ alkylaminocarbonyl, $C_4$-$C_7$ dialkylaminocarbonyl or $C_2$-$C_4$ alkylsulfonyl;

each $R^{24}$ and $R^{25}$ is independently $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_2$-$C_6$ alkoxyalkyl, $C_4$-$C_8$ cycloalkoxyalkyl, $C_3$-$C_6$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl;

$R^{26}$ is H, cyano, hydroxy, amino, $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_4$-$C_8$ cycloalkylalkyl, $C_2$-$C_6$ alkoxyalkyl, $C_1$-$C_6$ alkoxy, $C_1$-$C_6$ haloalkoxy, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_1$-$C_6$ alkylamino, $C_2$-$C_8$ dialkylamino, $C_1$-$C_6$ haloalkylamino or $C_2$-$C_8$ halodialkylamino;

$R^{27}$ is H, $C_1$-$C_6$ alkyl, $C_3$-$C_6$ alkenyl, $C_3$-$C_6$ alkynyl, $C_1$-$C_6$ haloalkyl or $C_3$-$C_6$ cycloalkyl; or $R^{26}$ and $R^{27}$ are taken together as $-(CH_2)_4-$, $-(CH_2)_5-$ or $-(CH_2)_2O(CH_2)_2-$;

$R^{28}$ is H, halogen, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl or $C_3$-$C_6$ dialkylaminocarbonyl;

each $R^{29}$ is independently halogen, $C_1$-$C_3$ alkyl or $C_1$-$C_3$ haloalkyl;

each $R^{33a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{33b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each m is independently 0, 1 or 2; and s and f are independently 0, 1 or 2 in each instance of $S(=O)_s(=NR^{11})_f$, provided that the sum of s and f is 1 or 2;

provided that:

(a) when $Y^1$ is a ring-forming chain consisting of 2 chain members and $Y^3$ is a ring-forming chain consisting of 2 or 3 chain members, then at least one of the chain members of $Y^1$ or $Y^3$ is other than $C(R^{14})_2$;

(b) when $Y^1$ is a ring-forming chain consisting of 2 chain members or $Y^3$ is a ring-forming chain consisting of 2 or 3 chain members and when a chain member is $-C(=O)-$, then said chain member is bonded to other than N-E in Formula 1;

(c) when $X^1$ is $-O-$, then $X^2$ is $-C(R^{14})-$ and the ring is fully saturated; and when $X^2$ is $-O-$, then $X^1$ is $-C(R^{14})-$ and the ring is fully saturated;

(d) when $Y^2$ is N, then the heterocyclic ring G is bonded to $Y^2$ through a carbon atom; and (f) when $R^{15}$ is hydroxy, then $R^{1a}$ is bonded through a carbon atom to A in Formula 1 or Formula 1A.

2. A compound of claim 1 wherein:

E is E-3;

$Y^1$ is $-N=C(R^{14})-$, $-C(R^{14})=N-$ or a ring-forming chain consisting of 2 chain members wherein one chain member is $-C(R^{14})_2-$ and the second chain member is selected from $-C(R^{14})_2-$, $-O-$, $-S-$ and $-N(R^{23})-$;

$Y^3$ is $-N=C(R^{14})-$, $-C(R^{14})=N-$ or a ring-forming chain consisting of 2 chain members wherein one chain member is $-C(R^{14})_2-$ and the second chain member is selected from $-C(R^{14})_2-$, $-O-$, $-S-$ and $-N(R^{23})-$; or $Y^3$ is $-C(R^{14})_2N=C(R^{14})-$, $-C(R^{14})_2C(R^{14})=N-$, $-N=C(R^{14})C(R^{14})_2-$, $-C(R^{14})=NC(R^{14})_2-$ or a ring-forming chain consisting of 3 chain members wherein two chain members are $-C(R^{14})_2-$ and the third chain member is selected from $-C(R^{14})_2-$, $-O-$, $-S-$ and $-N(R^{23})-$;

$W^3$ is $OR^{24}$, $SR^{25}$ or $NR^{26}R^{27}$;

$R^{1c}$ is an optionally substituted phenyl, an optionally substituted naphthalenyl or an optionally substituted 5- to 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ haloalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;

$R^6$ is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, $-NR^{20}R^{21}$ or $-ZQ$;

$R^{6a}$ is independently halogen, hydroxy, cyano, $C_1$-$C_2$ alkyl or $C_1$-$C_2$ alkoxy; or Z is independently a direct bond, O, $C(=O)$, $S(=O)_2$ or $CH(R^{12})$;

Q is a ring selected from Q-1 through Q-102 optionally substituted with from 0 to 5 $R^{6a}$ on carbon members and optionally substituted with $R^{6c}$ on nitrogen ring members;

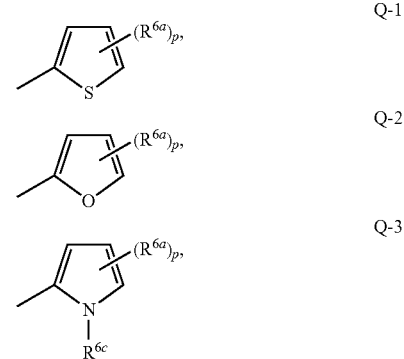

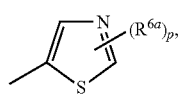 Q-4
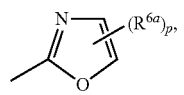 Q-5
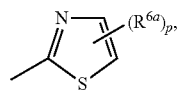 Q-6
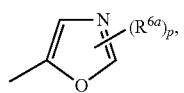 Q-7
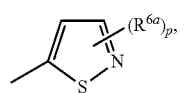 Q-8
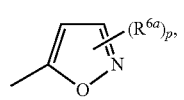 Q-9
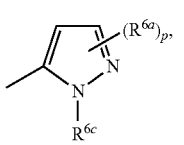 Q-10
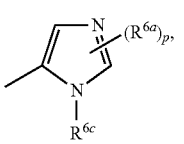 Q-11
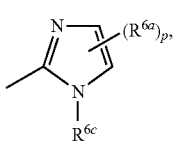 Q-12
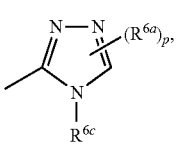 Q-13
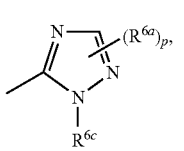 Q-14
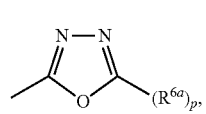 Q-15
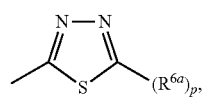 Q-16
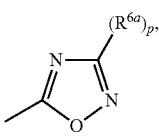 Q-17
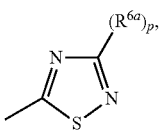 Q-18
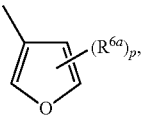 Q-19
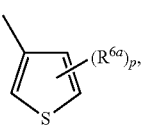 Q-20
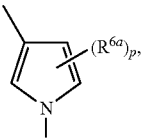 Q-21
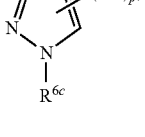 Q-22
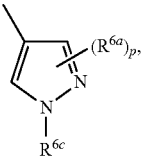 Q-23
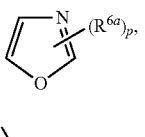 Q-24
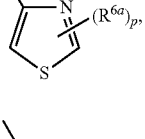 Q-25
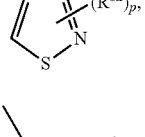 Q-26
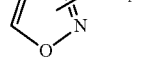 Q-27

| Q-28 through Q-54 structures (chemical substituent reference list) |

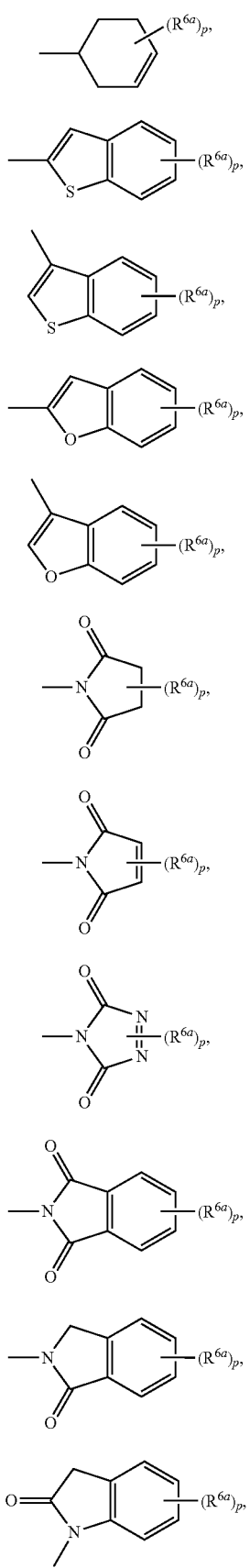
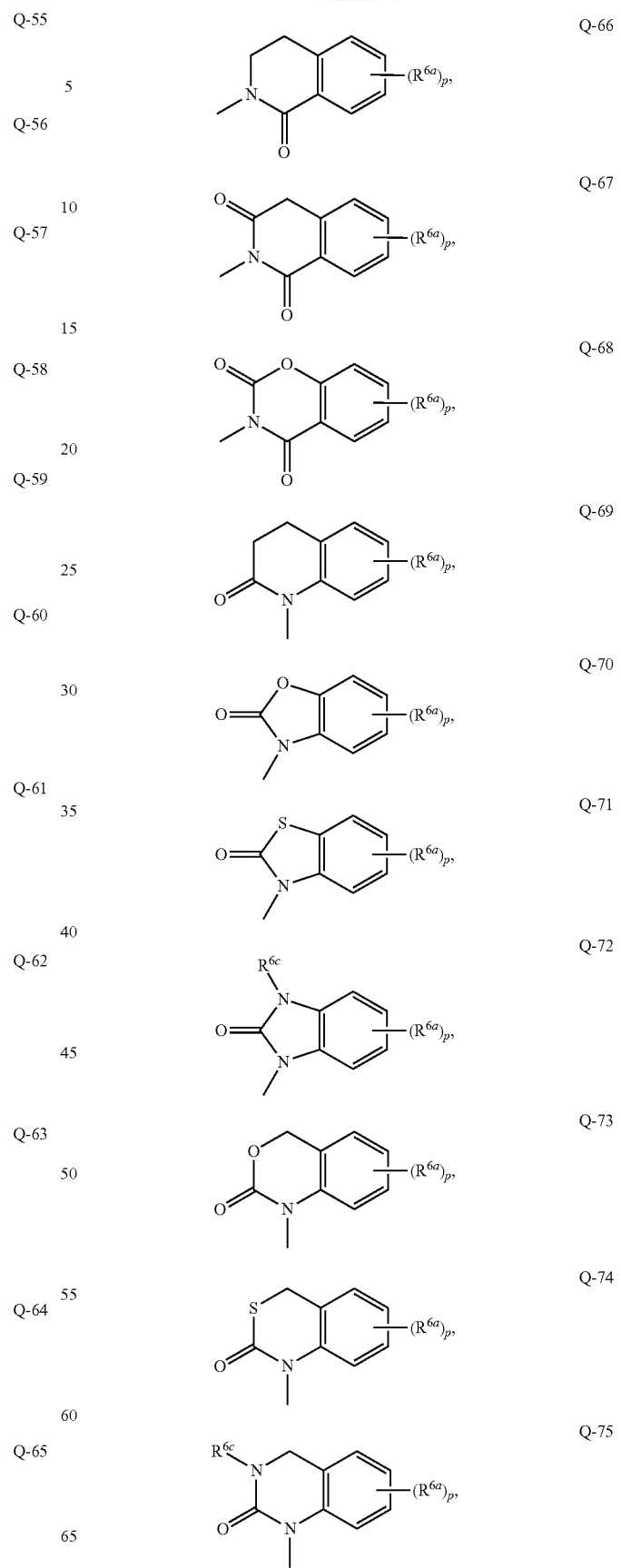

-continued
Q-76
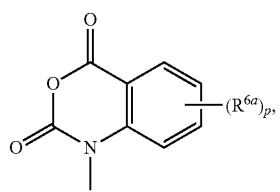
Q-77
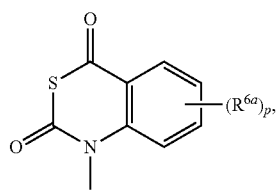
Q-78
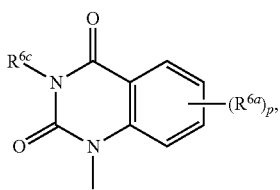
Q-79
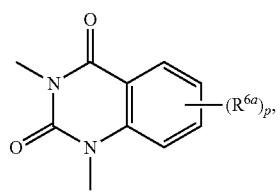
Q-80
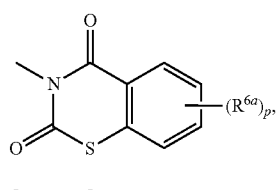
Q-81
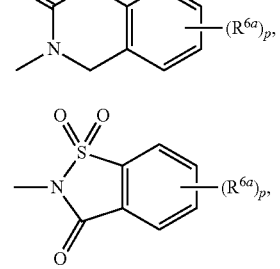
Q-82
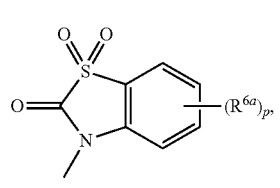
Q-83
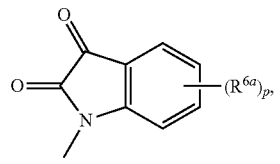
Q-84
-continued
Q-85
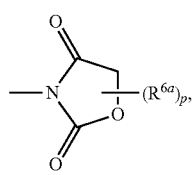
Q-86
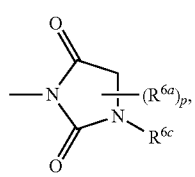
Q-87
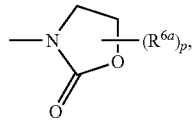
Q-88
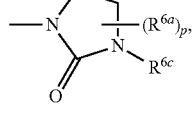
Q-89
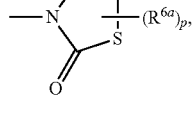
Q-90
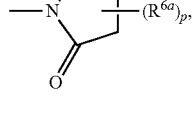
Q-91
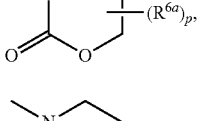
Q-92
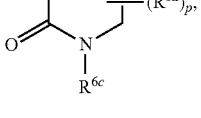
Q-93
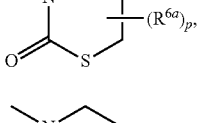
Q-94
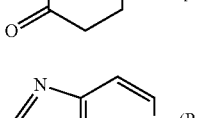
Q-95
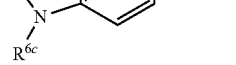

-continued

Q-96: 2-methylbenzoxazole with $(R^{6a})_p$

Q-97: 2-methylbenzothiazole with $(R^{6a})_p$

Q-98: N-substituted phthalimide-dithione-like (thione-oxo) with $(R^{6a})_p$

Q-99: N-substituted dithiophthalimide with $(R^{6a})_p$

Q-100: N-methyl benzoxazol-2-thione with $(R^{6a})_p$

Q-101: N-methyl benzothiazol-2-thione with $(R^{6a})_p$ and

Q-102: barbiturate-type ring with $R^{6c}$ and $(R^{6a})_p$ wherein p is an integer from 0 to 5;

$R^{6c}$ is independently selected from H, $C_1$-$C_3$ alkyl, $C_2$-$C_3$ alkylcarbonyl, $C_2$-$C_3$ alkoxycarbonyl and $C_1$-$C_3$ alkoxy;

$R^{11}$ is independently H, $C_1$-$C_6$ alkyl or $C_3$-$C_8$ cycloalkyl;

$R^{12}$ is independently H, $CH_3$, $CF_3$ or $CH_2CF_3$;

$R^{14}$ is H, cyano, hydroxy, $C_1$-$C_3$ alkyl, $C_1$-$C_3$ haloalkyl or $C_1$-$C_3$ alkoxy;

$R^{20}$ is independently H, $CH_3$, $CH_2CF_3$, $CF_3$ or cyclopropyl;

$R^{21}$ is independently $C_1$-$C_3$ alkyl or —$Z^1Q$;

$Z^1$ is independently C(=O) or S(=O)$_2$;

$R^{23}$ is independently H, —CHO, $C_1$-$C_4$ alkyl, $C_1$-$C_4$ alkenyl or $C_1$-$C_4$ haloalkyl each $R^{24}$ and $R^{25}$ is independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl;

$R^{26}$ is selected from H, cyano, hydroxy, amino and $C_1$-$C_6$ alkyl;

$R^{27}$ is selected from H, $C_1$-$C_6$ alky; or $R^{26}$ and $R^{27}$ are taken together as —$(CH_2)_4$—, —$(CH_2)_5$— or —$(CH_2)_2O(CH_2)_2$—;

$R^{28}$ is H, halogen, cyano or $C_1$-$C_4$ alkyl;

x is an integer from 1 to 5, and when x is 2, 3, 4 or 5, then at most one instance of $R^6$ is —ZQ;

m is 0 or 1; and s and f are 0 or 1 provided that the sum of s and f is 1.

3. A compound of claim 2 wherein:

$Y^1$, $Y^2$ and $Y^3$ in Formula 1 form a ring selected from L-1 through L-24;

L-1: 6-membered ring with N, O, positions 3,4,5, T, $(R^{14})_n$

L-2: 6-membered ring with N (position 2), O, T, $(R^{14})_n$

L-3: 6-membered ring with N, S, positions 3,4,5, T, $(R^{14})_n$

L-4: 6-membered ring with N (position 2), S, T, $(R^{14})_n$

L-5: 6-membered ring with N, N-T, O, positions 3,4, $(R^{14})_n$

L-6: 6-membered ring with N, N-T, O, positions 3,4, $(R^{14})_n$

L-7: 6-membered ring with N, N-T, S, positions 3,4, $(R^{14})_n$

L-8: 6-membered ring with N, N-T, S, positions 3,4, $(R^{14})_n$

L-9: 6-membered ring with N, N-$R^{23}$, positions 3,4,5, T, $(R^{14})_n$

L-10 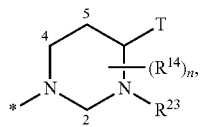
L-11 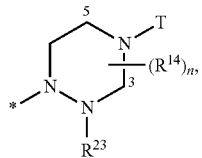
L-12 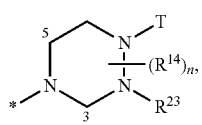
L-13 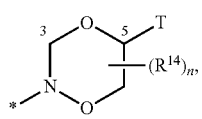
L-14 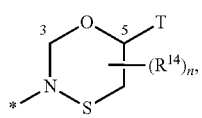
L-15 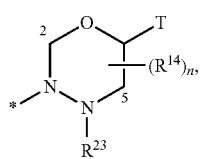
L-16 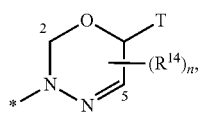
L-17 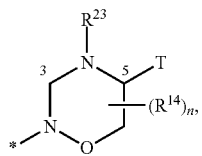
L-18 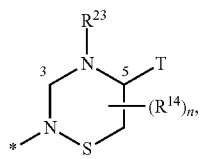
L-19 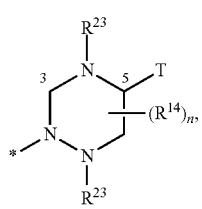
L-20 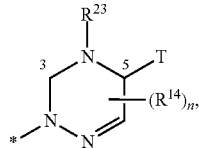
L-21 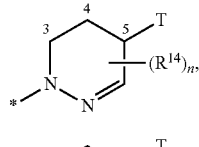
L-22 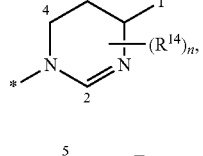
L-23 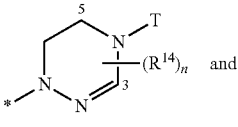 and
L-24 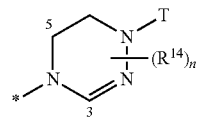
wherein the bond projecting to the left labeled with an astrisk is bonded to E in Formula 1 or Formula 1A, and the bond projecting to the right labeled with a T is bonded to G in Formula 1 or Formula 1A; and n is an integer from 0 to 4;
$Y^2$, $X^1$ and $X^2$ in Formula 1A form a ring selected from L-60 through L-65;
L-60 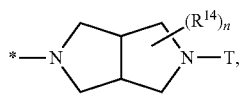
L-61 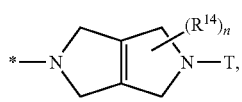
L-62 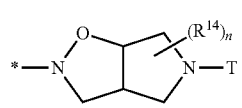
L-63 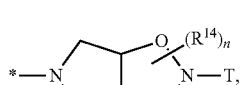
L-64  and
L-65 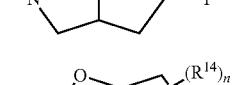

wherein the bond projecting to the left labeled with an asterisk is bonded to E in Formula 1 or Formula 1A, and the bond projecting to the right labeled with a T is bonded to G in Formula 1 or Formula 1A; and n is an integer from 0 to 4;

$W^3$ is $NR^{26}R^{27}$;

$R^{1c}$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

Z is a direct bond;

Q is selected from Q-45, Q-63, Q-65, Q-70, Q-71, Q-72, Q-84 and Q-85;

p is 0, 1, 2 or 3; and $R^{6a}$ is F, Cl, Br, hydroxy, cyano, methyl or methoxy.

4. A compound of claim 1 wherein:

E is E-1 or E-2;

$Y^1$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—;

$Y^3$ is —N=C($R^{14}$)—, —C($R^{14}$)=N— or a ring-forming chain consisting of 2 chain members wherein one chain member is —C($R^{14}$)$_2$— and the second chain member is selected from —C($R^{14}$)$_2$—, —O—, —S— and —N($R^{23}$)—; or $Y^3$ is —C($R^{14}$)$_2$N=C($R^{14}$)—, —C($R^{14}$)$_2$C($R^{14}$)=N—, —N=C($R^{14}$)C($R^{14}$)$_2$—, —C($R^{14}$)=NC($R^{14}$)$_2$— or a ring-forming chain consisting of 3 chain members wherein two chain members are —C($R^{14}$)$_2$— and the third chain member is selected from —C($R^{14}$)$_2$—, —O—, —S— and —N($R^{23}$)—;

x is an integer from 1 to 5, and when x is 2, 3, 4 or 5, then at most one instance of $R^6$ is —ZQ;

$R^6$ is H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{20}R^{21}$ or —ZQ;

$A^1$ is $CHR^{15}$ or $NR^{16}$;

$A^2$ is —O—, —S—, —N($R^7$)—, —C($R^8$)$_2$— or —OC($R^8$)$_2$—;

$W^1$ is O;

$W^2$ is O;

$R^{1a}$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

$R^2$ is H, cyano, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_1$-$C_4$ alkylthio, $C_1$-$C_4$ haloalkylthio, $C_1$-$C_4$ alkylamino, $C_2$-$C_4$ dialkylamino, $C_1$-$C_4$ haloalkylamino or $C_2$-$C_4$ halodialkylamino;

$R^3$ is H, $C_1$-$C_3$ alkyl, $C_1$-$C_3$ alkoxy or $C_1$-$C_3$ haloalkyl;

$R^4$ is H or methyl;

$R^5$ is H or $C_1$-$C_2$ alkyl;

$R^7$ is H, $C_1$-$C_2$ alkyl, $C_1$-$C_2$ haloalkyl, $CH_3C(=O)$, $CF_3C(=O)$ or $CH_3OC(=O)$;

each $R^8$ is independently H, $CH_3$ or $CH_2CF_3$;

Z is a direct bond;

Q is selected from Q-45, Q-63, Q-65, Q-70, Q-71, Q-72, Q-84 and Q-85;

p is 0, 1, 2 or 3;

each $R^{6a}$ is F, Cl, Br, hydroxy, cyano, methyl or methoxy;

$R^{14}$ is H, cyano, hydroxy, $C_1$-$C_3$ alkyl, $C_1$-$C_3$ haloalkyl or $C_1$-$C_3$ alkoxy;

$R^{15}$ is H, halogen, cyano, hydroxy, —CHO, $C_1C_4$ alkyl, $C_1$-$C_4$ haloalkyl, $C_2$-$C_5$ alkoxycarbonyl or $C_1$-$C_4$ alkoxy;

$R^{16}$ is H, methyl, methylcarbonyl or methoxycarbonyl;

$R^{20}$ is independently H, $CH_3$, $CH_2CF_3$, $CF_3$ or cyclopropyl;

$R^{21}$ is independently $C_1$-$C_3$ alkyl; and each $R^{23}$ is independently H or $CH_3$.

5. A compound of claim 4 wherein:

E is E-1;

$Y^1$, $Y^2$ and $Y^3$ in Formula 1 form a ring selected from L-1 through L-24;

$Y^2$, $X^1$ and $X^2$ in Formula 1A form a ring selected from L-60, L-61, L-64 and L-65;

J is;

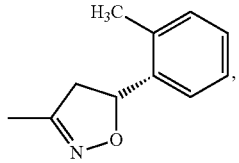
J-29-1

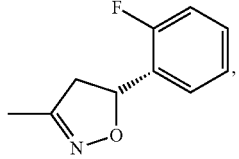
J-29-2

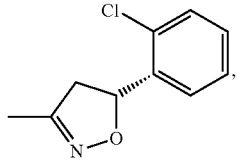
J-29-3

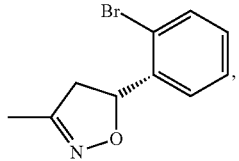
J-29-4

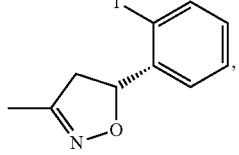
J-29-5

-continued
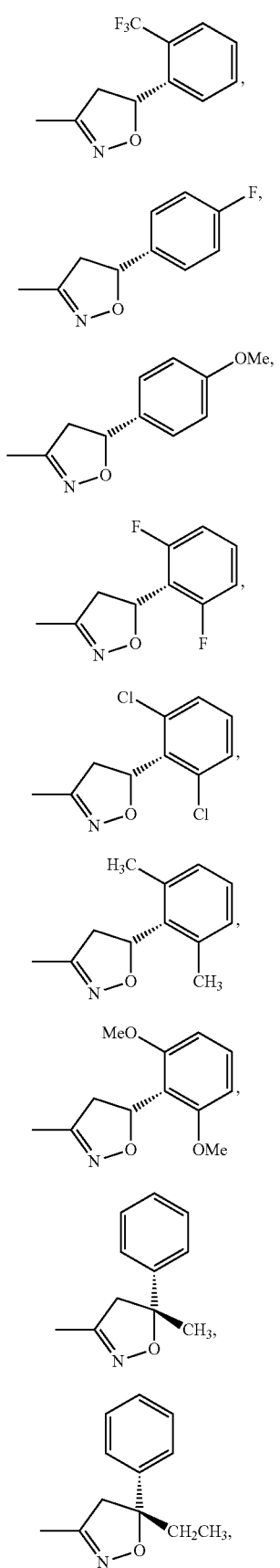
| | |
|---|---|
| J-29-6 | |
| J-29-7 | |
| J-29-8 | |
| J-29-9 | |
| J-29-10 | |
| J-29-11 | |
| J-29-12 | |
| J-29-13 | |
| J-29-14 | |
-continued
| | |
|---|---|
| 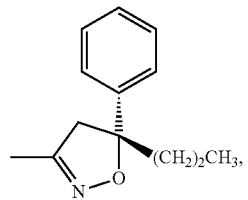 | J-29-15 |
| 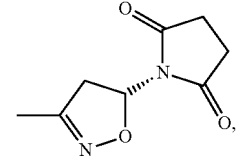 | J-29-37 |
| 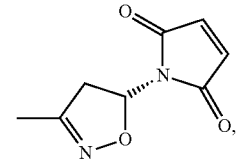 | J-29-38 |
| 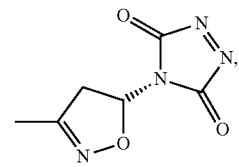 | J-29-39 |
| 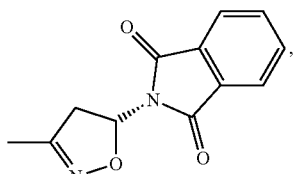 | J-29-40 |
| 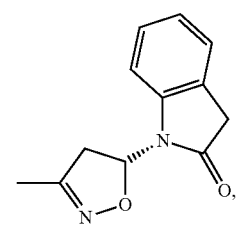 | J-29-41 |
| 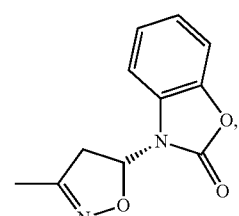 | J-29-42 |
| 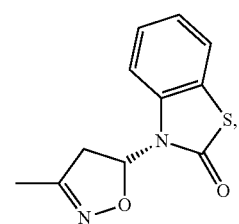 | J-29-43 |

-continued
J-29-44 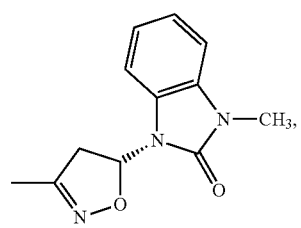
J-29-45 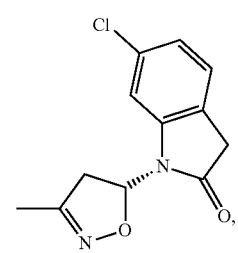
J-29-46 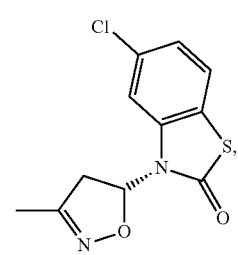
J-29-47 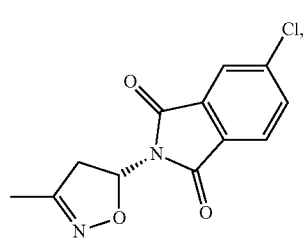
J-29-48 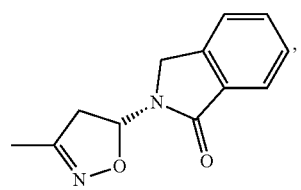
J-29-49 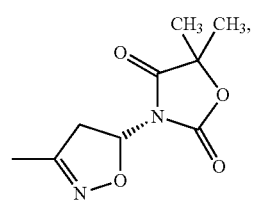
J-29-50 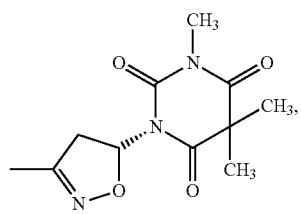
-continued
J-29-51 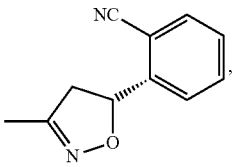
J-29-52 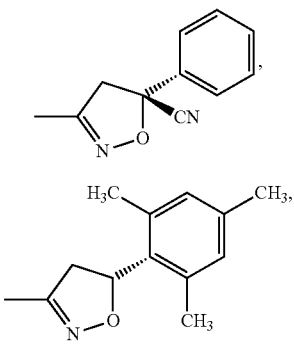
J-29-53 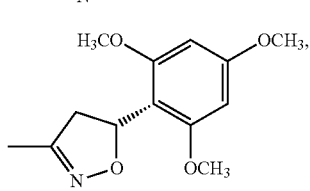
J-29-54 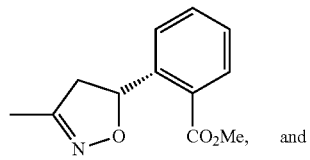
J-29-55 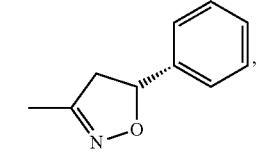, and
J-29-56 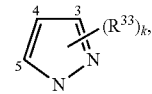,
wherein the bond shown projecting to the left is bonded to G in Formula 1 or Formula 1A;
$R^{1a}$ is selected from one of U-1 through U-50;
U-1 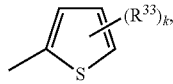
U-2 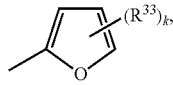
U-3 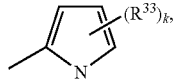
U-4

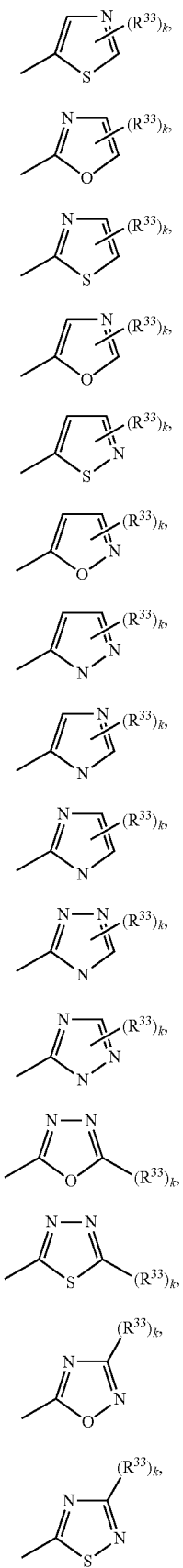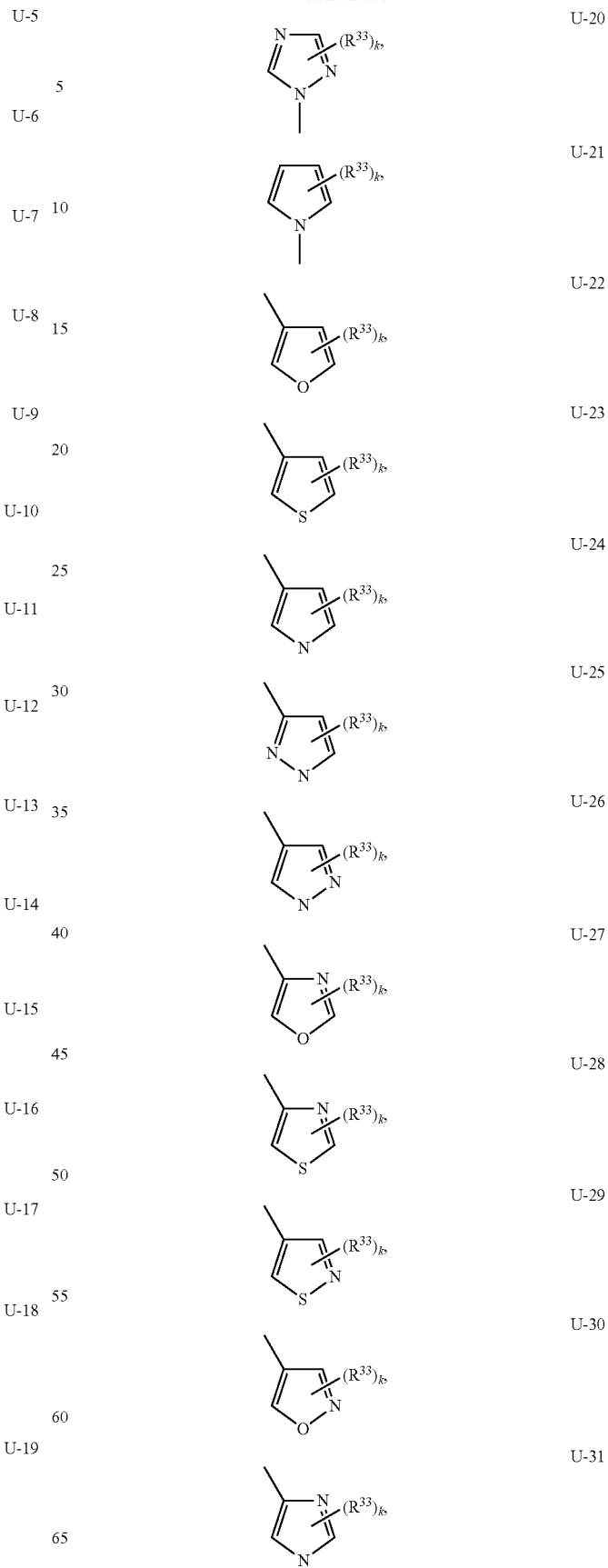

205

-continued

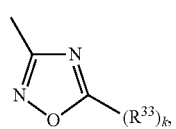 U-32

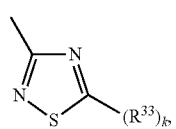 U-33

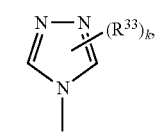 U-34

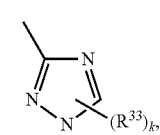 U-35

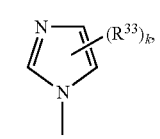 U-36

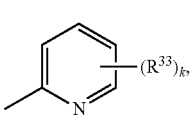 U-37

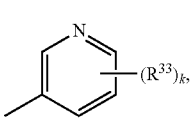 U-38

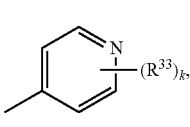 U-39

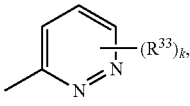 U-40

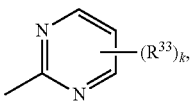 U-41

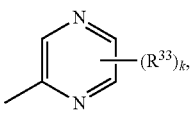 U-42

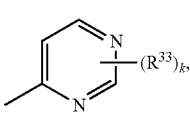 U-43

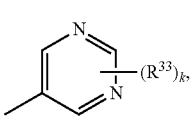 U-44

206

-continued

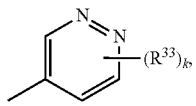 U-45

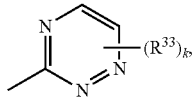 U-46

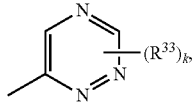 U-47

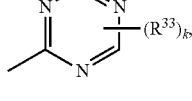 U-48

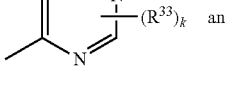 U-49 and

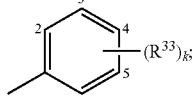 U-50 wherein when $R^{33}$ is attached to a carbon ring member, said $R^{33}$ is selected from $R^{33a}$, and when $R^{33}$ is attached to a nitrogen ring member, said $R^{33}$ is selected from $R^{33b}$; and k is 0, 1 or 2;
$R^{14}$ is H, cyano, hydroxy, $C_1$-$C_2$ alkyl or $C_1$-$C_2$ alkoxy;
$A^1$ is $CHR^{15}$;
$R^{15}$ is H, halogen, cyano, hydroxy, methyl or methoxy; and
$R^{23}$ is H.

6. A compound of claim 5 wherein:
$Y^1$, $Y^2$ and $Y^3$ in Formula 1 form a ring selected from L-1, L-2 and L-9;
$Y^2$, $X^1$ and $X^2$ in Formula 1A form a ring selected from L-6 and L-64;
$R^{1a}$ is U-1, U-20 or U-50;
$R^{15}$ is H;
k is 1 or 2;
each $R^{33a}$ is independently halogen, $C_1$-$C_3$ alkyl, $C_1$-$C_3$ haloalkyl or $C_2$-$C_3$ alkoxyalkyl; and
$R^{29a}$ is H.

7. A compound of claim 1 selected from
1-[4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone,
1-[2-acetyl-4-[4-[5-(2,6-difluorophenyl)-4,5-dihydro-3-isoxazolyl]-2-thiazolyl]tetrahydro-1(2H)-pyridazinyl]-2-[5-methyl-3-(trifluoromethyl)-1H-pyrazol-1-yl]ethanone;
1-[5-[4-[5-(2,6-Difluorophenyl)-4,5-dihydro-3-isoxazolyl]-2-thiazolyl]tetrahydro-2H- 1,2-oxazin-2-yl]-2-[5-methyl-3-trifluoromethyl)-1H-pyrazol-1-yl]ethanone; and
1-[5-[4-[5-(2,6-difluorophenyl)-4,5-dihydro-3-isoxazolyl]-2-thiazolyl]hexahydropyrrolol[3,4-c]pyrrol-2(1H)-yl]-2-[5-methyl-3-(trifluoromethyl)-1H-pyrazol-1-yl]ethanone.

8. A fungicidal composition comprising (a) a compound of claim 1; and (b) at least one other fungicide.

9. A fungicidal composition comprising (a) a compound of claim 1; and (b) at least one additional component selected from the group consisting of surfactants, solid diluents and liquid diluents.

10. A method for controlling plant diseases caused by fungal plant pathogens comprising applying to the plant or portion thereof, or to the plant seed, a fungicidally effective amount of a compound of claim 1.

11. A compound of claim 4 wherein:
E is E-1;
$Y^1$, $Y^2$ and $Y^3$ in Formula 1 form a ring selected from L-1 through L-24;
$Y^2$, $X^1$ and $X^2$ in Formula 1A form a ring selected from L-60, L-61, L-64 and L-65;
$R^{1a}$ is selected from one of U-1 through U-50;
$R^{14}$ is H, cyano, hydroxy, $C_1$-$C_2$ alkyl or $C_1$-$C_2$ alkoxy;
$A^1$ is $CHR^{15}$;
$R^{15}$ is H, halogen, cyano, hydroxy, methyl or methoxy; and
$R^{23}$ is H.

12. A compound of claim 11 wherein:
$Y^1$, $Y^2$ and $Y^3$ in Formula 1 form a ring selected from L-1, L-2 and L-9;
$Y^2$, $X^1$ and $X^2$ and in Formula 1A form a ring selected from L-6 and L-64;
$R^{1a}$ is U-1, U-20 or U-50;
$R^{15}$ is H;
k is 1 or 2;
each $R^{33a}$ is independently halogen, $C_1$-$C_3$ alkyl, $C_1$-$C_3$ haloalkyl or $C_2$-$C_3$ alkoxyalkyl;
$R^{29a}$ is H;
$R^6$ is —ZQ;
Q is selected from Q-45, Q-63, Q-65, Q-70, Q-71, Q-72 and Q-84;
each $R^{6a}$ is independently F, Cl, Br, hydroxy, cyano, methyl or methoxy;
$R^{6c}$ is H or methyl; and
p is 0, 1 or 2.

* * * * *